(12) United States Patent
Brecher et al.

(10) Patent No.: US 9,675,339 B2
(45) Date of Patent: Jun. 13, 2017

(54) DEVICES AND METHODS FOR MINIMALLY INVASIVE SUTURING

(71) Applicant: EndoEvolution, LLC, Raynham, MA (US)

(72) Inventors: Gerald I. Brecher, North Andover, MA (US); John C. Meade, Mendon, MA (US); John Aho, Lunenburg, MA (US); Roger Baske, Old Mill Creek, IL (US); James H. Bleck, Chelmsford, MA (US); John F. Carlson, Lake Elmo, MN (US); Thomas Eagan, Chelmsford, MA (US); Michael J. Helander, Somerset, WI (US); James W. Murray, Clear Lake, WI (US); Ashley Perkins, Lowell, MA (US); Wayne A. Shakal, Taylor Falls, MN (US); Jonathan Towle, Amherst, NH (US)

(73) Assignee: EndoEvolution, LLC, Raynham, MA (US)

( * ) Notice: Subject to any disclaimer, the term of this patent is extended or adjusted under 35 U.S.C. 154(b) by 0 days.

(21) Appl. No.: 15/377,562

(22) Filed: Dec. 13, 2016

(65) Prior Publication Data
US 2017/0105723 A1    Apr. 20, 2017

Related U.S. Application Data

(63) Continuation of application No. 13/204,820, filed on Aug. 8, 2011, which is a continuation-in-part of
(Continued)

(51) Int. Cl.
*A61B 17/04*    (2006.01)
*A61B 17/06*    (2006.01)
(Continued)

(52) U.S. Cl.
CPC ...... *A61B 17/0469* (2013.01); *A61B 17/0482* (2013.01); *A61B 17/0491* (2013.01);
(Continued)

(58) Field of Classification Search
CPC ............ A61B 17/0482; A61B 17/0491; A61B 17/0625; A61B 2017/2927;
(Continued)

(56) References Cited

U.S. PATENT DOCUMENTS

| 1,327,577 | A | 1/1920 | Turner |
| 1,822,330 | A | 9/1931 | Ainslie |

(Continued)

FOREIGN PATENT DOCUMENTS

| CN | 2169381 | 6/1994 |
| CN | 201082170 | 7/2008 |

(Continued)

OTHER PUBLICATIONS

Non-Final Office Action in U.S. Appl. No. 15/260,094, dated Jan. 17, 2017, 14 pages.
(Continued)

*Primary Examiner* — Christopher L Templeton
*Assistant Examiner* — Lucas Paez
(74) *Attorney, Agent, or Firm* — Crawford Maunu PLLC

(57) ABSTRACT

Devices and methods for minimally invasive suturing are disclosed. One suturing device for minimally invasive suturing includes a proximal section a distal end, and an intermediate region therebetween. The device includes a suture head assembly having a suturing needle with a pointed end and a second end. The suturing needle is capable of rotating about an axis approximately perpendicular to a longitudinal axis of the device, wherein the pointed end of the suturing needle is positioned within the suture head assembly prior to deployment of guides that are adapted and configured to
(Continued)

guide the needle around a circular path when advanced by a drive mechanism having a needle driver for engaging and rotating the suturing needle.

15 Claims, 116 Drawing Sheets

Related U.S. Application Data application No. 12/909,606, filed on Oct. 21, 2010, now Pat. No. 7,993,354.

(60) Provisional application No. 61/388,648, filed on Oct. 1, 2010.

(51) Int. Cl.
  *A61B 17/062* (2006.01)
  *A61B 17/00* (2006.01)

(52) U.S. Cl.
  CPC .... *A61B 17/0625* (2013.01); *A61B 17/06066* (2013.01); *A61B 2017/00407* (2013.01); *A61B 2017/0472* (2013.01)

(58) Field of Classification Search
  CPC .......... A61B 2017/06028; A61B 17/04; A61B 17/0483; A61B 17/062
  See application file for complete search history.

(56) References Cited

U.S. PATENT DOCUMENTS

| | | |
|---|---|---|
| 2,327,353 A | 8/1943 | Karle |
| 2,601,564 A | 6/1952 | Smith |
| 3,197,997 A | 8/1965 | Kurtz |
| 3,311,110 A | 3/1967 | Singerman et al. |
| 3,344,790 A | 10/1967 | Dorner |
| 3,762,418 A | 10/1973 | Wasson |
| 3,834,599 A | 9/1974 | Herr |
| 3,835,912 A | 9/1974 | Kristensen et al. |
| 3,910,282 A | 10/1975 | Messer et al. |
| 3,951,261 A | 4/1976 | Mandel et al. |
| 3,972,418 A | 8/1976 | Schuler et al. |
| 4,027,608 A | 6/1977 | Arbuckle |
| 4,235,177 A | 11/1980 | Arbuckle |
| 4,331,277 A | 5/1982 | Green |
| 4,437,465 A | 3/1984 | Nomoto et al. |
| 4,509,945 A | 4/1985 | Kramann et al. |
| 4,527,564 A | 7/1985 | Eguchi et al. |
| 4,557,265 A | 12/1985 | Andersson |
| 4,621,640 A | 11/1986 | Mulhollan et al. |
| 4,841,888 A | 6/1989 | Mills et al. |
| 4,899,746 A | 2/1990 | Brunk |
| 4,957,502 A | 9/1990 | Takase |
| 5,080,663 A | 1/1992 | Mills et al. |
| 5,089,012 A | 2/1992 | Prou |
| 5,201,760 A | 4/1993 | West |
| 5,210,376 A | 5/1993 | Caviar |
| 5,269,806 A | 12/1993 | Sardelis et al. |
| 5,305,281 A | 4/1994 | Lubeck |
| 5,306,281 A | 4/1994 | Beurrier |
| 5,308,353 A | 5/1994 | Beurrier |
| 5,318,578 A | 6/1994 | Hasson |
| 5,344,061 A | 9/1994 | Crainich |
| 5,358,498 A | 10/1994 | Shave |
| 5,364,408 A | 11/1994 | Gordon |
| 5,373,101 A | 12/1994 | Barabolak |
| 5,376,101 A | 12/1994 | Green et al. |
| 5,387,221 A | 2/1995 | Bisgaard |
| 5,437,681 A | 8/1995 | Meade et al. |
| 5,462,558 A | 10/1995 | Kolesa et al. |
| 5,472,081 A | 12/1995 | Kilgrow et al. |
| 5,474,568 A | 12/1995 | Scott |
| 5,478,344 A | 12/1995 | Stone et al. |
| 5,478,345 A | 12/1995 | Stone et al. |
| 5,480,409 A | 1/1996 | Riza |
| 5,503,266 A | 4/1996 | Kalbfeld et al. |
| 5,514,159 A | 5/1996 | Matula et al. |
| 5,540,705 A | 7/1996 | Meade et al. |
| 5,571,119 A | 11/1996 | Atala |
| 5,575,800 A | 11/1996 | Gordon |
| 5,578,044 A | 11/1996 | Gordon et al. |
| 5,643,295 A | 7/1997 | Yoon |
| 5,645,552 A | 7/1997 | Sherts |
| 5,665,096 A | 9/1997 | Yoon |
| 5,665,109 A | 9/1997 | Yoon |
| 5,669,490 A | 9/1997 | Colligan et al. |
| 5,675,961 A | 10/1997 | Cerwin et al. |
| 5,709,693 A | 1/1998 | Taylor |
| 5,713,910 A | 2/1998 | Gordon et al. |
| 5,715,942 A | 2/1998 | Li et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,814,069 A | 9/1998 | Schulze et al. |
| 5,814,071 A | 9/1998 | McDevitt et al. |
| 5,833,695 A | 11/1998 | Yoon |
| 5,860,992 A | 1/1999 | Daniel et al. |
| 5,891,160 A | 4/1999 | Williamson, IV et al. |
| 5,906,273 A | 5/1999 | Pohle et al. |
| 5,908,426 A | 6/1999 | Pierce |
| 5,908,428 A | 6/1999 | Scirica et al. |
| 5,911,727 A | 6/1999 | Taylor |
| 5,954,733 A | 9/1999 | Yoon |
| 5,968,077 A | 10/1999 | Wojciechowicz et al. |
| 5,993,466 A | 11/1999 | Yoon |
| 6,016,905 A | 1/2000 | Gemma et al. |
| 6,036,694 A | 3/2000 | Goble et al. |
| 6,048,351 A | 4/2000 | Gordon et al. |
| 6,053,908 A | 4/2000 | Crainich et al. |
| 6,056,771 A | 5/2000 | Proto |
| 6,071,289 A | 6/2000 | Stefanchik et al. |
| 6,096,051 A | 8/2000 | Kortenbach et al. |
| 6,126,666 A | 10/2000 | Trapp et al. |
| 6,135,385 A | 10/2000 | Martinez de Lahidalga |
| 6,136,010 A | 10/2000 | Modesitt et al. |
| 6,159,224 A | 12/2000 | Yoon |
| 6,261,307 B1 | 7/2001 | Yoon et al. |
| 6,270,508 B1 | 8/2001 | Klieman et al. |
| 6,322,581 B1 | 11/2001 | Fukuda et al. |
| 6,332,888 B1 | 12/2001 | Levy et al. |
| 6,346,111 B1 | 2/2002 | Gordon et al. |
| 6,443,962 B1 | 9/2002 | Gaber |
| 6,454,777 B1 | 9/2002 | Green |
| 6,454,778 B2 | 9/2002 | Kortenbach |
| 6,494,888 B1 | 12/2002 | Laufer et al. |
| 6,506,196 B1 | 1/2003 | Laufer |
| 6,558,400 B2 | 5/2003 | Deem et al. |
| 6,656,194 B1 | 12/2003 | Gannoe et al. |
| 6,663,639 B1 | 12/2003 | Laufer et al. |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,835,200 B2 | 12/2004 | Laufer et al. |
| 6,877,352 B1 | 4/2005 | Schlereth |
| 6,908,427 B2 | 6/2005 | Fleener et al. |
| 6,923,819 B2 | 8/2005 | Meade et al. |
| 6,955,643 B2 | 10/2005 | Gellman et al. |
| 7,004,951 B2 | 2/2006 | Gibbens, III |
| 7,033,370 B2 | 4/2006 | Gordon et al. |
| 7,041,111 B2 | 5/2006 | Chu |
| 7,144,401 B2 | 12/2006 | Yamamoto et al. |
| 7,166,116 B2 | 1/2007 | Lizardi et al. |
| 7,338,504 B2 | 3/2008 | Gibbens et al. |
| 7,615,060 B2 | 11/2009 | Stokes et al. |
| 7,628,796 B2 | 12/2009 | Shelton, IV et al. |
| 7,637,909 B2 | 12/2009 | Lechot et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,846,169 B2 | 12/2010 | Shelton, IV et al. |

(56) References Cited

U.S. PATENT DOCUMENTS

| | | | |
|---|---|---|---|
| 7,862,572 B2 | 1/2011 | Meade et al. |
| 7,887,554 B2 | 2/2011 | Stokes et al. |
| 7,976,533 B2 | 7/2011 | Larsson |
| 7,976,555 B2 | 7/2011 | Meade et al. |
| 7,993,354 B1 | 8/2011 | Brecher et al. |
| 8,066,737 B2 | 11/2011 | Meade et al. |
| 8,123,764 B2 | 2/2012 | Meade et al. |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,125,645 B1 | 9/2015 | Martin et al. |
| 9,173,655 B2 | 11/2015 | Martin |
| 9,220,496 B2 | 12/2015 | Martin et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | Brecher et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 2002/0107530 A1 | 8/2002 | Sauer et al. |
| 2002/0116011 A1 | 8/2002 | Chee Chung et al. |
| 2002/0173800 A1 | 11/2002 | Dreyfuss et al. |
| 2002/0193809 A1 | 12/2002 | Meade et al. |
| 2002/0198542 A1 | 12/2002 | Yamamoto et al. |
| 2003/0083674 A1 | 5/2003 | Gibbens |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034372 A1 | 2/2004 | Chu |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0035007 A1 | 2/2005 | Kennedy et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0262984 A1 | 12/2005 | Hetcher et al. |
| 2006/0069396 A1 | 3/2006 | Meade et al. |
| 2006/0111732 A1 | 5/2006 | Gibbens et al. |
| 2006/0224184 A1 | 10/2006 | Stefanchik et al. |
| 2006/0282089 A1 | 12/2006 | Stokes et al. |
| 2006/0282090 A1 | 12/2006 | Stokes et al. |
| 2006/0282091 A1 | 12/2006 | Shelton et al. |
| 2006/0282092 A1 | 12/2006 | Stokes et al. |
| 2006/0282093 A1 | 12/2006 | Shelton et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton et al. |
| 2006/0282099 A1 | 12/2006 | Stokes et al. |
| 2007/0135838 A1 | 6/2007 | Meyer |
| 2007/0239176 A1* | 10/2007 | Stokes ............. A61B 17/00234 606/144 |
| 2008/0132919 A1 | 6/2008 | Chui et al. |
| 2008/0140091 A1 | 6/2008 | DeDeyne et al. |
| 2009/0024145 A1 | 1/2009 | Meade et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2010/0152751 A1* | 6/2010 | Meade ............... A61B 17/0469 606/144 |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367240 A1 | 12/2016 | Shelton, IV et al. |
| 2016/0367243 A1 | 12/2016 | Martin et al. |

FOREIGN PATENT DOCUMENTS

| | | |
|---|---|---|
| DE | 4310315 | 10/1993 |
| EP | 0648474 | 4/1995 |
| EP | 2103262 | 9/2009 |
| EP | 2292157 | 3/2011 |
| EP | 2308391 | 4/2011 |
| EP | 2370002 | 10/2011 |
| EP | 1791476 | 12/2015 |
| FR | 2540377 | 8/1984 |
| GB | 18602 | 0/1908 |
| JP | 55151956 | 11/1980 |
| JP | 07178100 | 7/1995 |
| JP | 07328021 | 12/1995 |
| JP | H11276492 | 10/1999 |
| JP | 2000139931 | 5/2000 |
| JP | 2005253987 | 9/2005 |
| WO | WO9729694 | 8/1997 |
| WO | WO9912482 | 3/1999 |
| WO | WO9940850 | 8/1999 |
| WO | WO9947050 | 9/1999 |
| WO | WO0112084 | 2/2001 |
| WO | WO02102226 | 12/2002 |
| WO | WO03028541 | 10/2003 |
| WO | WO2004012606 | 2/2004 |
| WO | WO2004021894 | 3/2004 |
| WO | WO2004028402 | 4/2004 |
| WO | WO2004086986 | 10/2004 |
| WO | WO2006034209 | 3/2006 |
| WO | WO2007089603 | 8/2007 |
| WO | WO2008147555 | 12/2008 |
| WO | WO2010062380 | 6/2010 |

OTHER PUBLICATIONS

Preliminary Amendment filed in U.S. Appl. No. 15/260,094, dated Nov. 18, 2016, 7 pages.
International Preliminary Report on Patentability dated Jan. 13, 2008 and Written Opinion dated Jun. 13, 2008 for PCT/US05/33507.
International Preliminary Report on Patentability dated Jan. 27, 2006 and Written Opinion dated Nov. 1, 2007 for PCT/US07/02204.
International Search Report and Written Opinion dated Mar. 3, 2003 for PCT/US02/12560.
International Preliminary Examination Report dated Mar. 12, 2004 for PCT/US02/12560.
International Search Report and Written Opinion dated Jul. 5, 2010 for PCT/US09/06212.

(56) References Cited

OTHER PUBLICATIONS

Supplemental European Search Report dated Mar. 15, 2007 for EP140654.5.
European Search Report dated Feb. 8, 2011 for EP10009831.8.
European Search Report dated Feb. 9, 2011 for EP10009832.6.
Office Action dated Jul. 1, 2014 from Corresponding Japanese Application No. 2013-138559.
European Search Report dated Jun. 5, 2015 from corresponding European Application No. 12822057.1.
European Search Report dated Aug. 14, 2015 from corresponding European Application No. 11830008.
International Search Report issued in related PCT application No. PCT/US07/002204 dated Nov. 1, 2007.
Written Opinion issued in related PCT application No. PCT/US07/002204 dated Nov. 1, 2007.
Search Report dated May 20, 2010 from SG Application No. 200805426-4.
Extended Search Report dated Feb. 17, 2011 from corresponding European Application No. 05797831.4.
Extended Search Report dated Feb. 21, 2011 from corresponding European Application No. 10009831.8.
Extended Search Report dated Feb. 21, 2011 from corresponding European Application No. 10009832.6.
European Search Report dated Mar. 11, 2011 from corresponding European Application No. 07762862.6.
Japanese Office Action dated Oct. 18, 2011 from Corresponding Japanese Application No. 2008-552444.
International Preliminary Report on Patentability dated Feb. 11, 2014 from Corresponding PCT Application No. PCT/US12/049979.
International Search Report and Written Opinion of the International Searching Authority (ISA) dated Apr. 24, 2012 relating to PCT/US11/054334.
Examination Report issued by Hungarian IP Office on behalf of Singapore IP Office issued Feb. 8, 2012 in connection with Singapore Application No. 200907505-2.
Supplementary European Search Report dated Mar. 23, 2007 in connection with EP Application No. 02725747.6.
Supplementary European Search Report dated Oct. 6, 2009 in connection with EP Application No. 02725747.6.
Office Action with English translation in connection with Japanese Patent Application No. JP2007-532595 issued Jan. 1, 2011.
Extended Search Report in connection with EP05797831.4 issued Feb. 25, 2011.
Written Opinion issued Jan. 11, 2011 in connection with Singapore Patent Application No. 200907505-2.
International Search Report and Written Opinion dated Jan. 5, 2009 in connection with PCT/US08/006674.
International Preliminary Report on Patentability dated Nov. 24, 2009 in connection with PCT/US08/006674.
International Search Report issued in related PCT application No. PCT/US09/006212 dated Jul. 5, 2010.
International Search Report issued in related PCT application No. PCT/US05/33507 dated Jun. 13, 2008.
Extended Search Report dated Nov. 29, 2012 from corresponding European Application No. 09829467.1.

\* cited by examiner

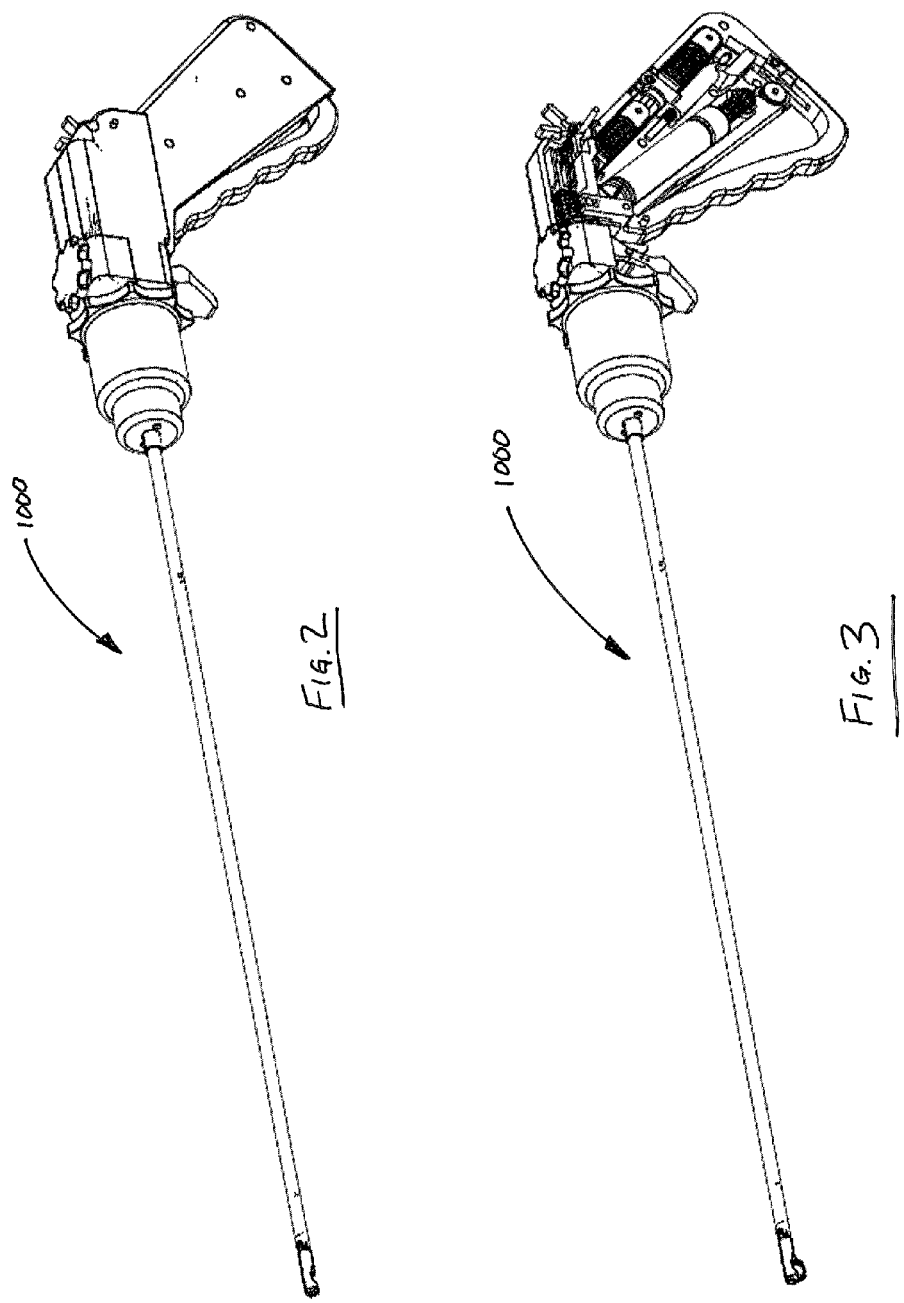

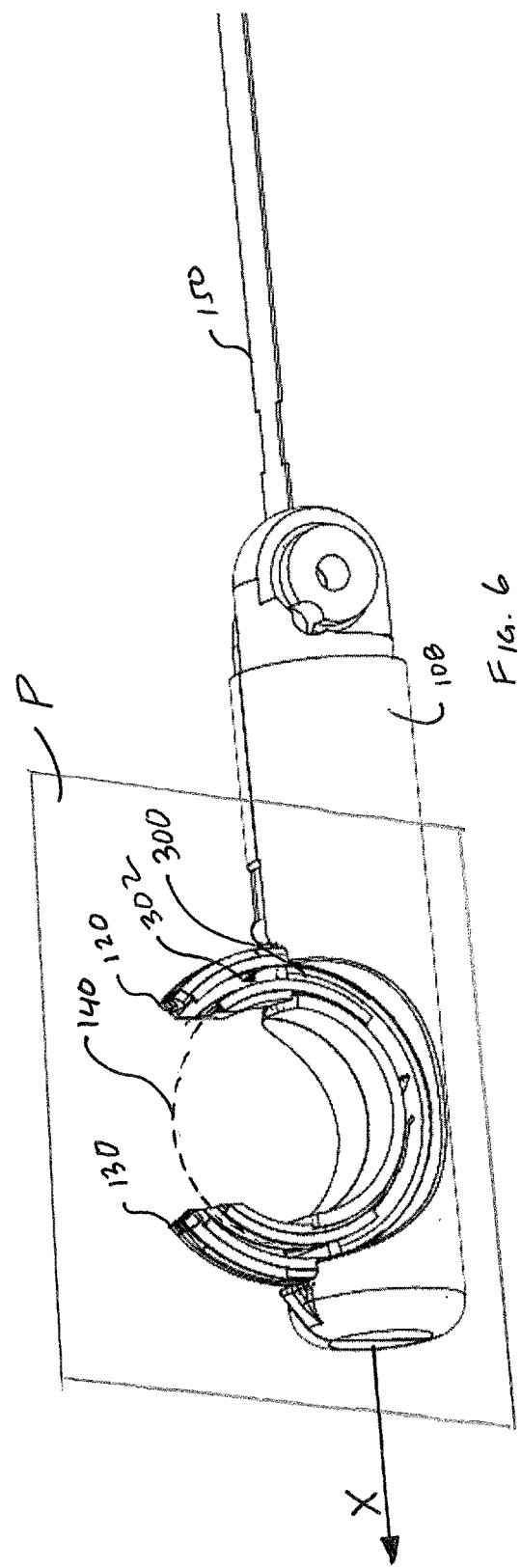

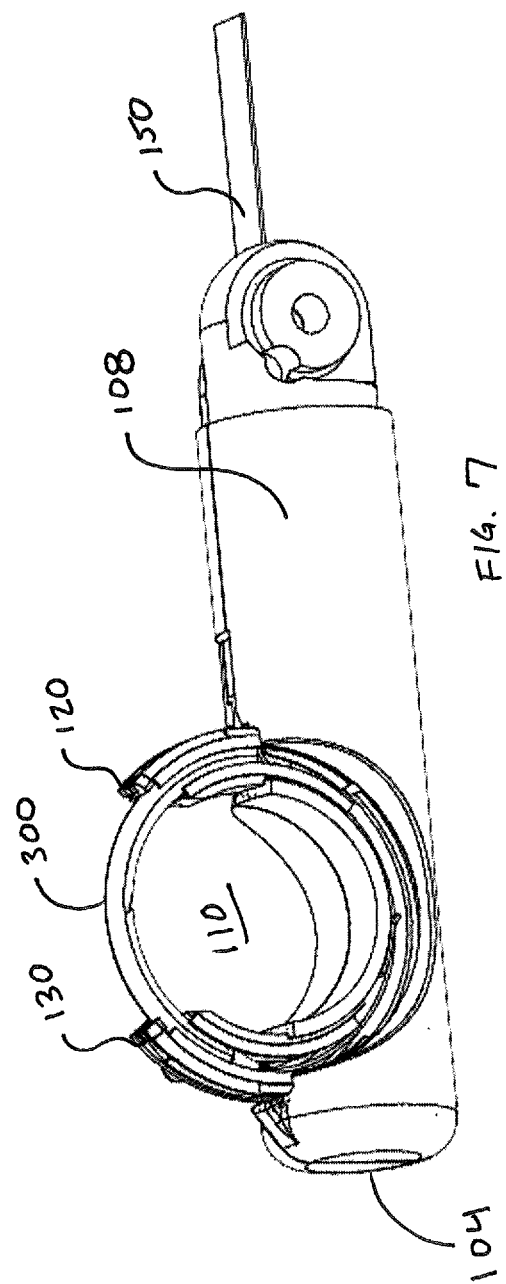

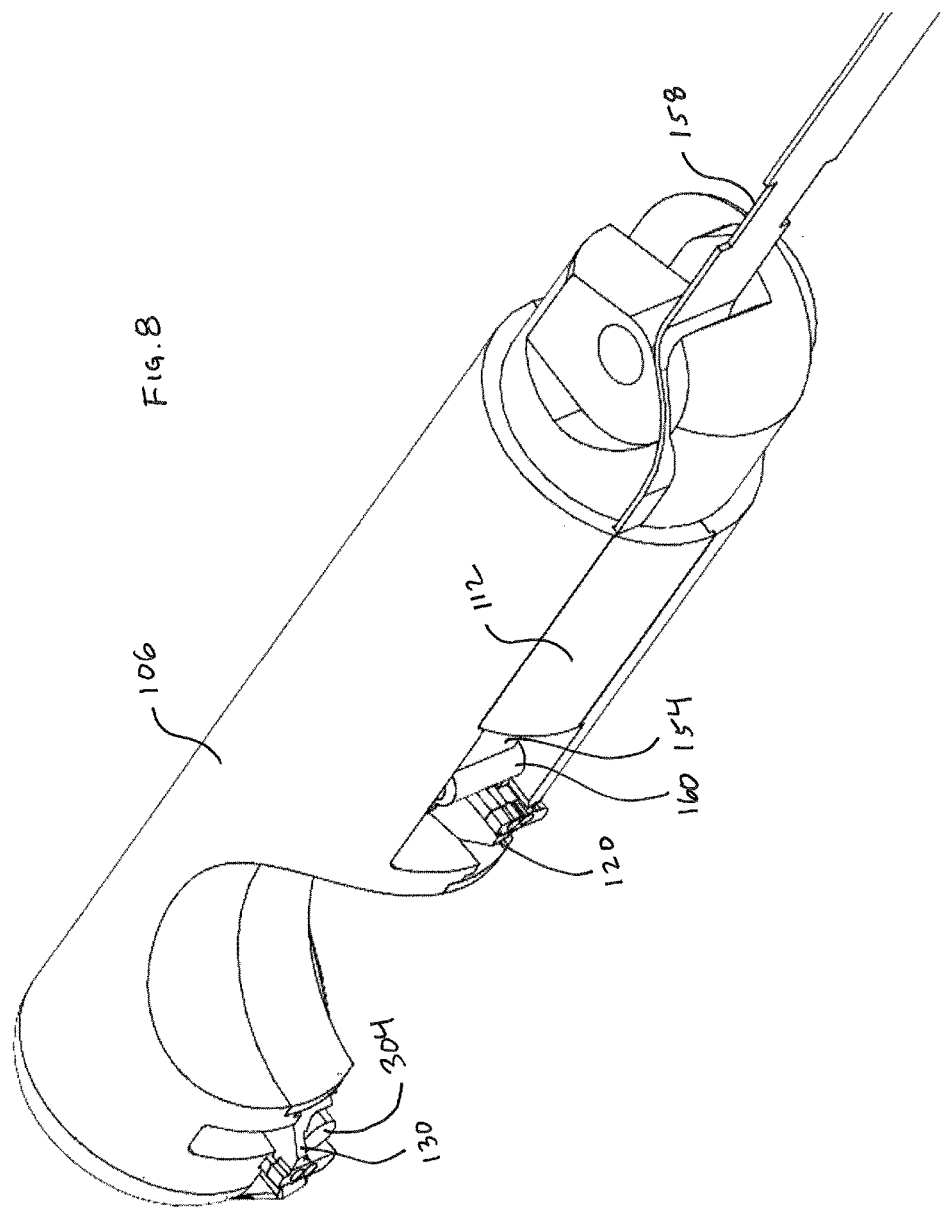

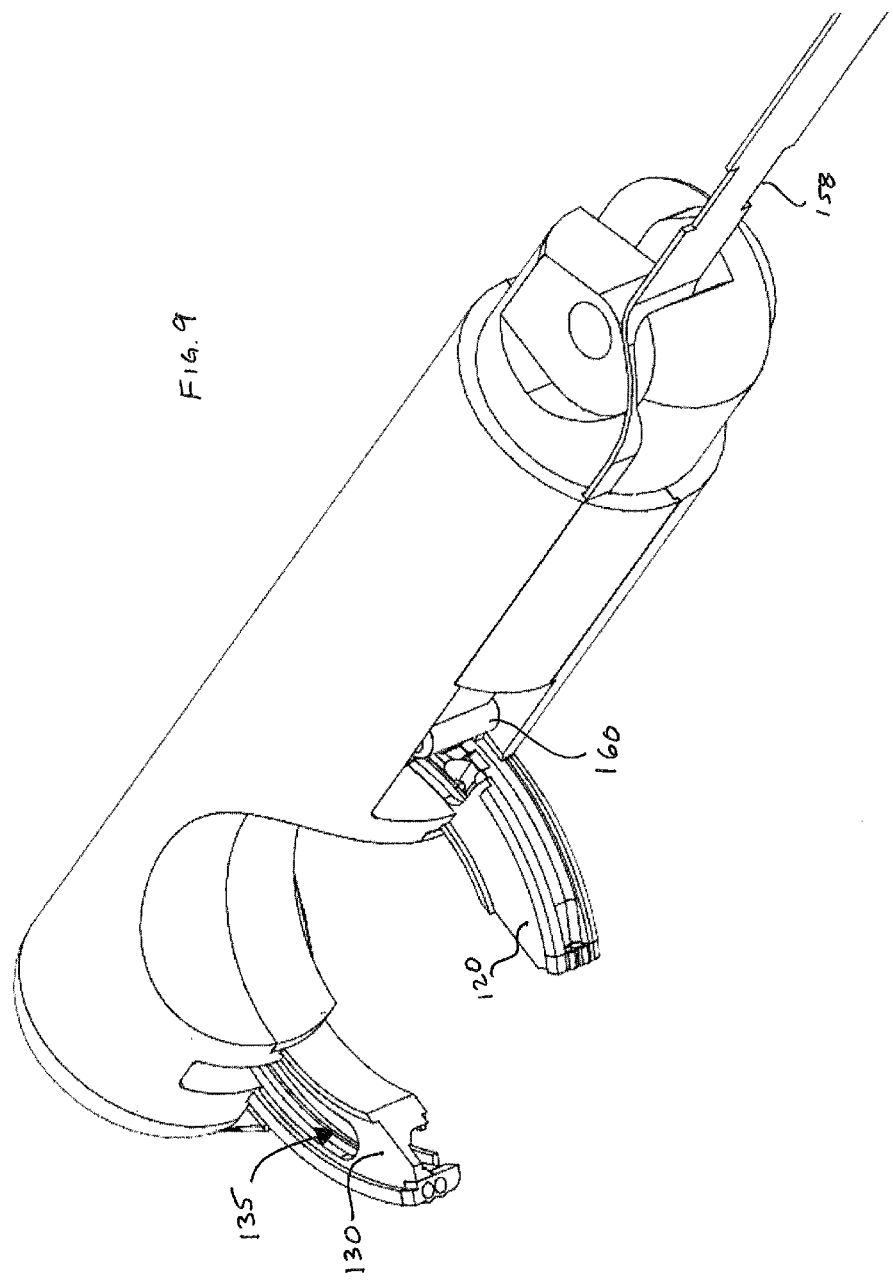

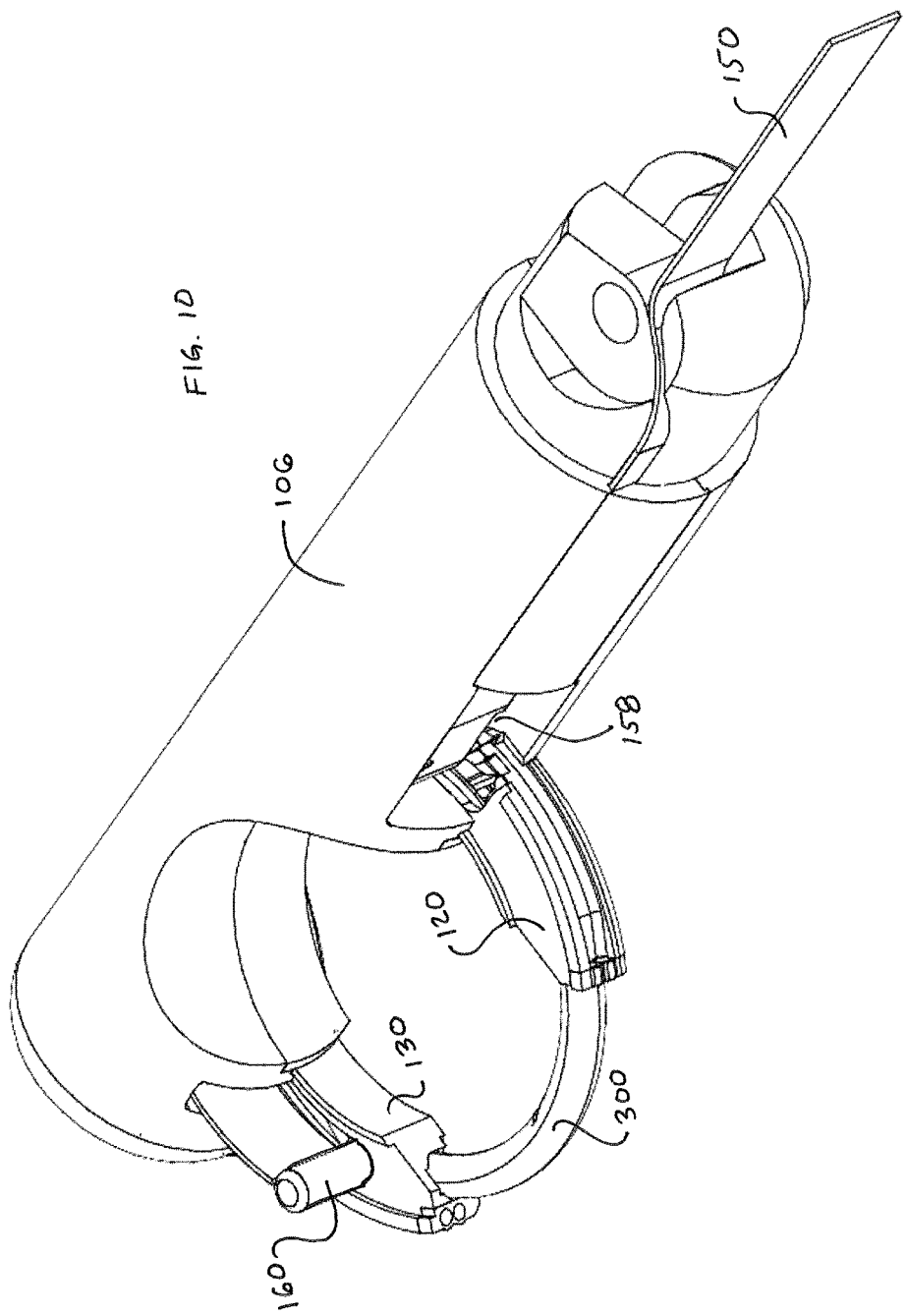

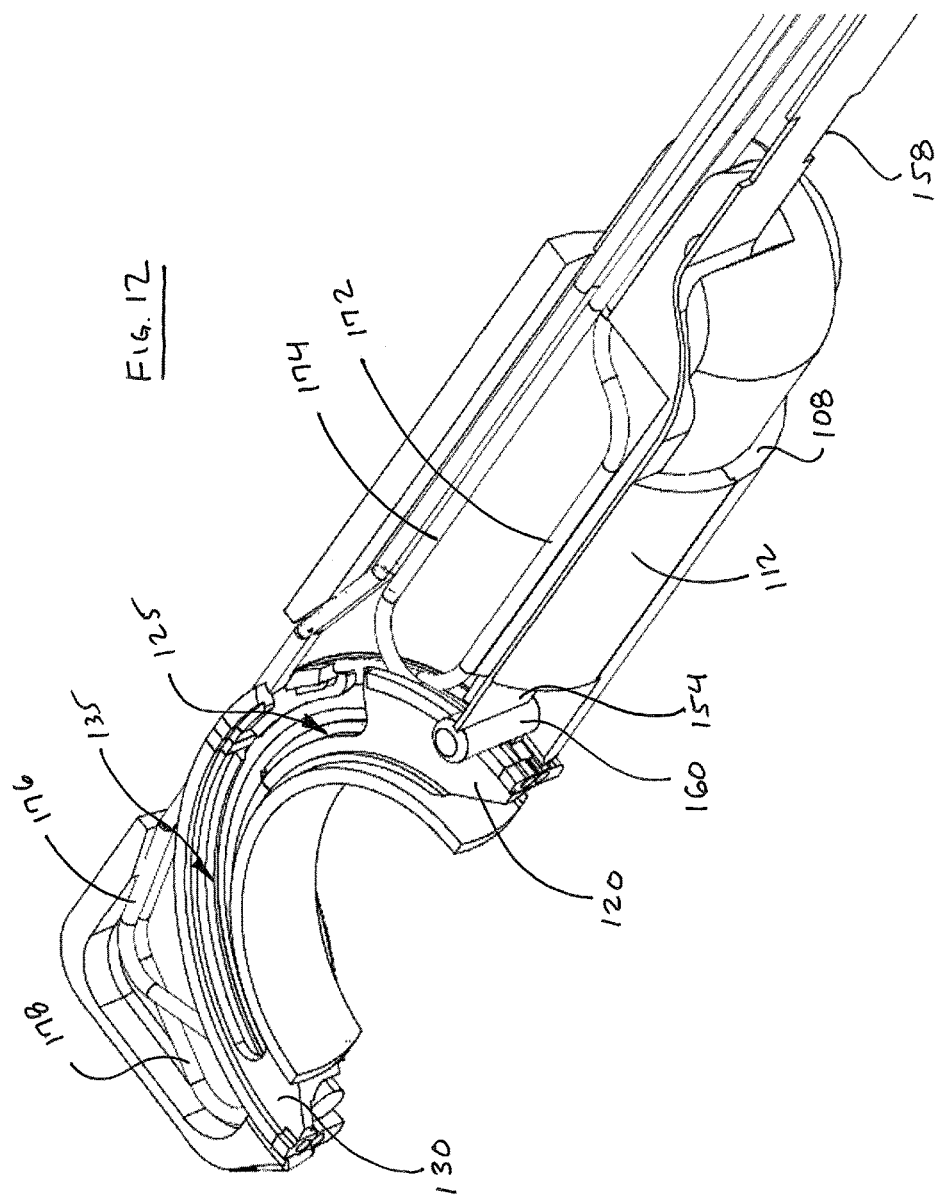

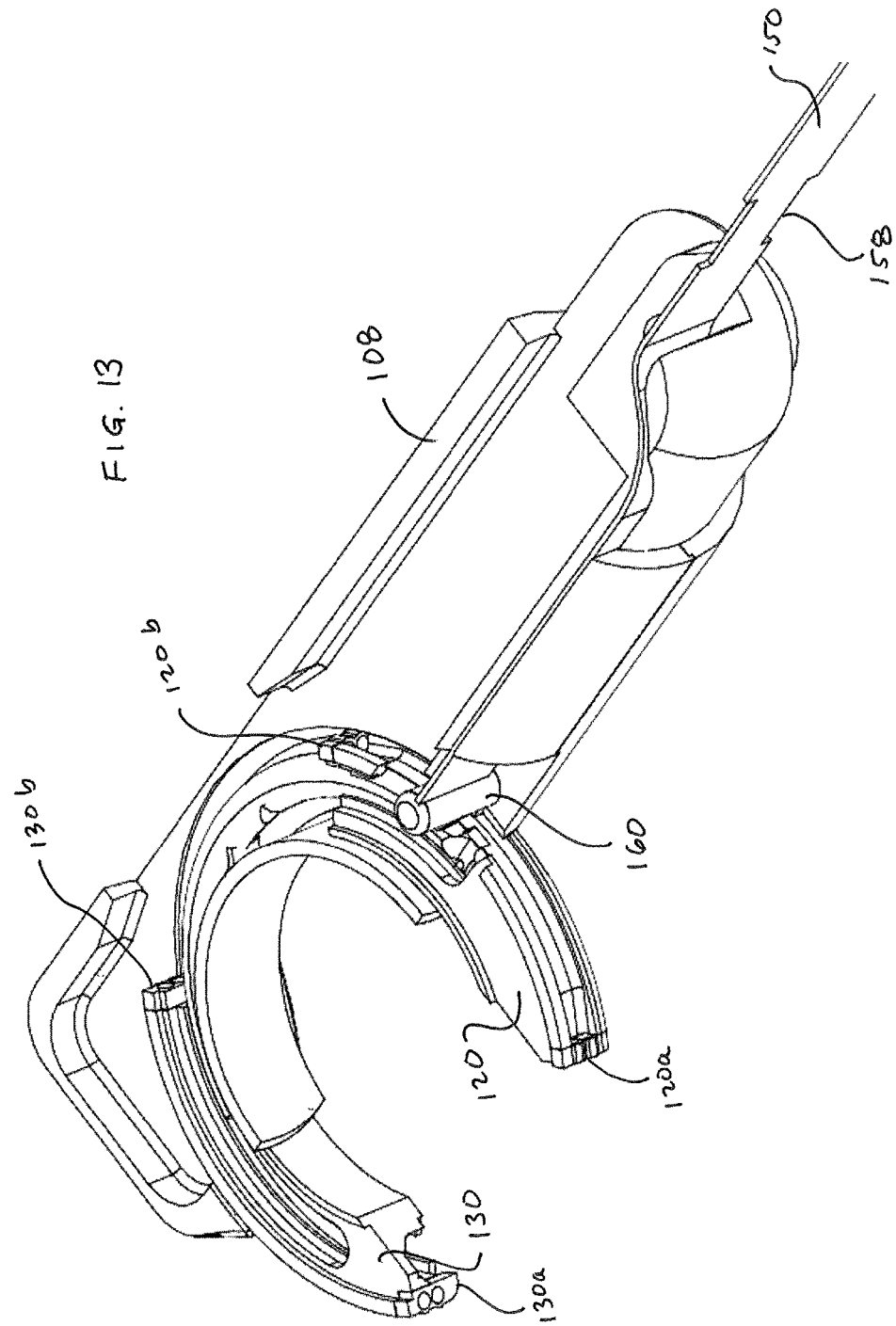

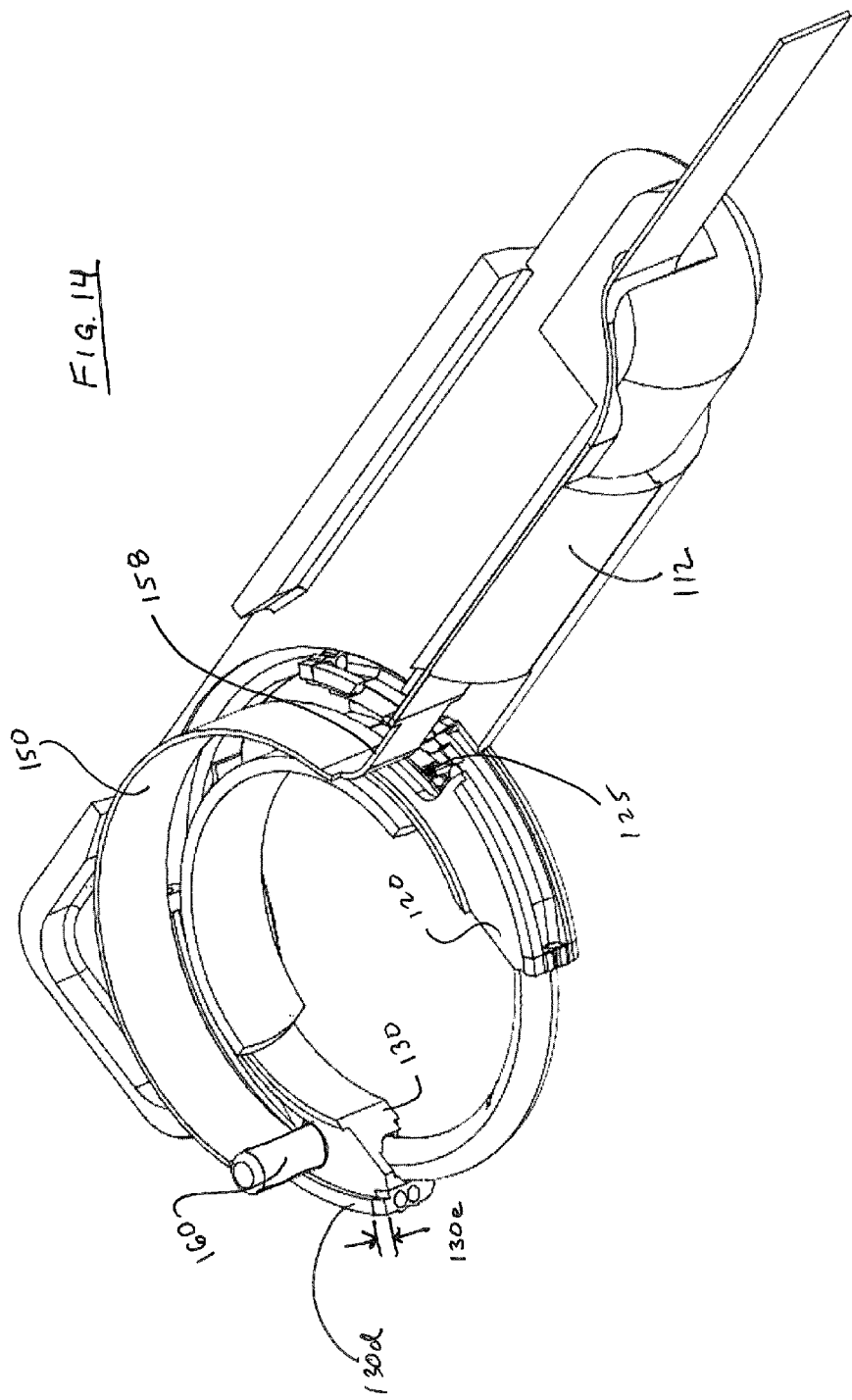

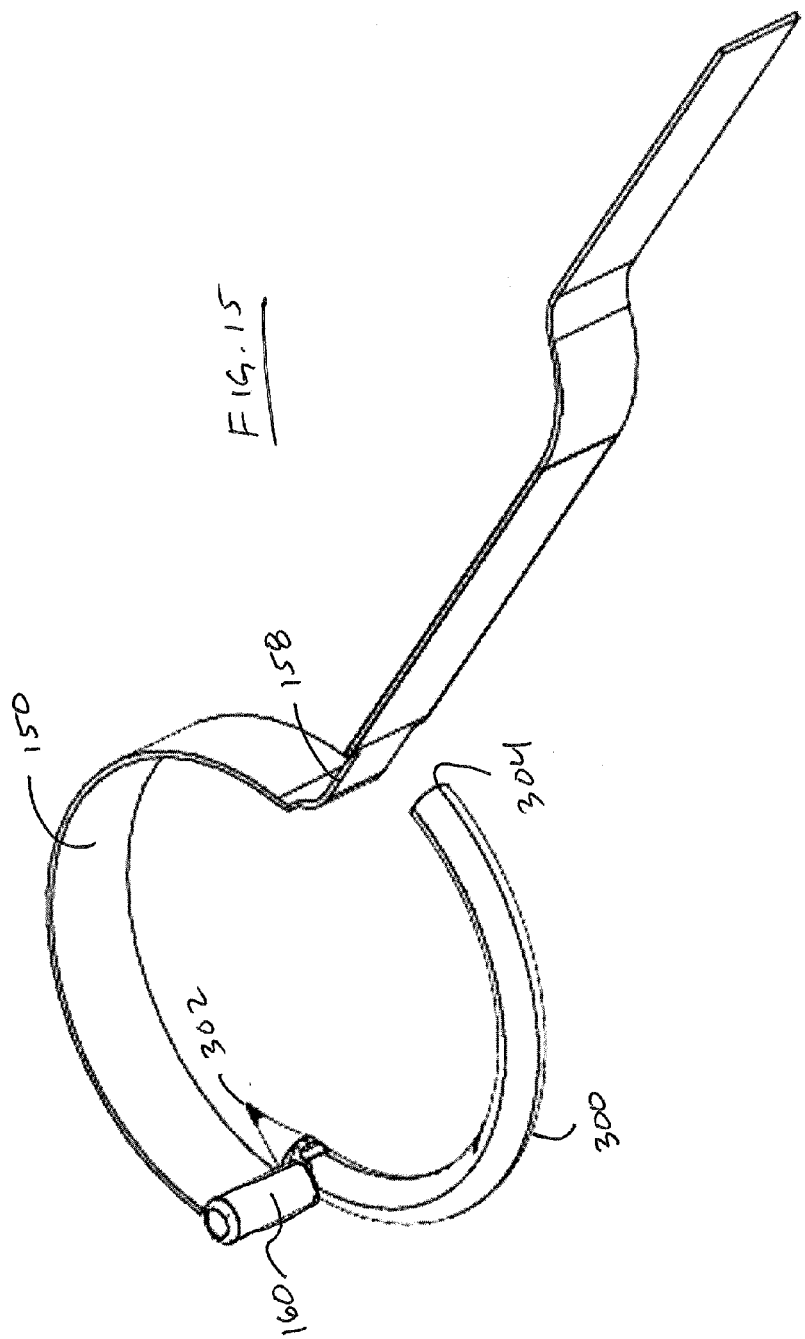

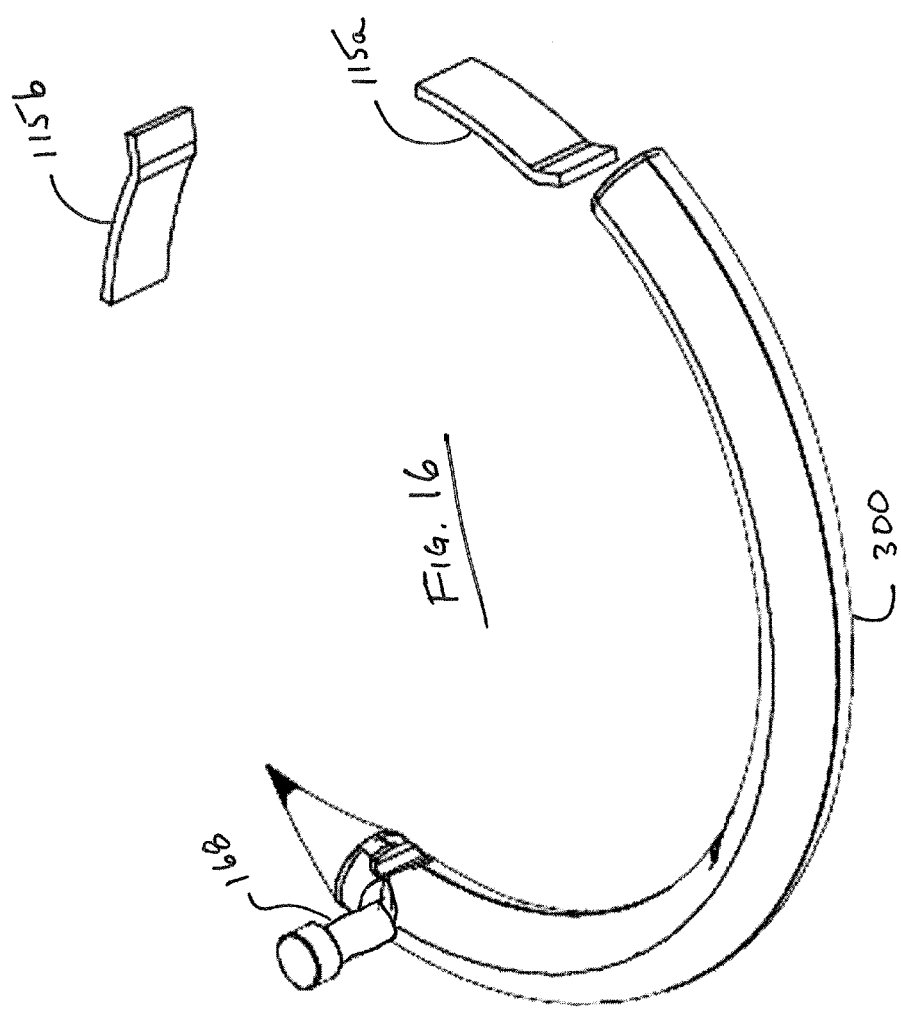

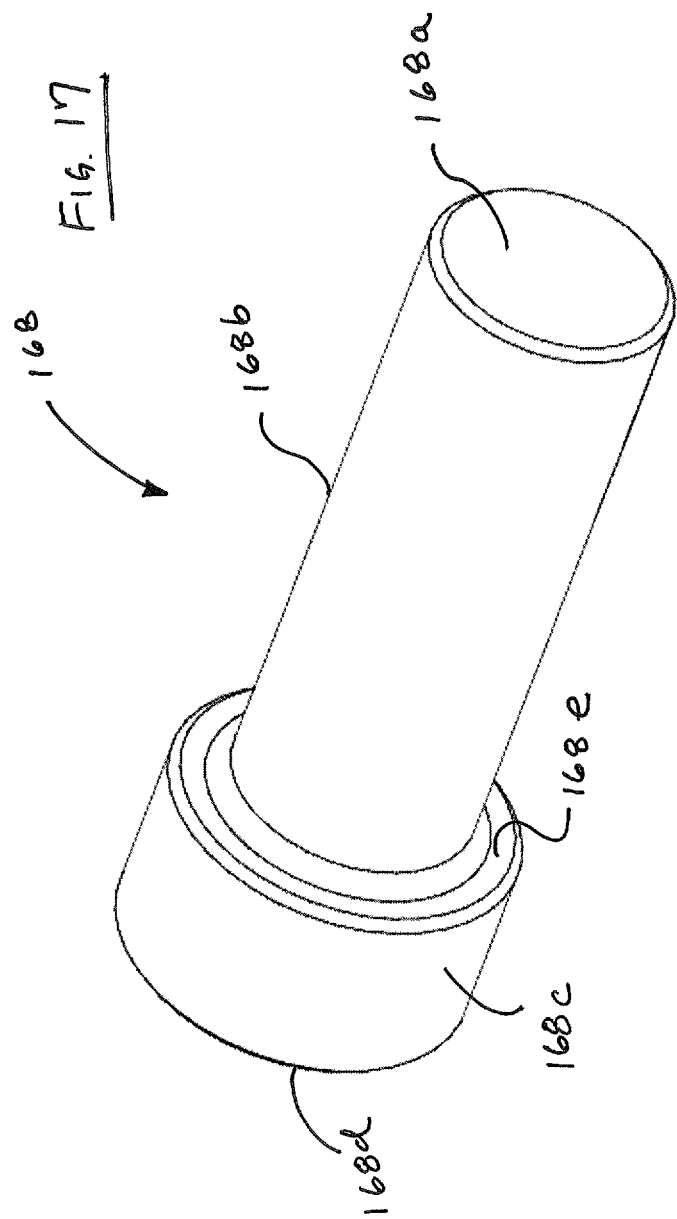

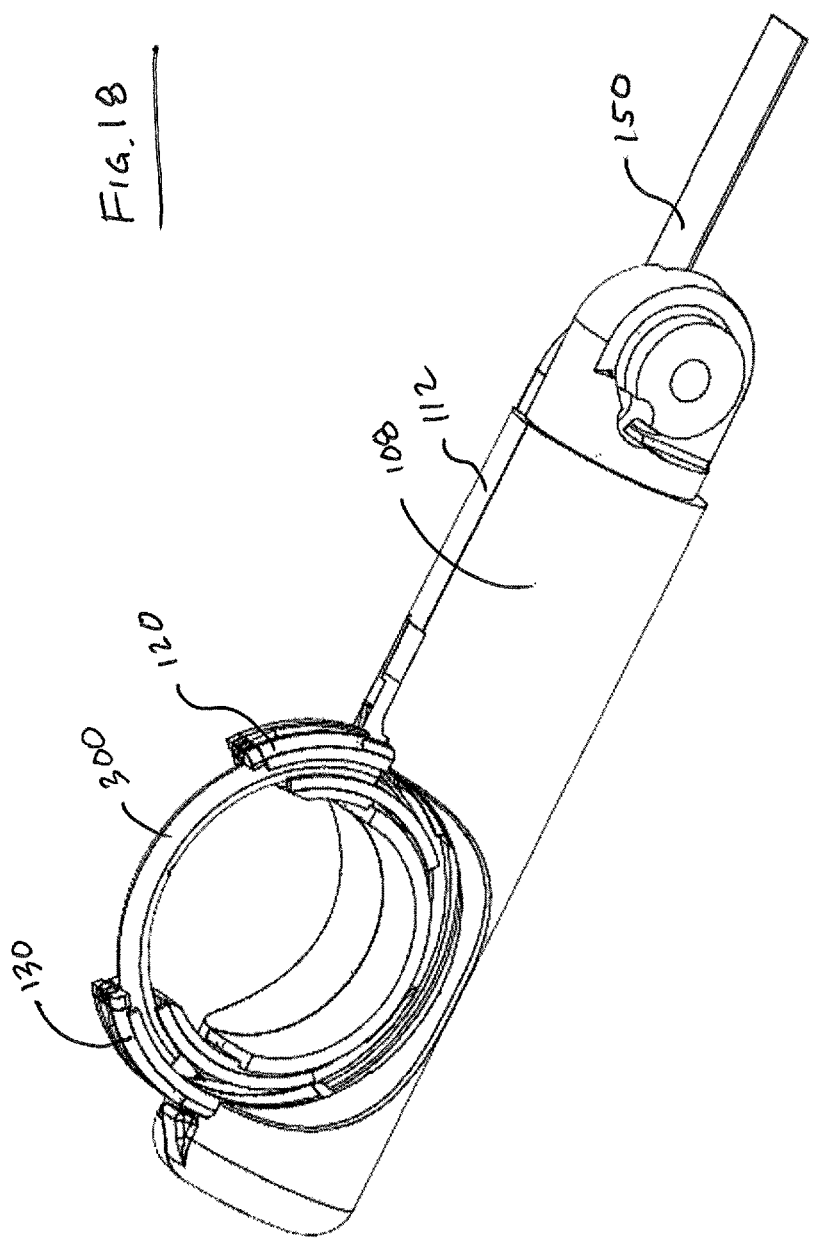

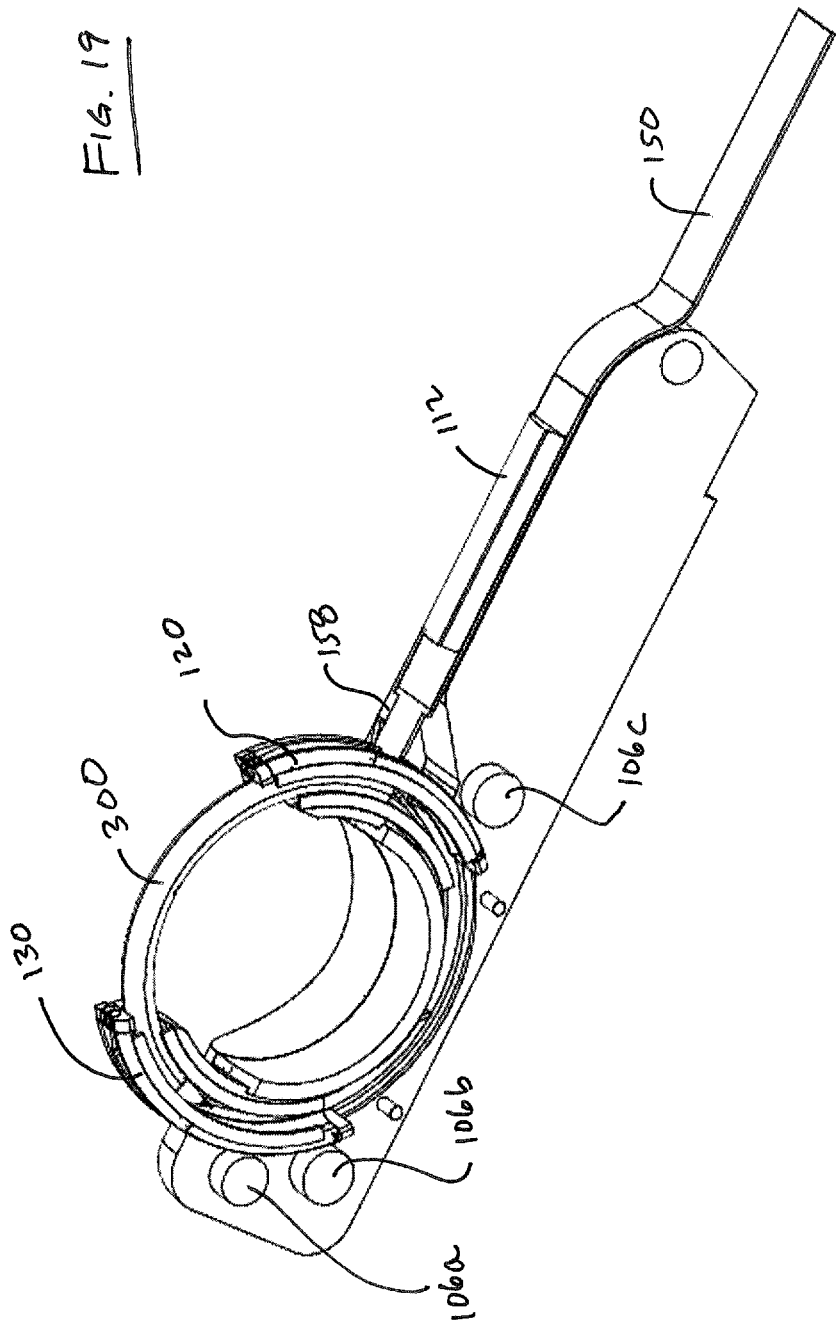

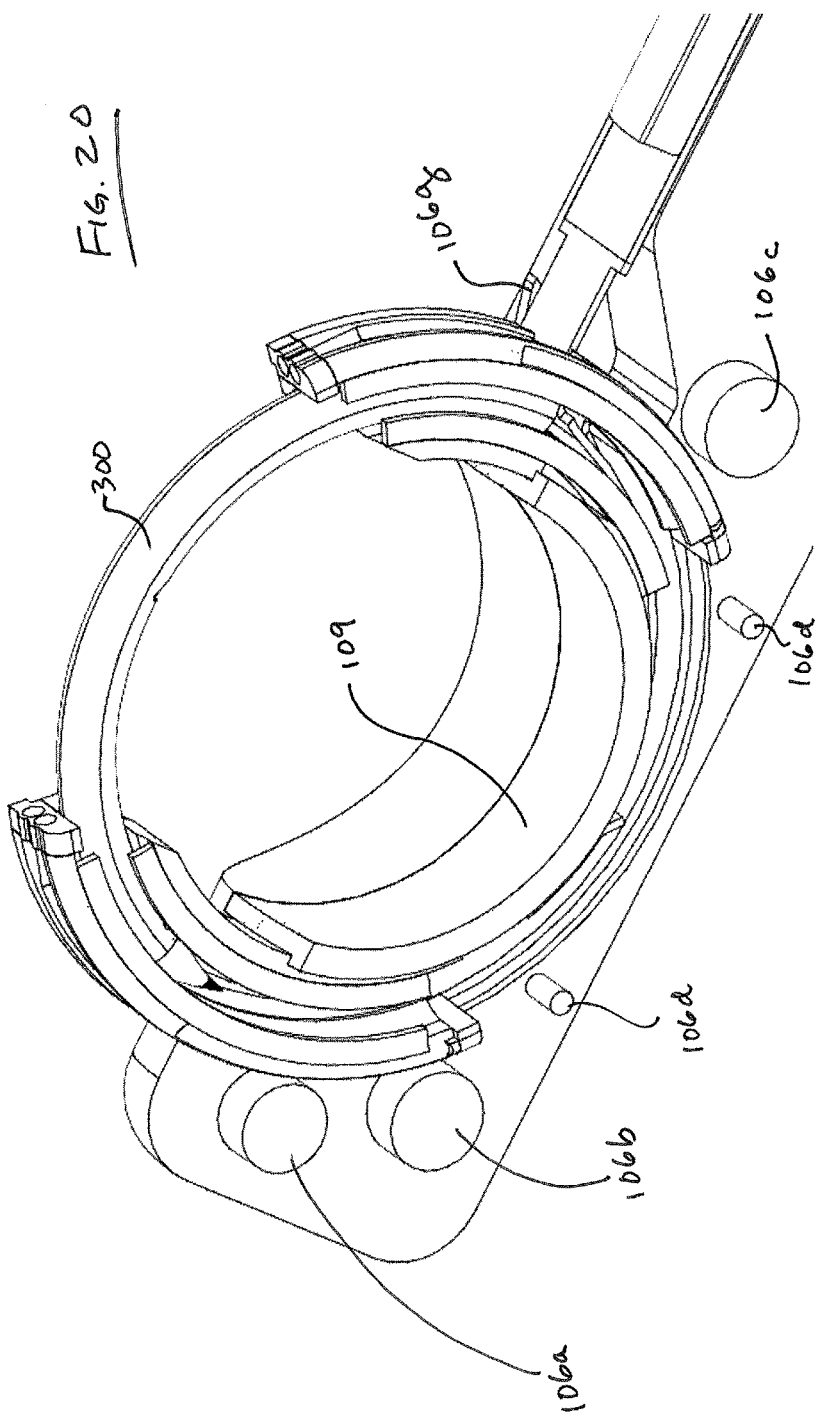

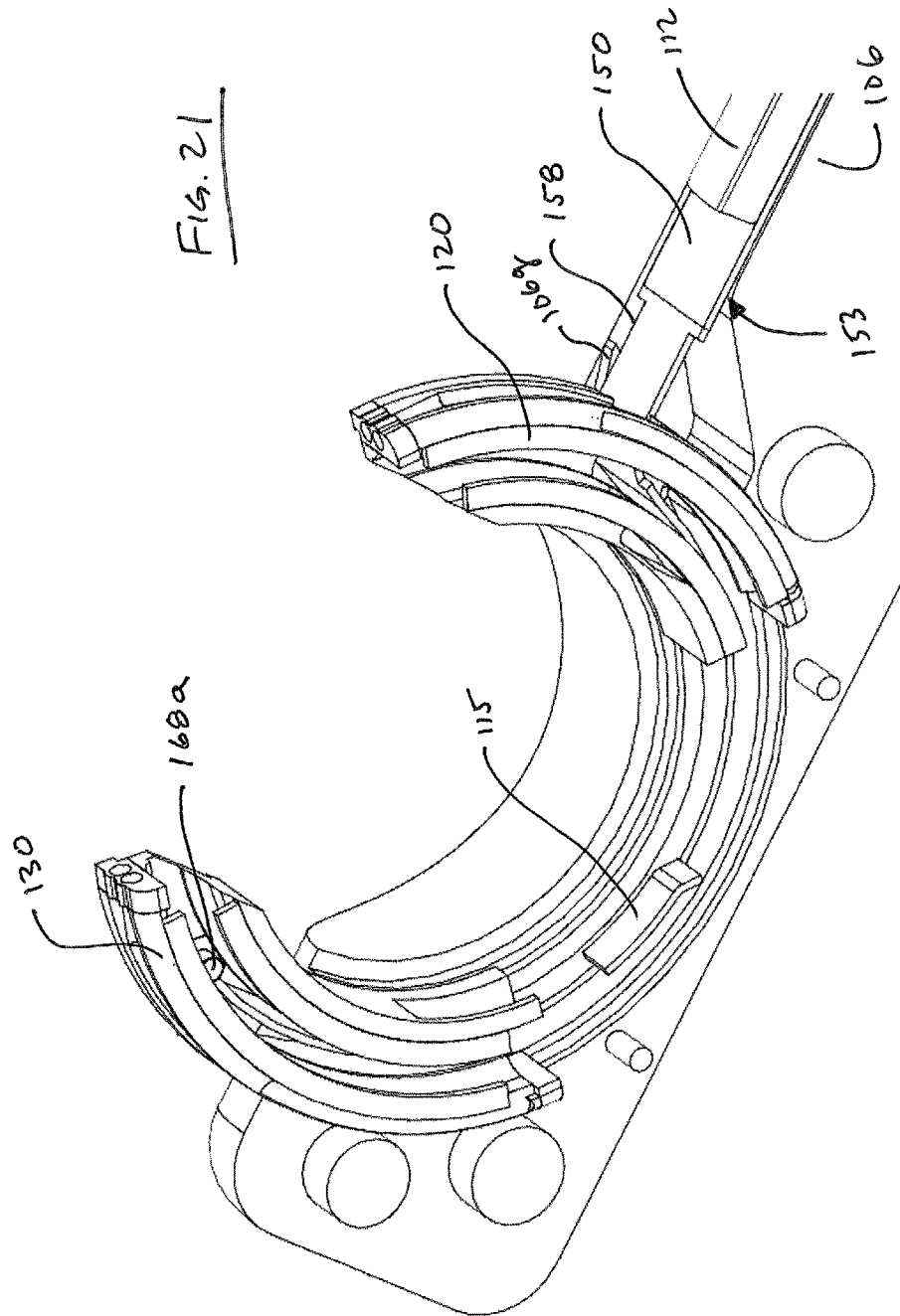

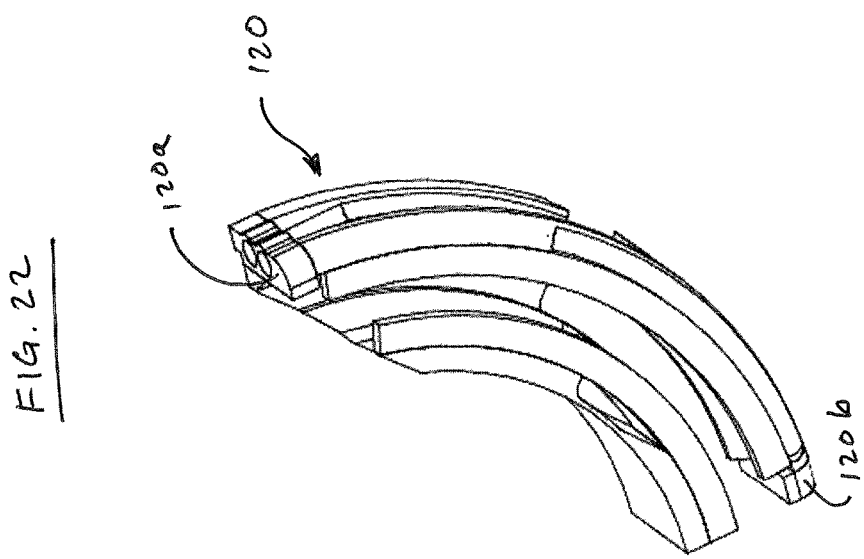
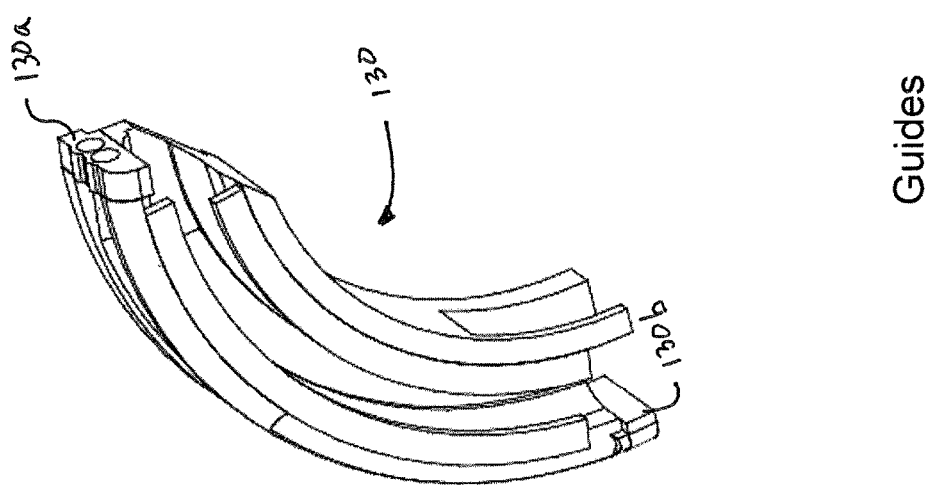
FIG. 22
Guides

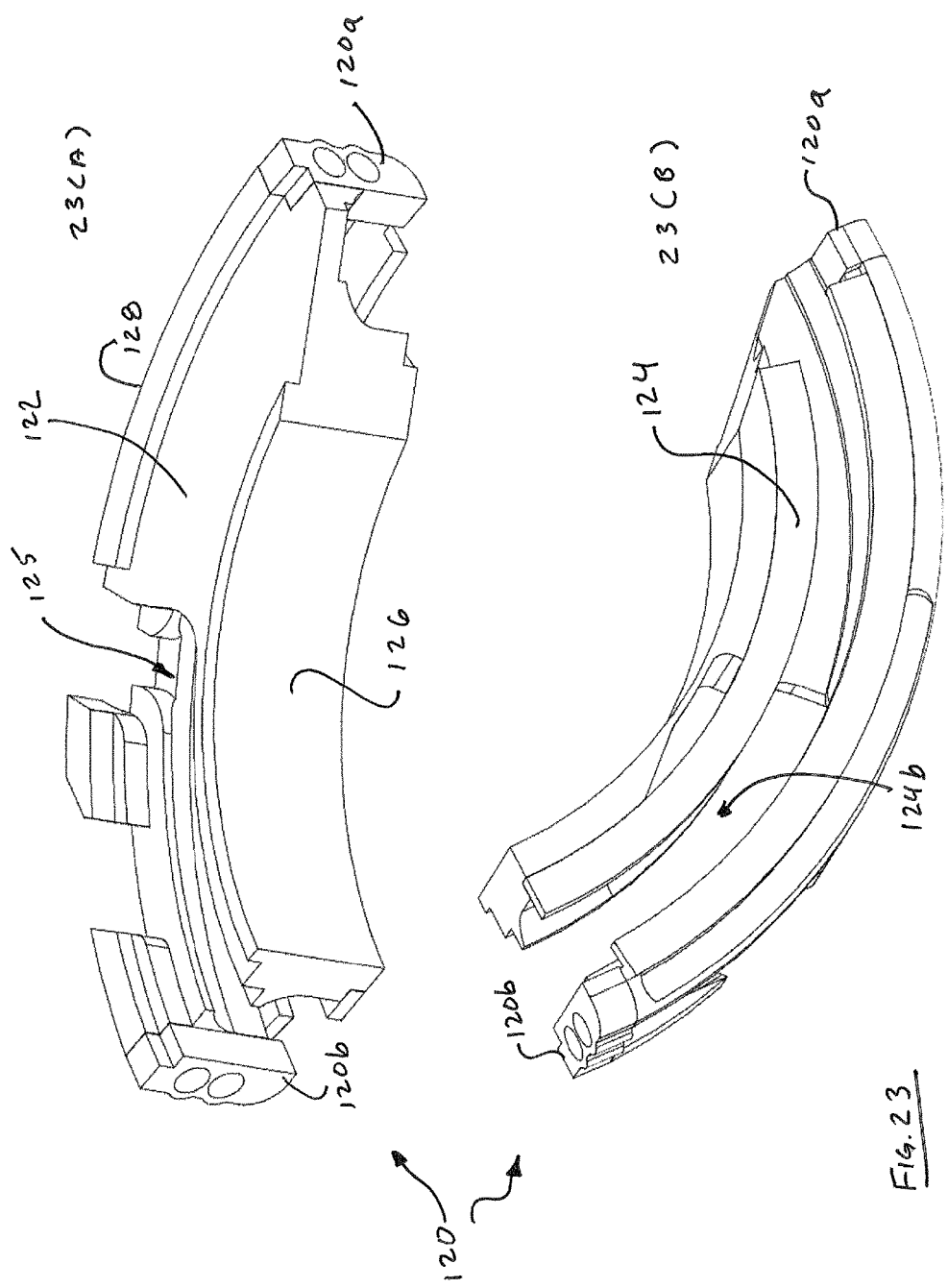

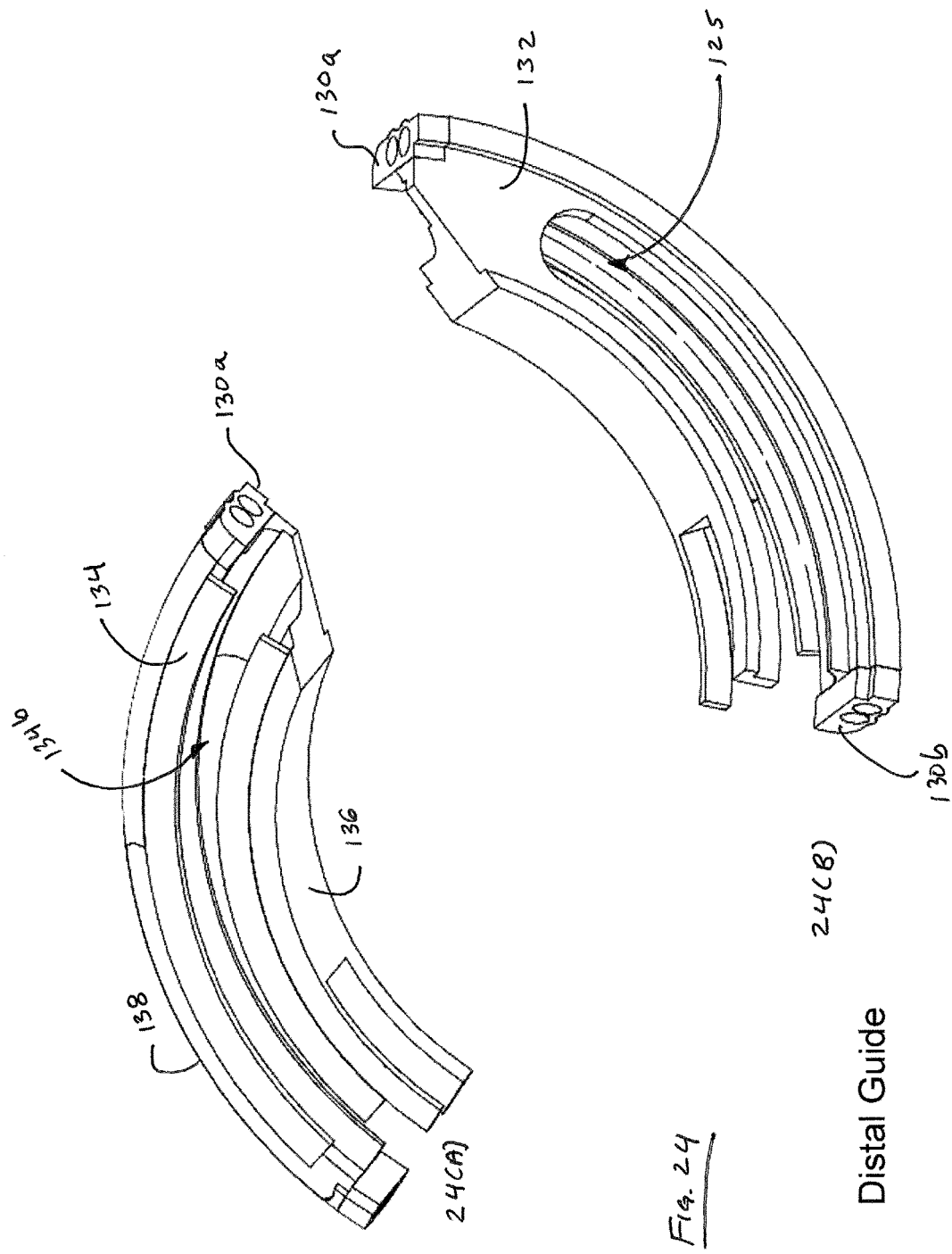

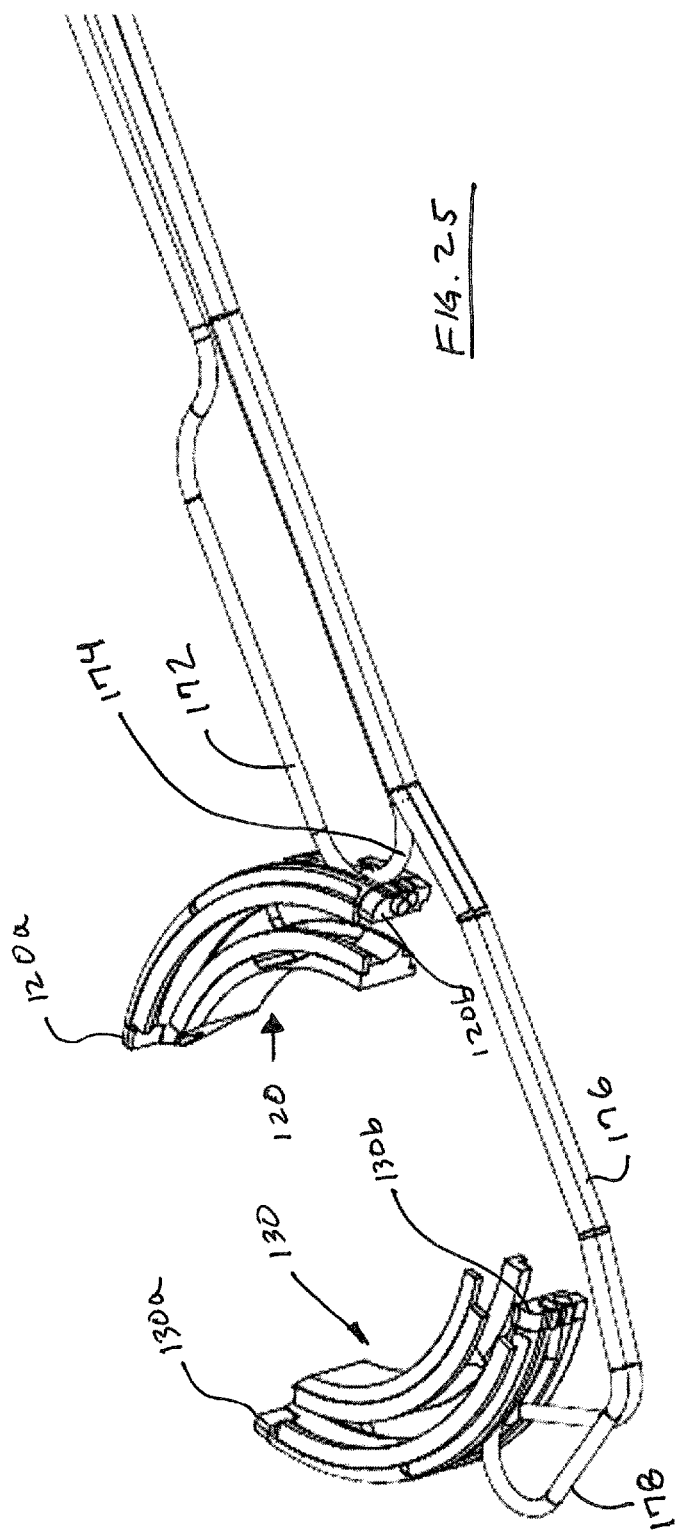

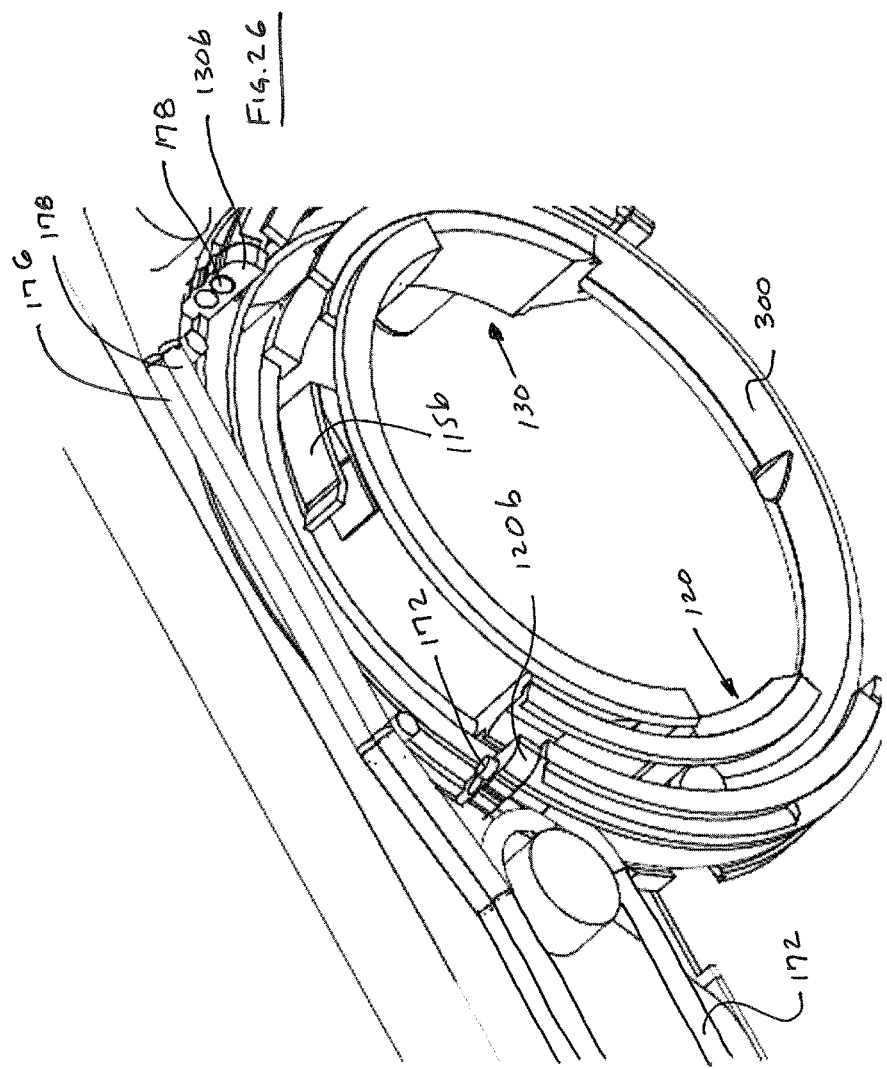

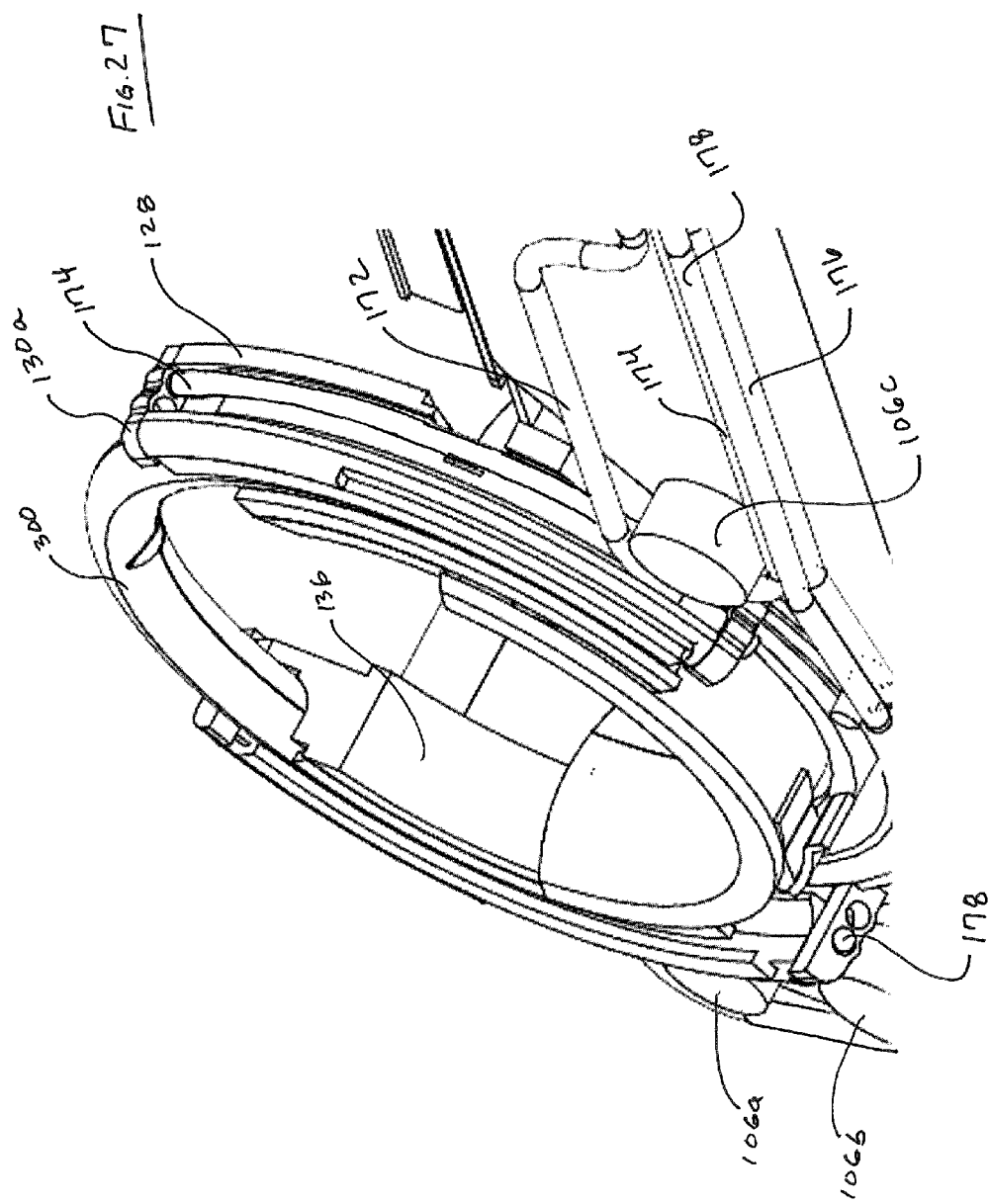

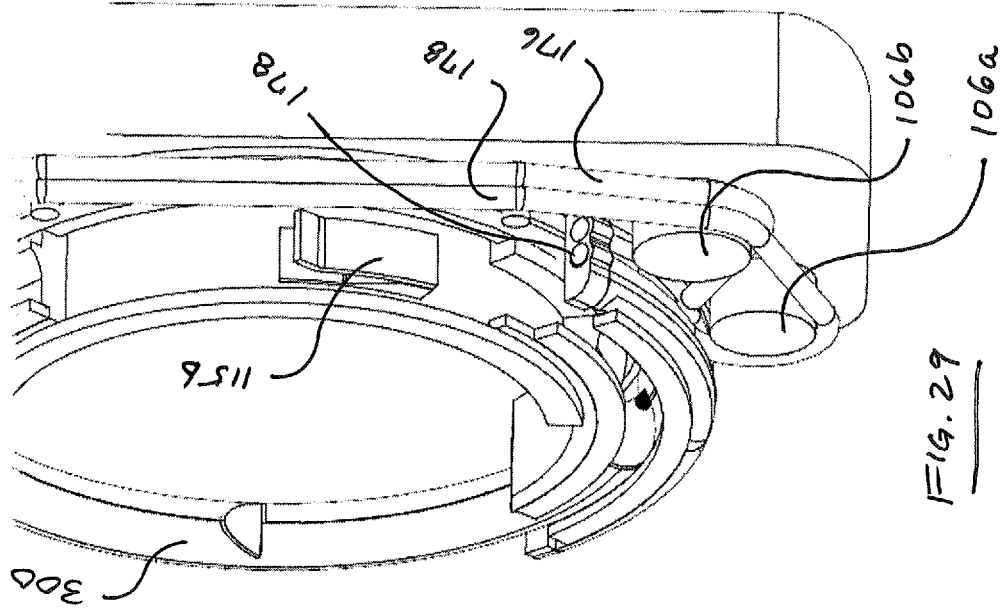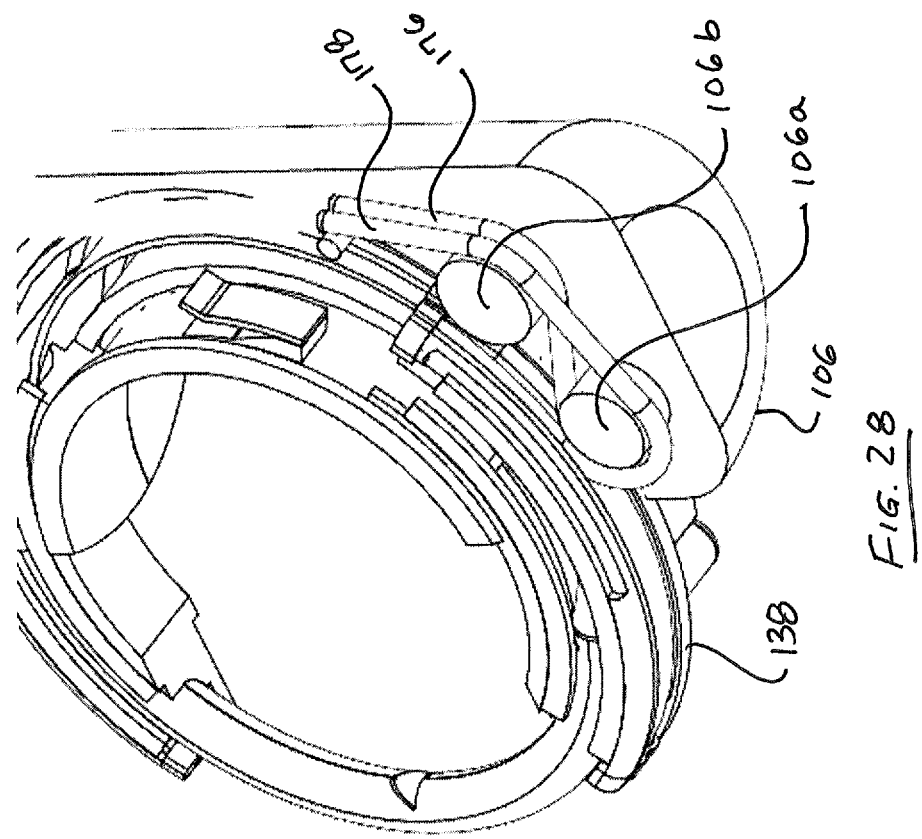

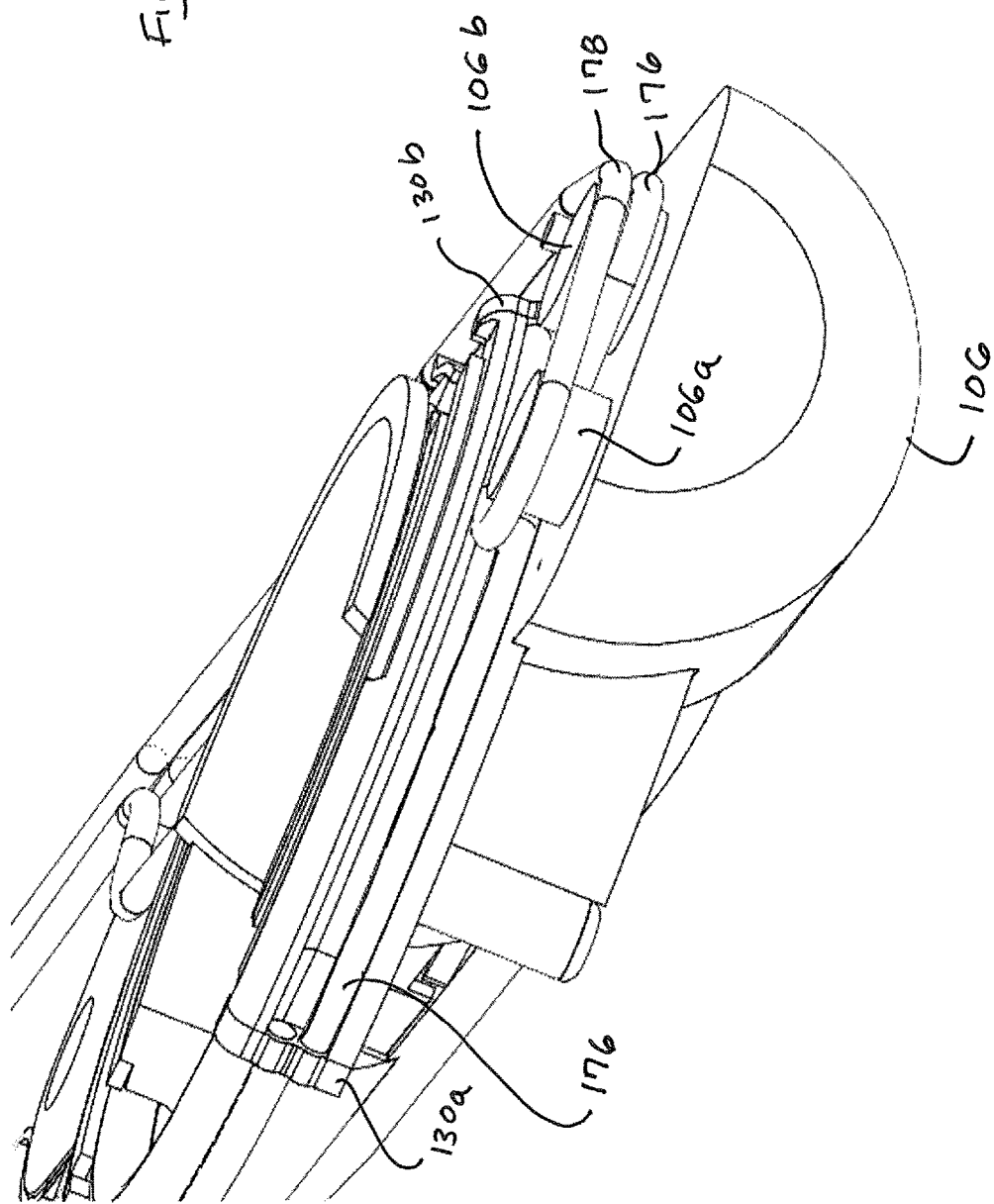

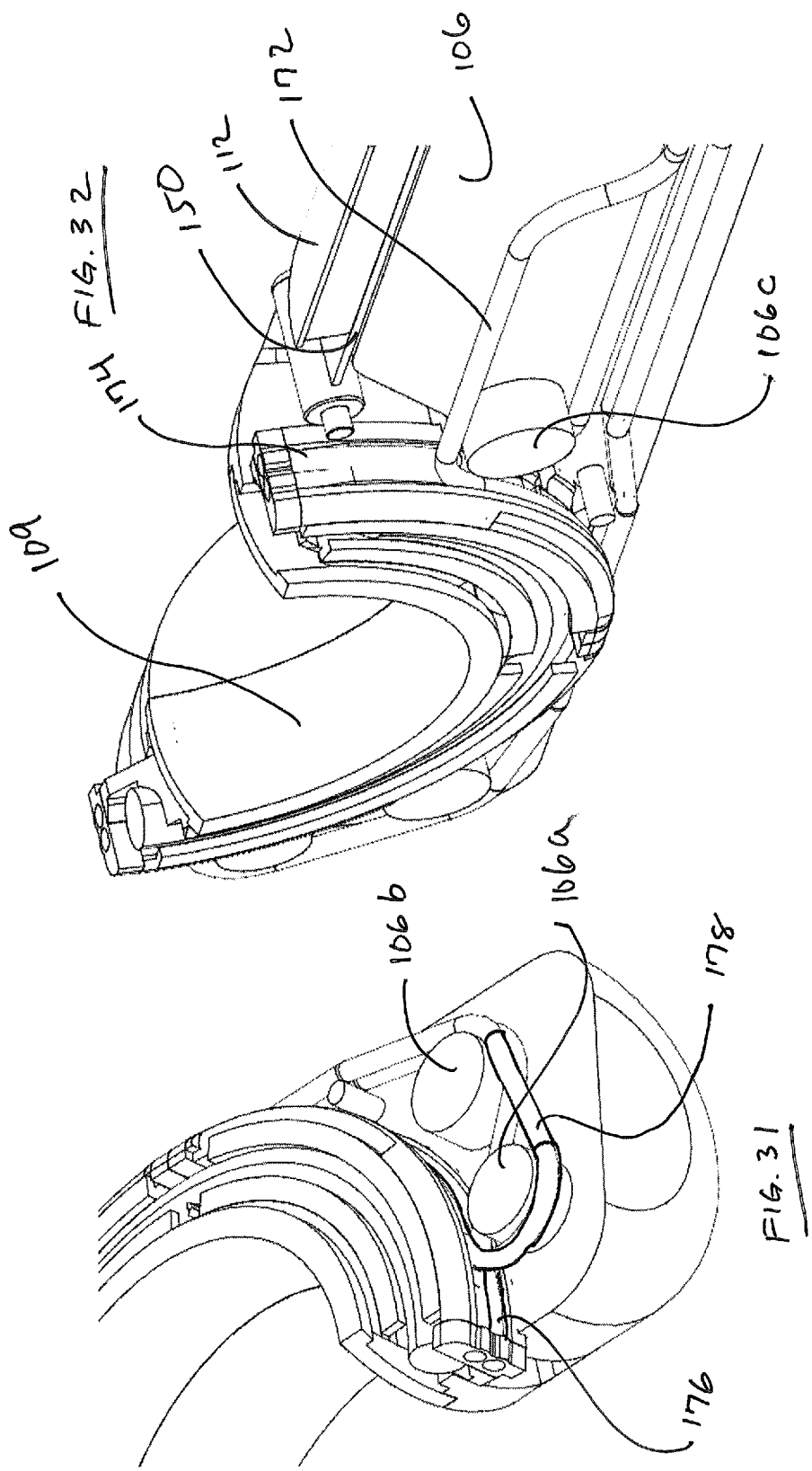

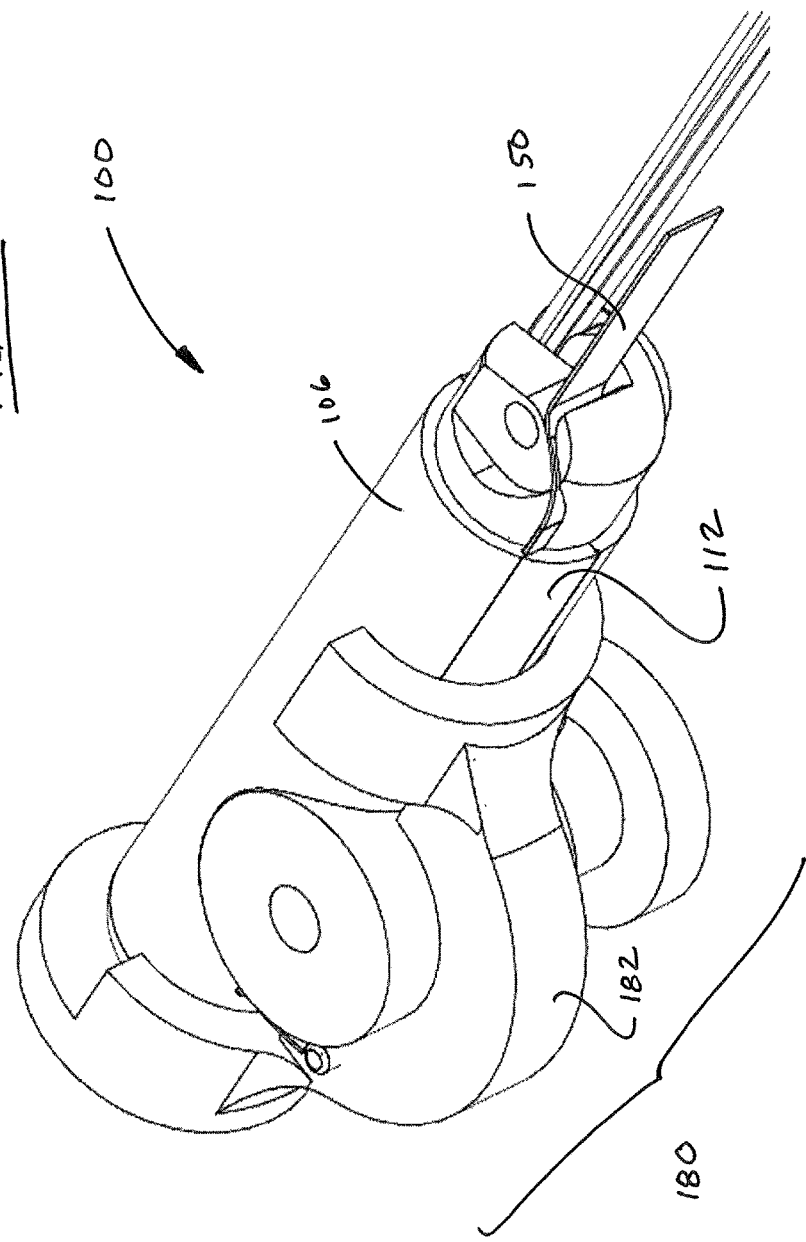

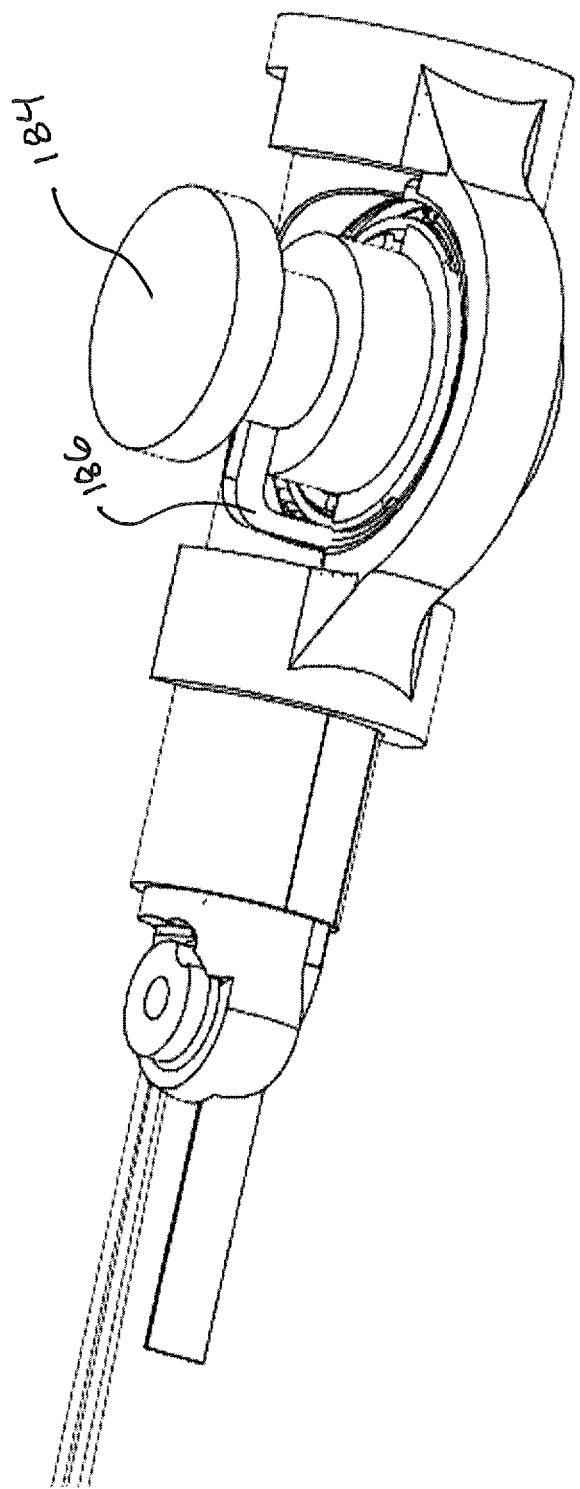

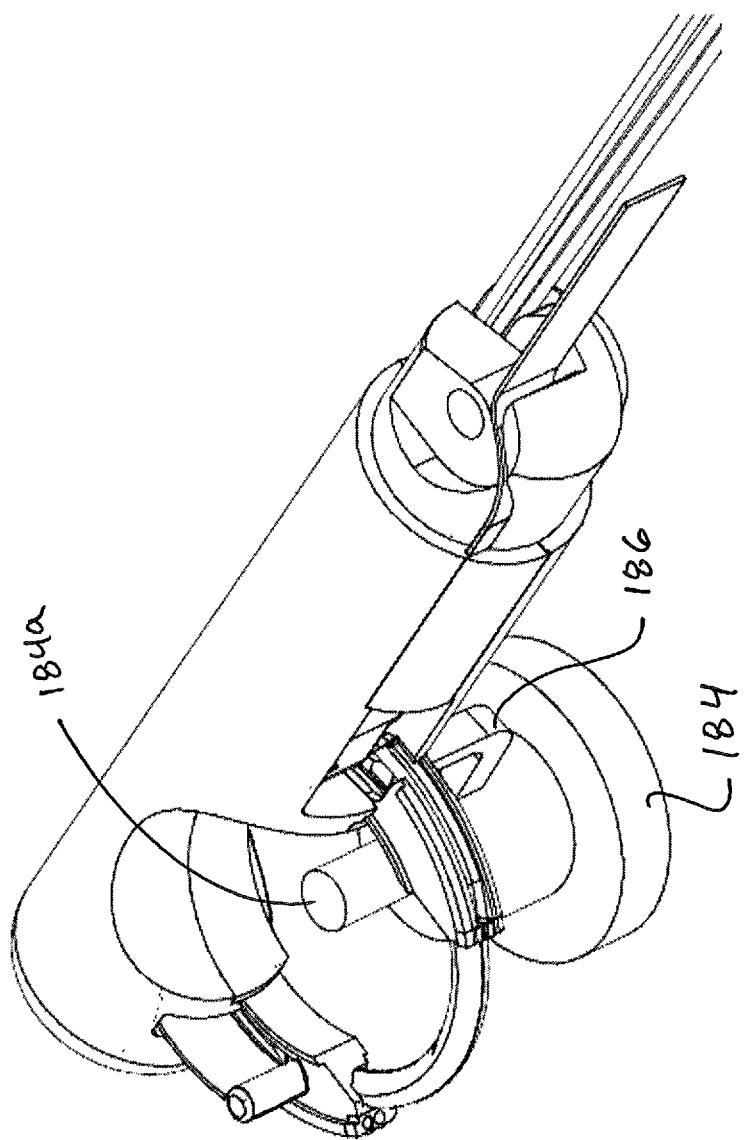

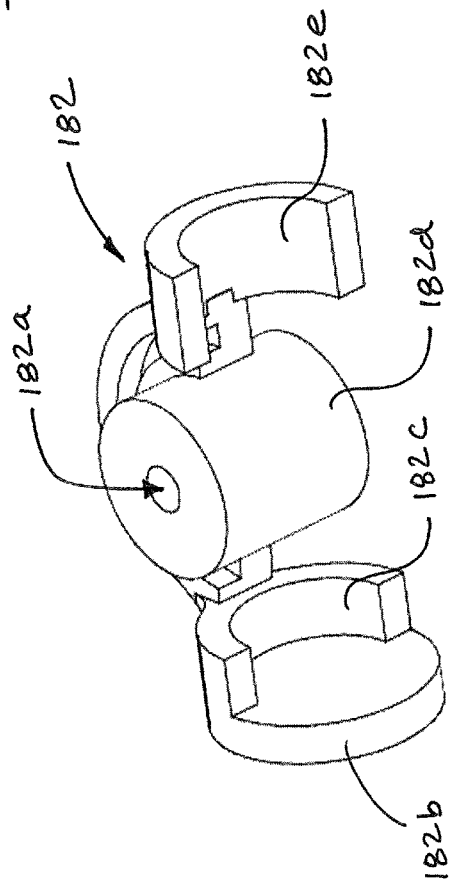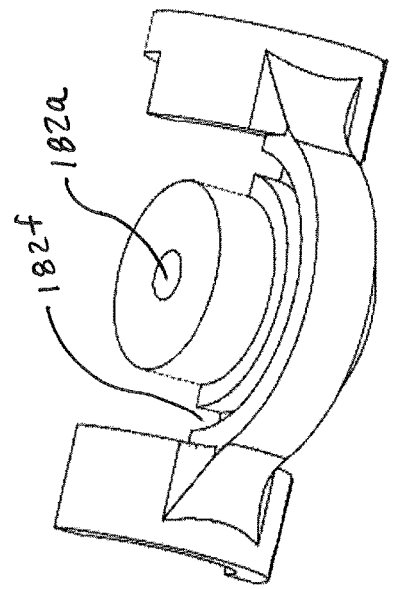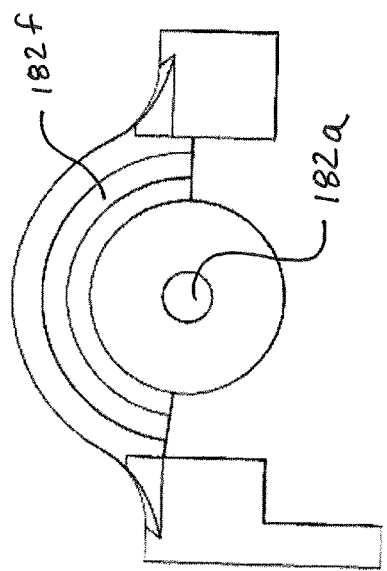

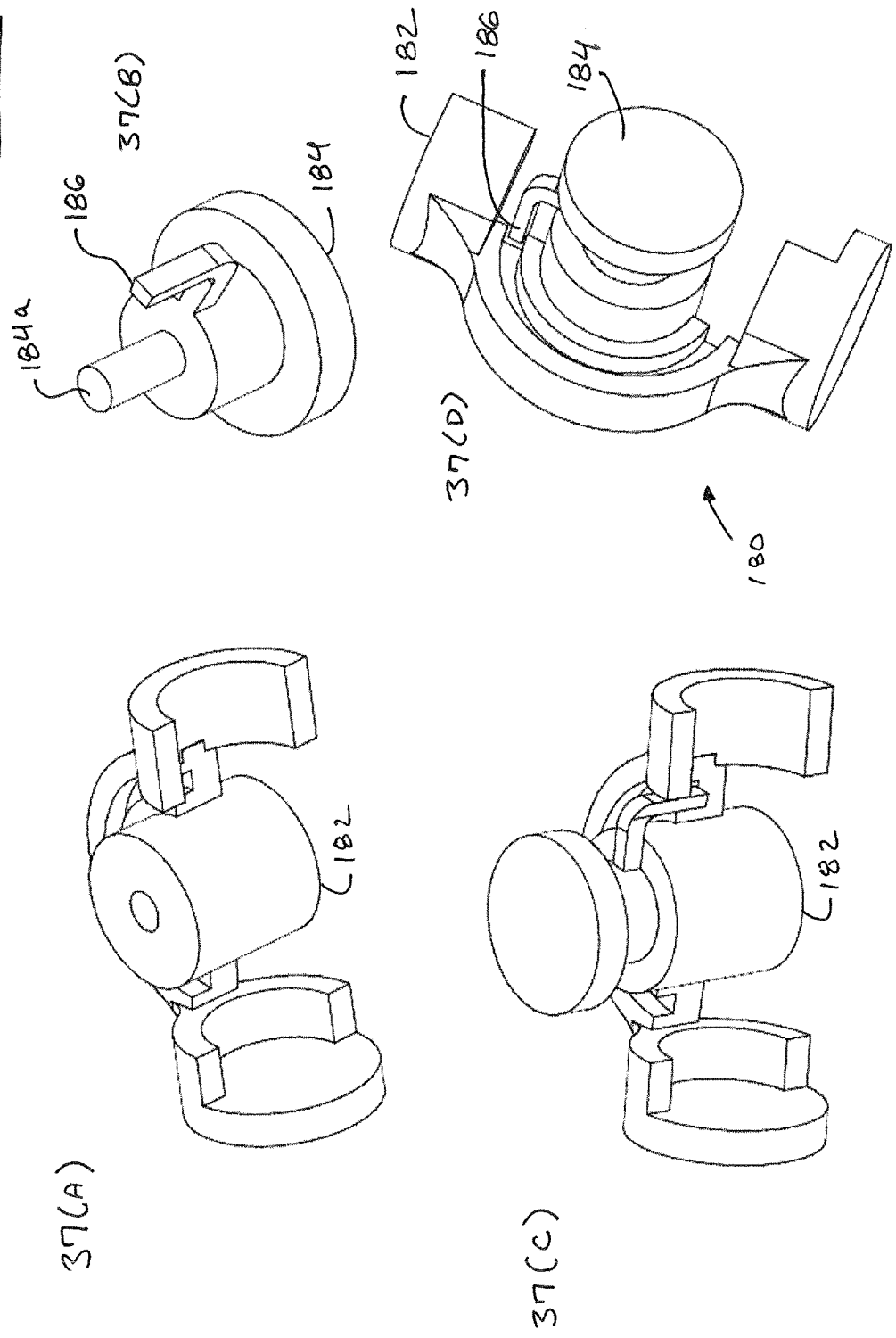

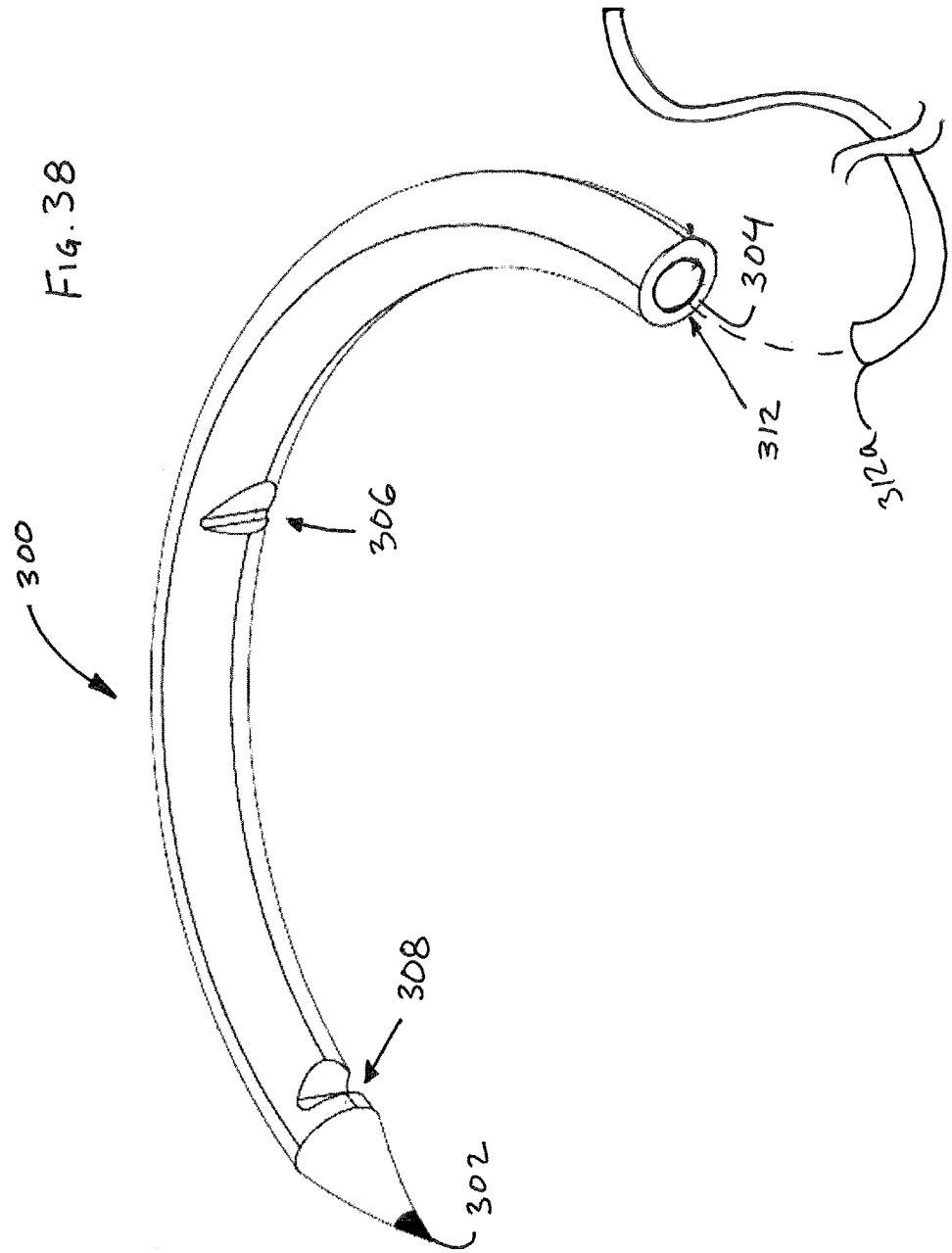

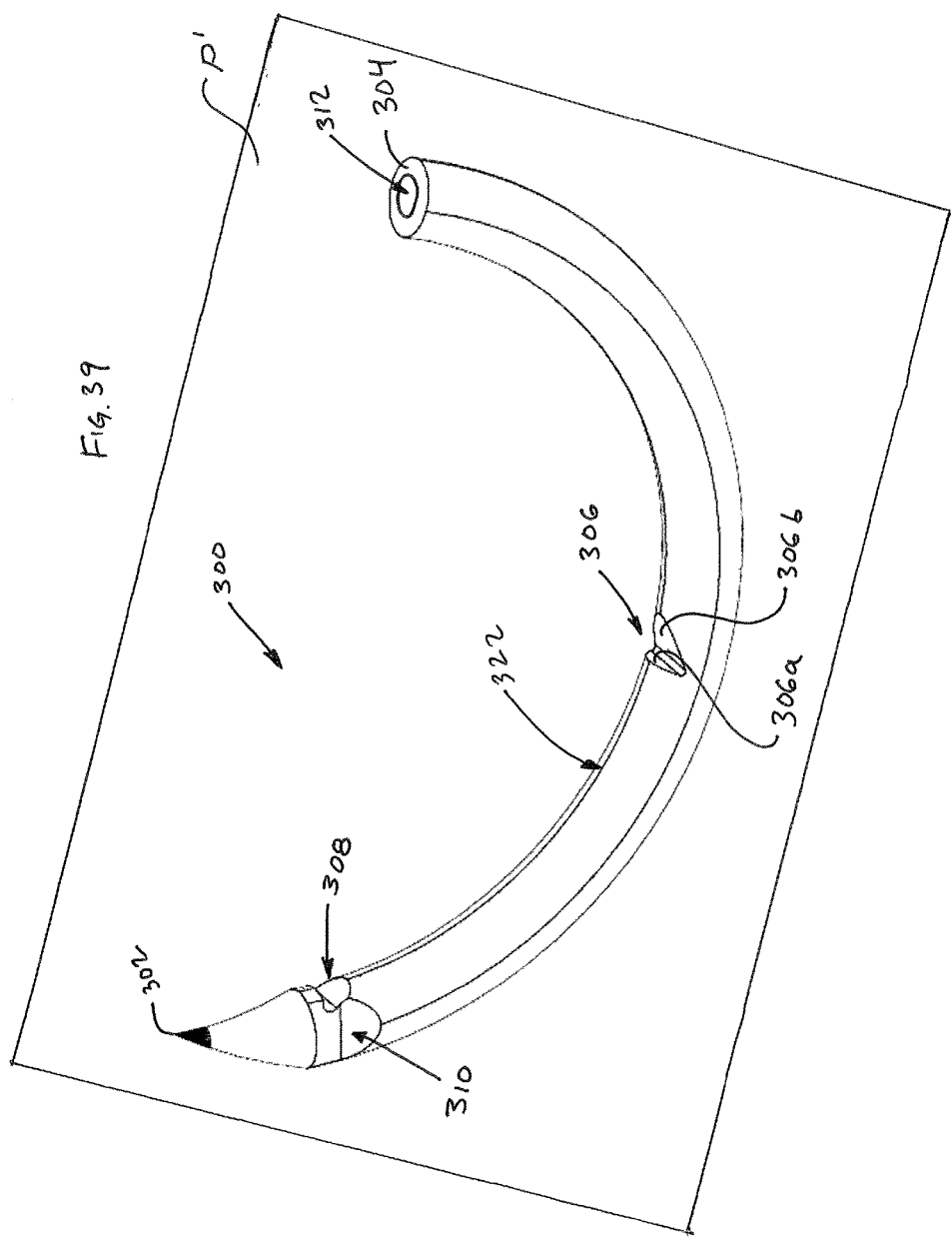

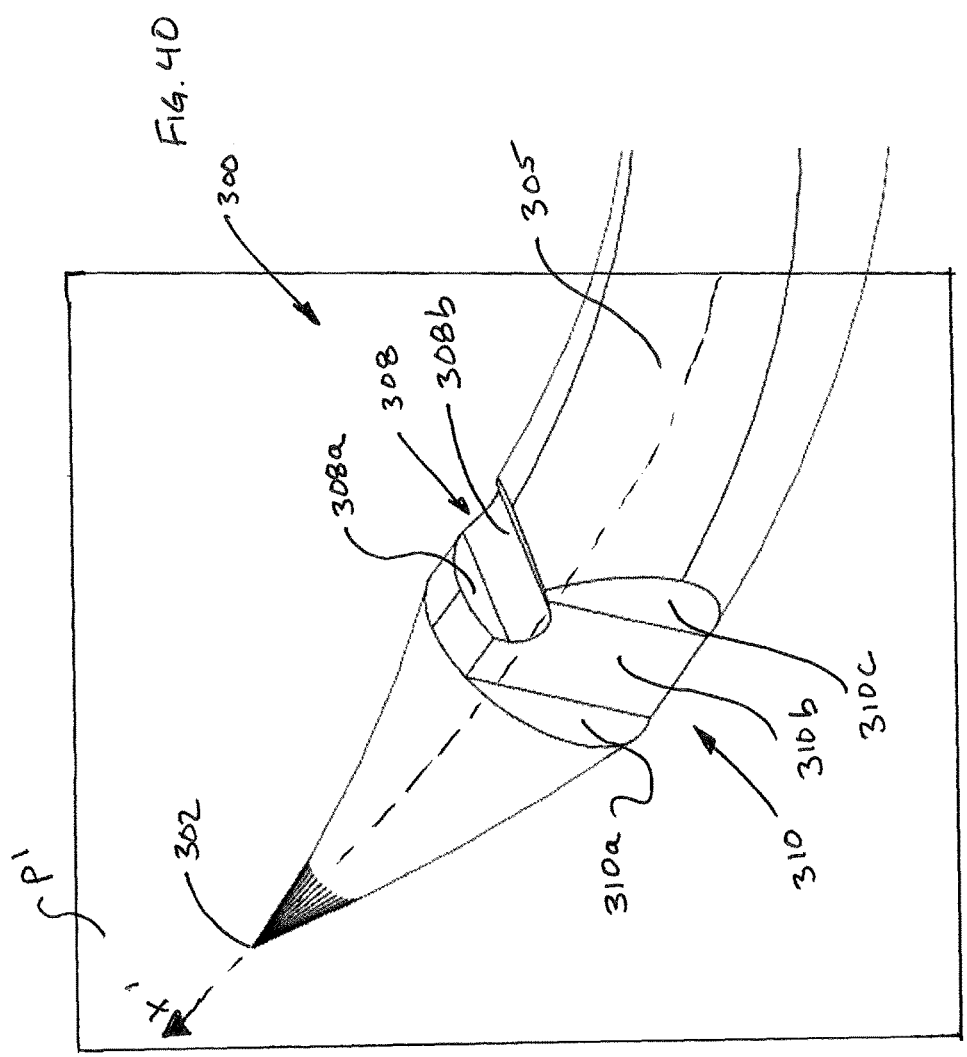

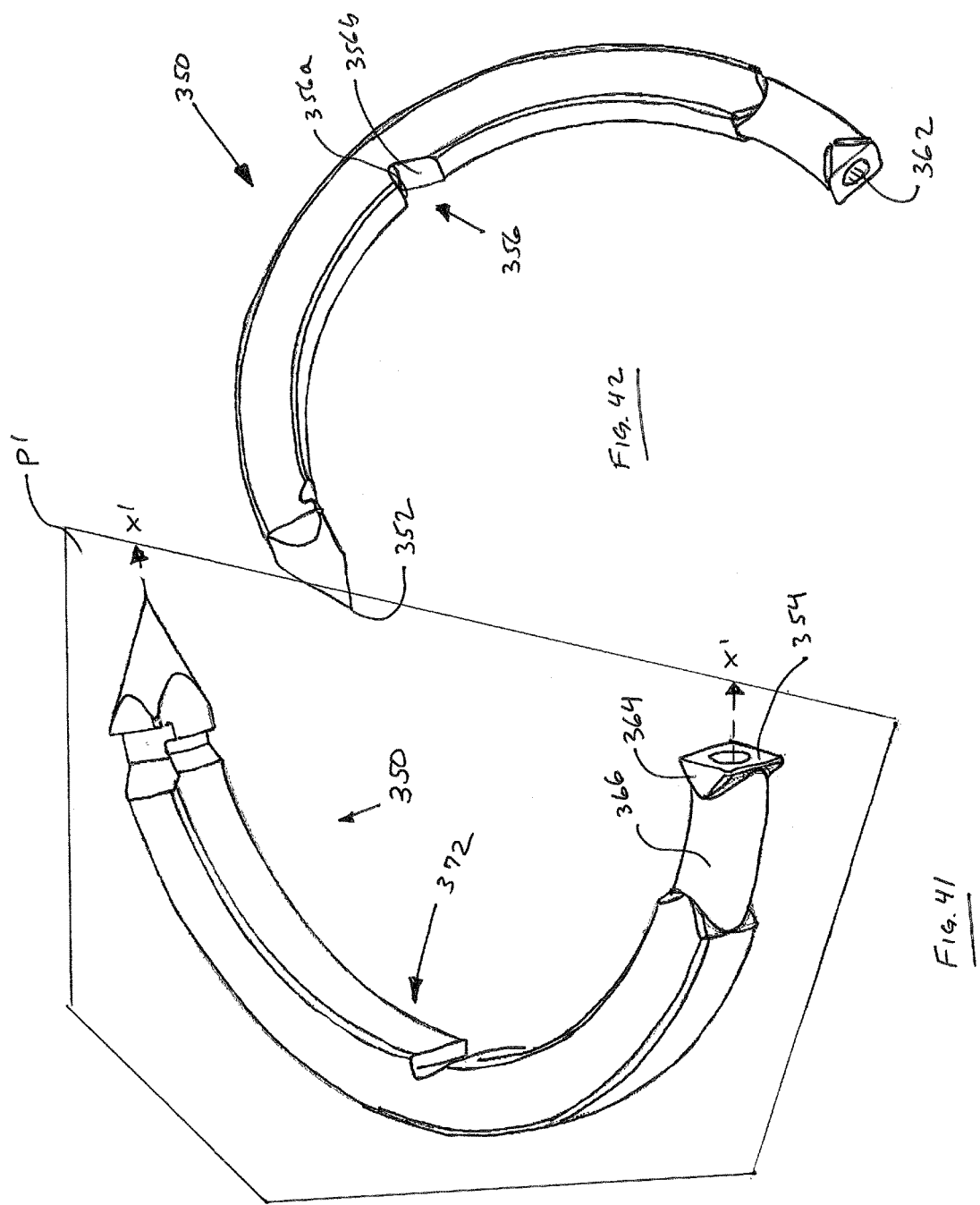

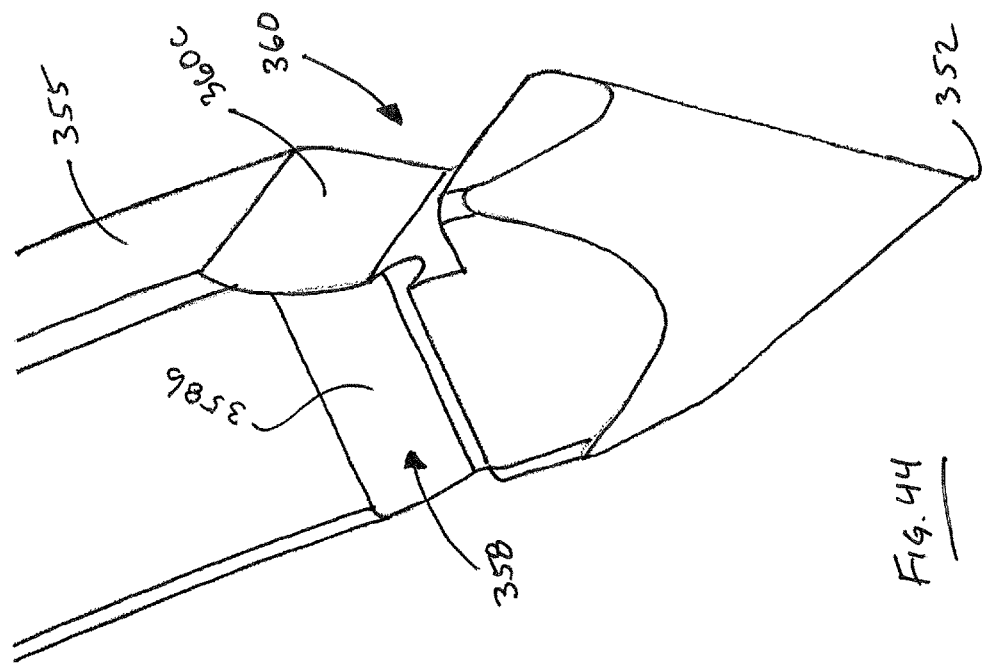
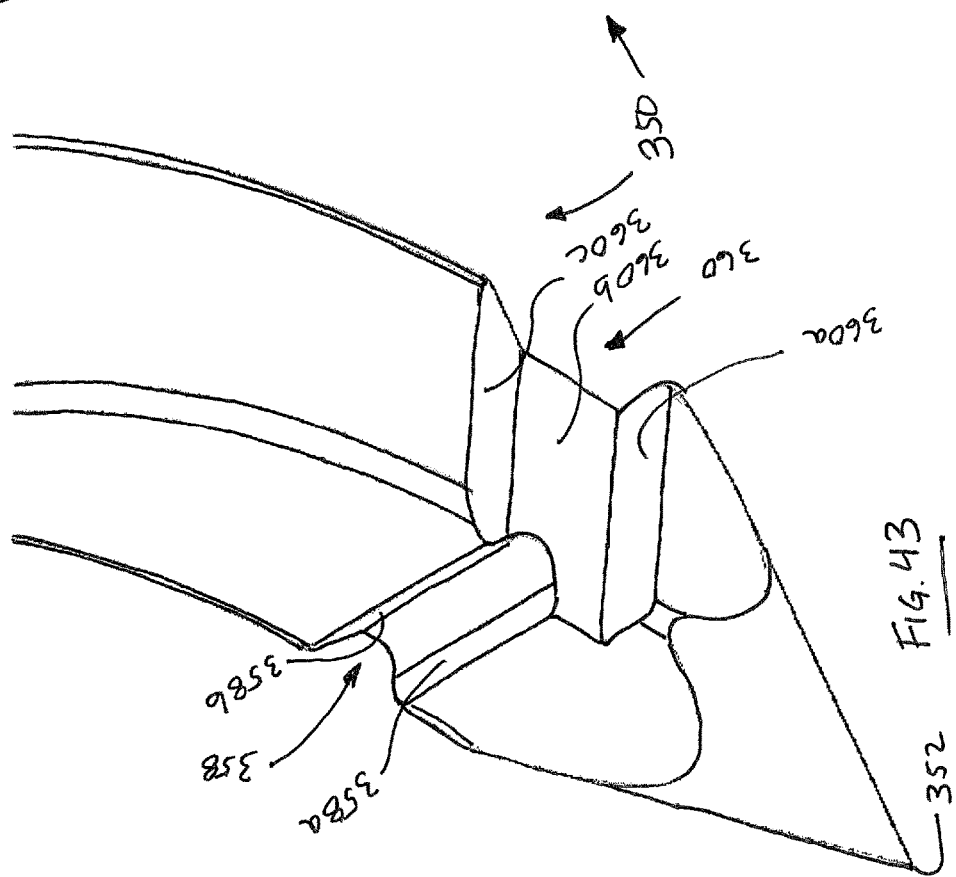

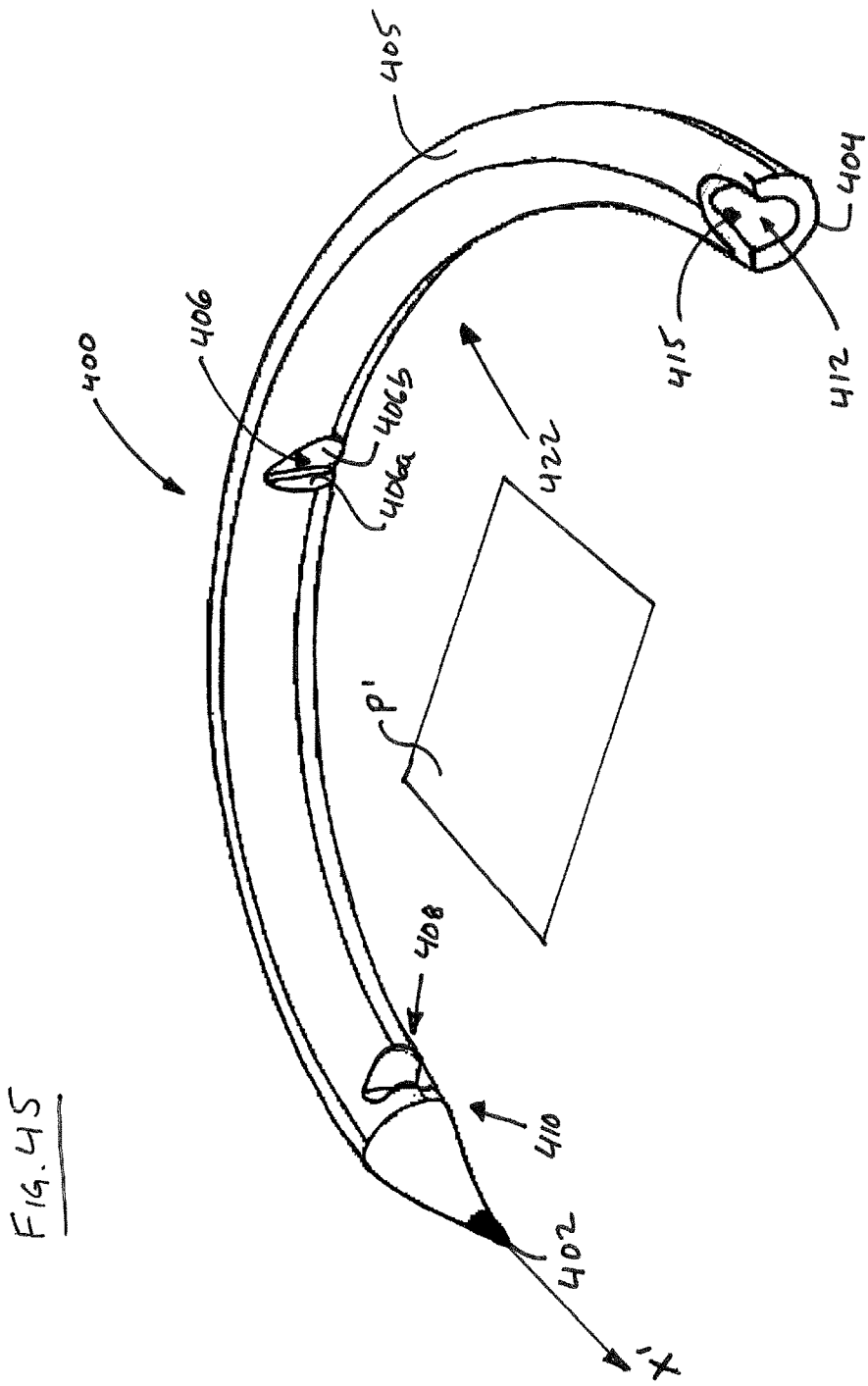

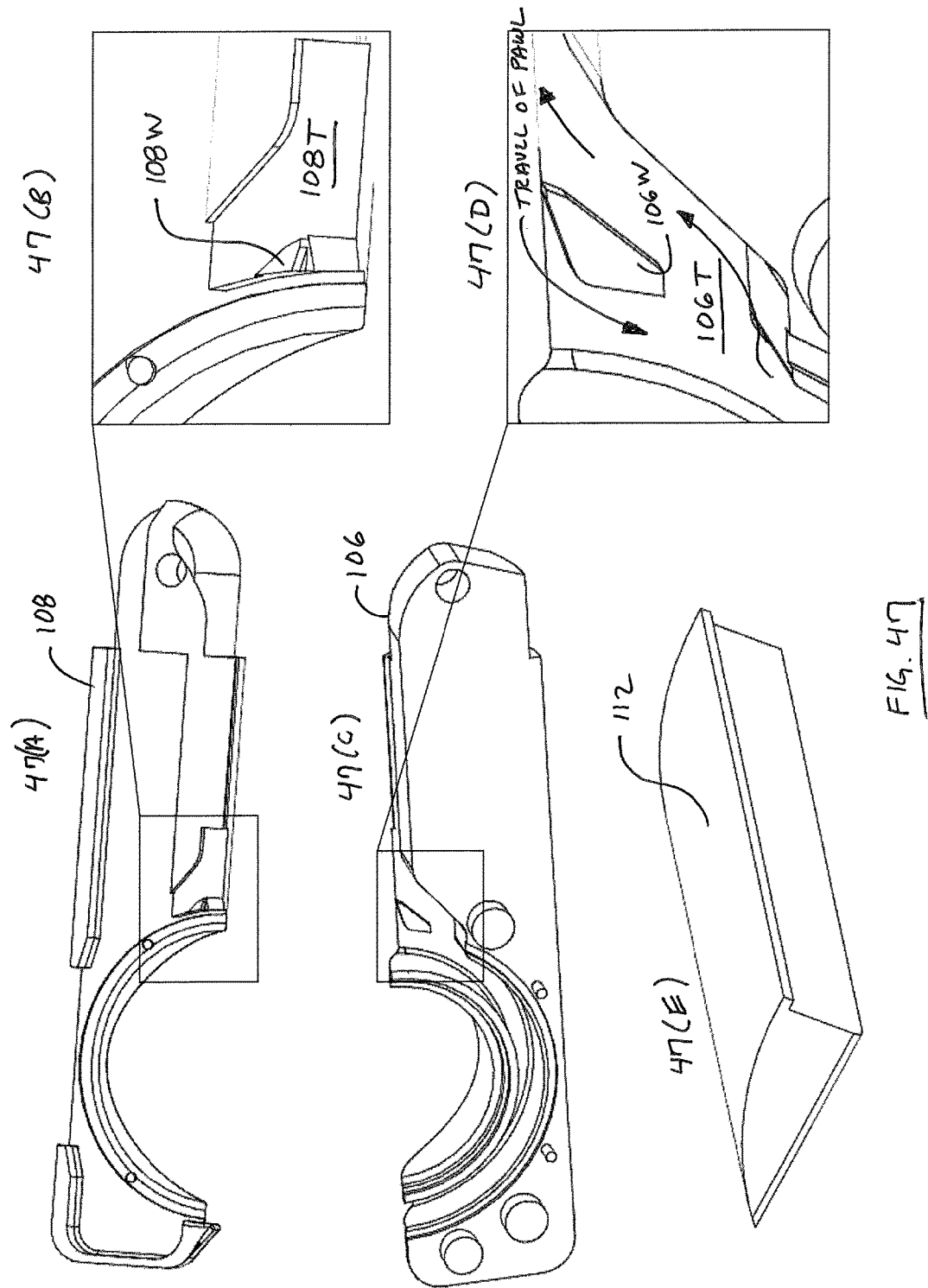

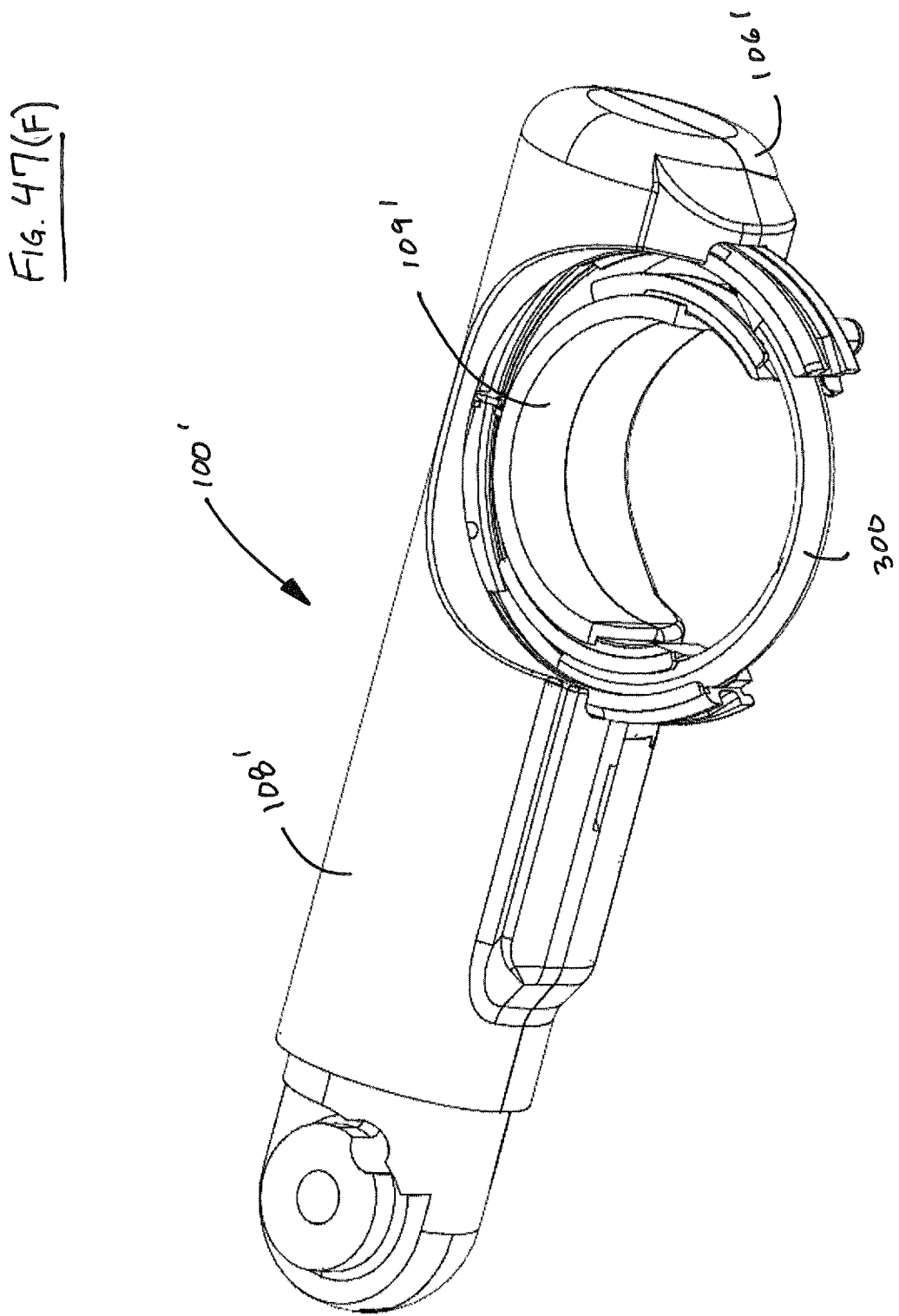

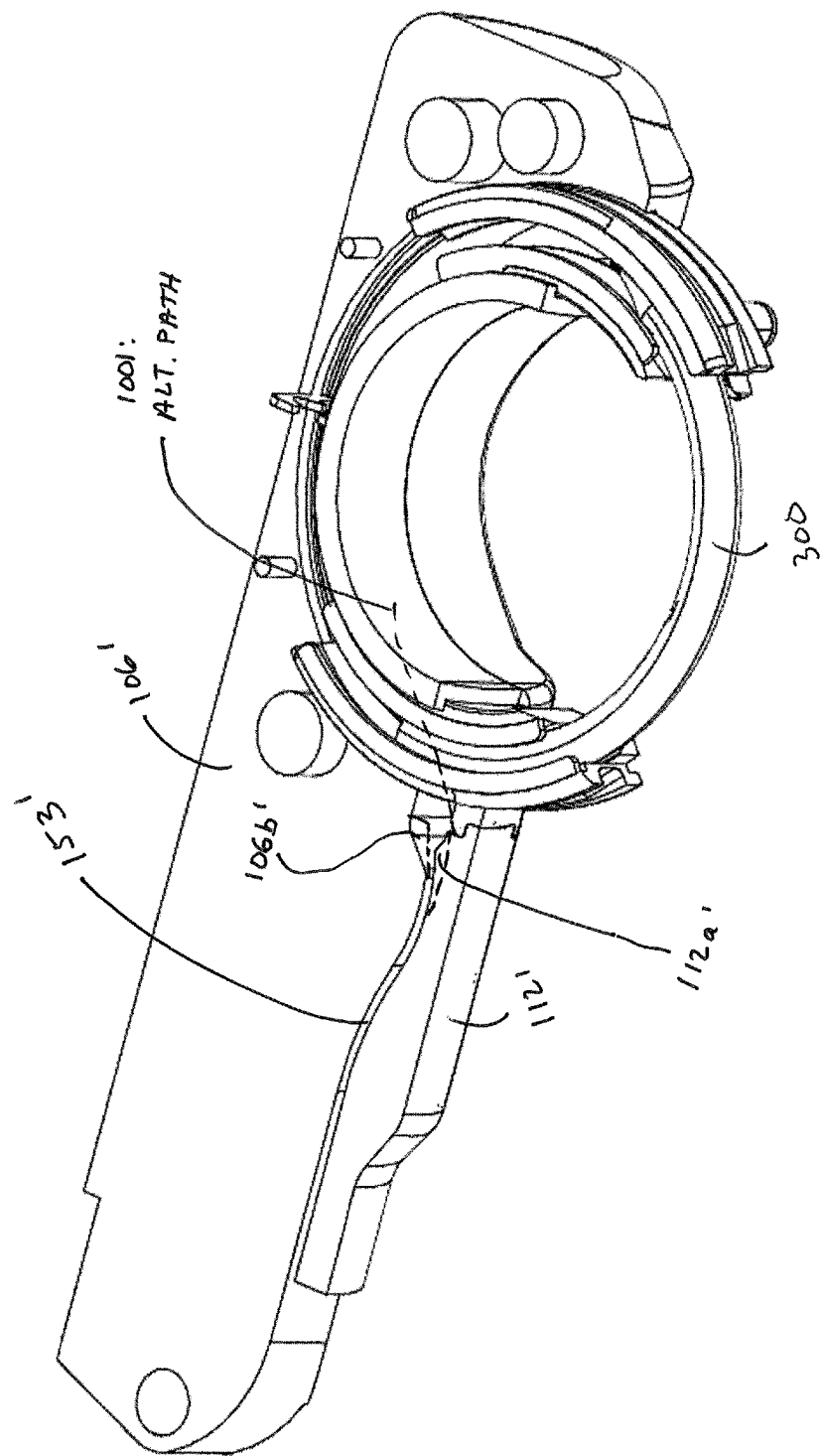

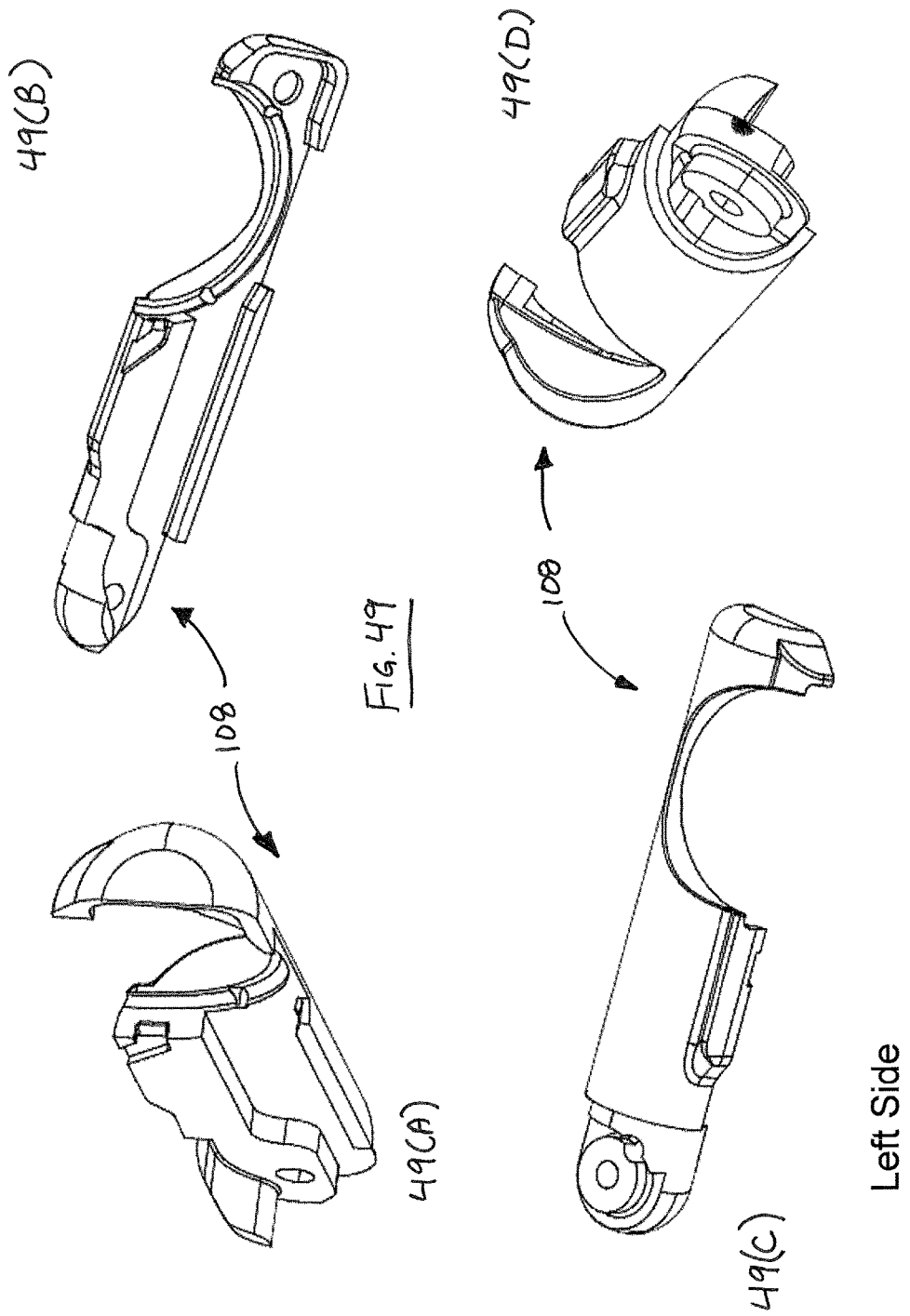

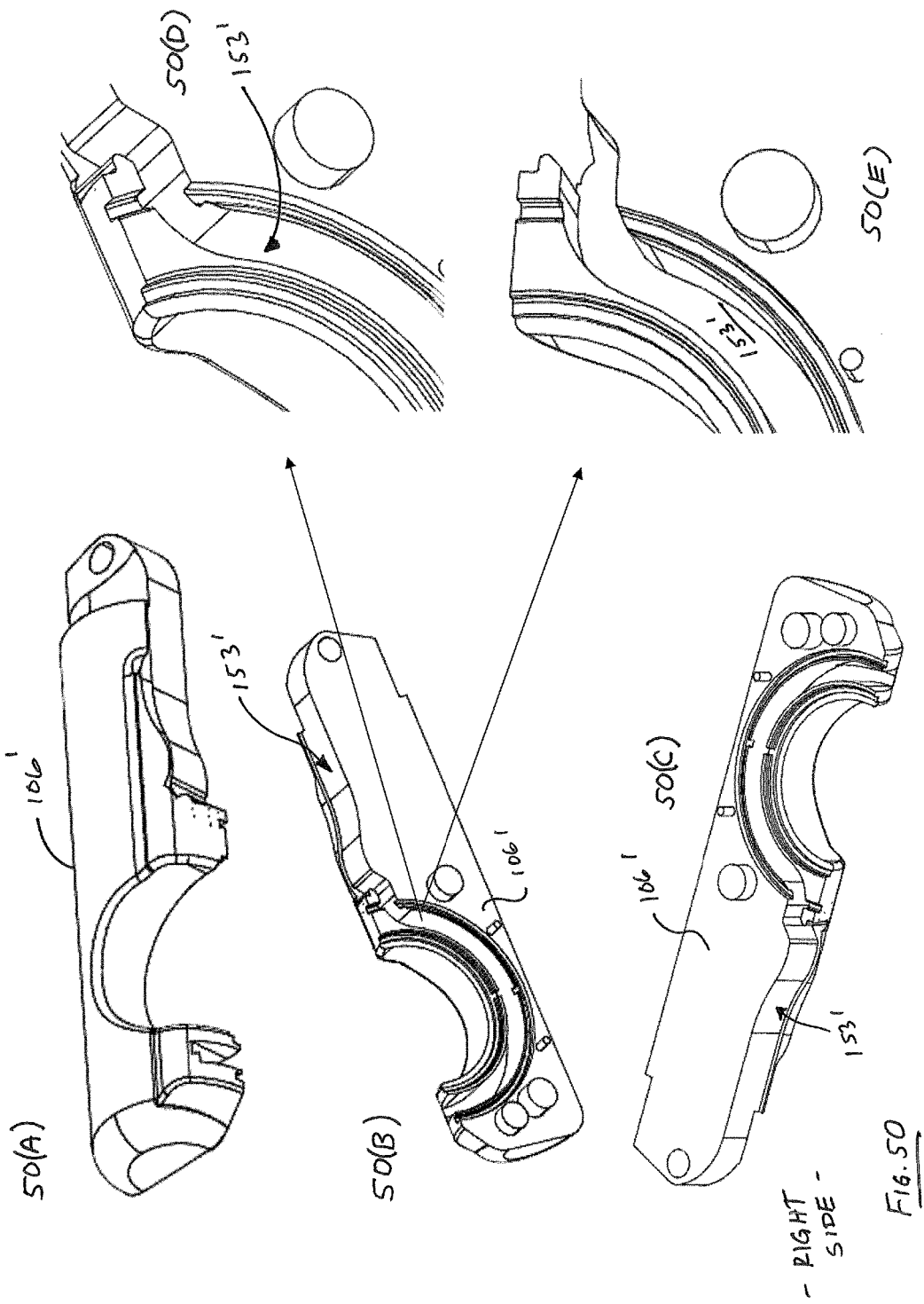

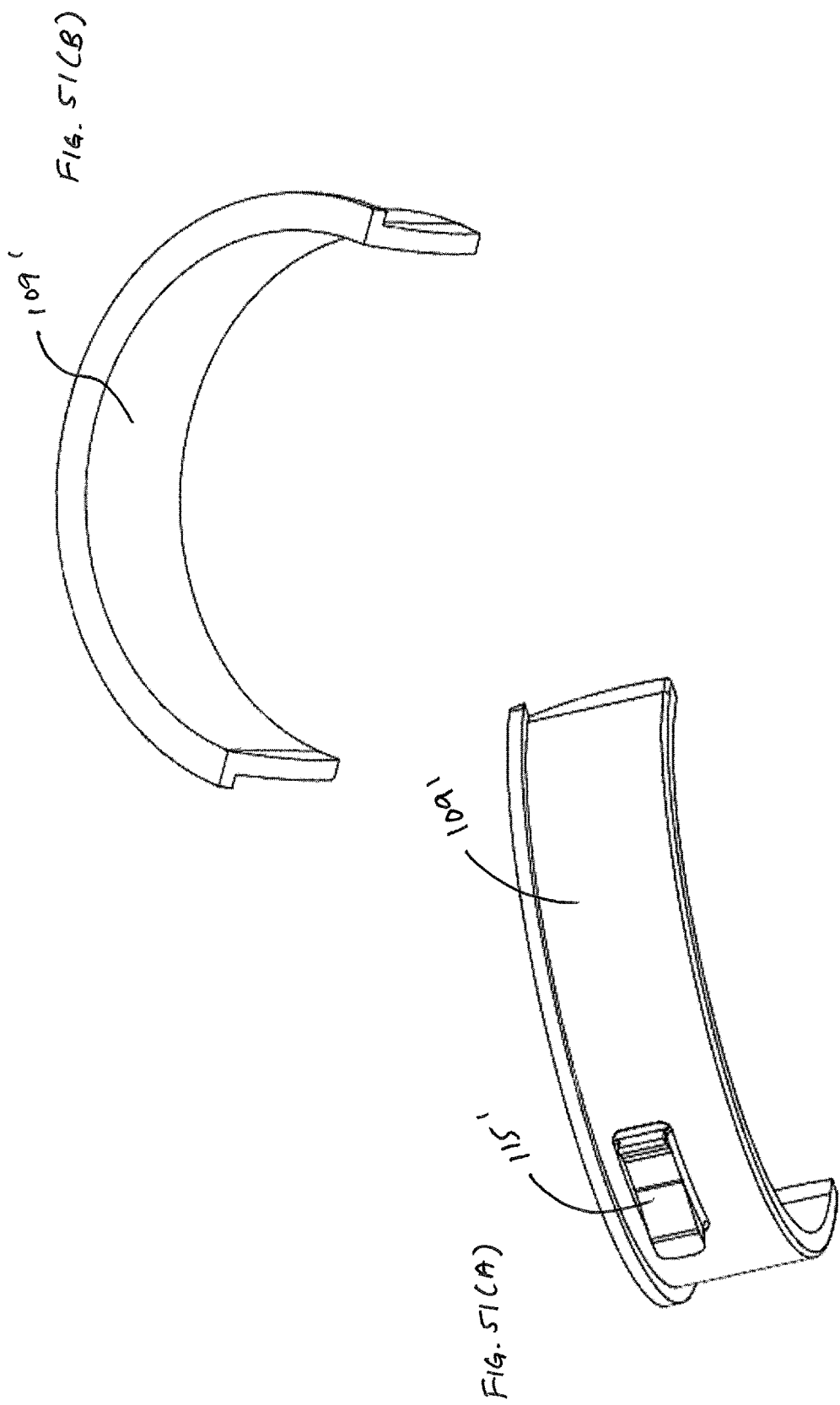

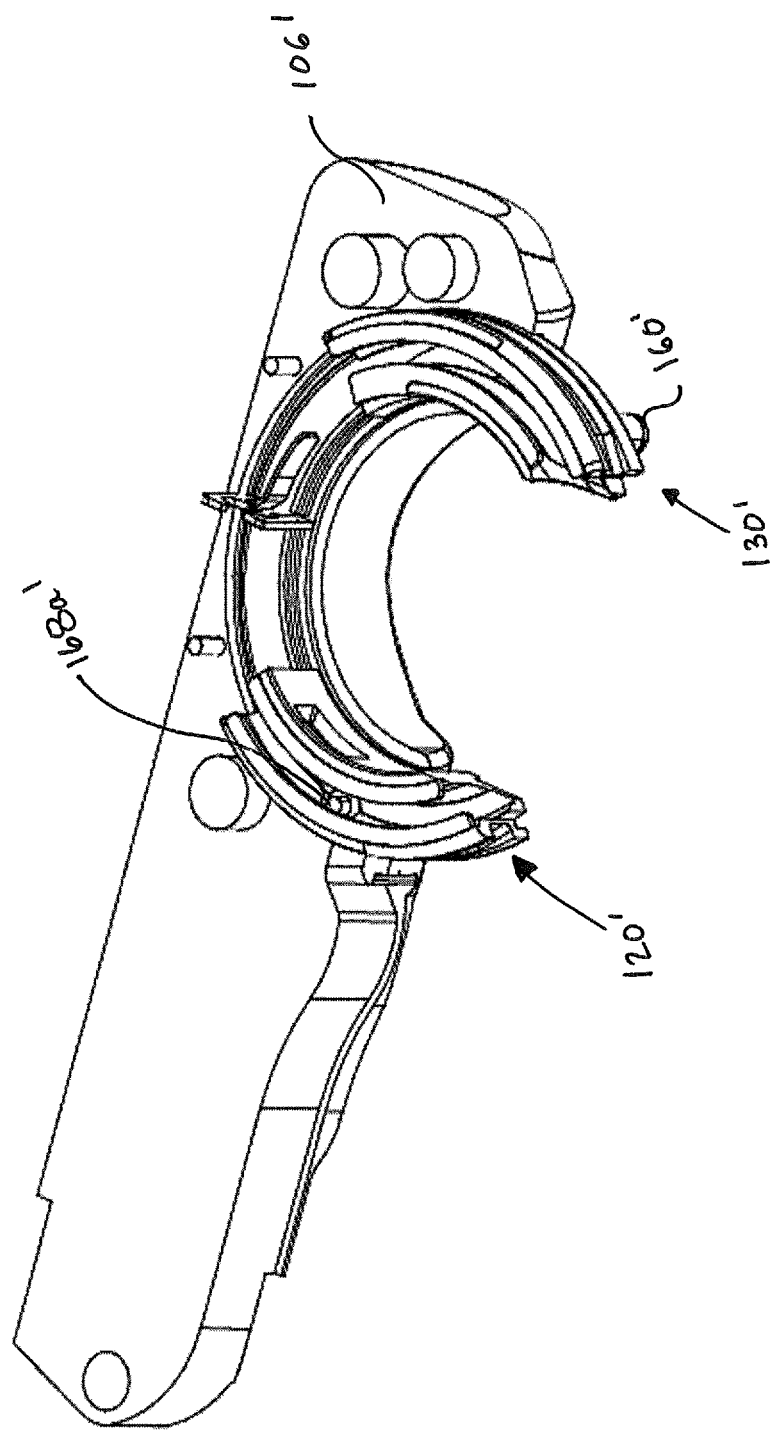

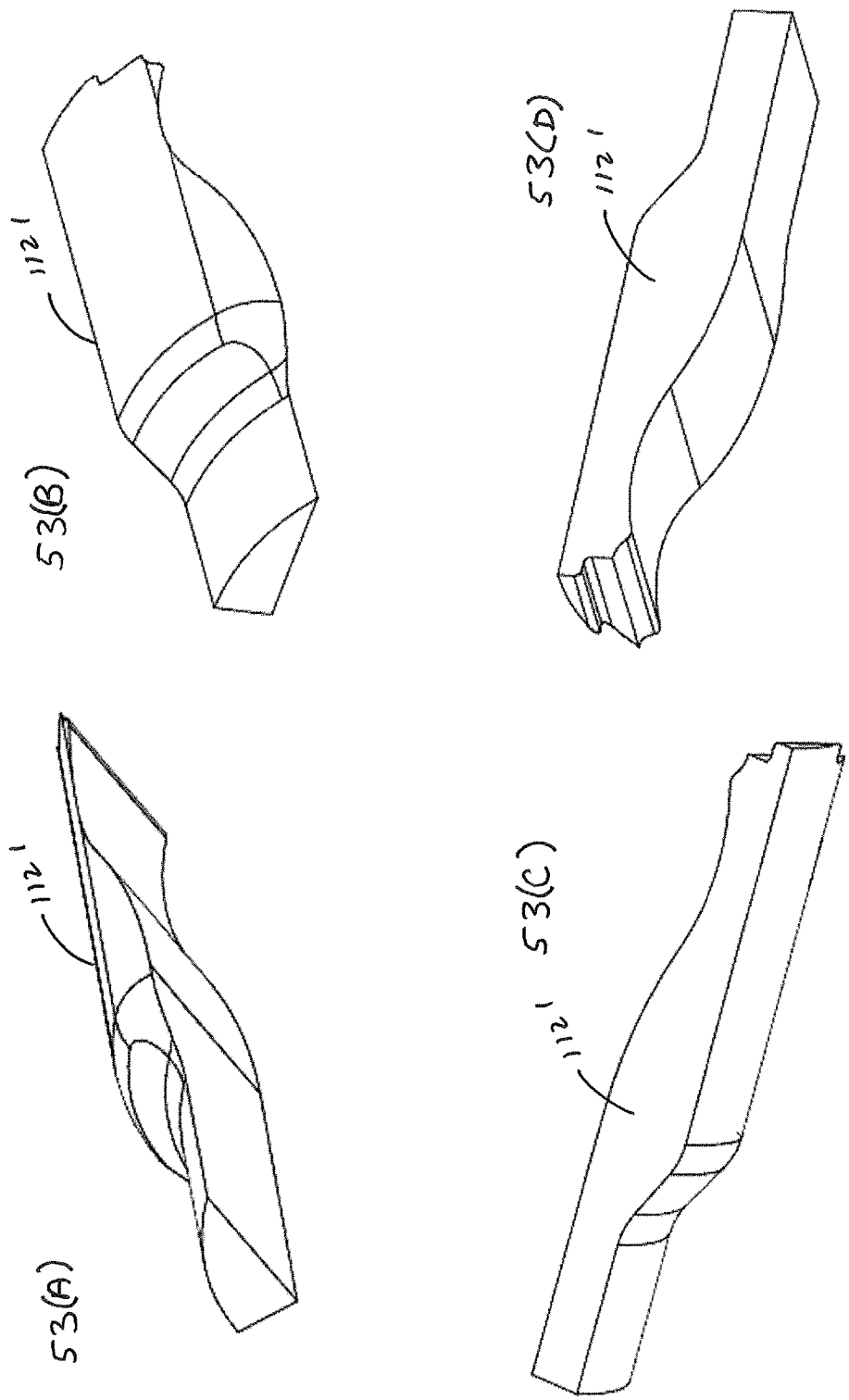

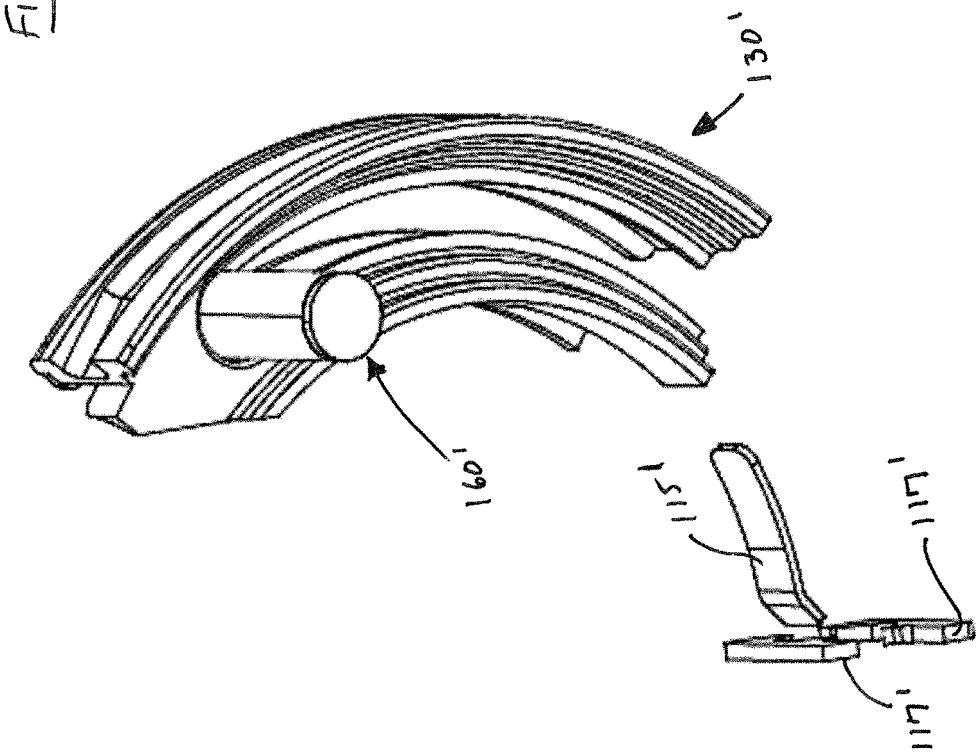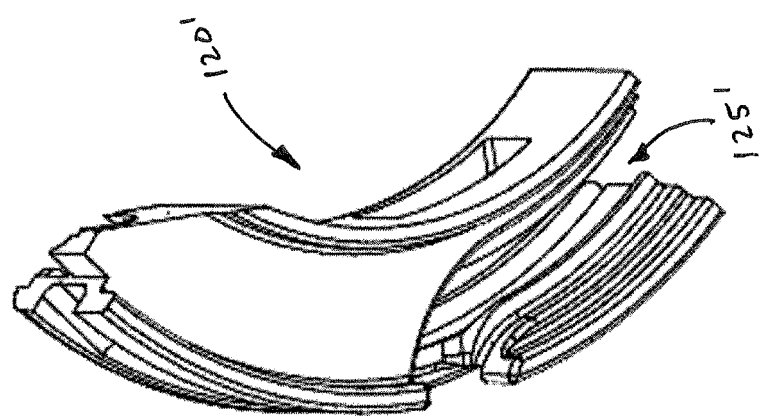

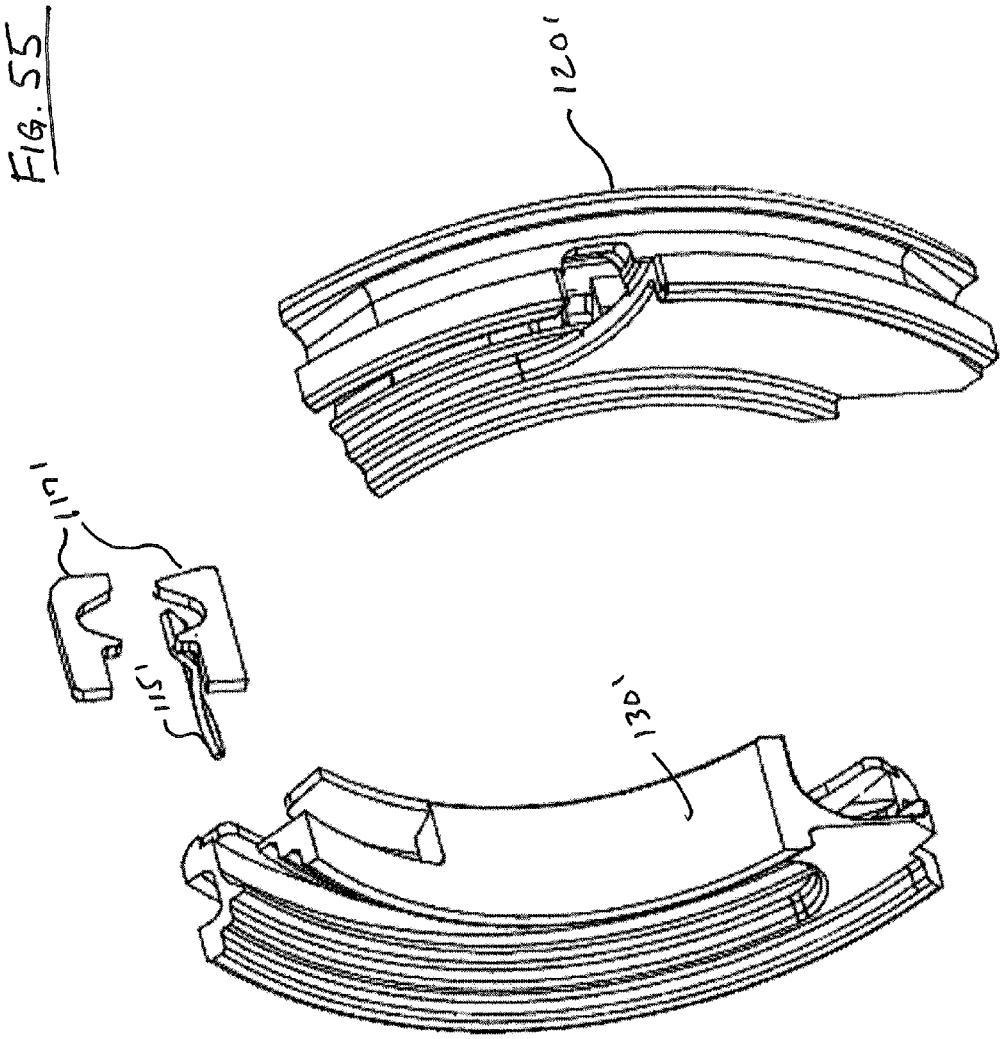

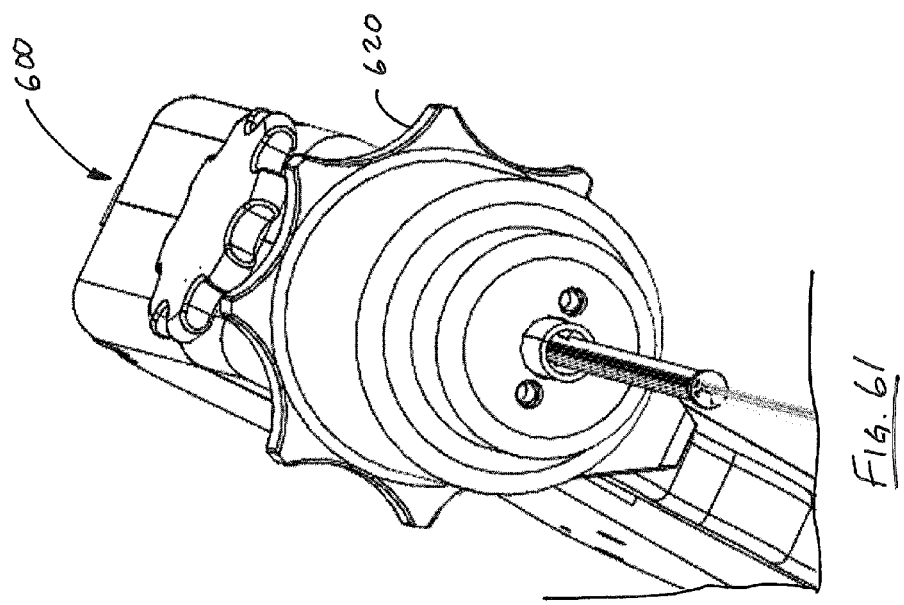
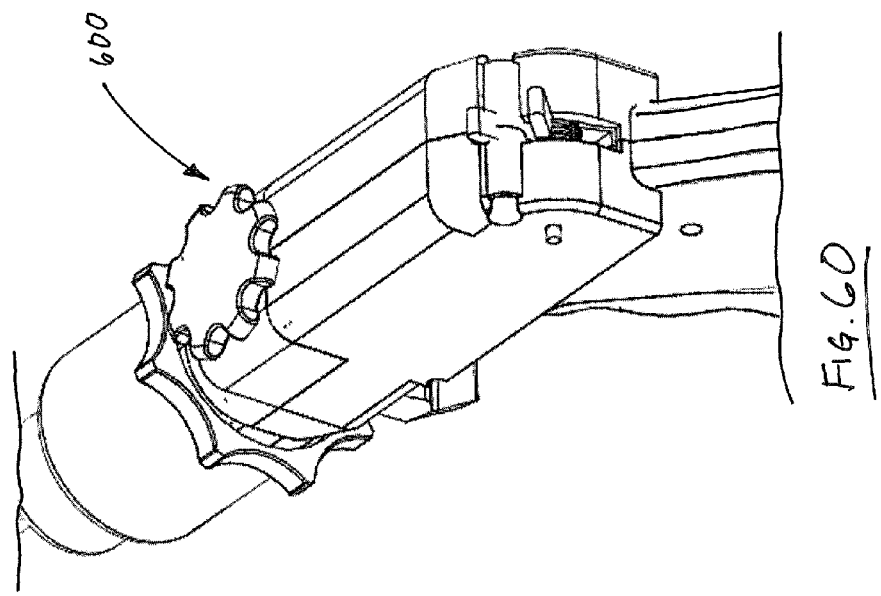

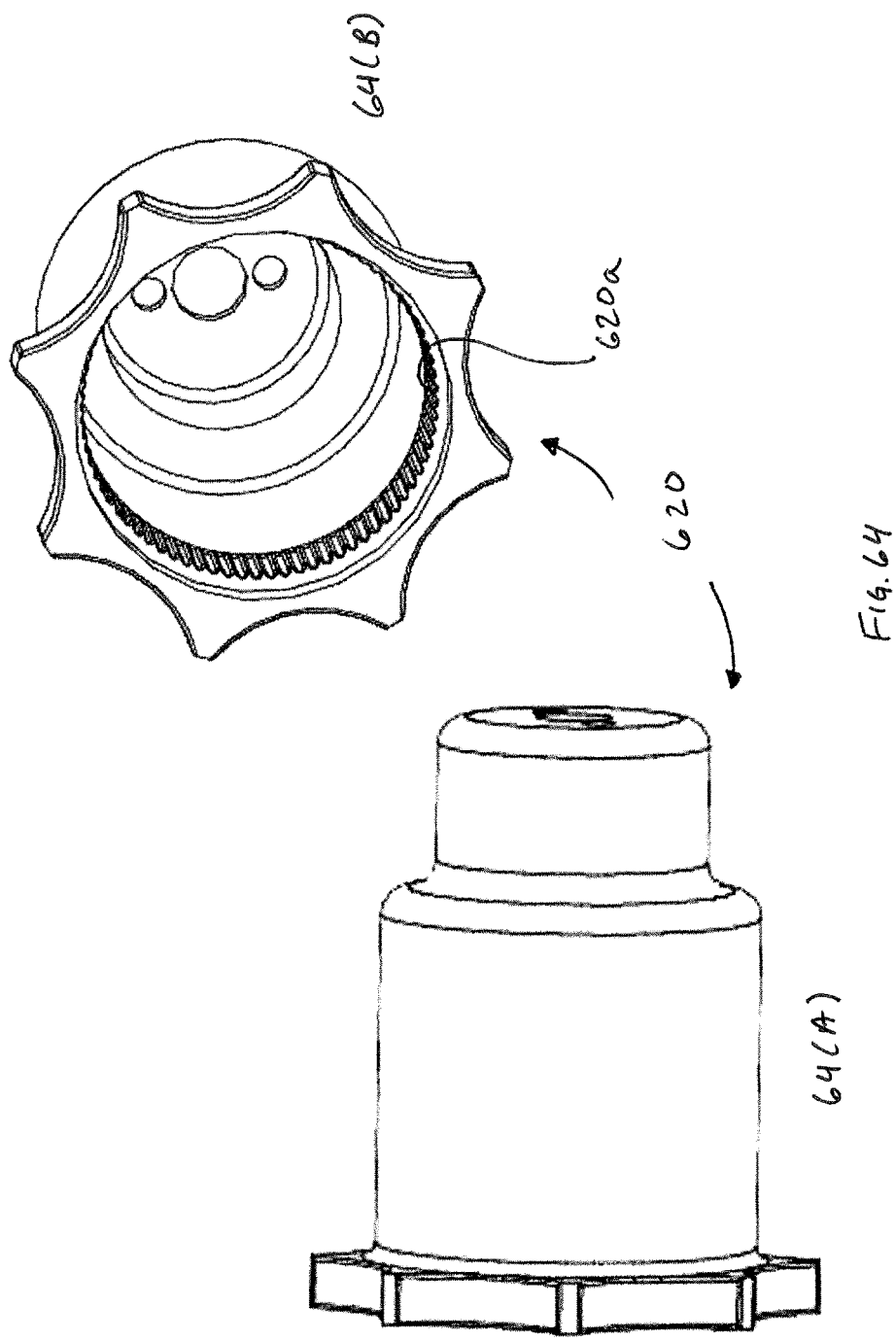

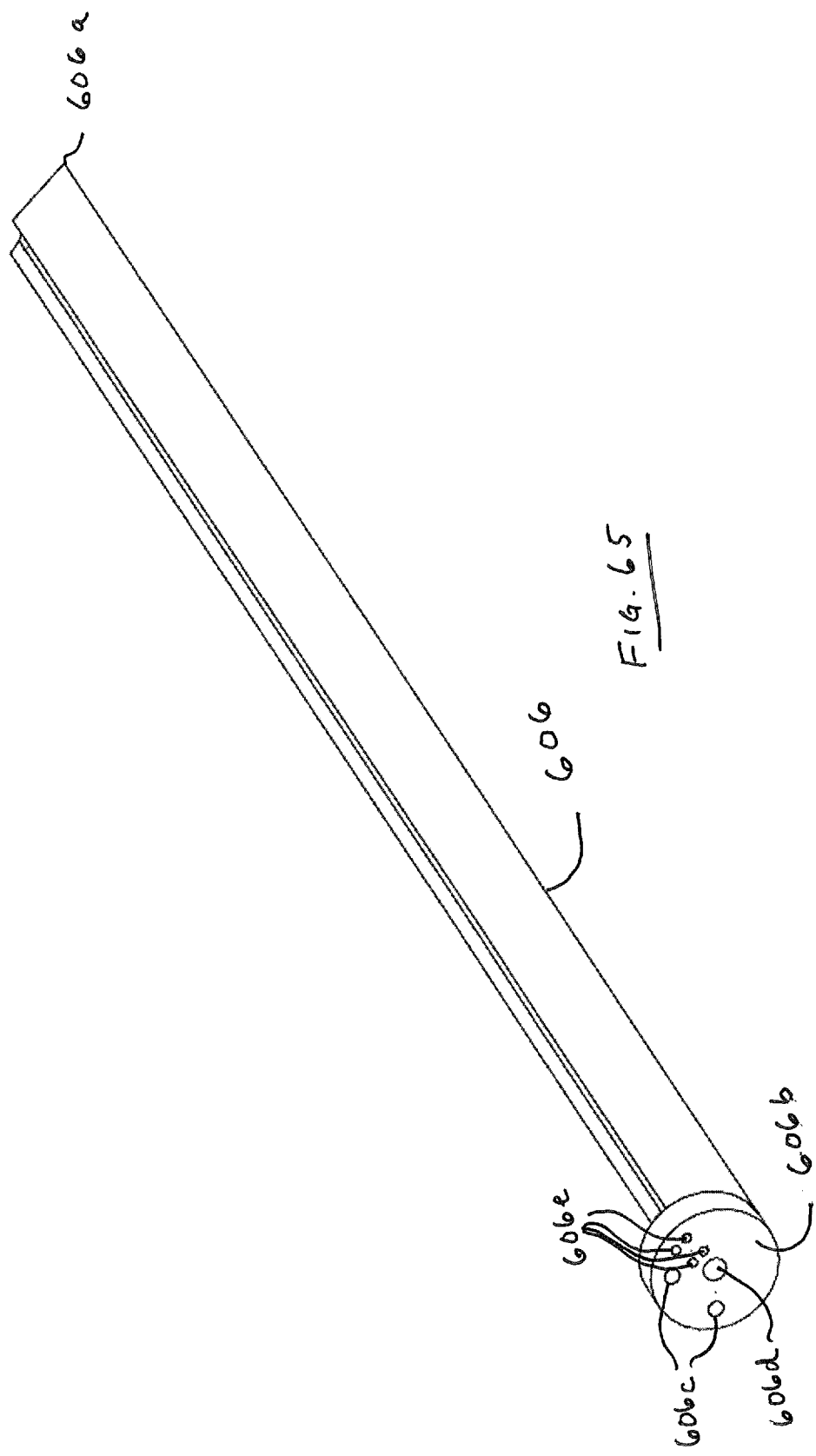

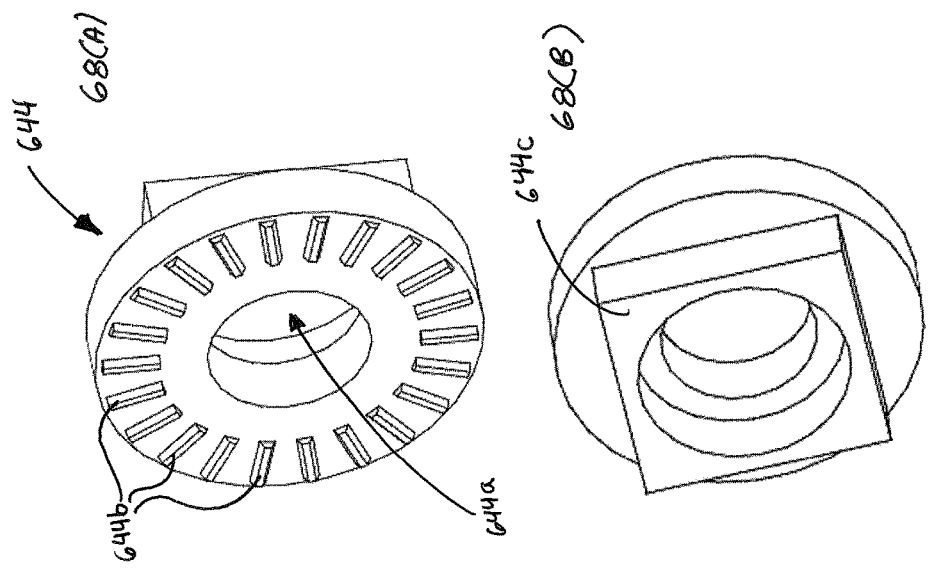
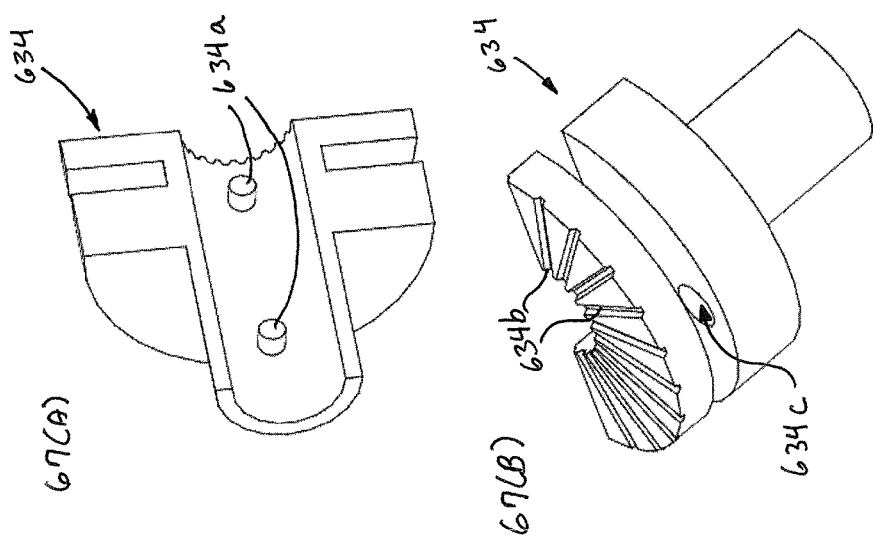

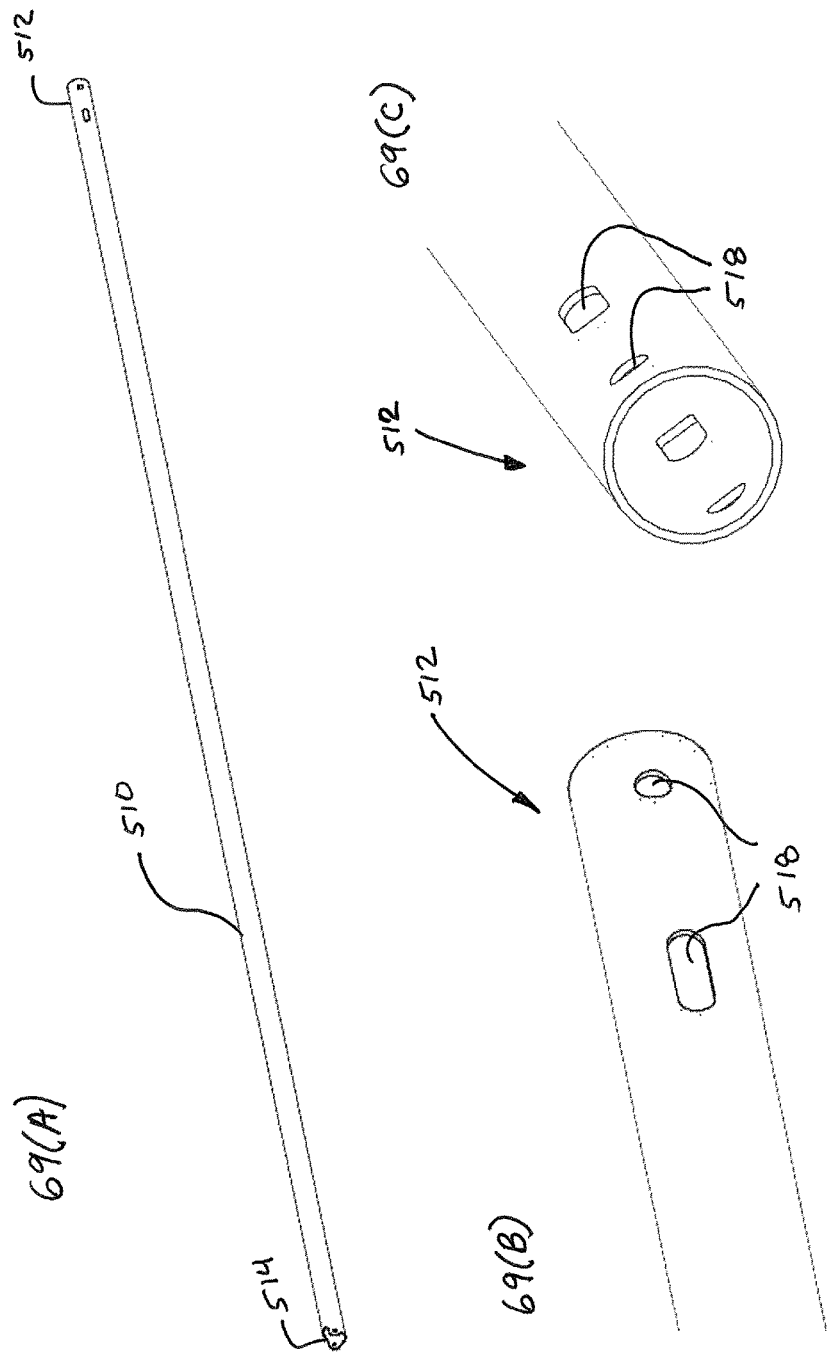

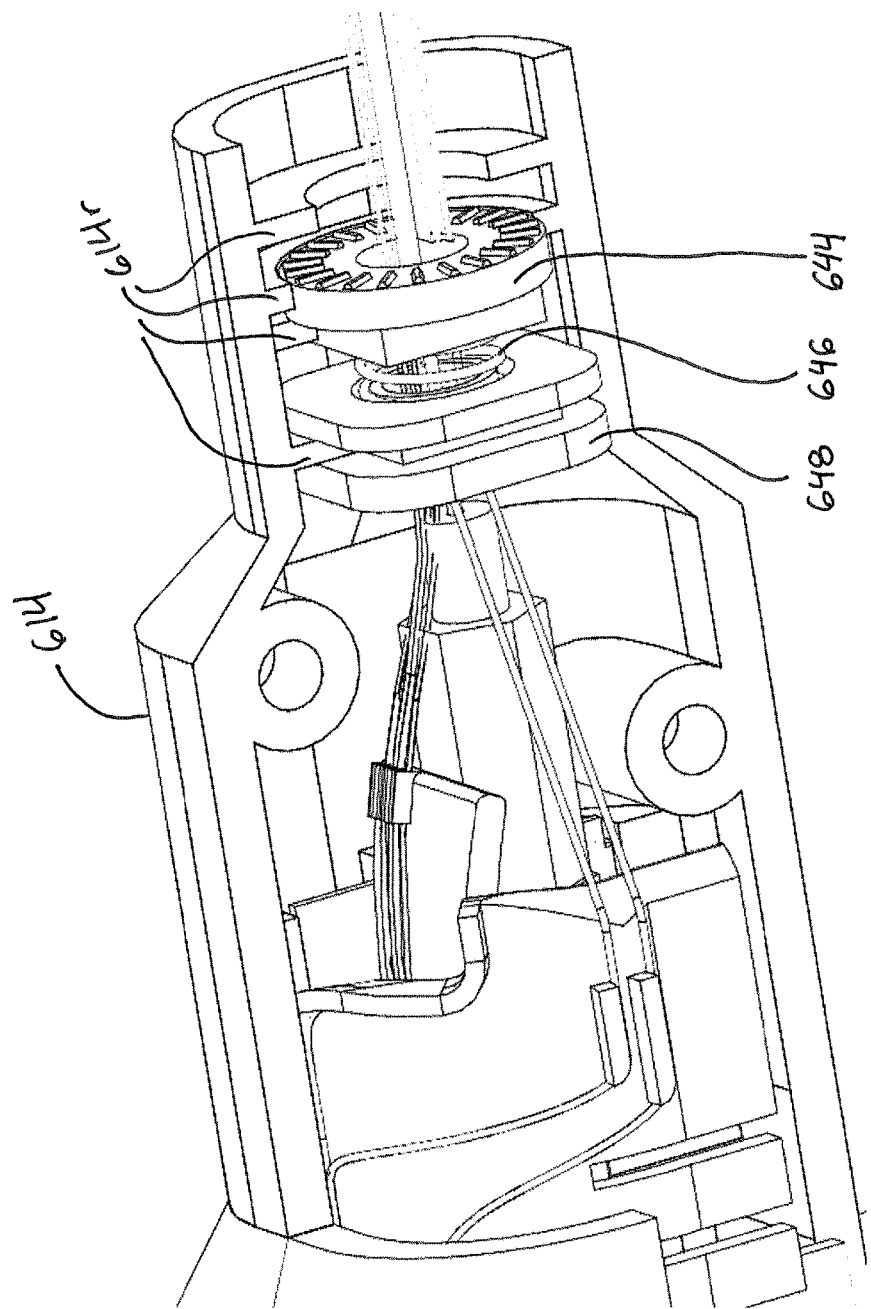

CABLE DISC

Trigger Pulled

Trigger Released

Trigger Pulled

Trigger Released

Trigger Released

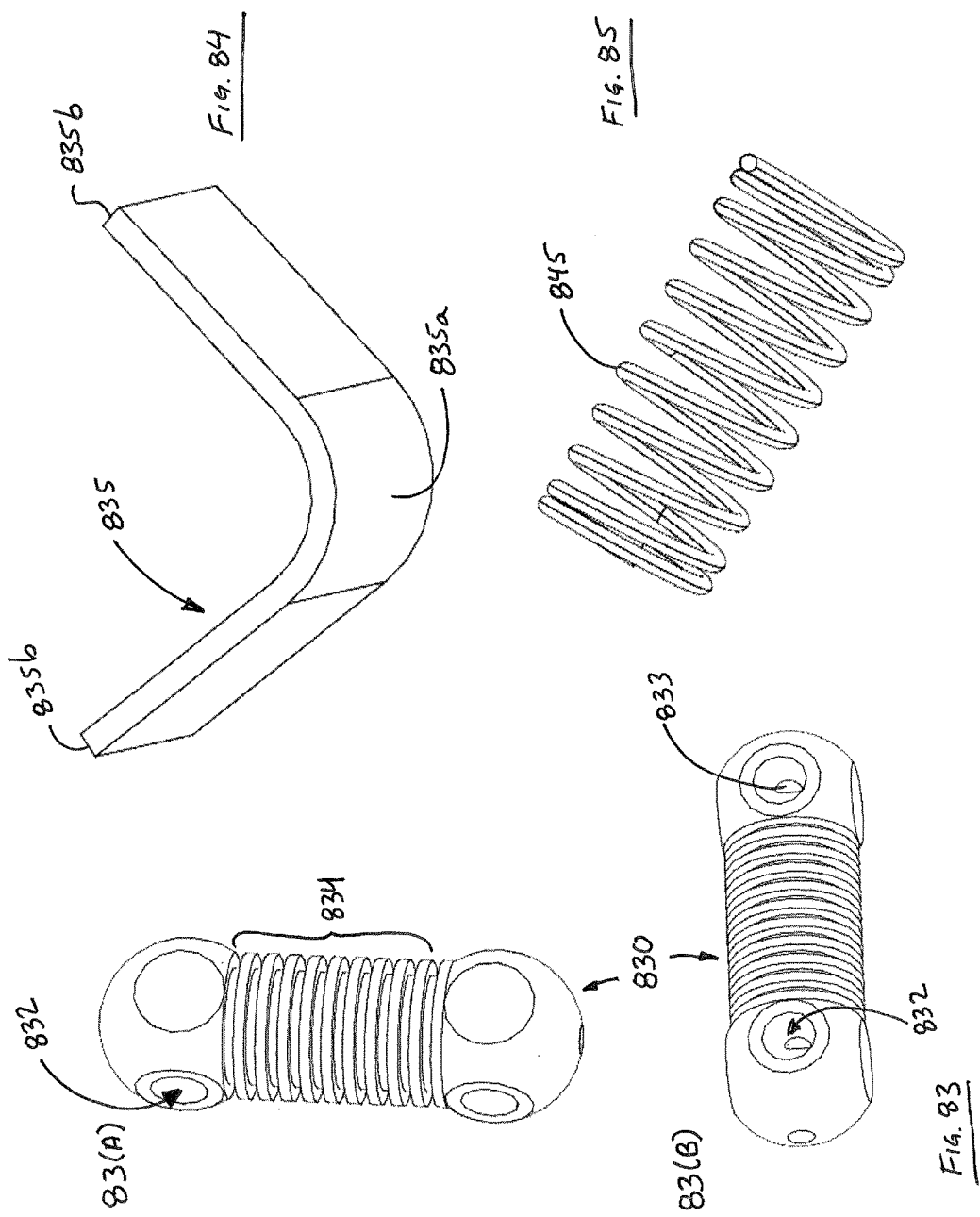

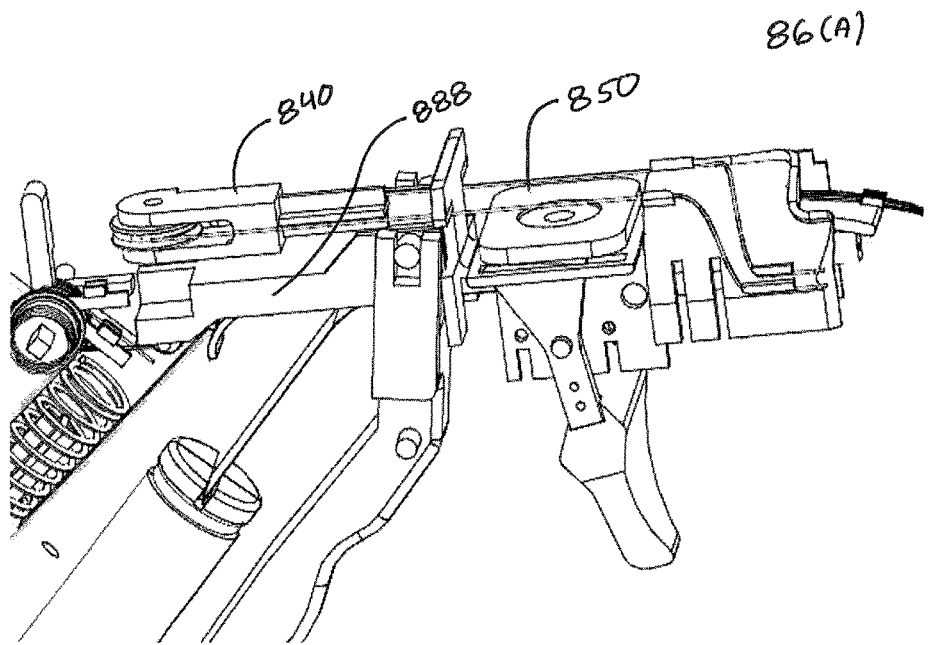
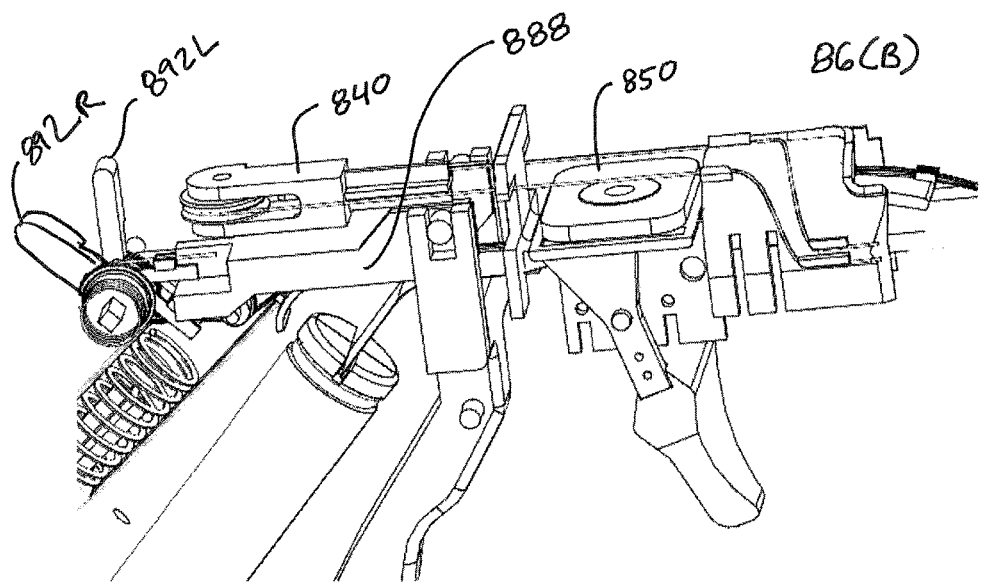
FIG. 86

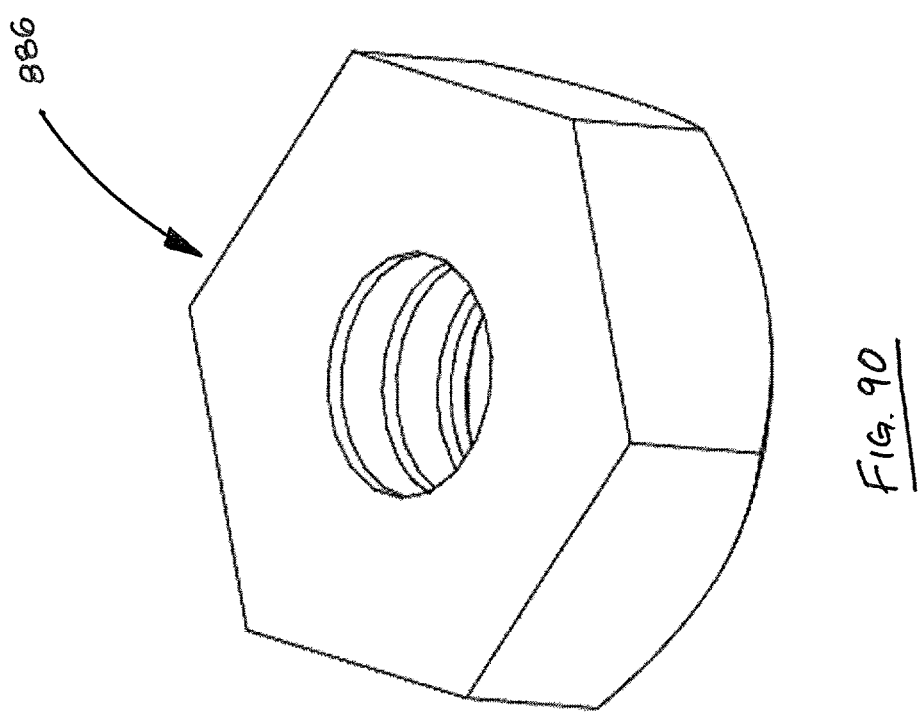

Trigger Released

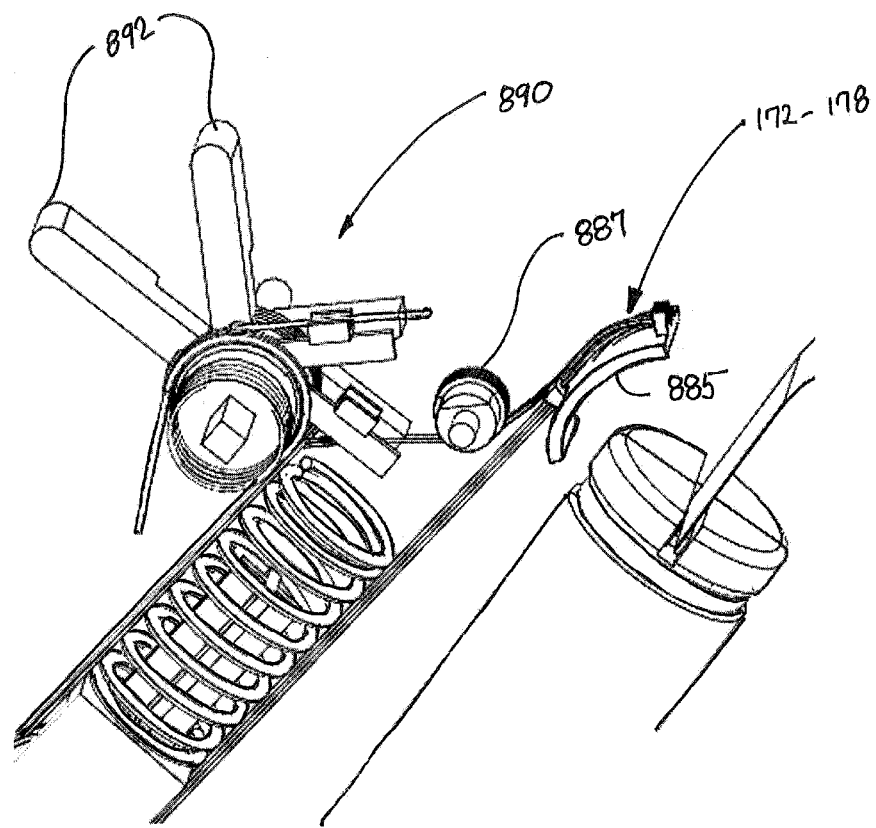
TRIGGER RELEASED
FIG. (92)

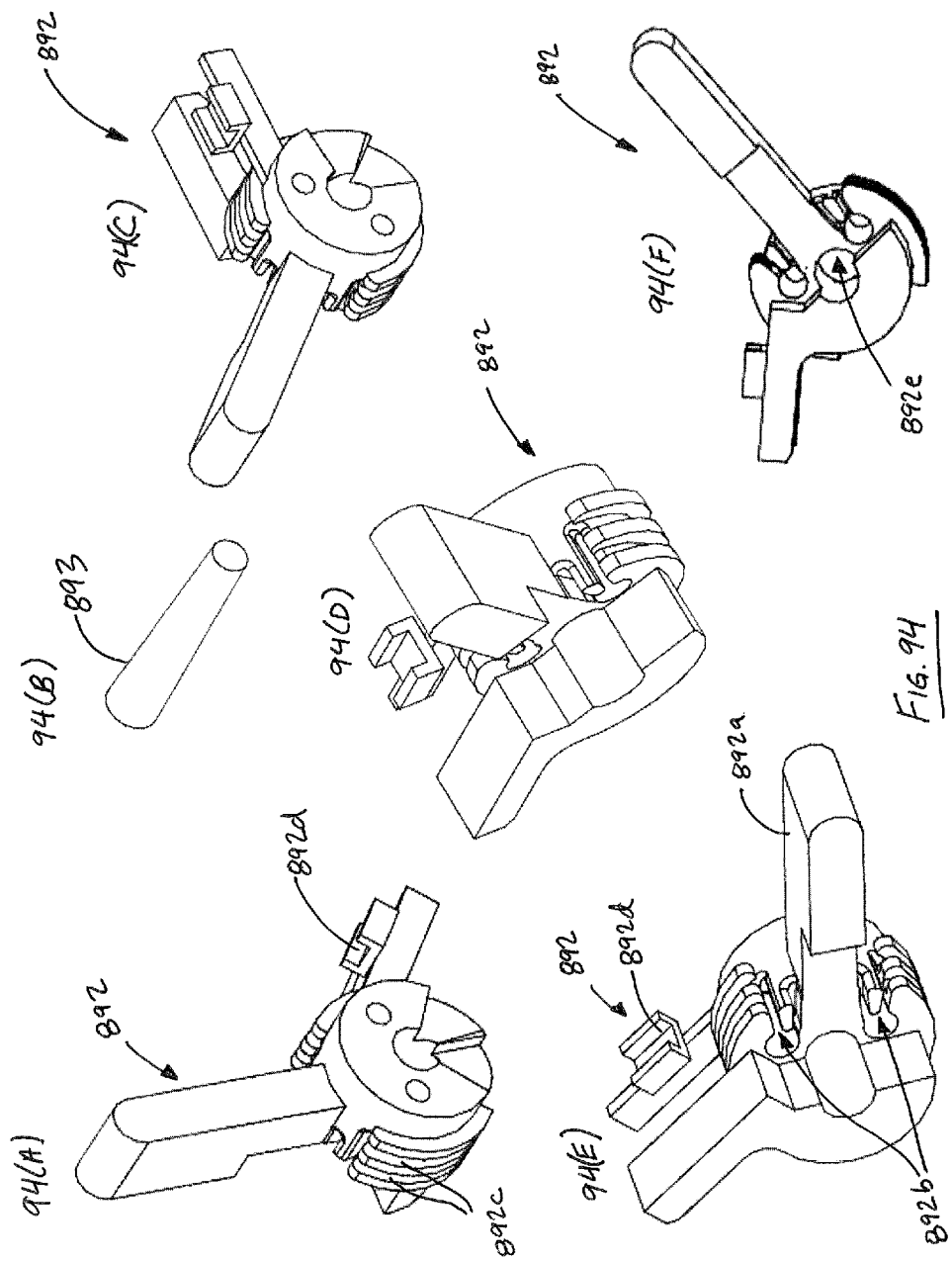

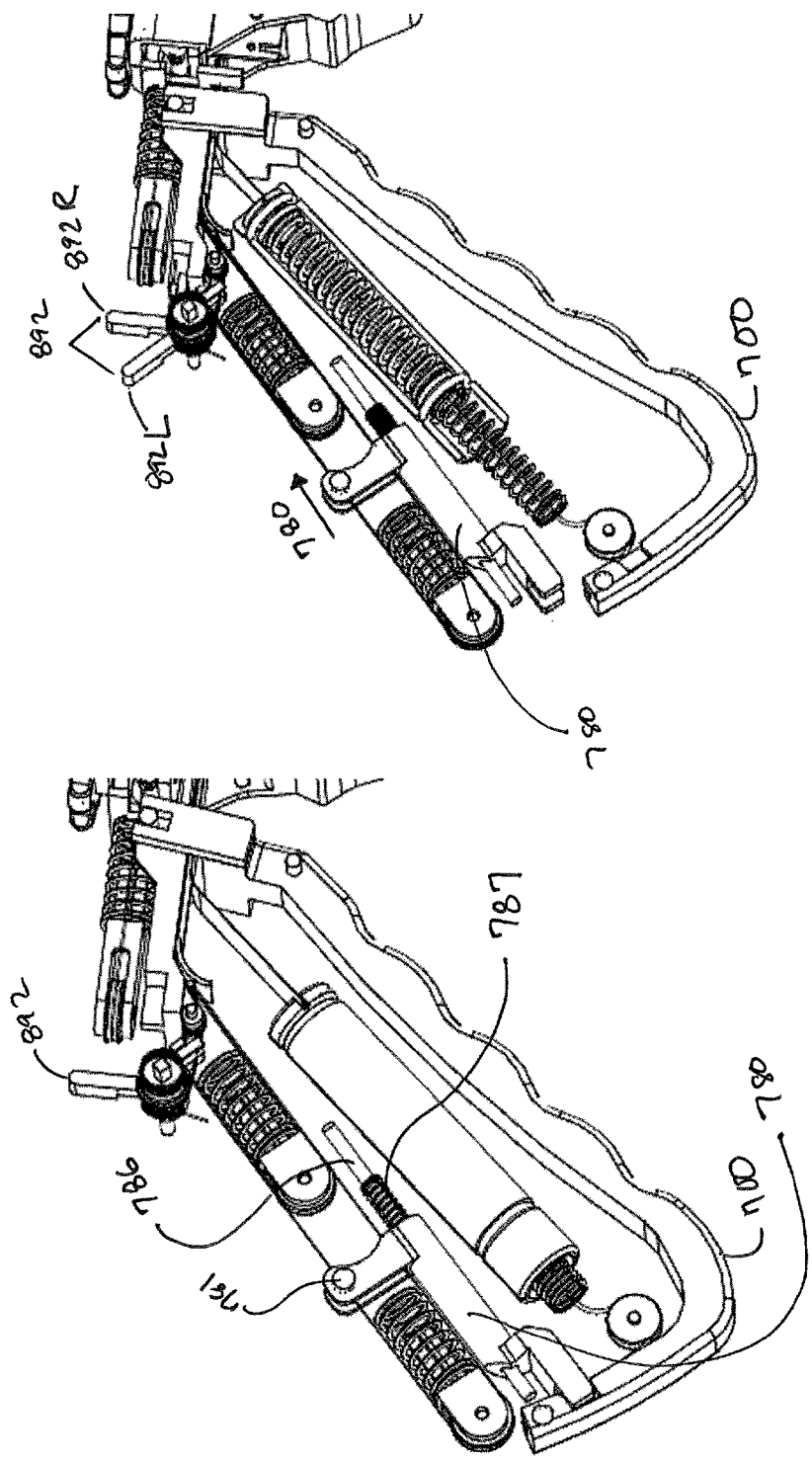

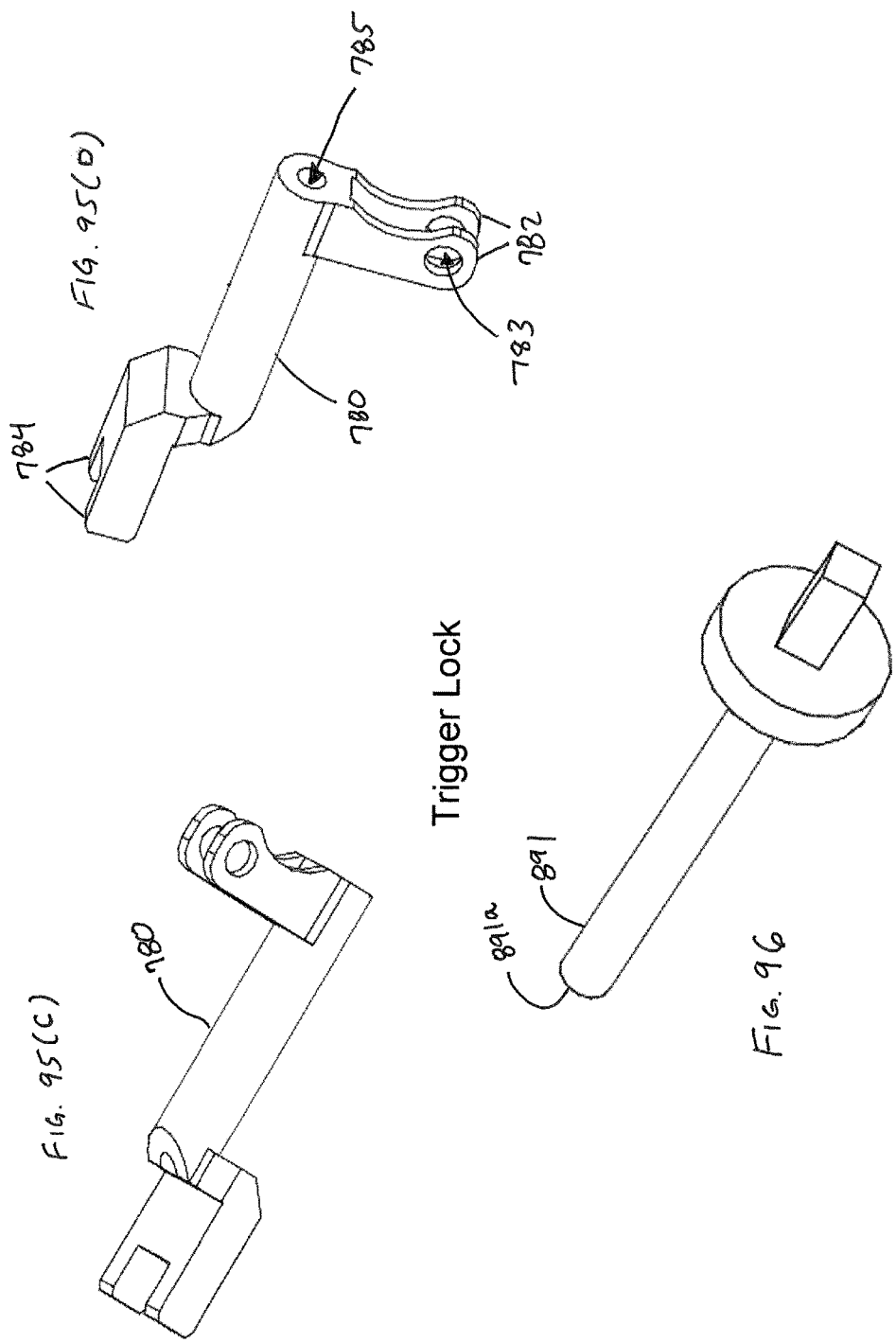

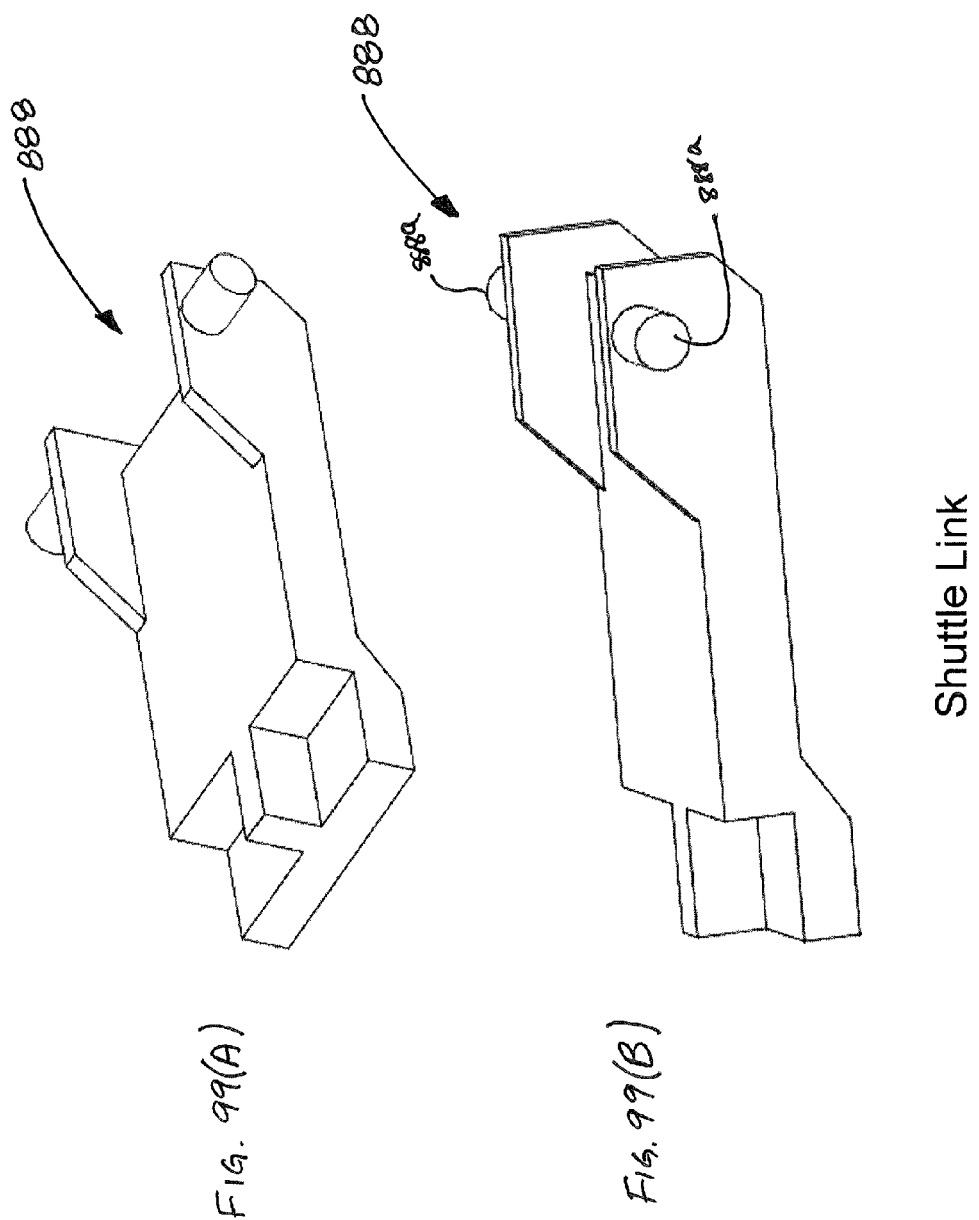

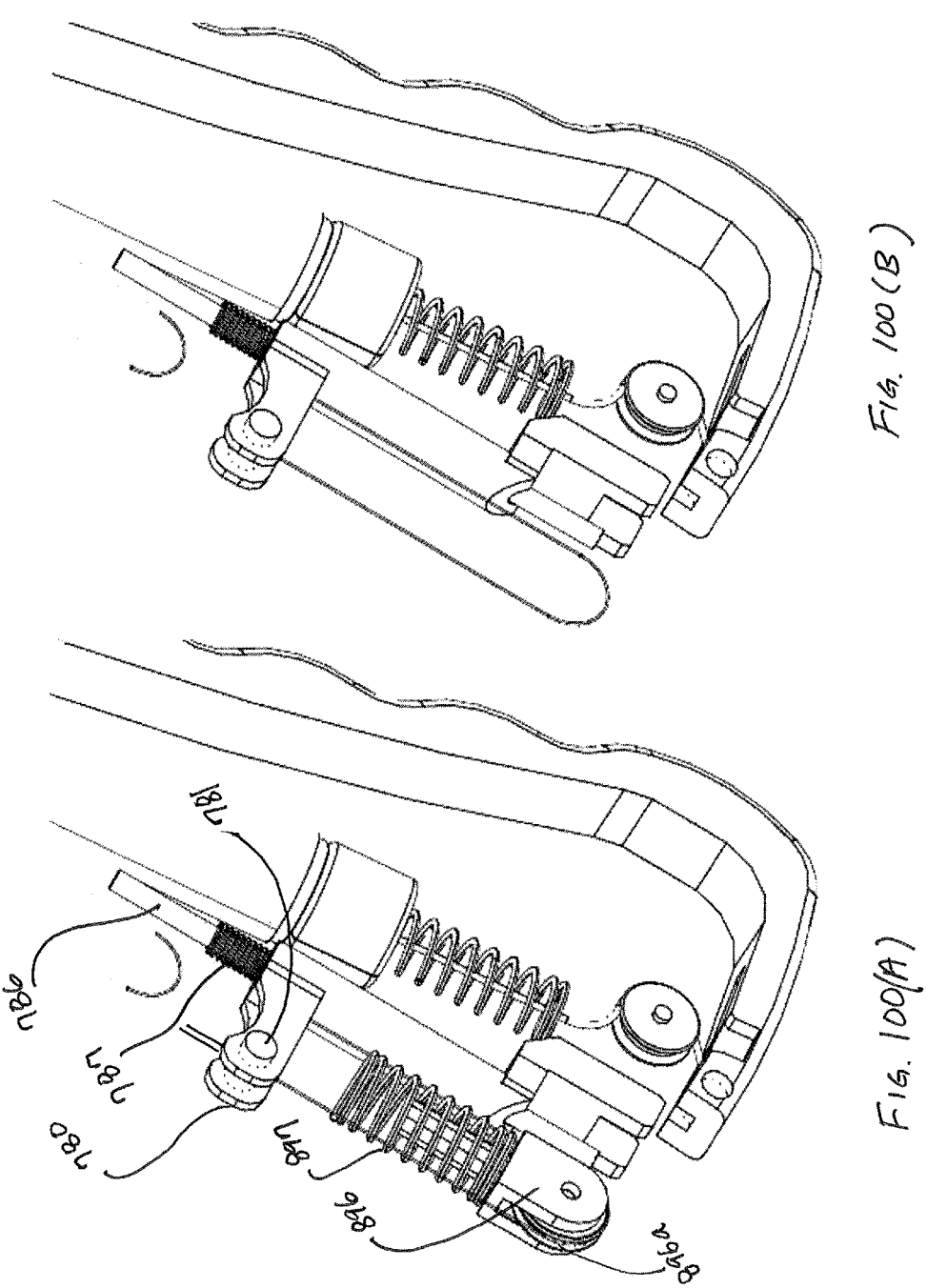

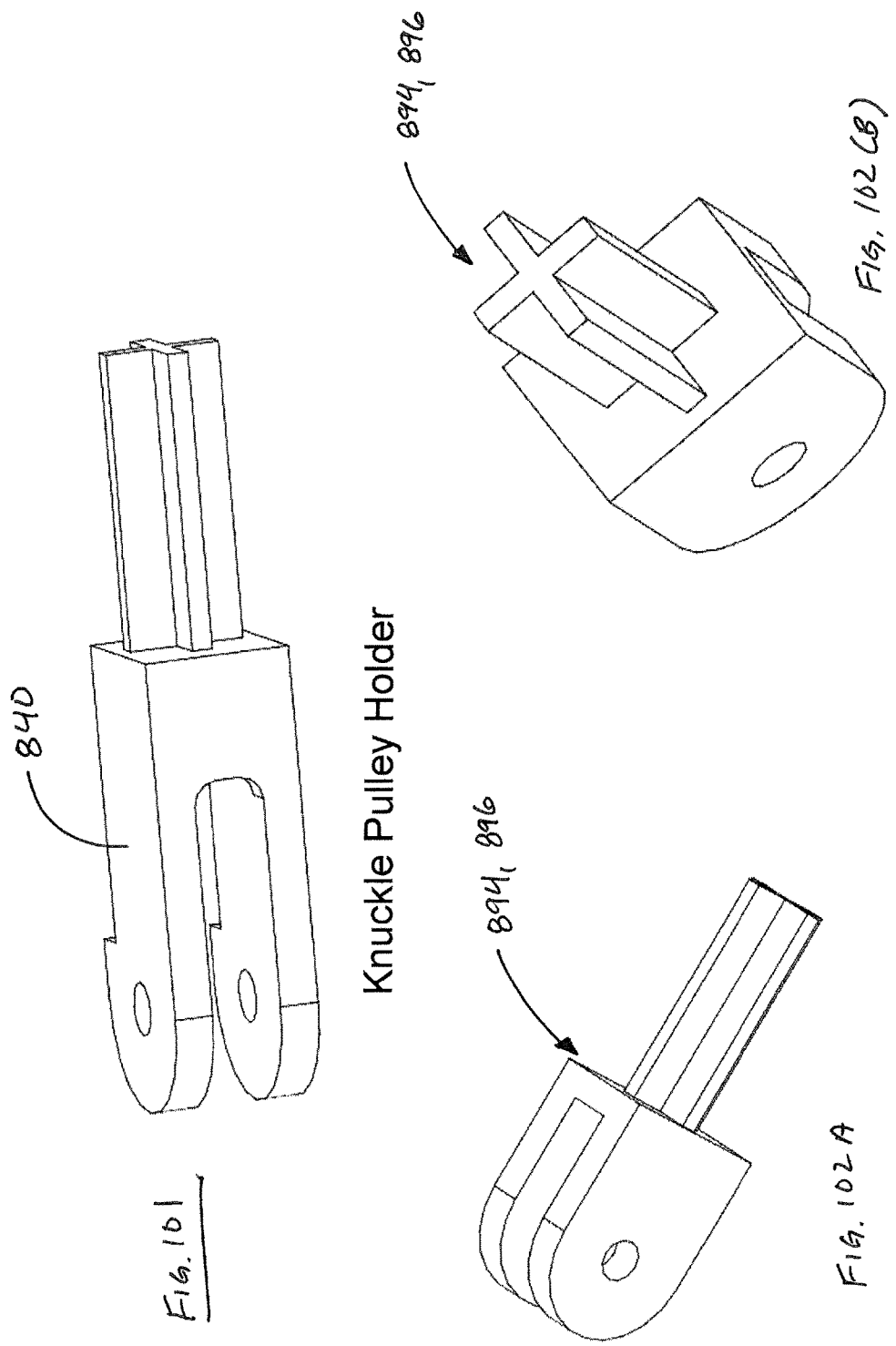

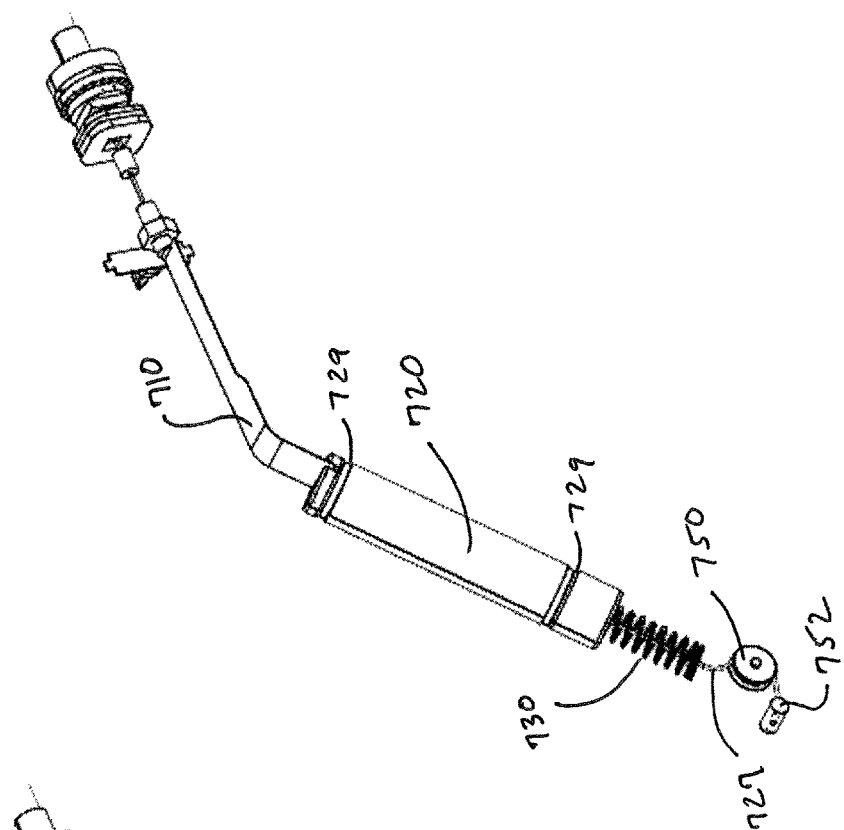
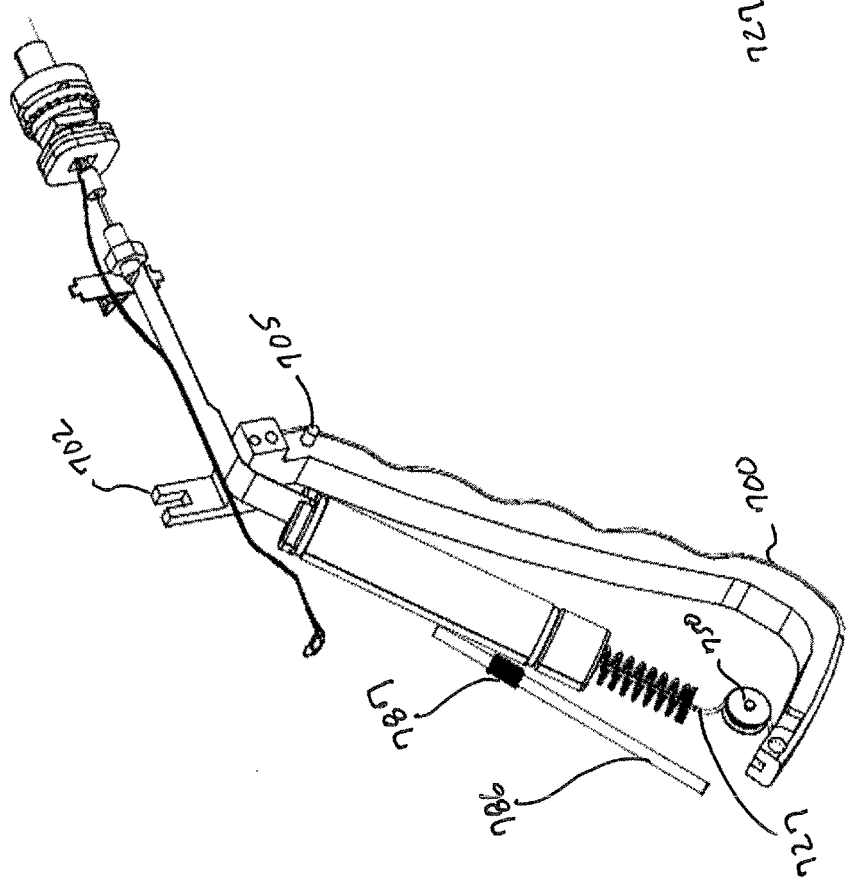

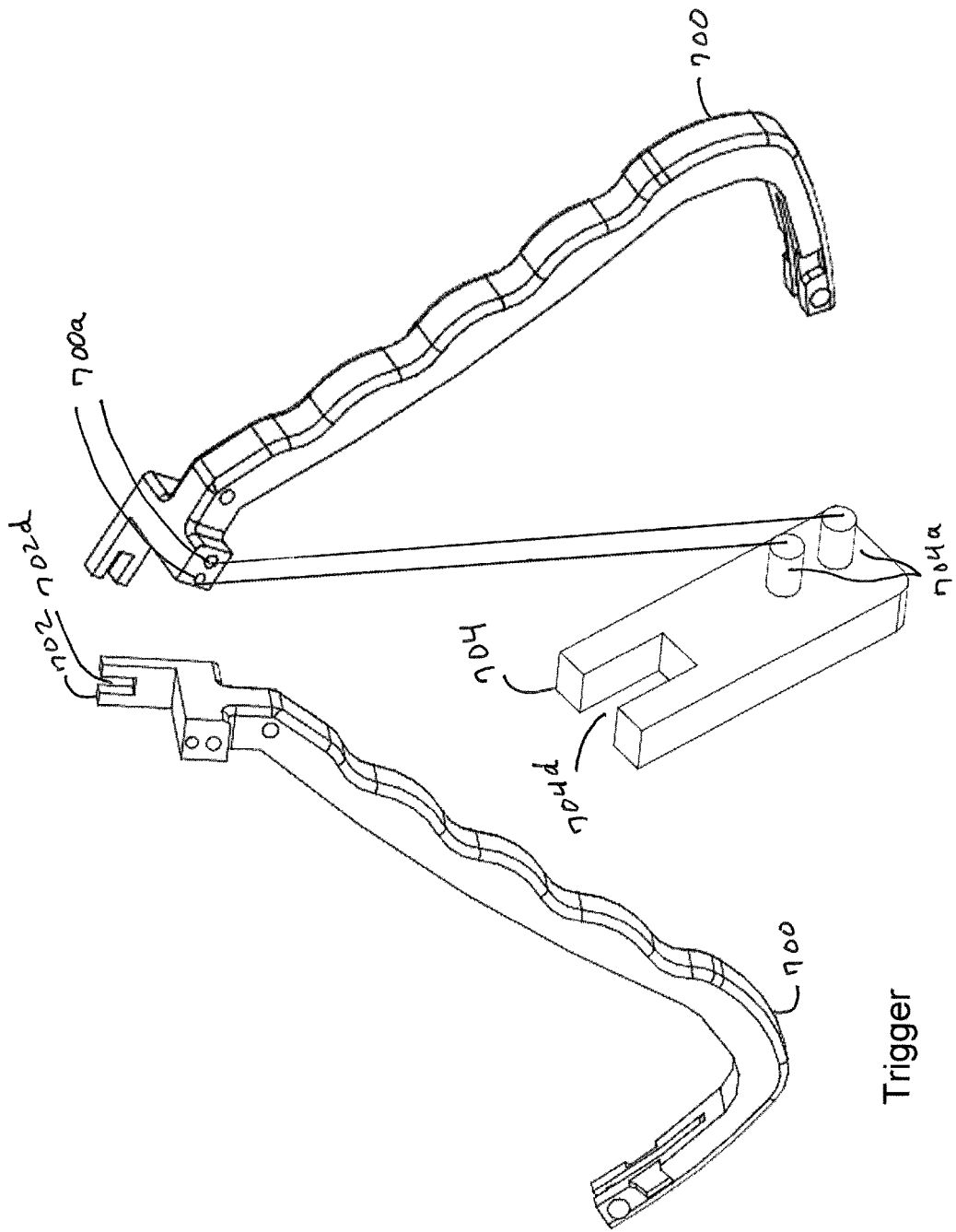

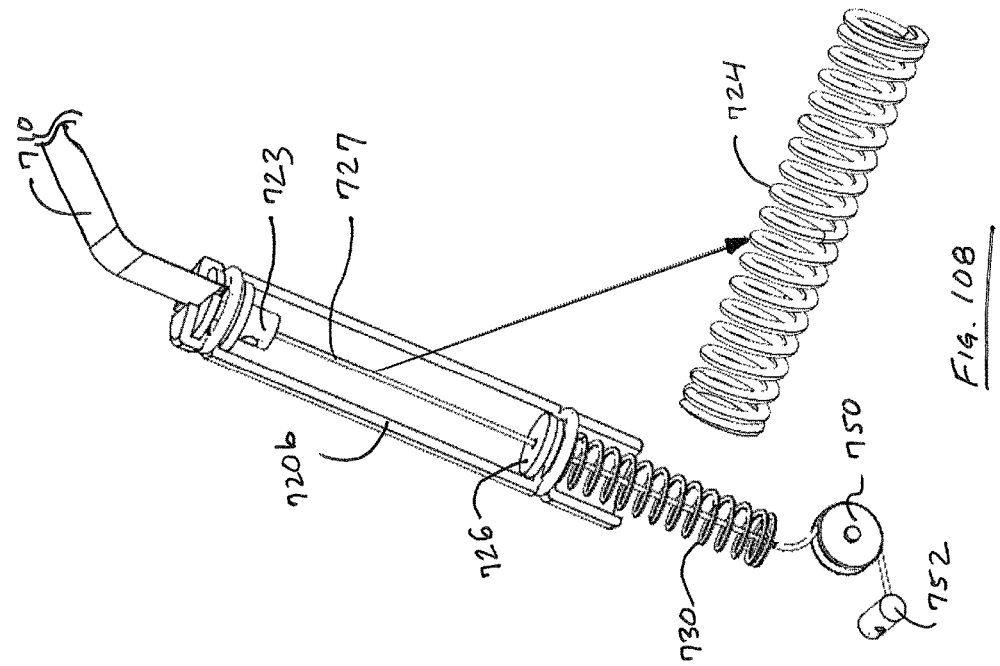
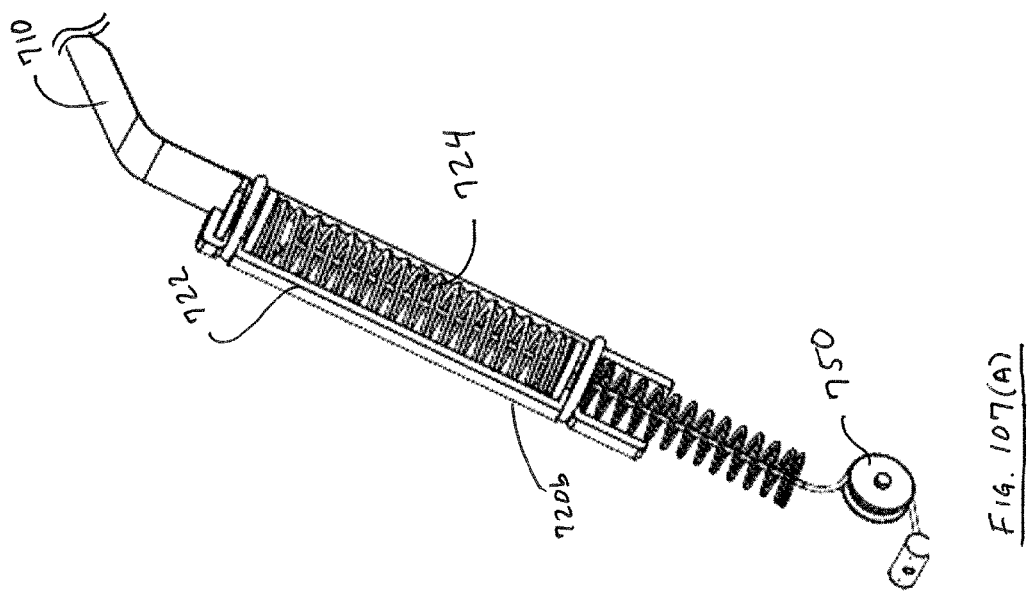

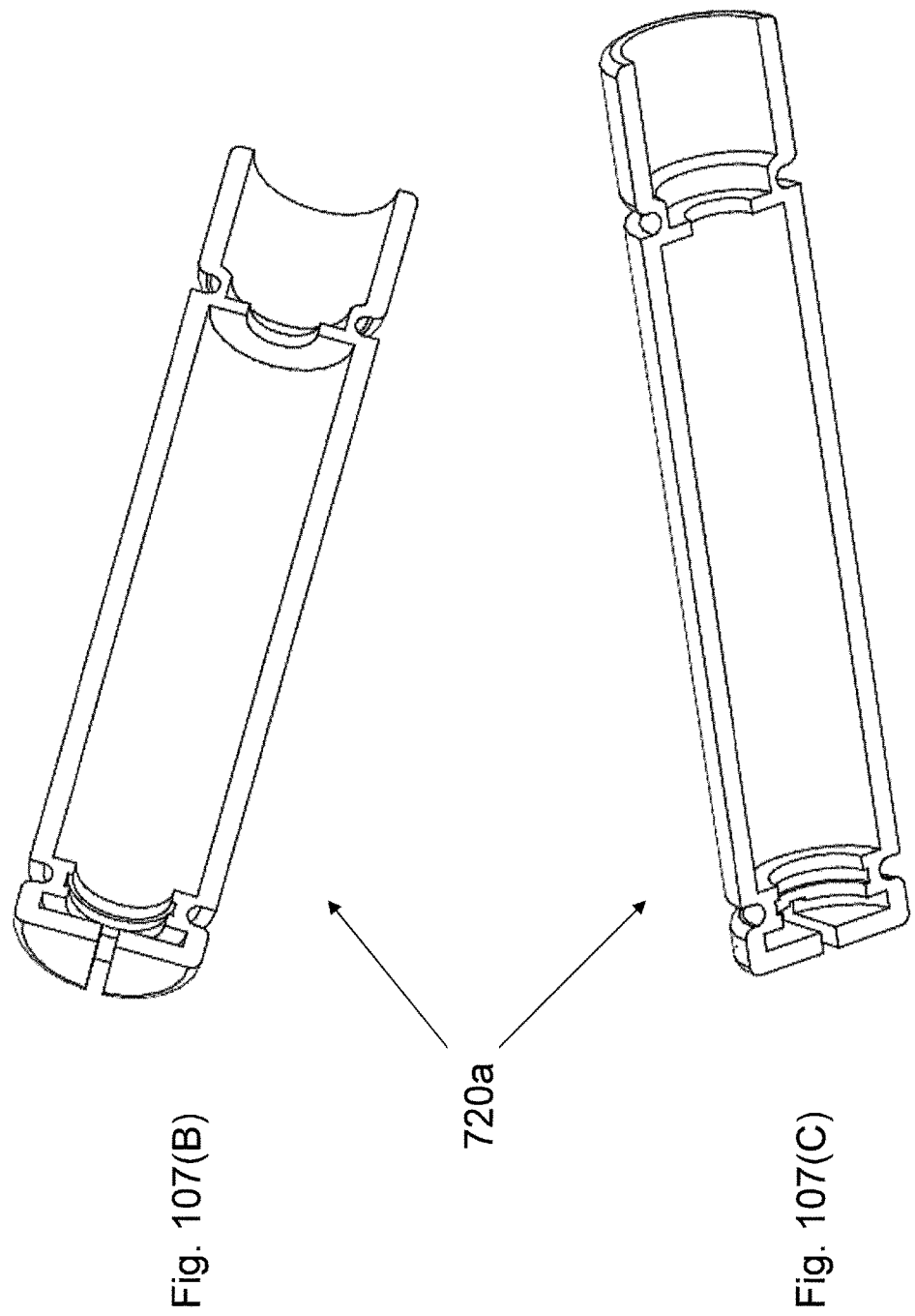

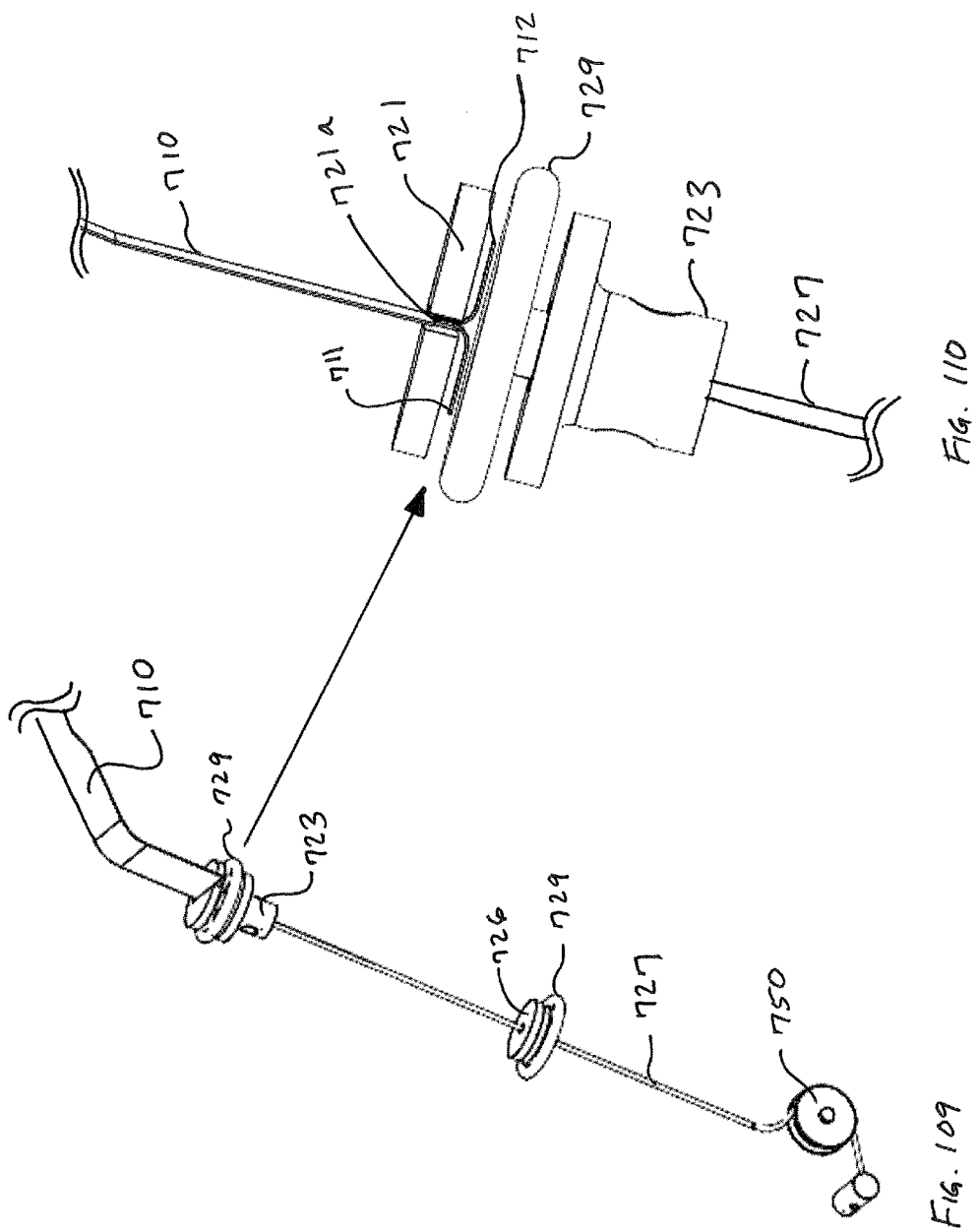

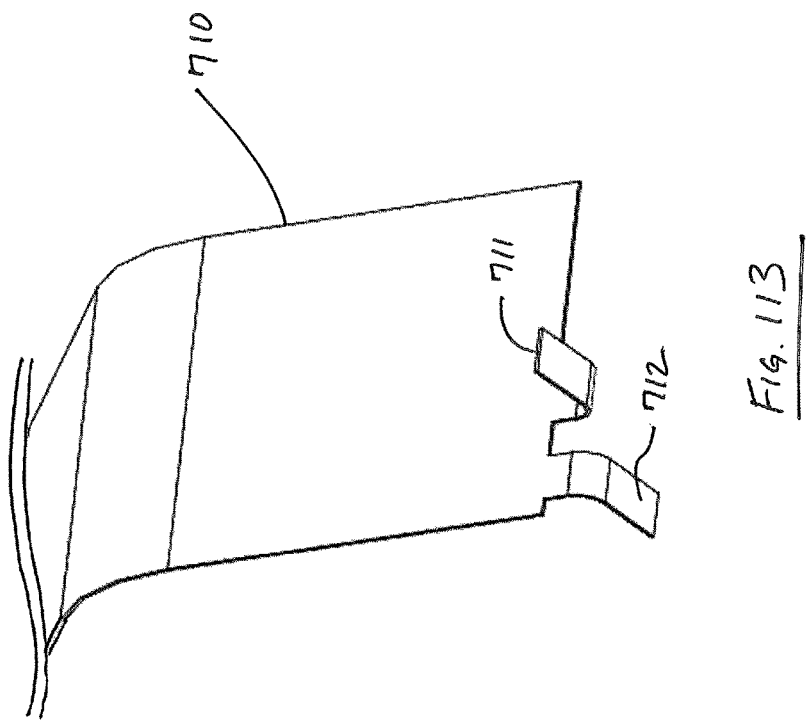
Fig. 113
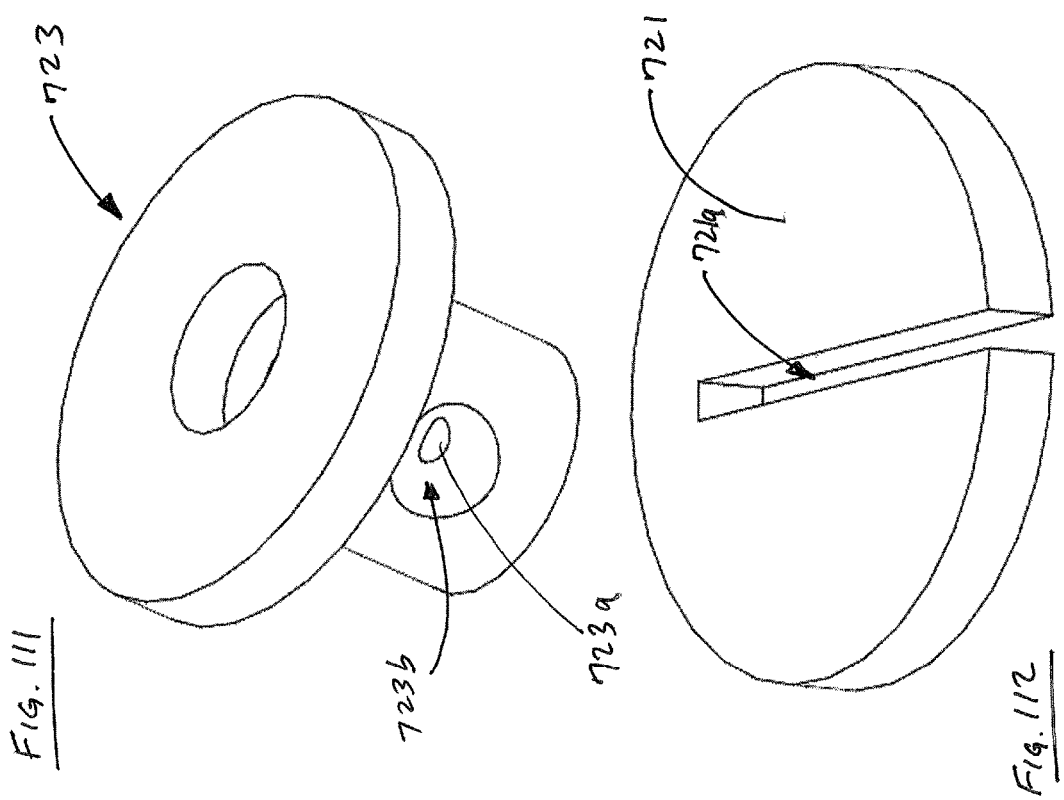
Fig. 111
Fig. 112

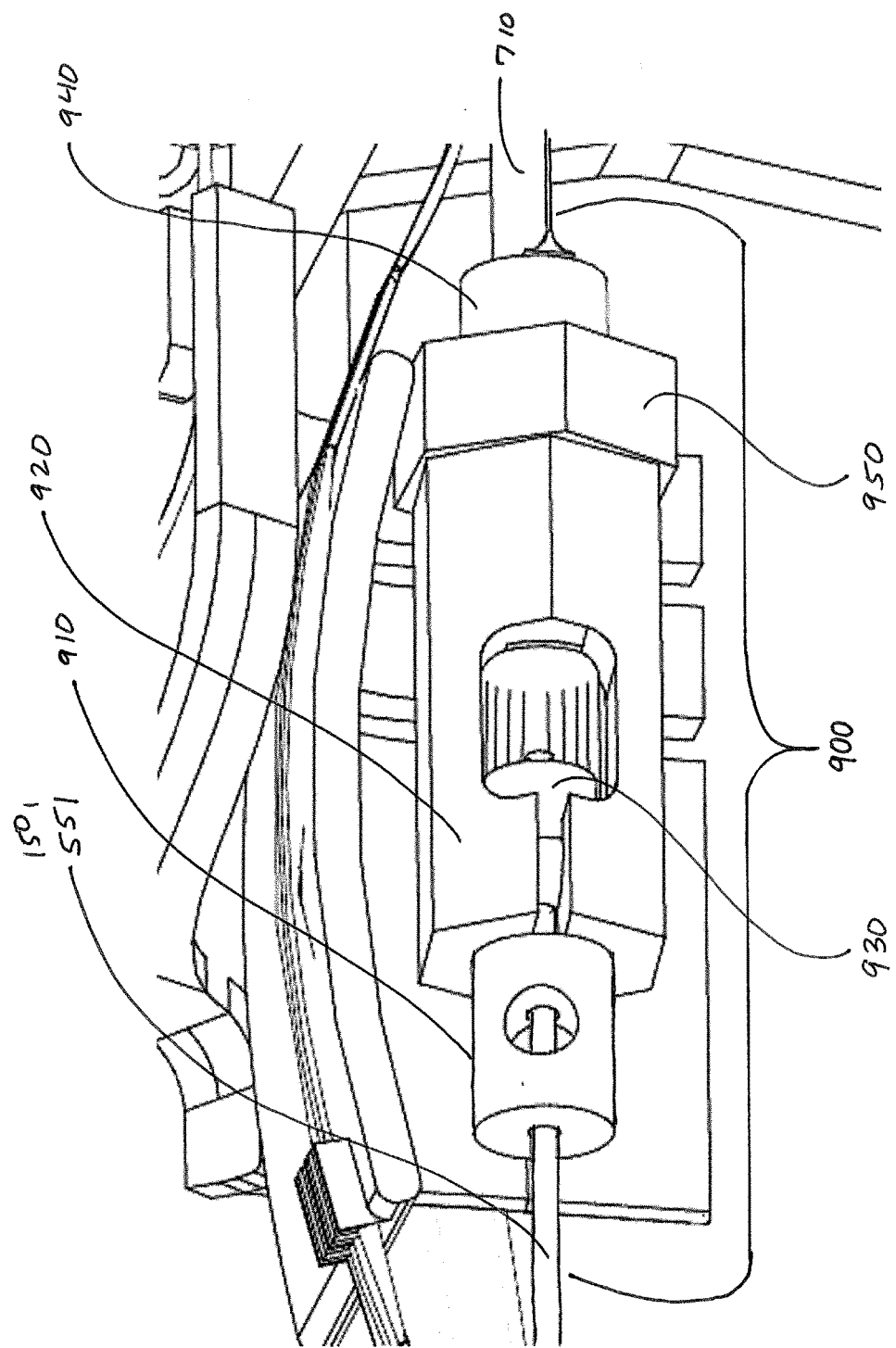

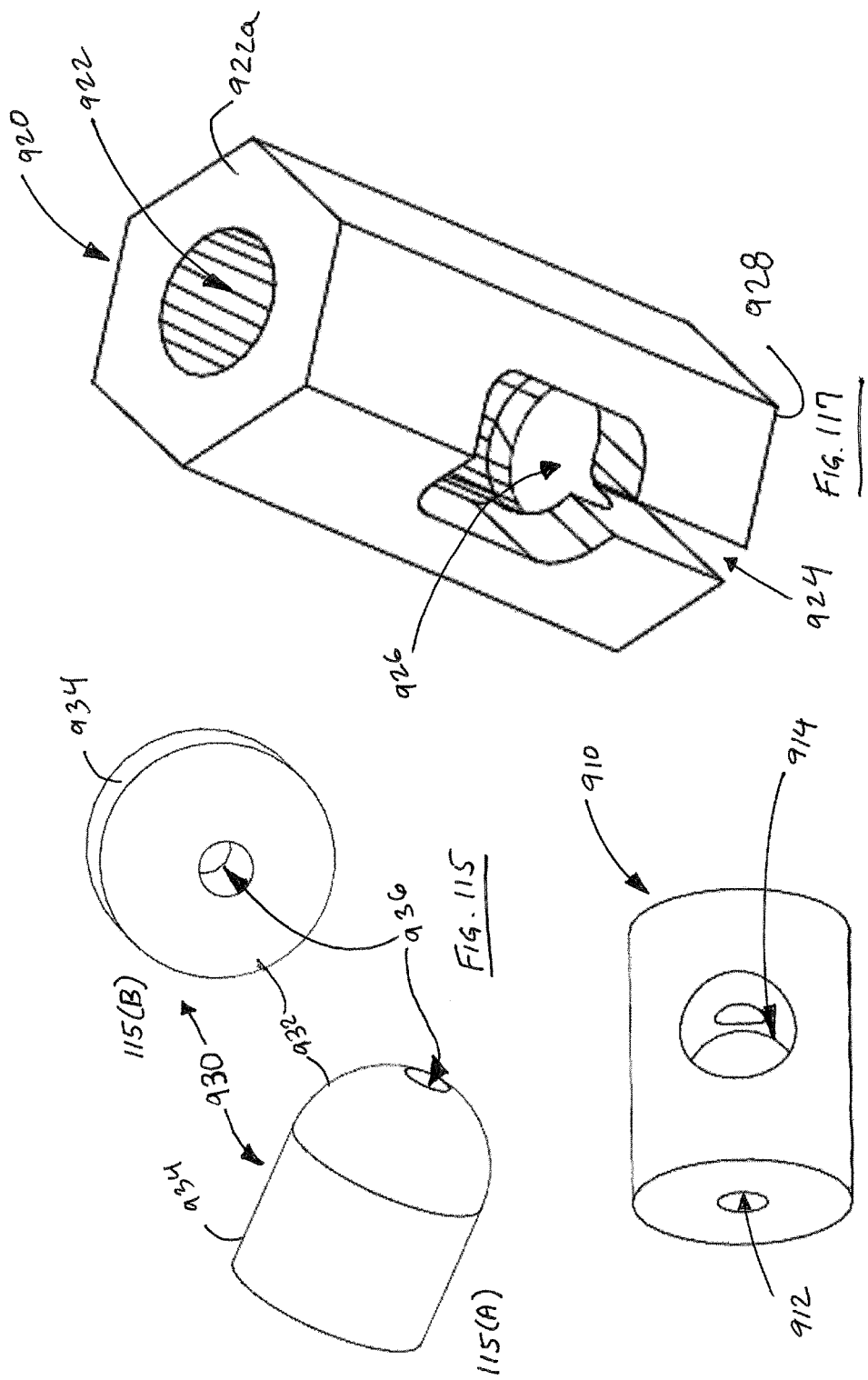

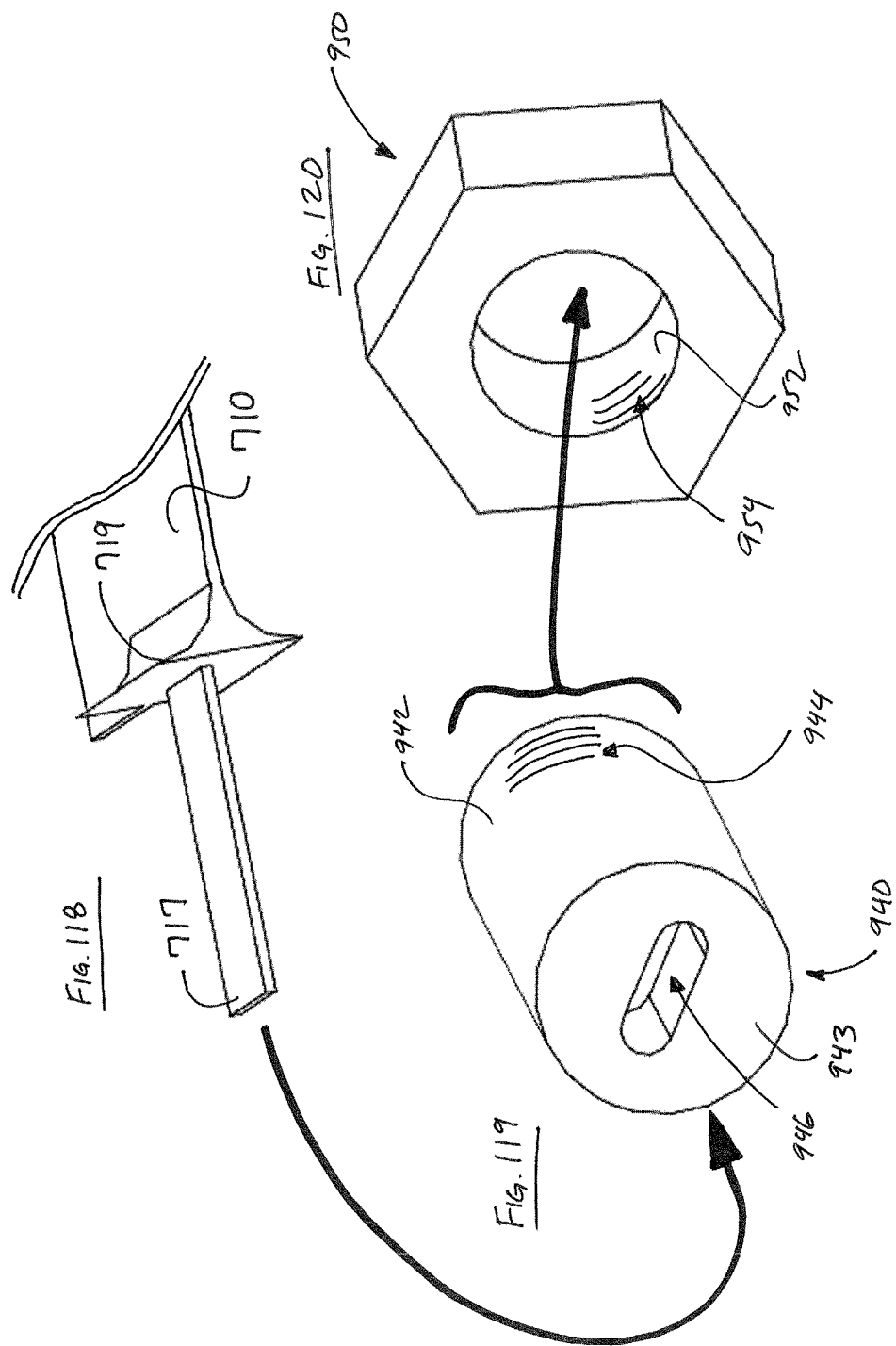

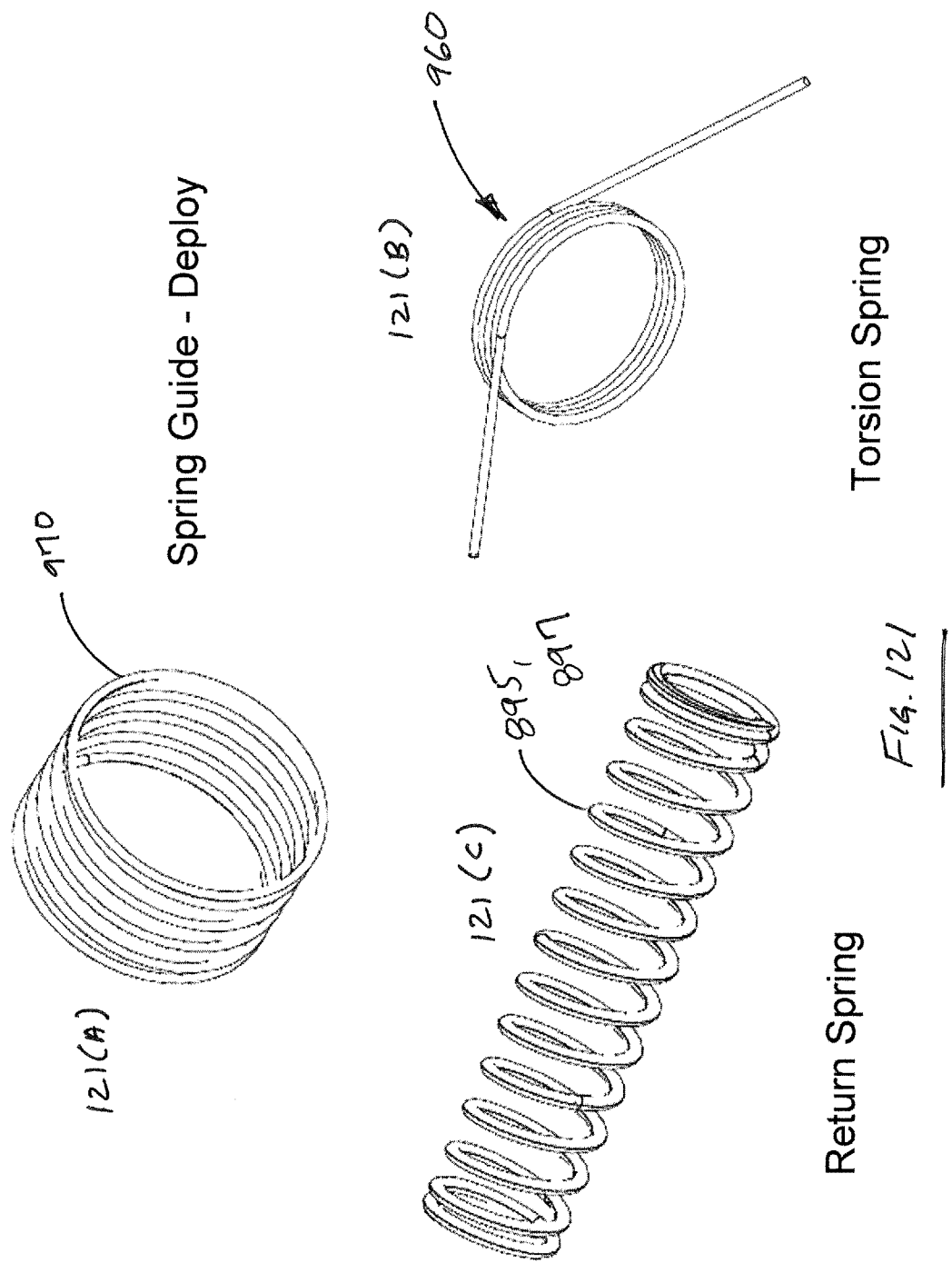

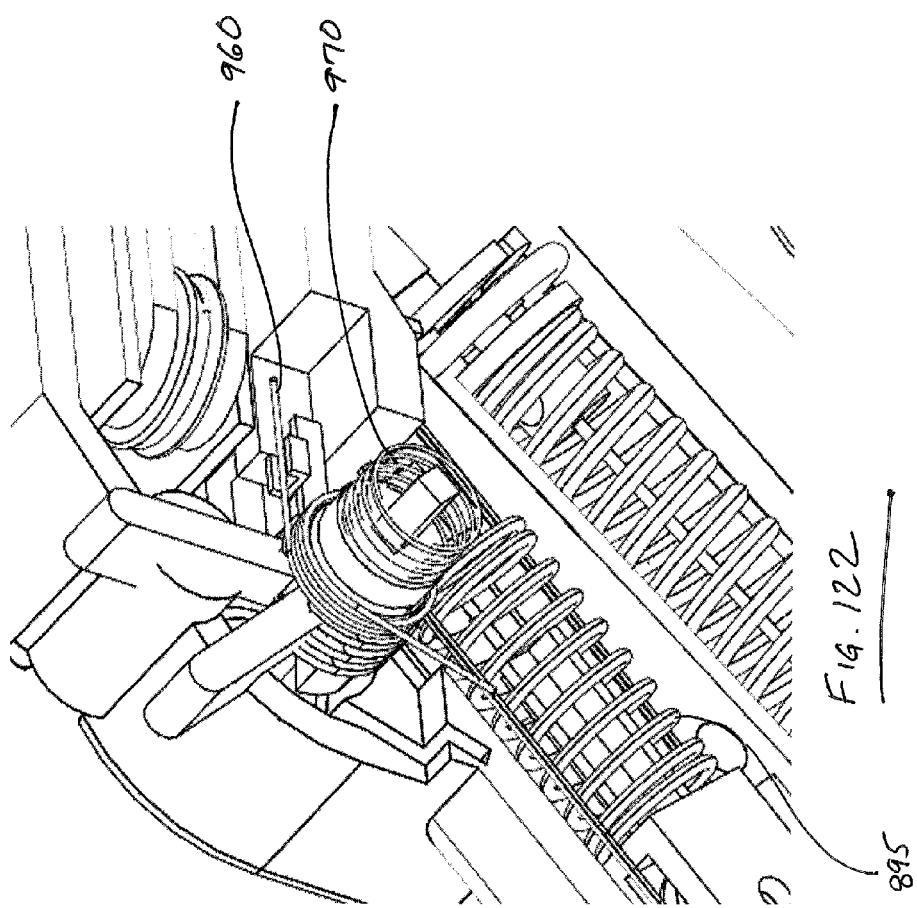

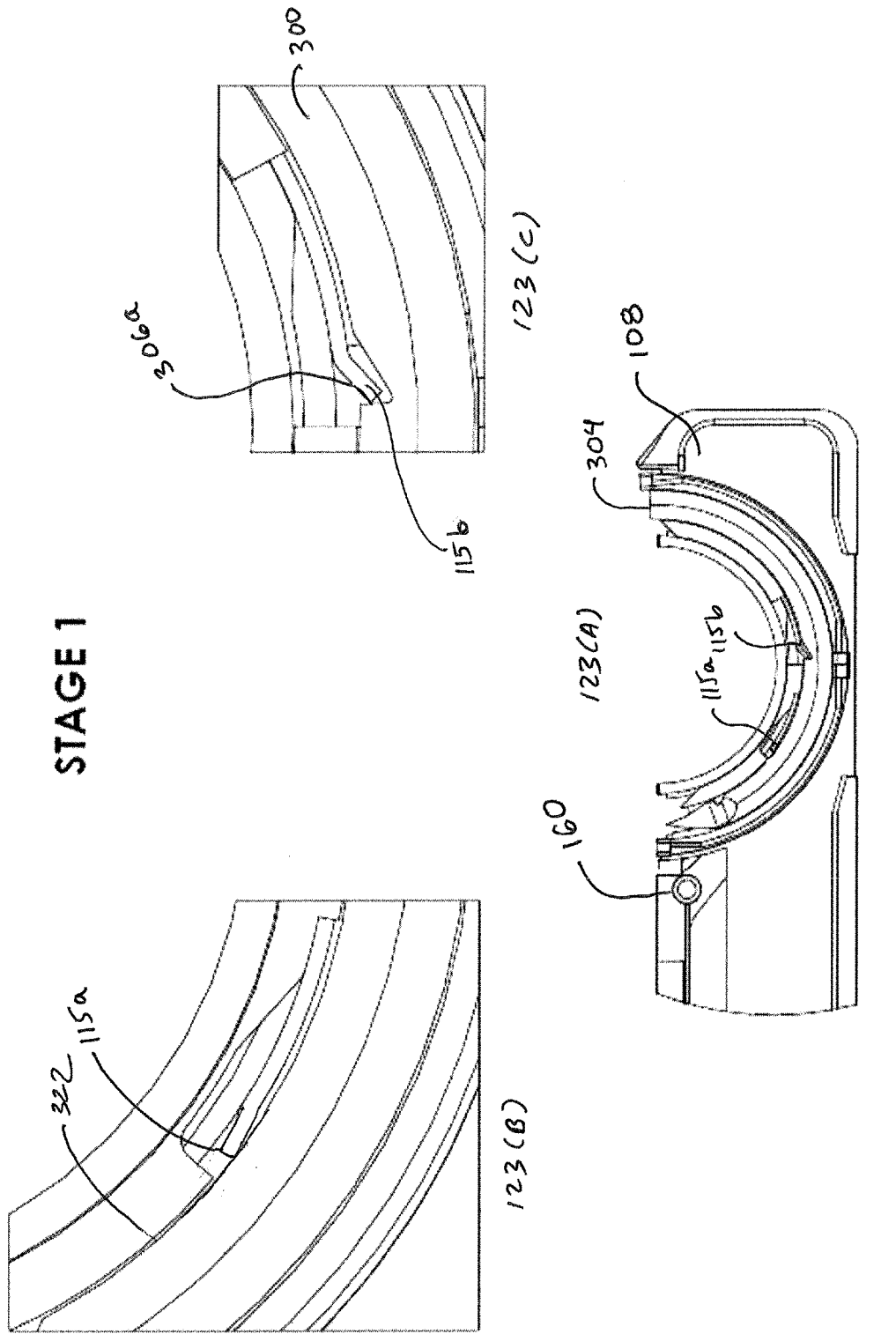

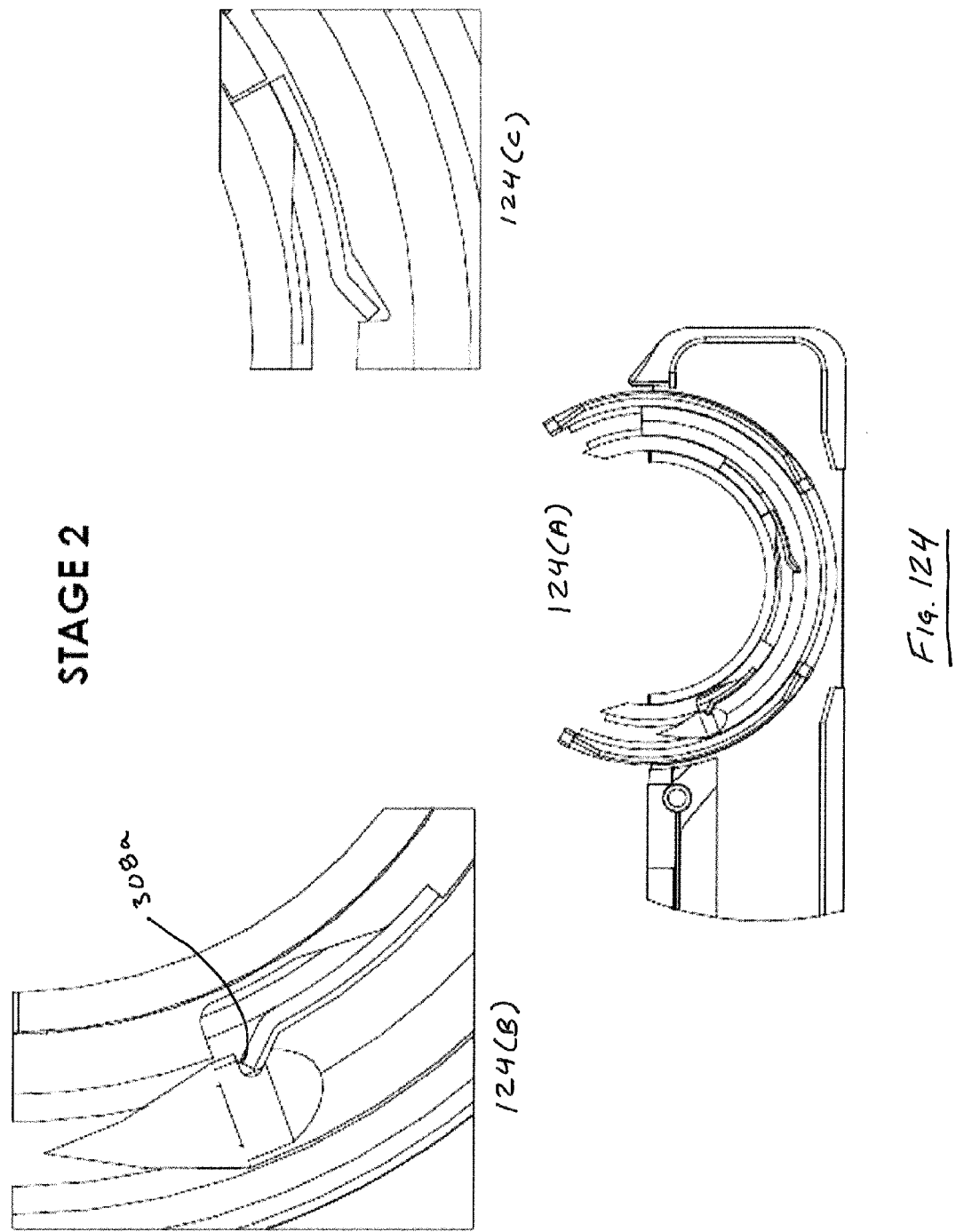

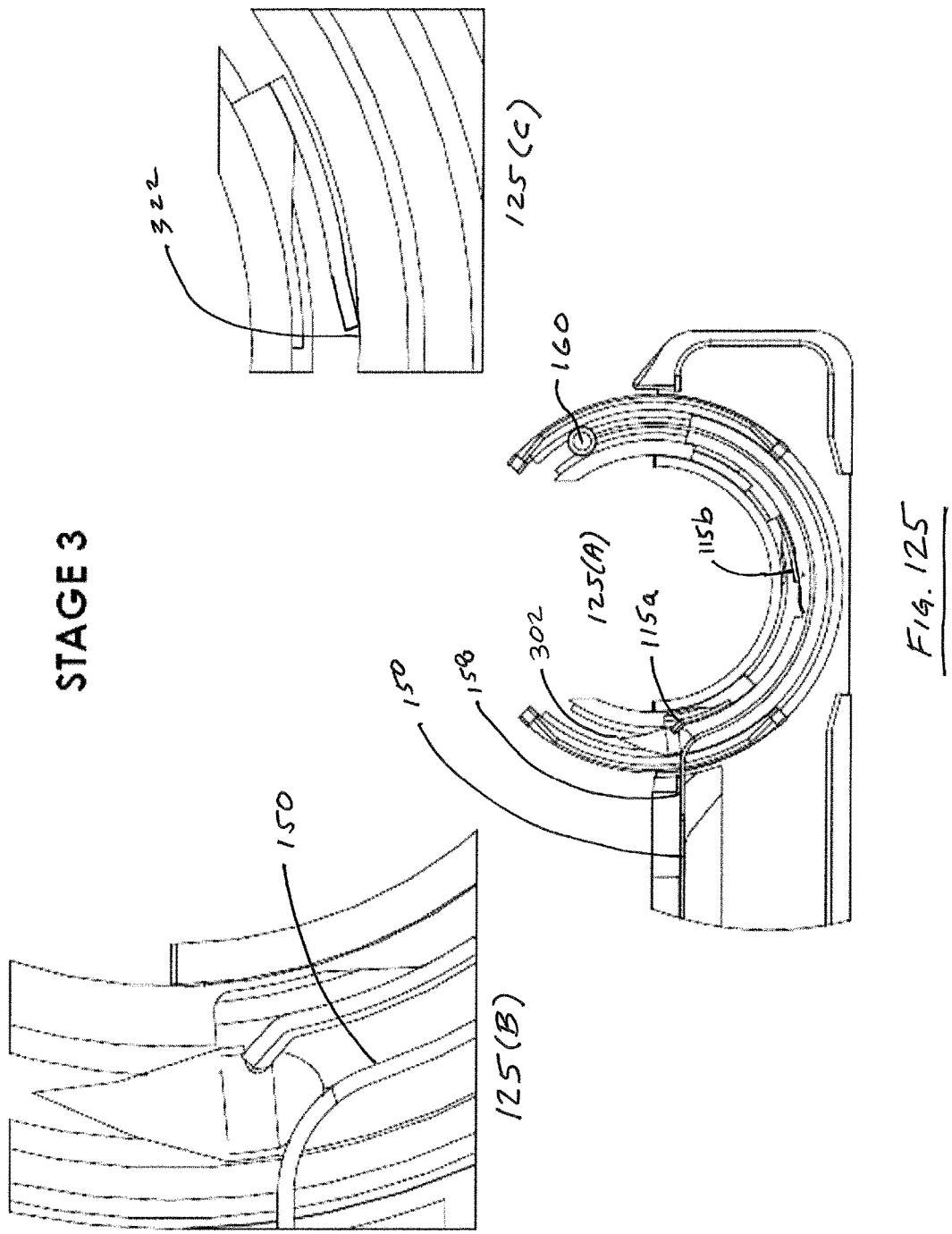

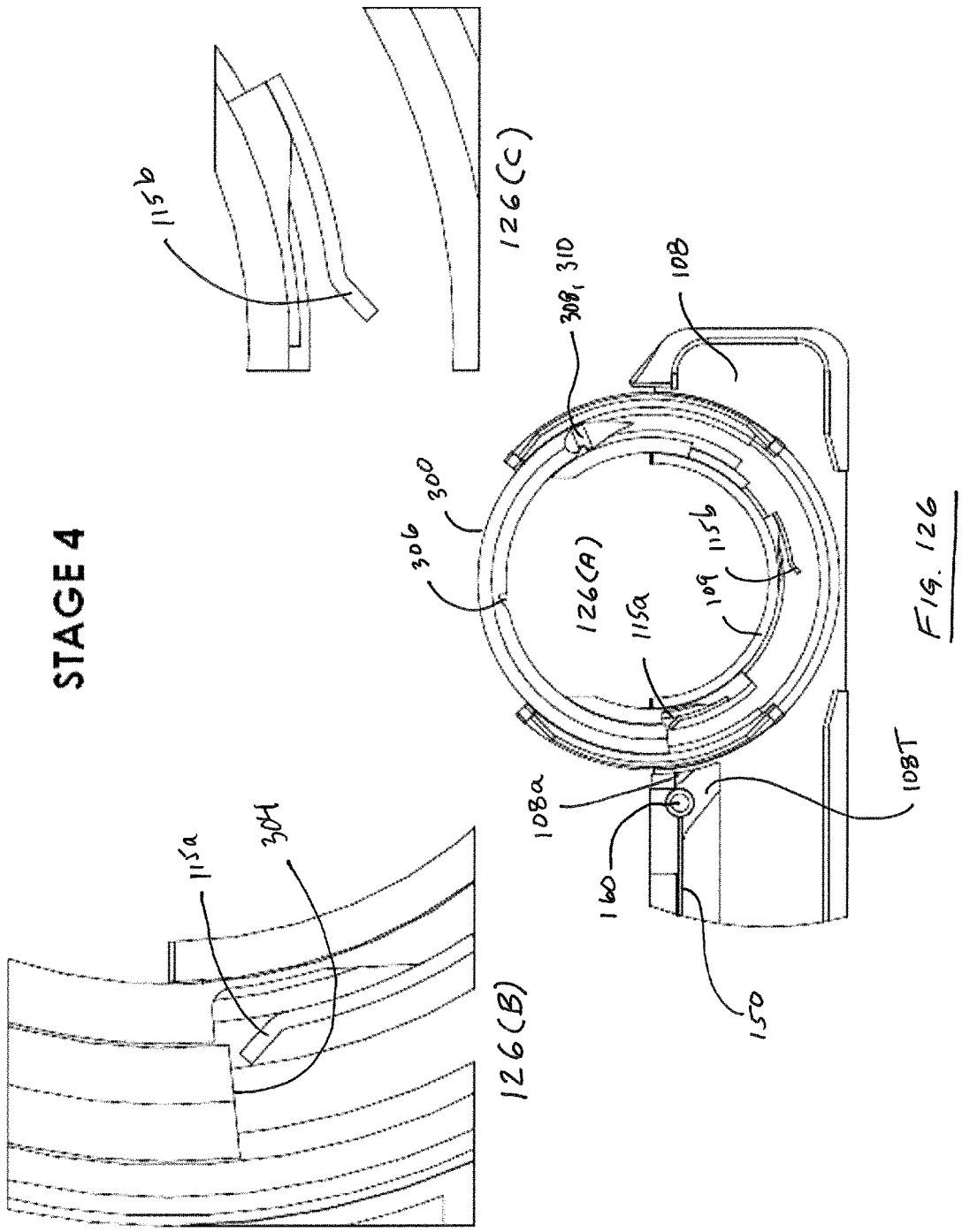

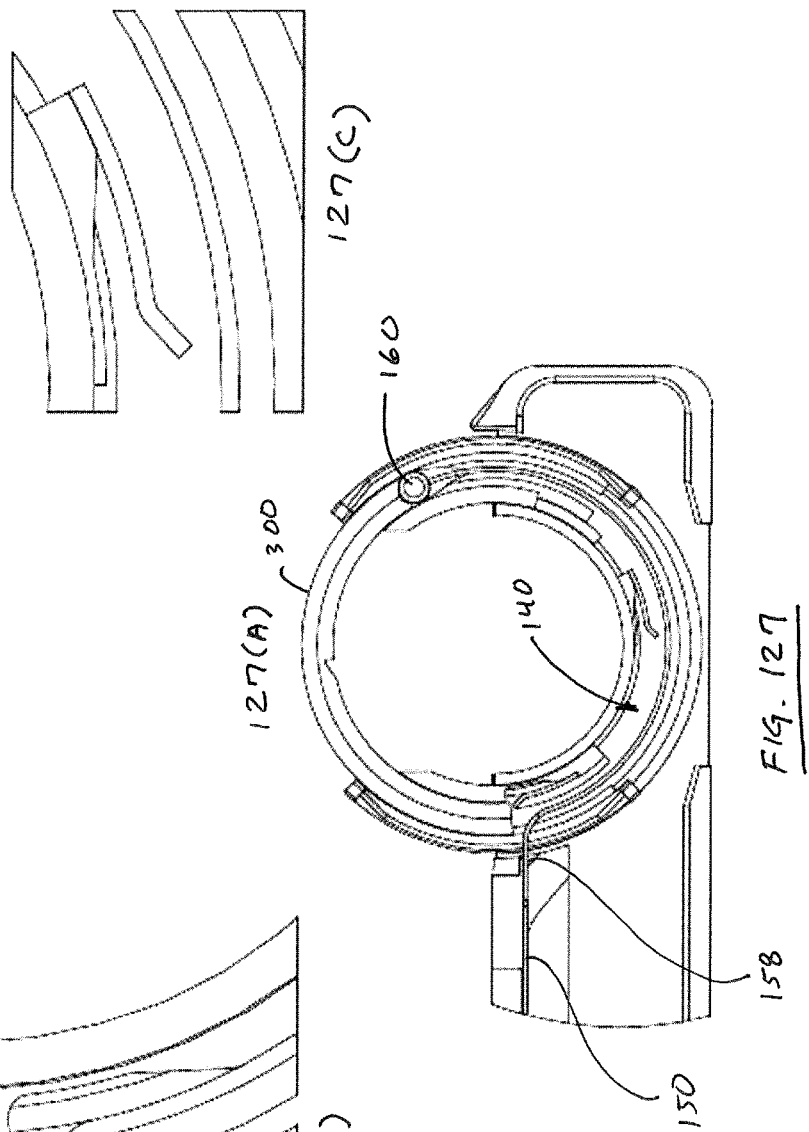
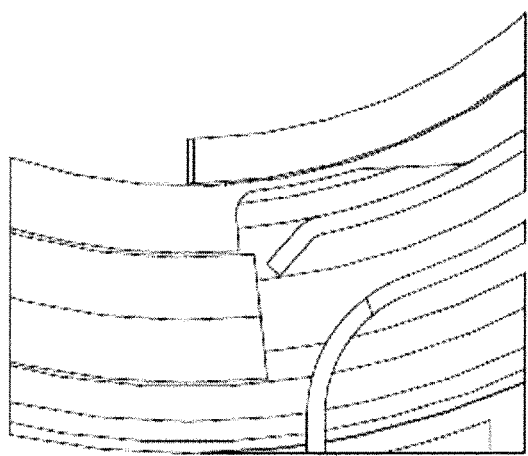

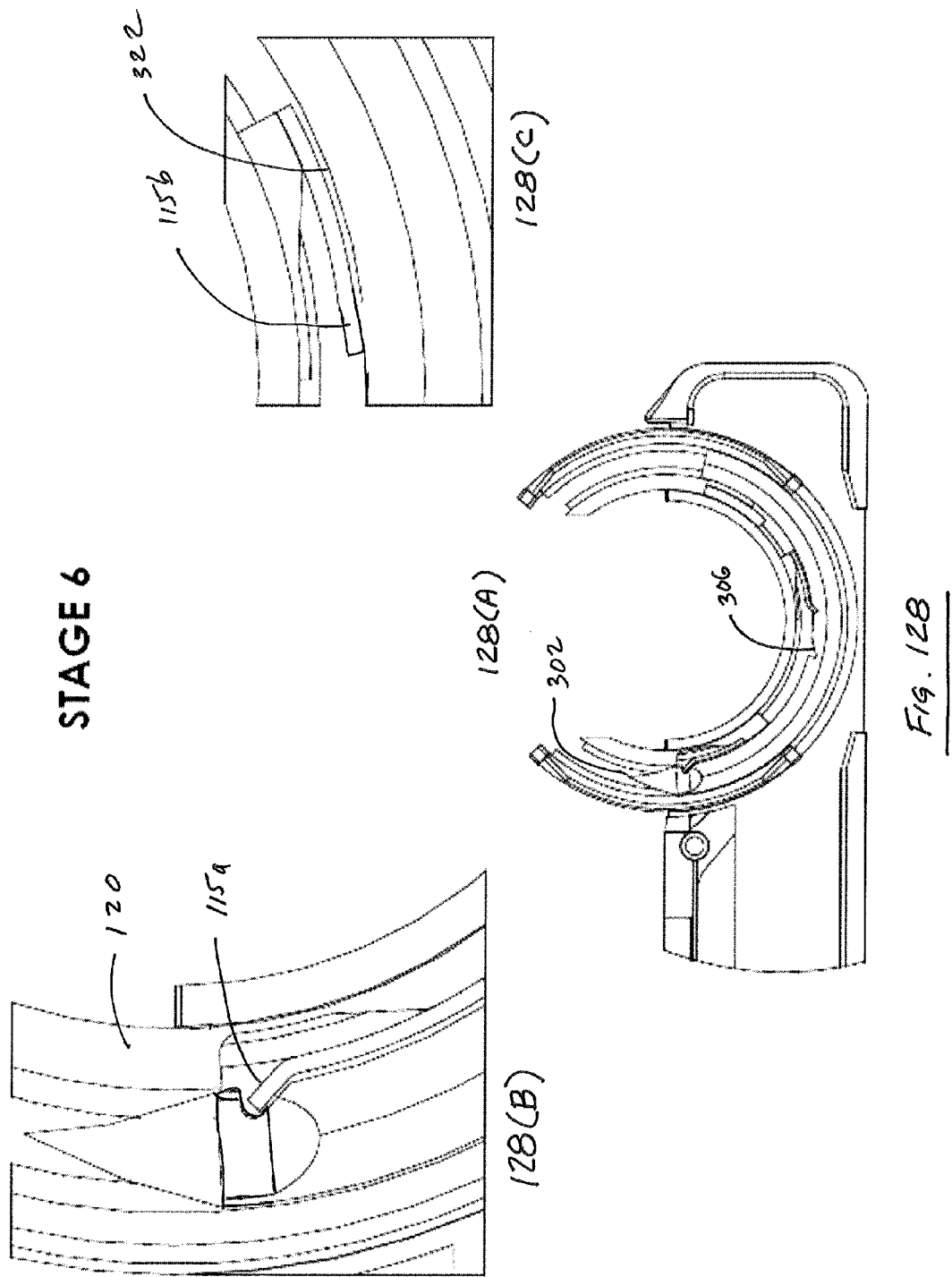

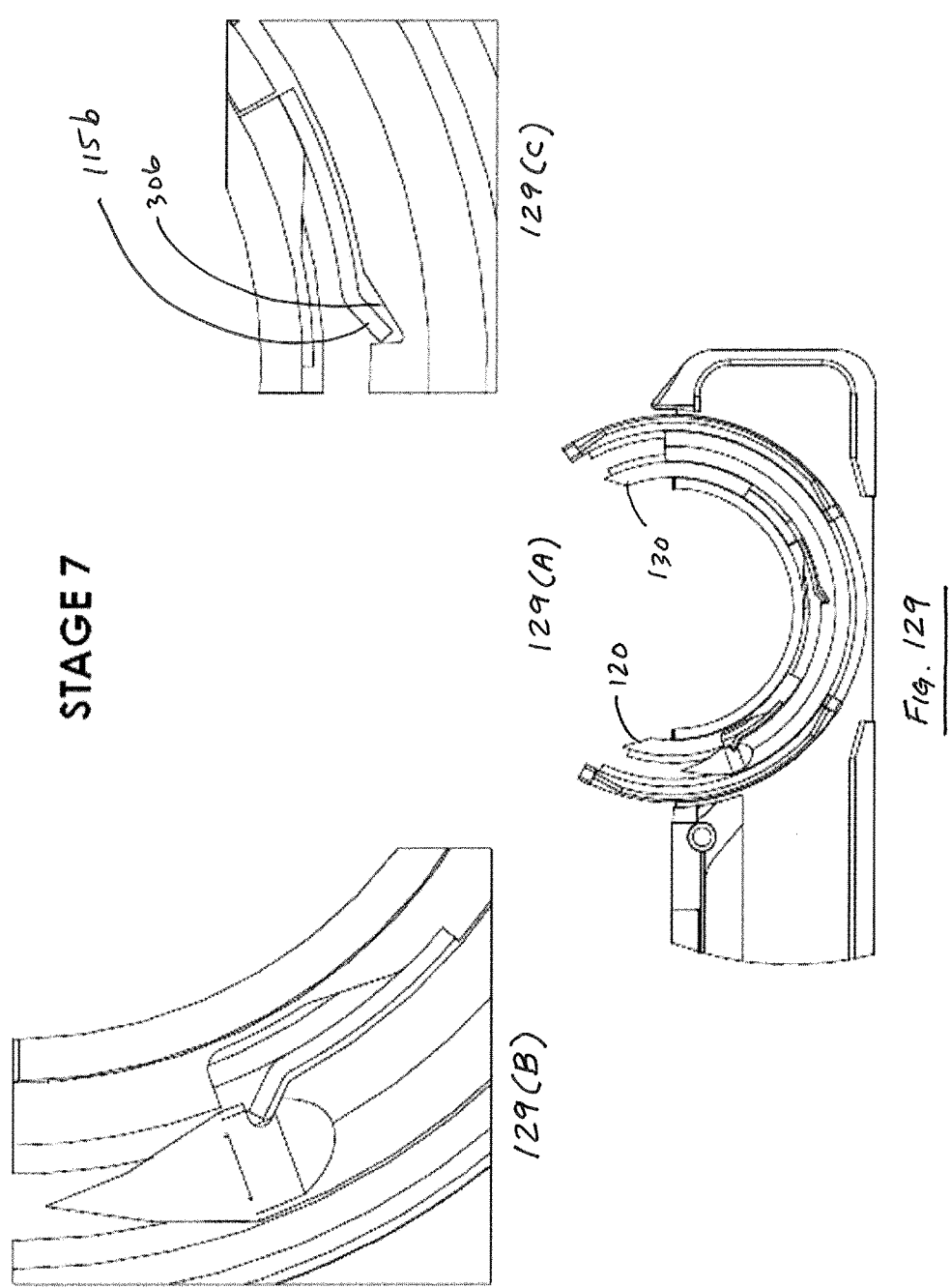

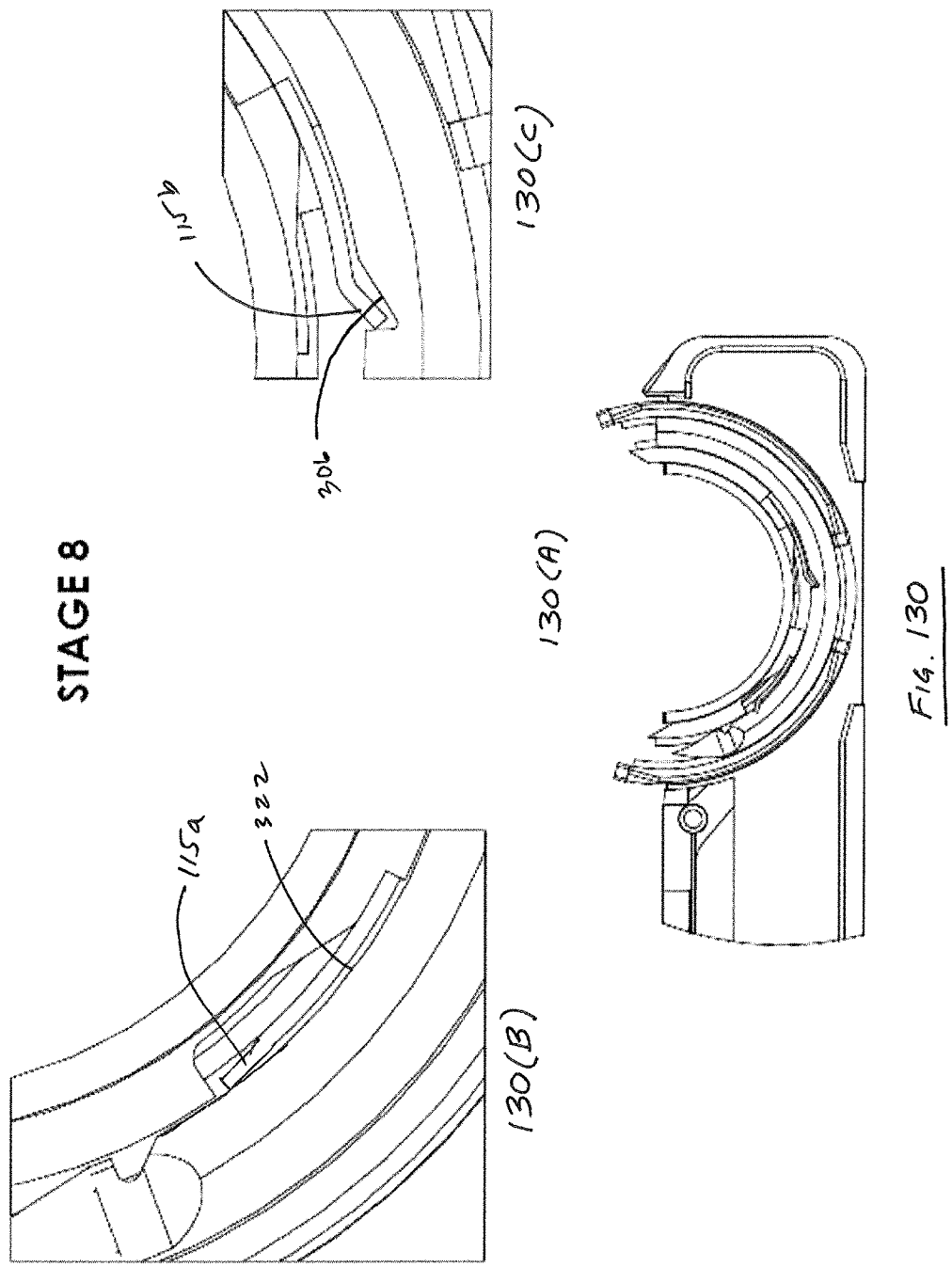

STAGE 9
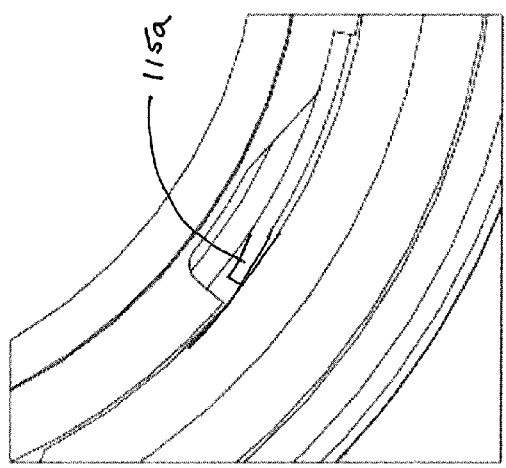
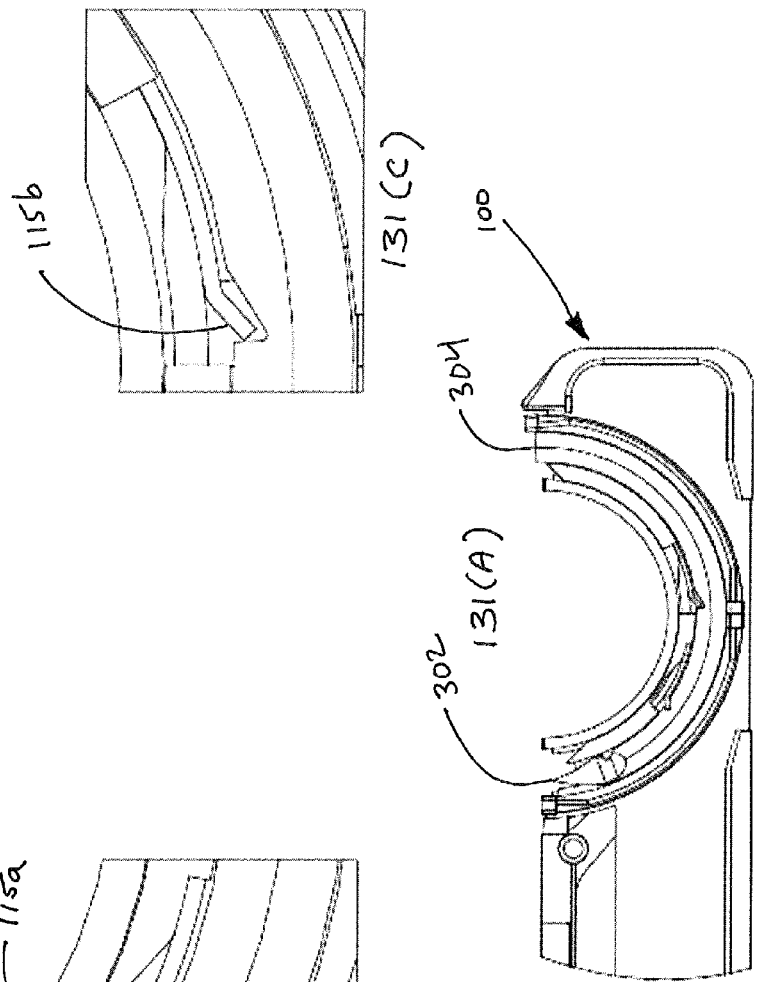
Fig. 131

DEVICES AND METHODS FOR MINIMALLY INVASIVE SUTURING

CROSS-REFERENCE TO RELATED APPLICATIONS

This patent application is a continuation of and claims the benefit of priority to U.S. patent application Ser. No. 13/204,820, filed Aug. 8, 2011, which in turn is a continuation-in-part of and claims the benefit of priority to U.S. patent application Ser. No. 12/909,606, filed Oct. 21, 2010 and issued as U.S. Pat. No. 7,993,354 on Aug. 9, 2011, which in turn claims the benefit of priority to U.S. Provisional Patent Application Ser. No. 61/388,648, filed Oct. 1, 2010. This application is also related to International Application No. PCT/US2009/006212 filed Nov. 20, 2009, which in turn claims priority to U.S. Provisional Application Ser. No. 61/200,180, filed Nov. 25, 2008. This application is also related to U.S. patent application Ser. No. 11/231,135, filed Sep. 20, 2005, which in turn claims the benefit of priority to U.S. Provisional Application Ser. No. 60/611,362, filed Sep. 20, 2004. This patent application is also related to International Application No. PCT/US2008/06674 filed May 23, 2008, which in turn claims priority to U.S. Provisional Application Ser. No. 60/939,887, filed May 24, 2007. This patent application is also related to U.S. patent application Ser. No. 12/175,442, filed Jul. 17, 2008. Each of the aforementioned applications is incorporated by reference herein in its entirety for any purpose whatsoever.

FIELD

The embodiments disclosed herein relate to medical devices for suturing tissue using curved suturing needles during minimally invasive suturing, methods for making such a device and methods for using such a device for suturing tissue.

BACKGROUND

Minimally invasive surgery (MIS) has allowed physicians to carry out many surgical procedures with less pain and disability than conventional, open surgery. Unlike conventional open surgery, where the surgical site is readily accessible through a large incision, enabling the surgeon to easily visualize and manipulate both tissue and instruments, MIS requires the surgeon to operate remotely by inserting and manipulating instruments through small punctures ("keyhole surgery") or through natural orifices, including for example the vagina, the esophagus, or the anus.

In MIS, a small puncture is typically made in the body. Medical instruments are then inserted through a cannula. A cannula has a small inside diameter, typically 5-10 millimeters (mm), and sometimes up to 20 millimeters (mm) or more. A number of such cannulas may be inserted into the body for any given operation. Minimally invasive surgical instruments are necessarily smaller, and are also generally longer and therefore are more difficult to manipulate with precision.

Perhaps the most problematic surgical task in MIS is suturing. Suturing requires coordinated manipulation with both hands of small needles and sutures that are difficult to visualize (particularly when only indirect, two-dimensional video imaging is available) as well as the several instruments (including needle-drivers and pick-up forceps) ordinarily used to suture by hand. In an environment characterized by limited space, limited visualization, and limited mobility, many surgeons find minimally invasive suturing by hand an extremely difficult, often virtually impossible, surgical task.

In the preferred method of suturing by hand, a grasping forceps ("needle driver") is held by the surgeon and is used to grip a curved needle near the needle's tail. Pronation of the surgeon's wrist drives the needle into the tissue. When the point of the curved needle emerges from the tissue, the surgeon releases the needle from the grip of the needle driver and grasps the point with another forceps ("pick-ups"). The surgeon then pulls the curved needle by the needle point, preferably in a circular path following the arc of the needle's curvature to follow the most atraumatic path through the tissue, until the entire length of the needle has exited the tissue. Each time a stitch is placed, the curved needle is thus driven around in a complete circular arc. Individual (interrupted) stitches are placed by tying off the suture following placement of each stitch. Running (continuous) stitches are placed by repeatedly driving the curved needle in a complete circular arc repeatedly until the desired length of suture and number of stitches has been placed. In order to place additional interrupted or continuous stitches, the surgeon must let go of the point of the needle and re-grasp the needle near the needle's tail.

In the manual suturing technique described above, the direct handling of the needle can result in accidental needle pricks through a surgeon or nurse's gloves, posing a potential risk of infection for the surgeon, nurse, staff, and patient, or cause the needle to become contaminated with pathogenic bacteria that can cause onset of infection at the site of the sutures. There is also a risk of the needle penetrating internal organs or vessels and causing a serious, and often fatal infection.

Various devices for suturing for MIS are described in U.S. Pat. No. 5,643,295 entitled "Methods and Apparatus for Suturing Tissue"; U.S. Pat. No. 5,665,096 entitled "Needle Driving Apparatus and Methods of Suturing Tissue"; U.S. Pat. No. 5,665,109 entitled "Methods and Apparatus for Suturing Tissue"; U.S. Pat. No. 5,759,188 entitled "Suturing Instrument with Rotatably Mounted Needle Driver and Catcher"; U.S. Pat. No. 5,860,992 entitled "Endoscopic Suturing Devices and Methods"; U.S. Pat. No. 5,954,733 entitled "Suturing Instrument with Rotatably Mounted Needle Driver and Catcher"; U.S. Pat. No. 6,719,763 entitled "Endoscopic Suturing Device"; and U.S. Pat. No. 6,755,843 entitled "Endoscopic Suturing Device", all of which are incorporated by reference in their entireties for the teachings therein.

Assignees' U.S. Pat. No. 5,437,681, U.S. Pat. No. 5,540,705 and U.S. Pat. No. 6,923,819 disclose a suturing device with thread management comprising a protective cartridge, suturing needle and needle rotation drive, the disclosures of which are hereby incorporated by reference. The devices described in the above-mentioned patents and patent application comprise a mechanism for driving a protected needle however, the needle is rotated about an axis that is parallel to the axis of the device. In addition, the orientation and size of the suturing device makes it difficult to visualize and cumbersome to use for MIS.

Therefore, there remains a need in the art for a minimally invasive suturing device that is easily manipulated within the small diameter of the cannula; functions in an environment characterized by limited space, limited visualization, and limited mobility; mimics the preferred method of suturing used by surgeons; permits the surgeon to secure and tie knots quickly and with controlled tension; places continuous stitches; and protects users from accidental needle sticks during needle handling, as well as internal organs and vessels from inadvertent needle-pricks.

SUMMARY

Devices and methods for minimally invasive suturing of tissue internal to a body are disclosed herein.

According to aspects illustrated herein, there is provided a medical device for closing openings internal to a patient's body, which closely emulates or replicates the manual suturing actions carried out by a surgeon. The device offers several advantages over conventional methods used by surgeons for suturing tissue during minimally invasive surgery in that the device provides a hand-held suturing instrument that requires no external motive source. The presently disclosed embodiments provide relative ease of operation for the surgeon with only one hand.

According to aspects illustrated herein, a suture head assembly may be removably attached to an actuator mechanism of the suturing device. The diameter of the device is small enough to fit into a 5 mm cannula in some embodiments, thus making the device extremely easy to maneuver, as well as suture, during endoscopic or other MIS procedures. In surgical procedures, it is desirable to make as few incisions as possible, and for those incisions to be as small as possible. As such, devices with reduced profile are highly advantageous. Also, the suture head assembly of the device can be laterally articulated to the left of center, to the right of center, up, and down, once inside the cannula, which is ideal for use in the course of endoscopic surgery, including laparoscopy, thoracoscopy and arthroscopy, as well as other less-invasive surgical procedures.

Devices of the present disclosed embodiments closely emulate or replicate the manual suturing actions carried out by a surgeon. For example, during manual suturing by hand, the needle is held in forceps and travels in a circular arc with no obstructions anywhere in the interior of the arc. The design of the suturing devices of the present disclosed embodiments allows for a lack of obstruction in the center of the arc of the needle during suturing. In other words, there is no hub at the center of the circular arc of the suturing needle. The entire area within the circular arc of the needle is unobstructed. This allows for the user to have better visualization during operation, unlike the present mechanical suturing methods, while maintaining control over needle movement.

A benefit provided by suturing devices of the presently disclosed embodiments is that the devices enable maneuvering a suturing material through a tissue incision in a manner substantially similar to the way a surgeon would do so by hand. In particular, some embodiments of the suturing device first push a suturing needle from the tail of the needle and drives the point of the needle through the tissue. The device then picks up the point of the needle that passed through the tissue, and pulls the remainder of the suturing needle and the suture attached to the suturing needle through the tissue. The suturing needle thus consistently follows the arc of the needle's own curve, which is the preferred method of suturing, in the most atraumatic way of passing a needle through tissue. A benefit provided by the suturing device of the presently disclosed embodiments is the ability of the suturing needle to pull the suturing thread entirely through the tissue segments being closed, following each stitch. When using the suturing device of the presently disclosed embodiments, no ancillary instruments or tools such as needle holders, pick-up forceps or the like are needed to complete the stitch. A forceps or grasping instrument can be used to tighten the knots.

According to aspects illustrated herein, there is provided an embodiment of a suturing device that includes a suturing needle that is protected by a housing, the suturing needle is not exposed to or handled directly by the user, thereby preventing inadvertent needle sticks. The configuration of the suturing device of the presently disclosed embodiments also protects against inadvertent penetration of internal organs or vessels by the needle, since the housing acts as a shield between the organs and the needle.

In one embodiment, a suturing device is provided having a suturing head. The suturing head includes a housing defining at least one passage therein and a deployable needle track. The deployable needle track is disposed in the housing, and the needle track is adapted and configured to be deployed, or expanded from a stored or contracted condition wherein the needle track is essentially disposed within the housing to an expanded, or deployed condition wherein the needle track extends outwardly from the housing to form an arcuate needle track. The device further includes an arcuate or circular needle disposed in the deployable needle track, the needle having a first end, a second end, and a generally toroidal body. The device further includes a drive for advancing the needle about a 360° path about the needle track when the deployable needle track is in a deployed condition. The drive is adapted and configured to advance the needle in multiple 360° revolutions about the needle track when the deployable or expandable needle track is in a deployed or expanded condition without removing the needle from the needle track. The drive selectively engages with and disengages from the needle to advance the needle about a 360° rotation.

In accordance with further aspects, the housing of the suturing device can be generally cylindrical, and have an outer diameter of about 5.0 mm. The circular path of the needle track can have a diameter of about 10 mm. If desired, the needle can have a non-circular cross-section. Preferably, the device further includes means for deploying the needle track from the stored condition to the deployed condition. The needle track can occupy about 270° of the 360° needle path when the needle track is deployed. It will be appreciated however that the present disclosure is directed to a device having a deployable, or, angularly expandable, needle track that can expand to a final extent that is greater or less than 270°, such as in increments of one degree. For example, a needle track can be provided that expands from about 180° to about 190°, about 200°, about 210°, about 220°, about 230°, about 240°, about 250°, about 260°, about 270°, about 280°, about 290°, about 300°, about 310°, about 320°, or about 300°, among others. For example, depending on the diameter of the device and the dimensions of the needle track, it may only be necessary to have guides that increase the angular extent of the needle track by about 10°, about 20°, about 30°, about 40°, about 50°, about 60°, about 70°, about 80°, about 90°, about 100°, about 110°, about 120°, about 130°, about 140°, about 150°, or about 160° from the undeployed (unexpanded) configuration to the deployed (expanded) configuration. The drive can include an elongate flexible member that reciprocates along a longitudinal axis of the device. The drive can engage with and advance the needle along the needle track when the elongate flexible member is advanced proximally with respect to the housing. The needle can include first and second notches along an inner face of the needle for engaging an antirotate mechanism disposed on at least one of the housing and the deployable needle track. The needle can further include a notch on a top face of the needle for engaging a portion of the drive, wherein the notch on the top face of the needle intersects one of the notches disposed on the inner face of the needle.

In accordance with a preferred embodiment, the deployable needle track includes at least one arcuate guide that is adapted to be deployed from the housing along an arcuate path. Preferably, the deployable needle track includes a pair of arcuate guides that are adapted to be deployed from the housing along an arcuate path. The pair of arcuate guides are preferably deployed from the housing along the arcuate path by pulling in a first pair of pull wires, wherein one pull wire is attached to each guide. The pair of guides are further preferably adapted and configured to be retracted into the housing by pulling in a second pair of pull wires, wherein one pull wire in the second pair of pull wires is attached to each guide. The first pair of pull wires is preferably connected to the second pair of pull wires to make a pair of continuous mechanical loops, wherein the loops are connected at a distal end to the guides, and at a proximal end to a pair of handles, wherein movement of the handles results in movement of the guides.

The disclosure also provides a suturing needle having an arcuate body with a leading tip and a trailing end, wherein the arcuate body defines a first notch along an inner radial region needle and a second notch having a projection that lies within a plane that is defined by a central curved axis of the needle, and further wherein the first notch and second notch intersect. If desired, the needle can further includes a generally square cross-section. The needle body can include a portion with a round cross section that separates a main portion of the needle with a generally square cross section from a tail portion with a generally square cross section. The needle can further define a third notch in the needle proximate its trailing end for receiving a portion of a drive pawl. Moreover, the needle can define an arcuate keel along its length to stabilize its movement in the suturing device.

According to aspects illustrated herein, there is provided a method for suturing tissue during minimally invasive surgery that includes inserting a distal end of a suturing device having a suturing needle with a pointed end into a body; positioning the suturing needle to span a plurality of separated tissue segments; activating an actuator a first time causing the pointed end of the suturing needle to extend beyond a protective housing of a cartridge to engage the plurality of separated tissue segments; and activating the actuator a second time to cause the suturing needle to complete a revolution and pull a suture extending from the suturing needle through the plurality of separated tissue segments to form a stitch.

In accordance with a further aspect, a suturing device having a suturing head is provided. The suturing head includes a housing defining at least one passage therein, the housing having a proximal end, a distal end and a peripheral side joining the proximal and distal ends. The head further includes a deployable needle track disposed at least partially within the housing, the needle track being adapted and configured to be deployed from a stored condition wherein the needle track is essentially disposed within the housing and has an angular extent of about 180° to a deployed condition wherein the needle track has an angular extent in excess of 180° and extends outwardly from the peripheral side of the housing to form an arcuate needle track that lies in a plane that is parallel to a longitudinal axis of the housing. Preferably, the needle track is angularly expandable along a circular path that defines the path of travel of the needle such that the track expands angularly about the circular path from a contracted condition to an expanded condition. The suturing head further includes an arcuate needle disposed in the deployable needle track, the needle having a first end, a second end, and a generally toroidal body. The suturing head further includes a drive for advancing the needle in multiple 360° revolutions about the needle track when the deployable needle track is in a deployed condition, wherein the drive selectively engages with and disengages from the needle to advance the needle about a 360° rotation.

In accordance with a further aspect, housing is generally cylindrical, and has a diameter of about 5.0 mm and the path of the needle track has a diameter of about 10 mm. However, it will be appreciated that the diameter can be larger or smaller as desired. The needle can have a substantially circular cross section, a circular cross section, a non-circular cross-section, a square or triangular cross section, or may have a cross section that varies along its length that transitions from one shape to another, such as from a square to a circle to a square. The device preferably further includes means for deploying the needle track from the stored condition to the deployed condition. The needle track preferably occupies about 270° of a 360° needle path when the needle track is deployed, but the angular extent of the track can be more or less than 270°, as desired, in one degree increments, for example.

In accordance with a further aspect, the drive preferably includes an elongate flexible member that reciprocates along a longitudinal axis of the device. The drive preferably engages with and advances the needle along the needle track when the elongate flexible member is advanced proximally with respect to the housing. The deployable needle track preferably includes at least one arcuate guide that is adapted to be deployed from the housing along an arcuate path. The deployable needle track preferably includes a pair of arcuate guides that are adapted to be deployed from the housing along an arcuate path. The pair of arcuate guides are preferably deployed from the housing along the arcuate path by pulling in a first pair of pull wires, wherein one pull wire is attached to each guide. The pair of arcuate guides is preferably adapted and configured to be retracted into the housing by pulling in a second pair of pull wires, wherein one pull wire in the second pair of pull wires is attached to each guide. The first pair of pull wires is preferably connected to the second pair of pull wires to make a pair of continuous mechanical loops, wherein the loops are connected at a distal end to the guides, and at a proximal end to a pair of handles, wherein movement of the handles results in movement of the guides.

In another embodiment, a suturing device is provided having a suturing head. The suturing head includes an elongate housing having a proximal end, a distal end and a peripheral side joining the proximal and distal ends, wherein the housing defines a longitudinal axis from its proximal end to its distal end. The suturing head further includes a deployable needle track disposed at least partially within the housing, at least a portion of the needle track being adapted and configured to be deployed along an arcuate path from a undeployed condition wherein the needle track has an arcuate extent of about 180 degrees and is essentially disposed within the housing to a deployed condition wherein the needle track has an arcuate extent in excess of 180 degrees, and wherein the needle track lies in a plane that is parallel to a longitudinal axis of the housing. The suturing head further includes an arcuate needle disposed in the deployable needle track, the needle having a first end, a second end, and a generally toroidal body. The suturing head also includes a drive for advancing the needle in multiple 360° revolutions about the needle track when the deployable needle track is in a deployed condition, wherein the drive selectively engages with and disengages from the needle to advance the needle about a 360° rotation.

In accordance with a further aspect, the housing can be generally cylindrical or rectilinear, as desired. The deployable or expandable needle track can include one or more arcuate guides that are adapted to be deployed from the housing along an arcuate path. The deployable or expandable needle track can include a pair of arcuate guides that are adapted to be deployed from the housing along an arcuate path. Accordingly, a pair of arcuate guides can be deployed from the housing along the arcuate path by pulling on a first pair of pull wires, wherein one pull wire is attached to each guide. In one embodiment, the deployable or expandable needle track occupies about 270° of a 360° needle path when the needle track is in the expanded condition, but the angular extent of the track can be more or less than 270°, as desired, in one degree increments, for example.

These and other advantages of the presently disclosed embodiments are illustrated through the embodiments described hereinafter. The presently disclosed embodiments accordingly comprise the features of construction, combination of elements and arrangement of parts that will be exemplified in the following detailed description.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments, wherein:

FIGS. 1-3 generally depict a suturing device made in accordance with the present disclosure.

FIGS. 4-32 and 47(A)-47(D) illustrate aspects of a first embodiment of a suturing head of a suturing device made in accordance with the present disclosure.

FIGS. 33-37 illustrate aspects of an embodiment of a needle loader made in accordance with the present disclosure.

FIGS. 38-40 illustrate aspects of a first embodiment of a suturing needle made in accordance with the present disclosure.

FIGS. 41-44 illustrate aspects of a second embodiment of a suturing needle made in accordance with the present disclosure.

FIG. 45 illustrates aspects of a third embodiment of a suturing needle made in accordance with the present disclosure.

FIGS. 47(E)-55 illustrate aspects of a second embodiment of a suturing head of a suturing device made in accordance with the present disclosure.

FIGS. 60-122 illustrate aspects of a handle portion of the suturing device illustrated in FIGS. 1-3.

FIGS. 123-131 illustrate operation of the suturing head of FIGS. 4-32 and 47(A)-47(D).

While the drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Reference will now be made in detail to the present preferred embodiments of the disclosure, examples of which are illustrated in the accompanying drawings. The method and corresponding steps of the disclosed embodiments will be described in conjunction with the detailed description of the system.

Broadly speaking, the disclosure provides embodiments of suturing devices having features that permit the device to be constructed on a smaller scale and having a smaller profile than embodiments discussed in the prior art and in patent applications incorporated herein by reference. In particular, embodiments made in accordance with the present disclosure have been constructed that are adapted and configured to fit through a 5 mm trocar. Advantageously, the disclosed embodiments still use a comparatively large suturing needle, thereby permitting substantial tissue capture during operation, resulting in effective suturing.

Figure 1:
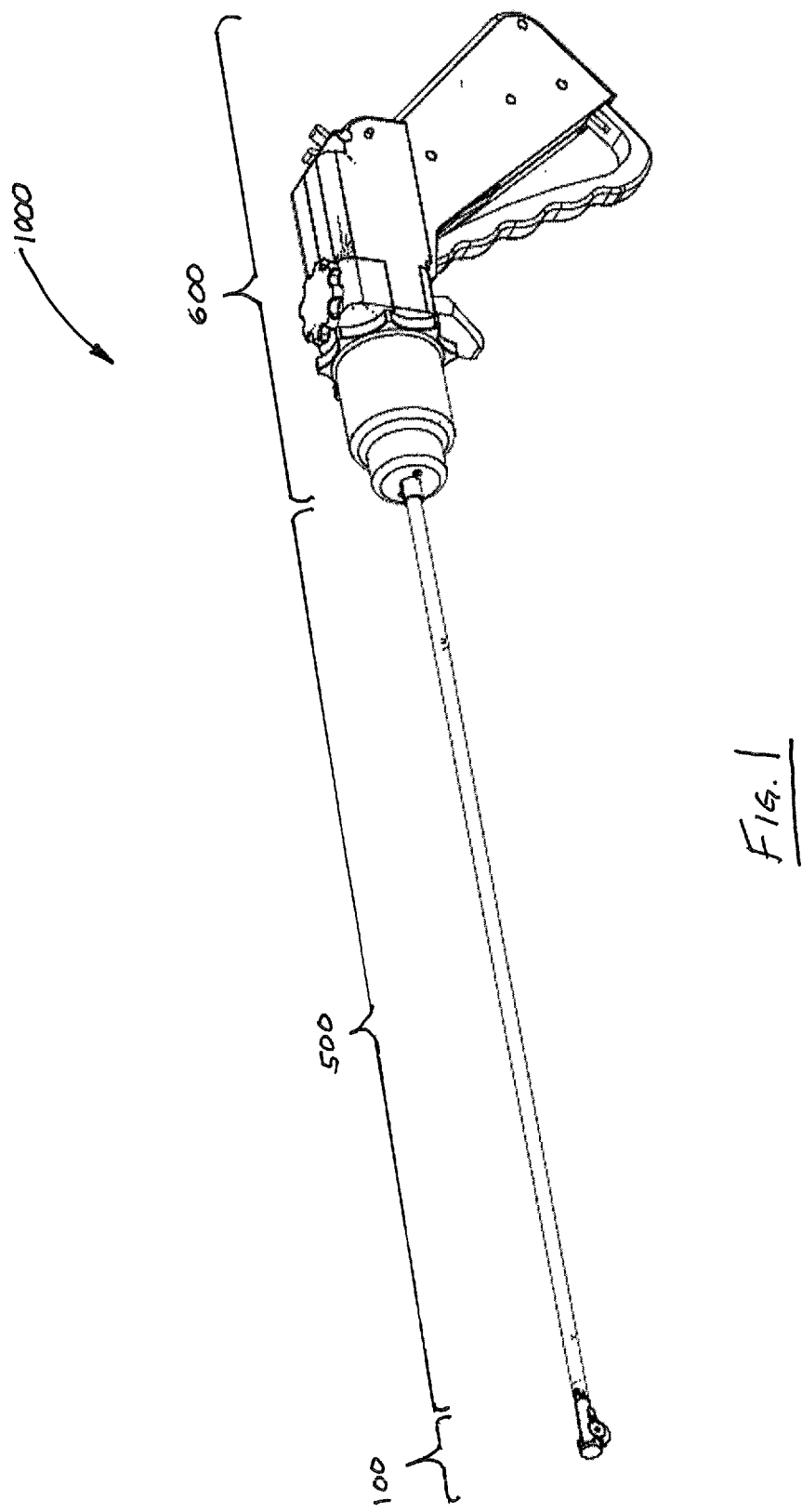

For purposes of illustration and not limitation, as embodied herein, an exemplary embodiment of a suturing device 1000 is illustrated in FIG. 1. Device 1000 includes three regions, including a suture head 100, an intermediate region 500, and a handle 600. Each of these regions is discussed in detail below. FIGS. 2-3 illustrate device 1000 with certain portions removed. In particular, FIG. 2 illustrates device 1000 with a needle loader removed (discussed in further detail below), while FIG. 3 illustrates device 1000 with certain portions of the handle housing removed.

Figure 4:
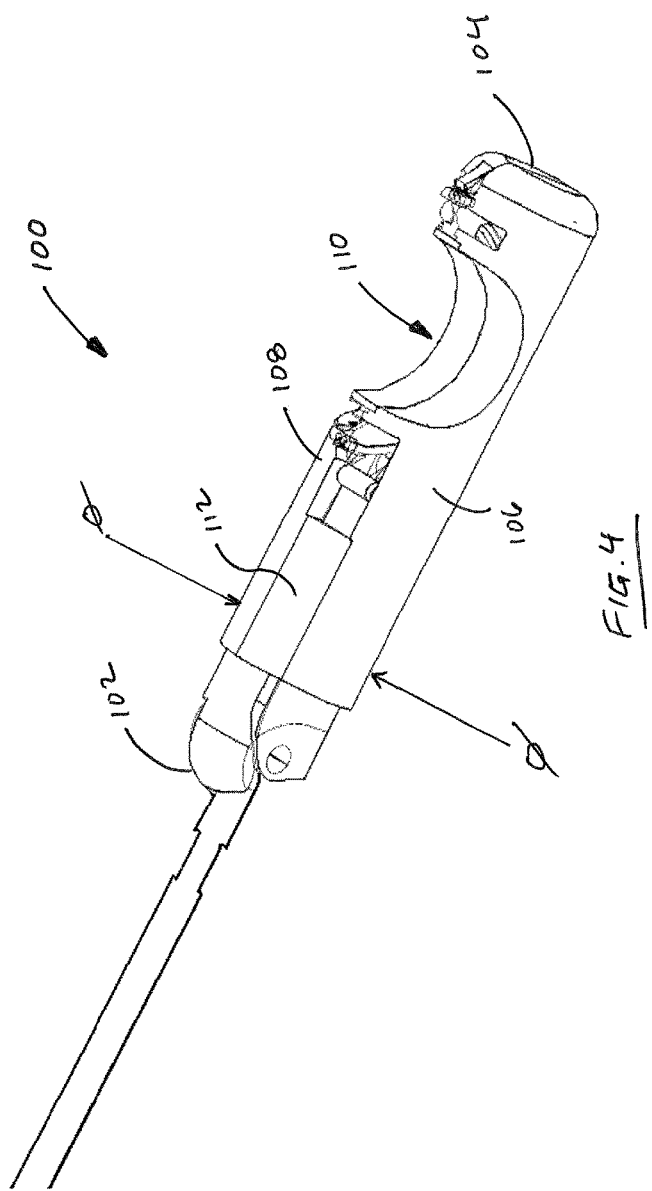

For purposes of illustration, and not limitation, suture head 100, separated from the remainder of device 1000, is illustrated in FIG. 4. Suture head 100 includes a proximal end 102, a distal end 104, and is formed by the cooperation of three main housing components (106, 108, 112) that define a gap 110 for receiving tissue of a patient to be sutured together. Suture head 100 is adapted and configured to direct a semi-circular needle (300, 350, 400) about a semicircular track and across gap 110 to form a series of sutures through tissue to be sutured.

Figure 5:
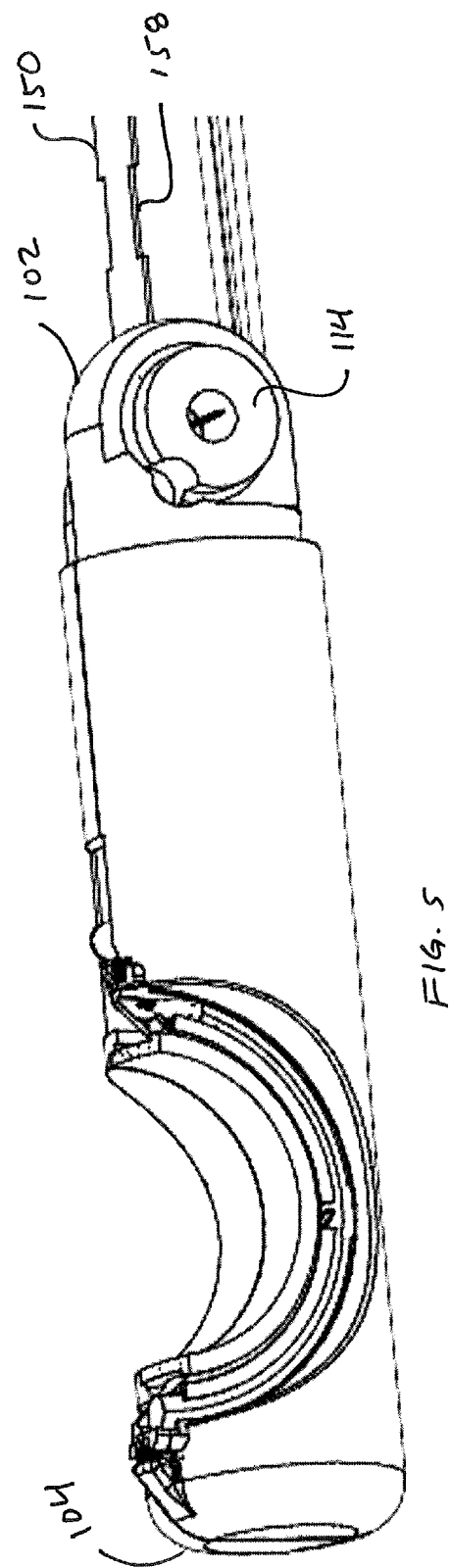
Figure 11A:
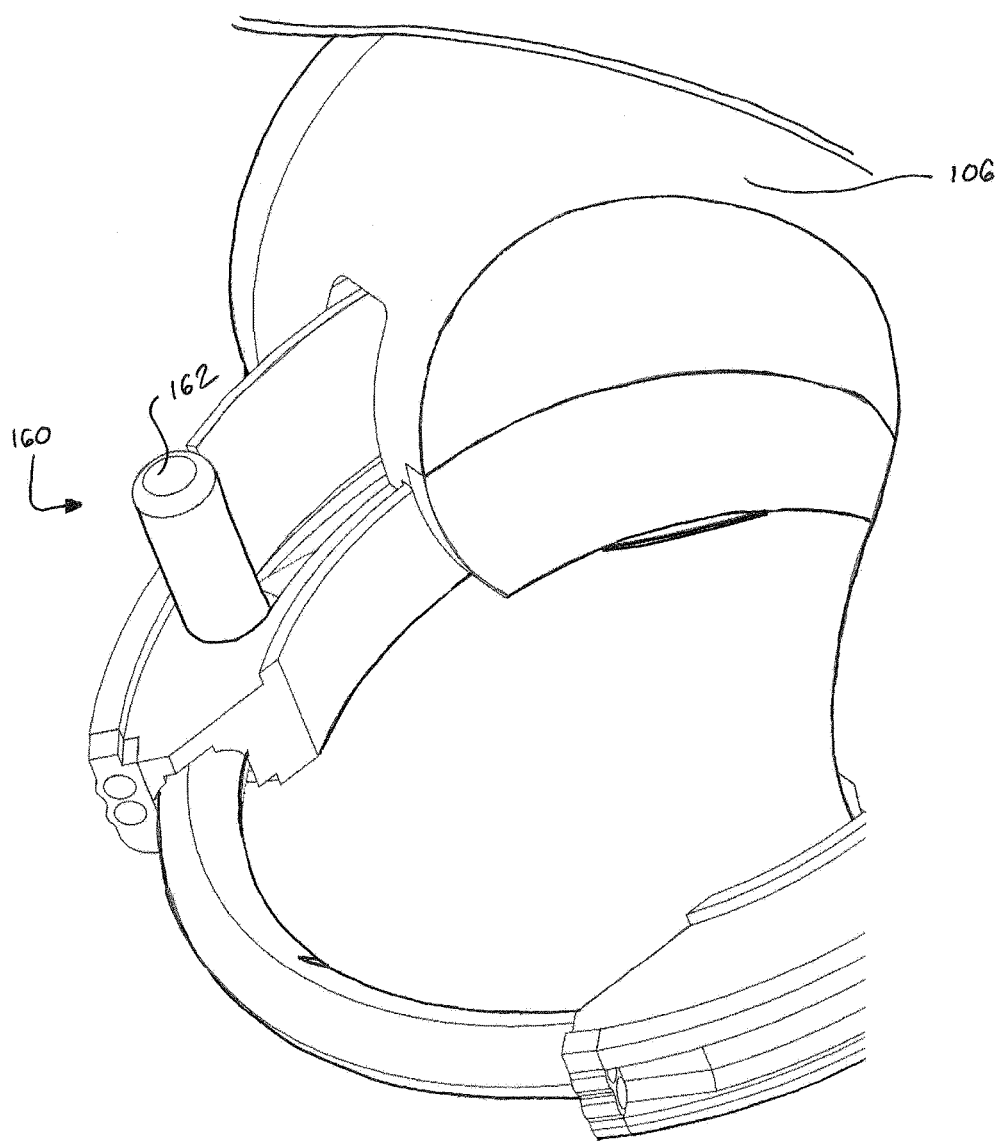
Figure 11B:
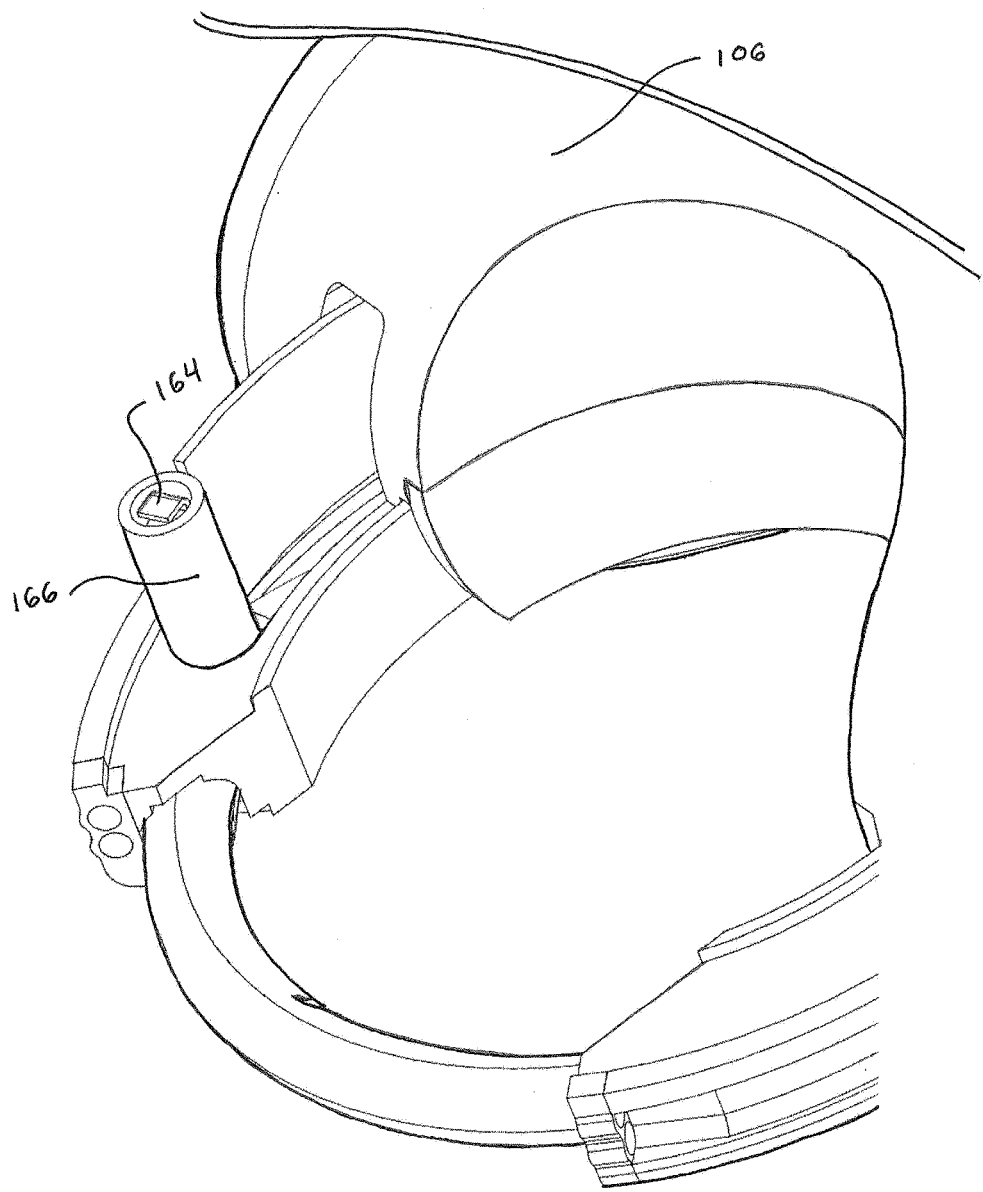
Figure 11C:
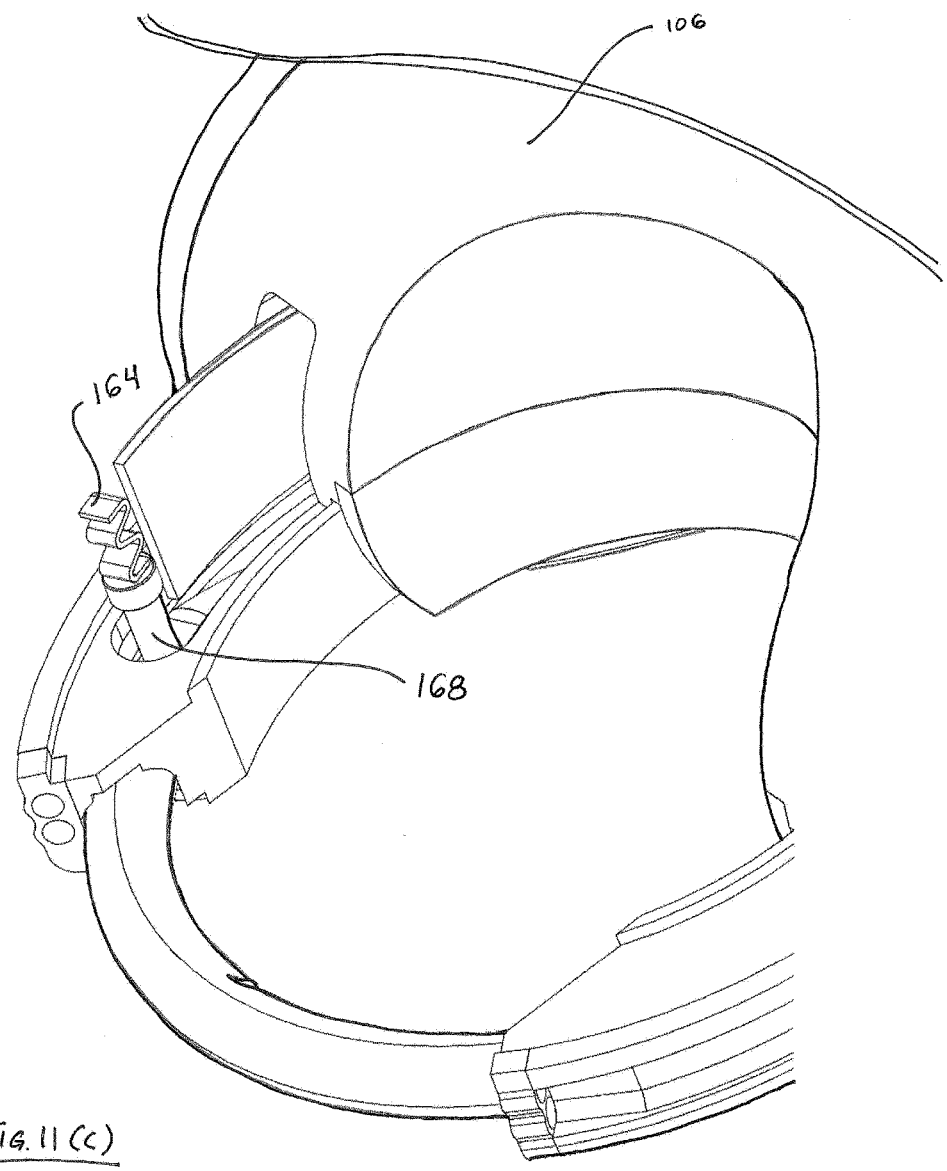
Figure 11D:
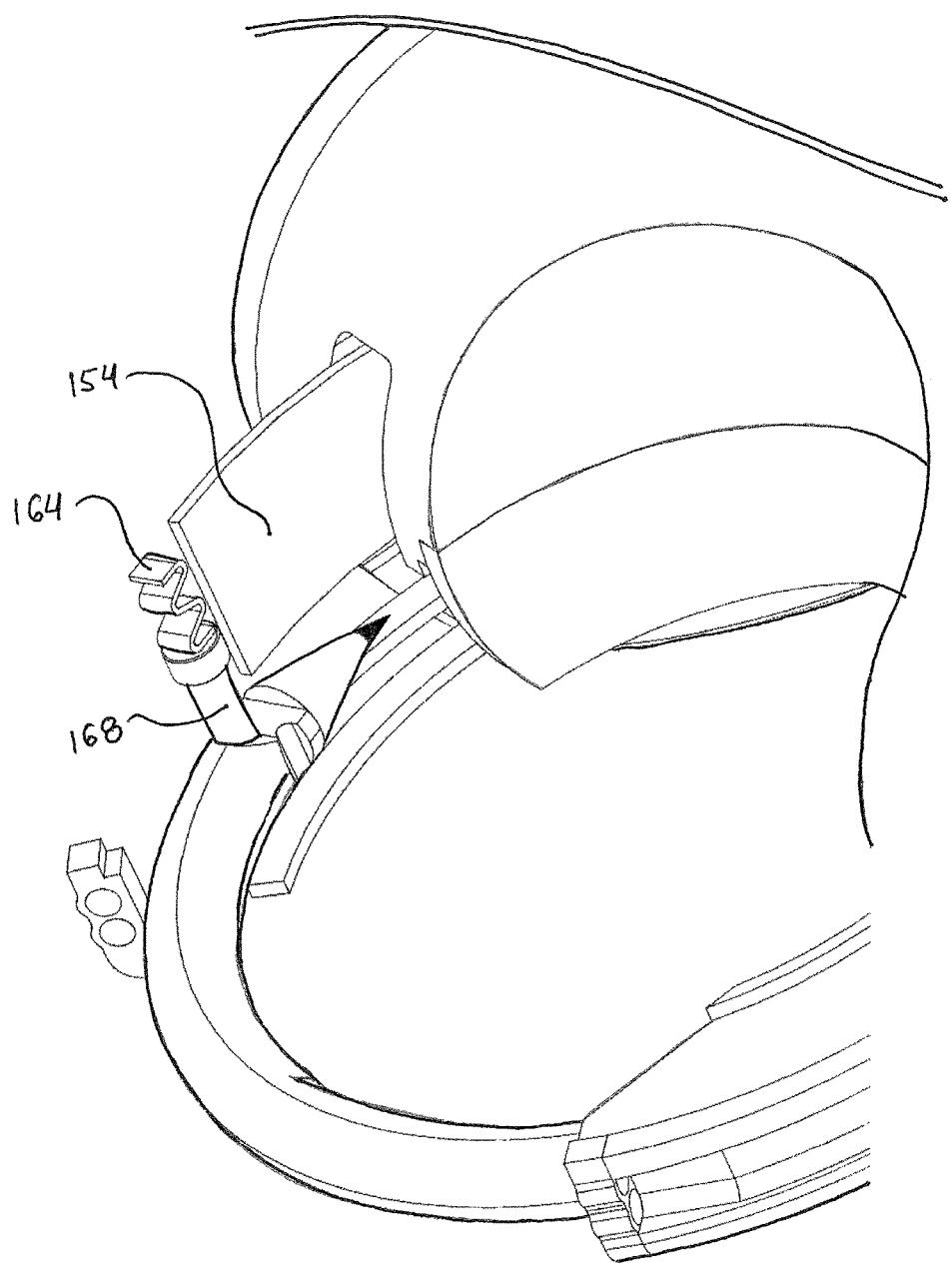

Prior to advancing needle across gap 110, suture head 100 must be converted from a delivery configuration to a deployed configuration. As illustrated in FIG. 4 and FIG. 5, suture head 100 is initially provided in a compact form having a predetermined transverse dimension, or diameter, φ. This transverse dimension, φ, can be any desired dimension, and is preferably about 5 millimeters. In particular, the dimension φ is preferably selected so that suture head 100 can pass through a standard 5 mm trocar into a patient's abdomen, for example, during a laparoscopic surgical procedure. FIG. 5 shows suture head 100 from the opposite angle as compared to FIG. 4, including pivot boss 114, which mates with intermediate portion 500 of device 1000.

Suture head 100 is illustrated in deployed configuration in FIG. 6. As illustrated in FIG. 6, in a deployed configuration, proximal guide 120 and distal guide 130 are moved outwardly from their nested position defined by housing components 106, 108, discussed in further detail below. When deployed as in FIG. 6, guides 120, 130 define a circular needle path or track 140 that lies in a plane P that is parallel to a longitudinal axis X of device 1000. In addition, as illustrated, leading tip 302 of needle 300 is advanced slightly by virtue of being dragged along by virtue of a pawl 125 in proximal guide 120 engaging a notch 306 disposed along an interior surface of needle 300, discussed in detail below.

After guides 120, 130 are in a deployed condition and needle track 140 is defined, needle 300 can then be advanced through track by advancing pawl 160 to a distal extremity along its path of reciprocation. FIG. 7 illustrates needle 300 spanning the gap 110, wherein needle 300, being about 180° in arcuate extent, is essentially located outside of the enclosure defined by housing segments 106, 108, 112.

FIGS. 8-10 illustrate the functionality of suture head 110 from the opposite side of the head. FIG. 8 illustrates suture head 100 in a delivery configuration with the guides 120, 130 retracted. As can be seen, engagement pawl 160 is withdrawn to a position proximal to the needle 300, and the trailing end 304 of needle 300 is visible. FIG. 9 illustrates suture head in a deployed configuration wherein guides 120, 130 are deployed. As seen in FIG. 9, distal guide 130 defines an arcuate recess 135 that receives the pawl 160 at the distal extremity of its reciprocating movement, best observed in FIG. 10. As is evident from FIG. 10, notch 158 in drive member 150 is advanced in a distal direction as is pawl 160.

FIGS. 11(A)-11(D) illustrate the structure of the engagement pawl 160. Pawl 160 includes a housing 166 attached (e.g., welded) to the distal end 154 of drive member 150. Housing 166 is preferably a metallic tubular structure, and houses a pawl spring 164 biased between a movable pin 168 and cap portion 162. Cap 162 is preferably attached to housing 166, such as be welding.

FIG. 12 illustrates suture head 100 with cover portion 106 removed, revealing the reciprocating guide path followed by drive member 150 and pawl 160, as well as guides 120, 130. Guides 120, 130 are advanced from the delivery configuration to the deployed configuration by four advancement wires, cables or filaments, 172, 174, 176, 178 that are directed around a series of bosses in housing portion 106, discussed below. In particular, each guide 120, 130 includes crimps 102a, 120b, 130a, 130b that integrally form a end of each of the guides 120, 130. Each crimp includes passages formed therein for receiving an end of wires 172-178. Wires 172-178 can take any suitable form, most preferably multi-strand 300 series Stainless Steel cables 0.009" in diameter. These ends are then crimped, adhered or otherwise attached to the crimps. Then by applying tension to one wire in each pair attached to each guide, the guides 120, 130 are pulled into or out of the suture head 100.

FIG. 13 illustrates the guides 120, 130 in a deployed condition and does not display wires 172-178 simply for purposes of clarity. FIG. 14 illustrates drive member 150 with pawl 160 at the full distal extent of its travel, riding within groove 135 in the side of guide 130. The elevation 130e of wall 130d can be increased and can be thickened to coincide with groove 135 to provide an enhanced bearing surface for pawl 160. Stops (not shown) are preferably provided in the form of raised surfaces on guides 120, 130 and the housing components to help prevent guides 120, 130 from falling out of suture head.

As is also evident, groove 125 in the side of guide 120 becomes accessible for the passage of pawl when the guides are in a deployed condition. As illustrated in FIG. 14, guide 150 traverses an arcuate path along guides and follows the path of the needle. FIG. 15 illustrates the spatial relationship of drive member 150 with respect to needle with other device components removed. FIG. 16 illustrates the relative positions of needle 300 with respect to antirotate springs 115 and drive pin 168 housed within pawl 160. FIG. 17 illustrates drive pin 168 in detail, wherein pin 168 includes a distal face 168a that contacts a body of the needle, a circumferential generally cylindrical face 168b, the distal extremity of which also contacts a surface of a notch in needle 100, or the distal end 304 of needle, a proximal face 168d that contacts pawl spring 164, an enlarged head portion 168c, and a circumferential distal face 168e that contacts with a narrowed portion of the housing 166 of pawl 160 that prevents pin 168 from falling out of housing 166.

FIGS. 18-21 are additional views of suture head 100 showing a progressive removal of components. FIG. 18 shows the suture head 100 in tact, while FIGS. 19-20 shows the positioning of bosses 106a, 106b, 106c on housing portion 106 that define bearing points for guide cables 172, 174, 176, 178 (not shown). Spacers 106d may also be provided to maintain a desired distance between housing components 106, 108 to permit the movement of components within suture head 100, and can also act as bearing surfaces for wires 176, 178 (FIG. 29). FIGS. 20-21 illustrate removal of guard 109 which provides inner support for guides 120, 130 to bear against. Guides 120, 130 ride in arcuate channels defined by the cooperation of components 106, 108 and 109.

FIG. 22 illustrates proximal and distal guides 120, 130 in the same spatial relationship as in FIG. 21. Views of the proximal guide 120 are depicted in FIGS. 23(A)-23(B). Guides 120, 130 are preferably made from a metallic material by assembling a series of metallic subcomponents, such as by laser welding, and are unitary and integral once assembled. Guides can be thought of as having a "top" face that faces the drive member 150, and a bottom "face" that faces housing portion 108. Proximal guide 120 defines a curved channel 125 in the top face 122 thereof. Proximal guide 120 further defines a lower face 124, having a groove 124b defined therein, an inner face 126 that bears against the inner surface of guard 109 and an outer face 128 that bears against housing components 106, 108. As illustrated in FIGS. 24(A)-24(B), distal guide 130 defines a curved channel 135 in the top face 132 thereof for guiding the pawl 160. Distal guide 130 further defines a lower face 134, having a groove 134b defined therein, an inner face 136 that bears against the inner surface of guard 109 and an outer face 138 that bears against housing components 106, 108.

FIGS. 25-32 illustrate the cooperation between wires/filaments 172-178 and guides 120, 130. As shown in these figures, wires/filaments 172, 174, 176 and 178 cooperate with bosses 106a, 106b, 106c and the other components of suture head 100 to permit guides 120, 130 to be selectively advanced and retracted. Wire 178 terminates in crimp 130b of guide 130. Applying tension to wire 178, which wraps around boss 106a (FIG. 28) results in guide 120 being advanced out of the suture head 100. Conversely, applying tension to wire 176, which terminates in crimp 130a of guide 130 (FIG. 30) causes guide 130 to be retracted into suture head 100. Similarly, applying tension to wire 172, which wraps around boss 106c and is attached to guide 120 at crimp 120b, causes guide 120 to be advanced out of suture head, while applying tension to wire 174, which wraps around boss 106c in a direction opposite to wire 172, pulls at the attachment point at crimp 120a, causing the guide 120 to be withdrawn back into the housing.

FIGS. 33-37 illustrate an embodiment of a needle loader 180 that is configured for loading a suturing needle (300, 350, 400) into suture head 100. Needle loader 180 has two main components, including a main body portion 182 and an advancement portion 184. Pin 184a of advancement portion is received in opening 182a of main body portion 182. Main body portion 182 defines a groove 182f for receiving a suturing needle (300, 350, 400). Main body portion 182 includes a central portion 182 d and clip portions 182c, 182e that fit over suture head 100. If desired, clip portions 182c, 182e may be adapted to snap fit over suture head 100. A distal stop plate 182b is provided to facilitate axial alignment between loader 180 and suture head 100. Advancement portion 184 rotates within opening 182a of main body portion 182, and further includes a needle pushing arm 186. In operation, a needle is situated within track 184f with suturing material attached to the trailing end, as discussed herein. The loader 180 is then snapped onto suture head. Arm 186 is preferably situated at this time proximate the trailing end of the needle. Arm 186 is then rotated such that needle (300, 350, 400) is advanced into the needle track 140. If needed, needle (300, 350, 400) can be advanced back into the needle loader 180, by virtue of the fact that arm 186 is dimensioned to pass through the grooves 124b, 134b of proximal guide 120 and distal guide 130, respectively.

FIGS. 38-40 illustrate a first embodiment of a suturing needle 300. Needle 300 includes an arcuate body defined by a leading end 302, a trailing end 304 and a generally toroidal surface 305. Needle 300 includes a plurality of notches 306, 308, 310 formed therein, as well as an opening 312 in trailing end 304 for receiving an end of a length of suturing material 312a. Notches 306, 308 are located on an inner radial region 322 of needle, while notch 310 has a projection that lies within a plane P' that is defined by the central curved axis X' of the needle. Notch 310 includes a first portion 310a that is generally perpendicular to the plane P' and a portion 310b that generally lies in plane P', and a sloped portion 310c. The notches 306, 308 have projections that are generally perpendicular to the plane P'. Notches 308, 306 have first portions 306a, 308a that are generally parallel to a cross section of the needle in that location, and sloped portions 306b, 308b that are angled (such as by an angle of 60 degrees) with respect to portions 306a, 308a. Notches 308, 310 intersect to facilitate the function of the particular embodiments of suturing head 100, 100' described herein.

FIGS. 41-44 illustrate a second embodiment of a suturing needle 350. Needle 350 includes an arcuate body defined by a leading end 352, a trailing end 354 and a generally toroidal surface 355. Needle 350 includes a plurality of notches 356, 358, 360 formed therein, as well as an opening 362 in trailing end 354 for receiving an end of a length of suturing material. Notches 356, 358 are located on an inner radial region 372 of needle, while notch 360 has a projection that lies within a plane P' that is defined by the central curved axis X' of the needle. Notch 360 includes a first portion 360a that is generally perpendicular to the plane P' and a portion 360b that generally lies in plane P', and a sloped portion 360c. The notches 356, 358 have projections that are generally perpendicular to the plane P'. Notches 358, 356 have first portions 356a, 358a that are generally parallel to a cross section of the needle in that location, and sloped portions 356b, 358b that are angled (such as by an angle of 60 degrees) with respect to portions 356a, 358a. Notches 358, 360 intersect to facilitate the function of the particular embodiments of suturing head 100, 100' described herein. Needle 350 further includes a generally square cross-section having a rounded portion 366 and a tail portion 364, also having a round cross section. Stated another way, the needle body includes a portion with a round cross section 366 that separates a main portion of the needle with a generally square cross section from a tail portion 364 with a generally square cross section. It is believed that using a needle with a square cross section helps the needle 350 cross the gap 110 of suture head and re-enter suture head with superior alignment as compared to needle 300.

FIG. 45 illustrates a third embodiment of a suturing needle 400. Needle 400 includes an arcuate body defined by a leading end 402, a trailing end 404 and a generally toroidal surface 405. Needle 400 includes a plurality of notches 406, 408, 410 formed therein, as well as an opening 412 in trailing end 404 for receiving an end of a length of suturing material. Notches 406, 408 are located on an inner radial region 422 of needle, while notch 410 has a projection that lies within a plane P' that is defined by the central curved axis X' of the needle. The notches 406, 408, 410 are generally similar to those described with respect to needle 300. The principal difference between needles 300, 400 are the addition of an additional notch 415 cut into the needle proximate its trailing end 404. Notch 415 has a projection in the plane P' and is shaped to receive the housing 166 of the pawl 160. It is believed that using a needle with notch 415 helps the needle 400 cross the gap 110 of suture head and re-enter suture head with superior alignment as compared to needle 300.

Figure 46:
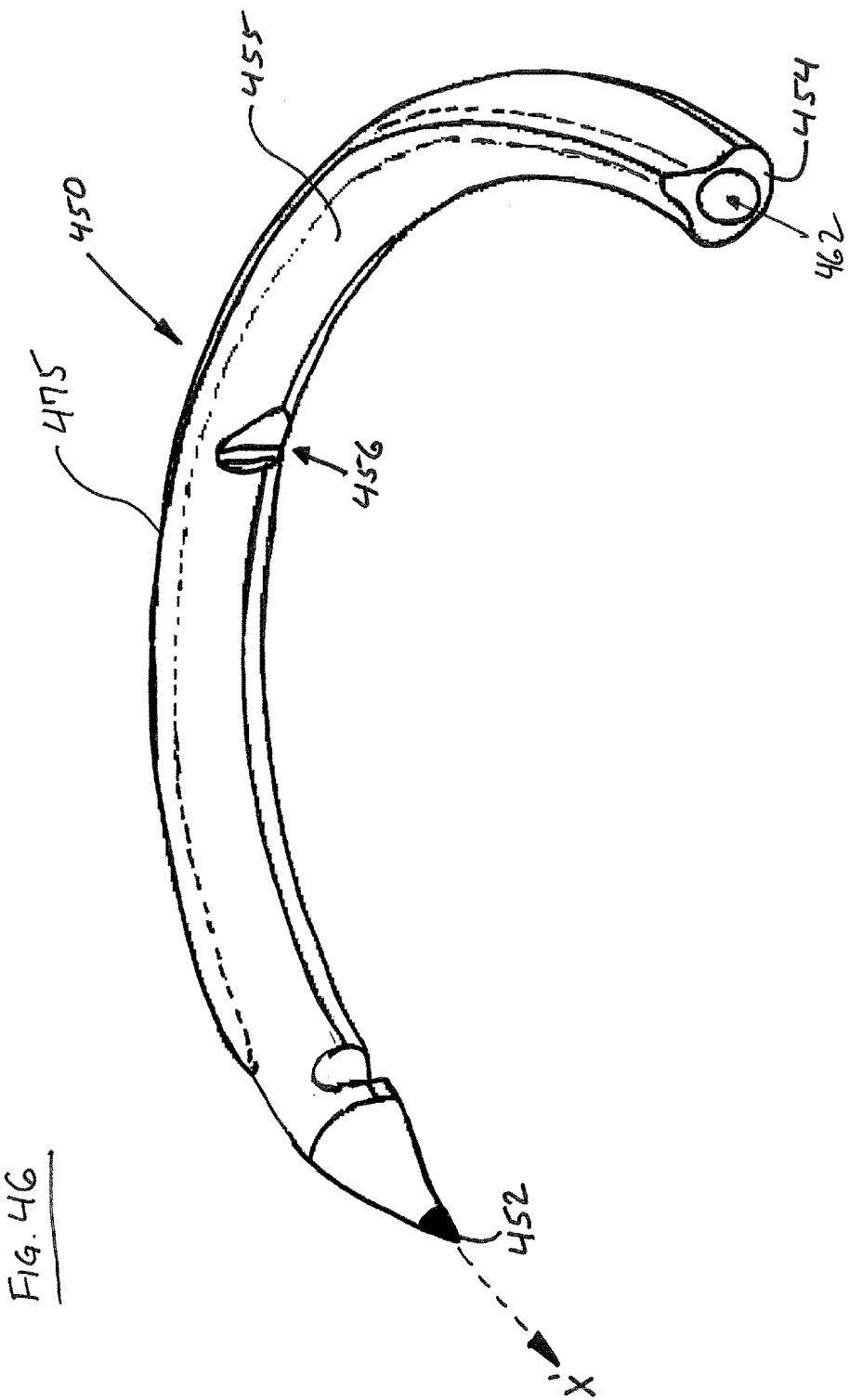
FIG. 46 illustrates aspects of a fourth embodiment of a suturing needle made in accordance with the present disclosure.
Figure 56:
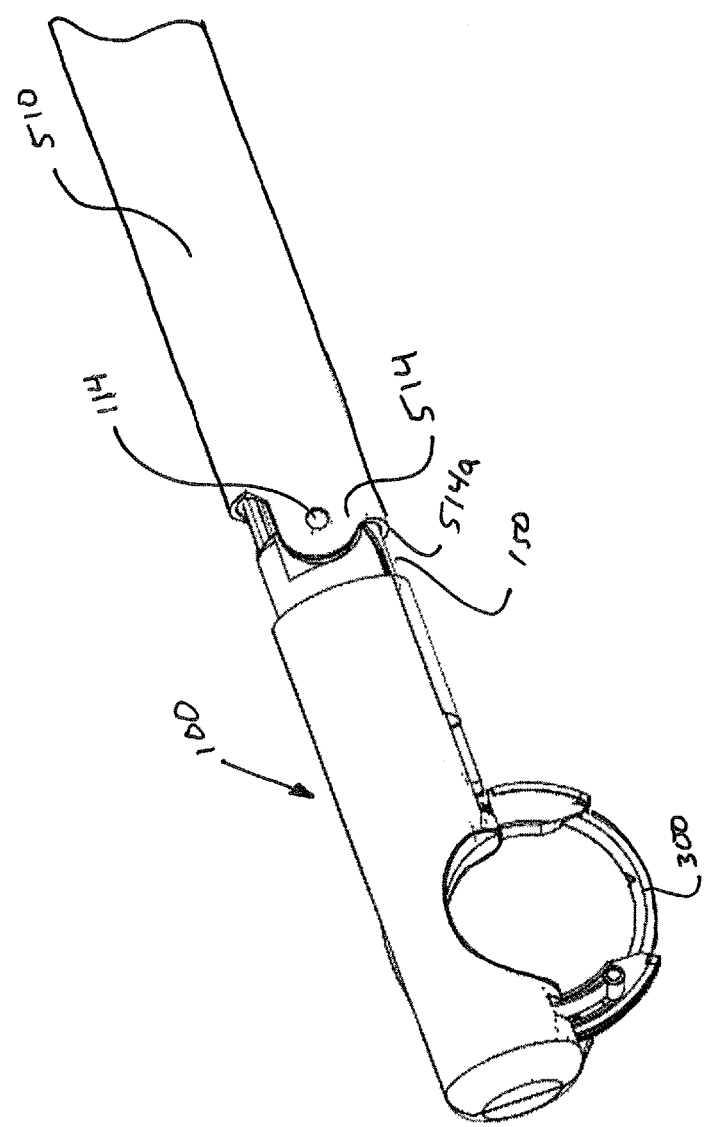
FIGS. 56-59 illustrate aspects of an intermediate region of the suturing device illustrated in FIGS. 1-3.
Figure 57:
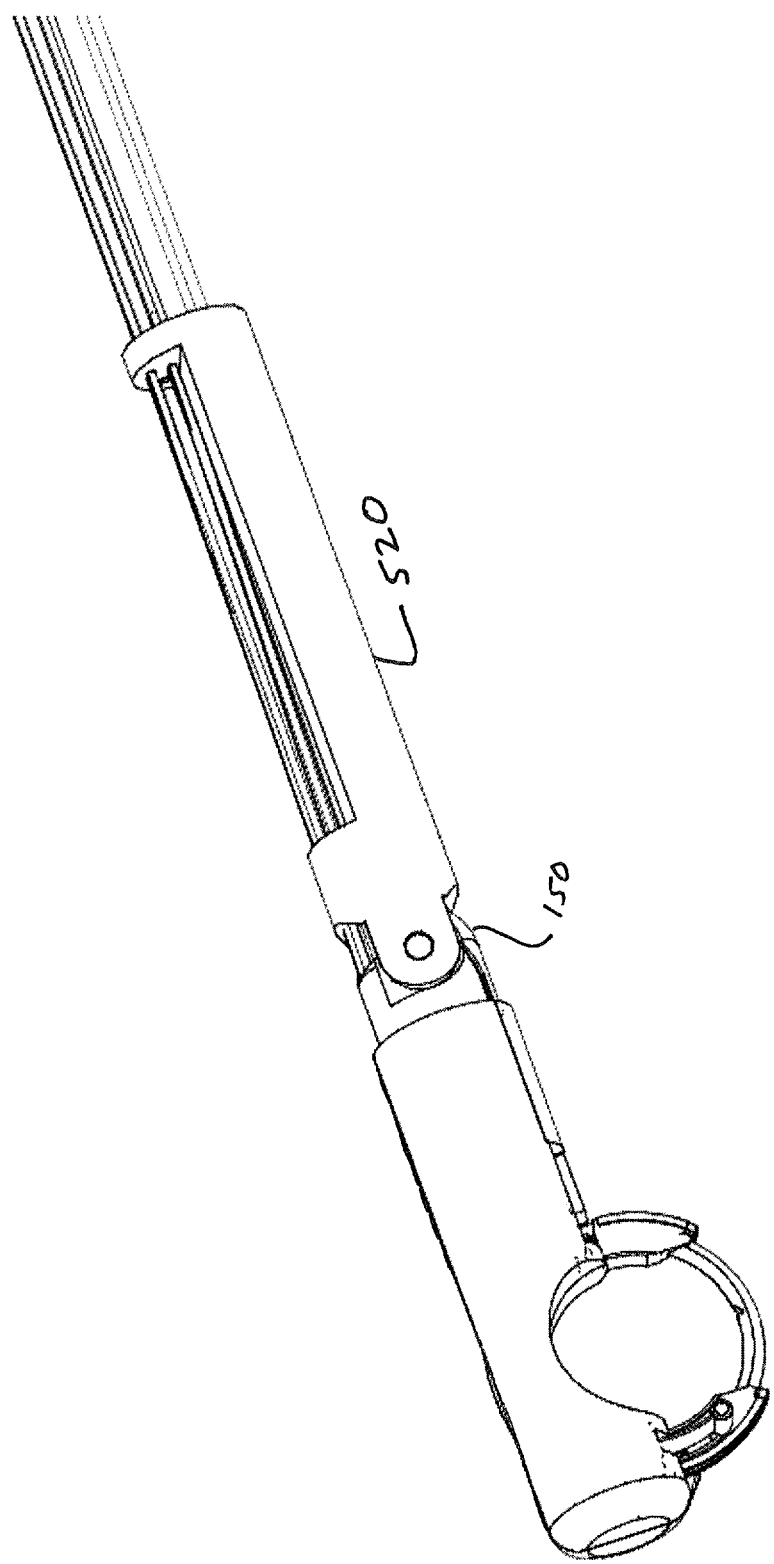
Figure 58:
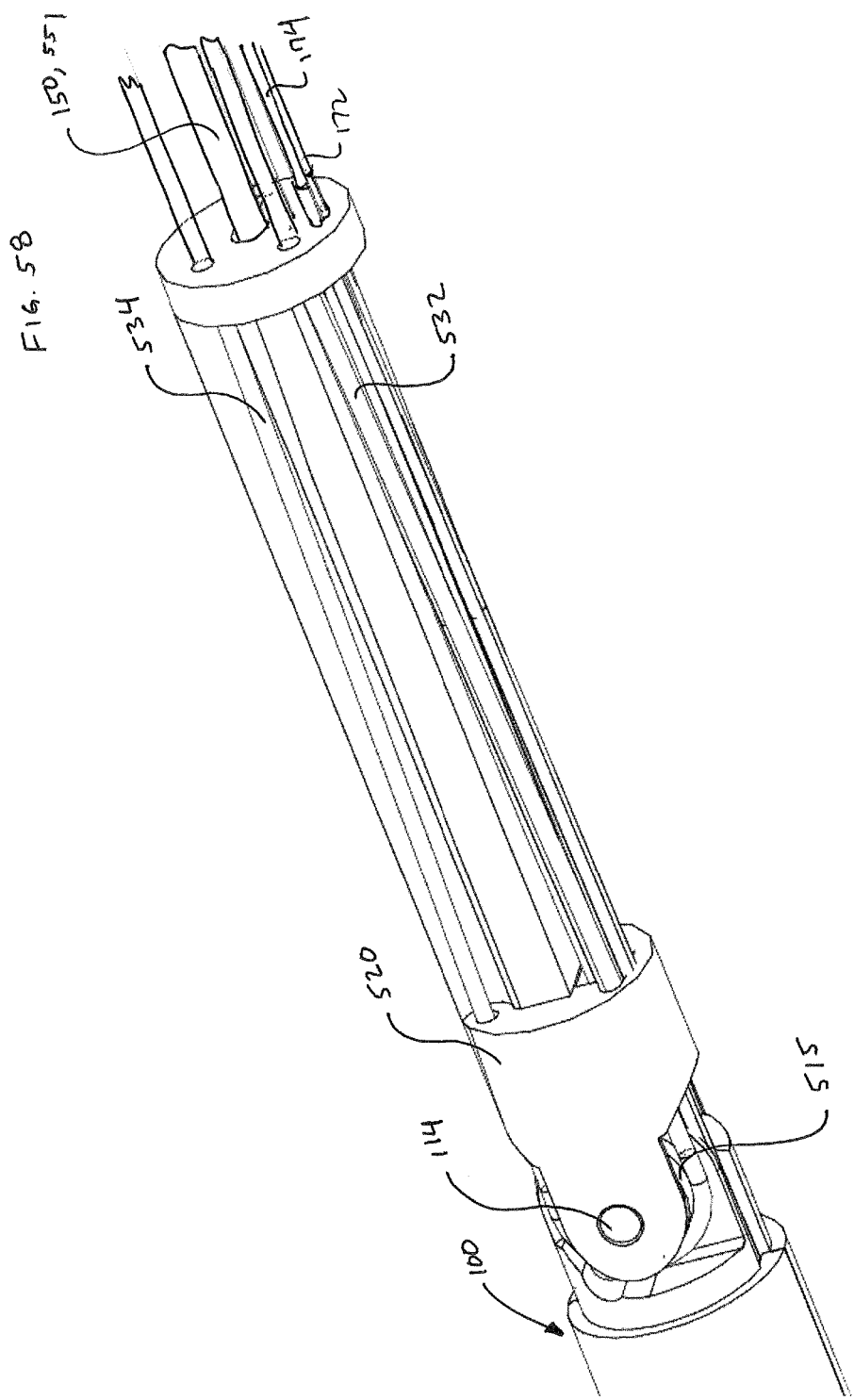
Figure 59:
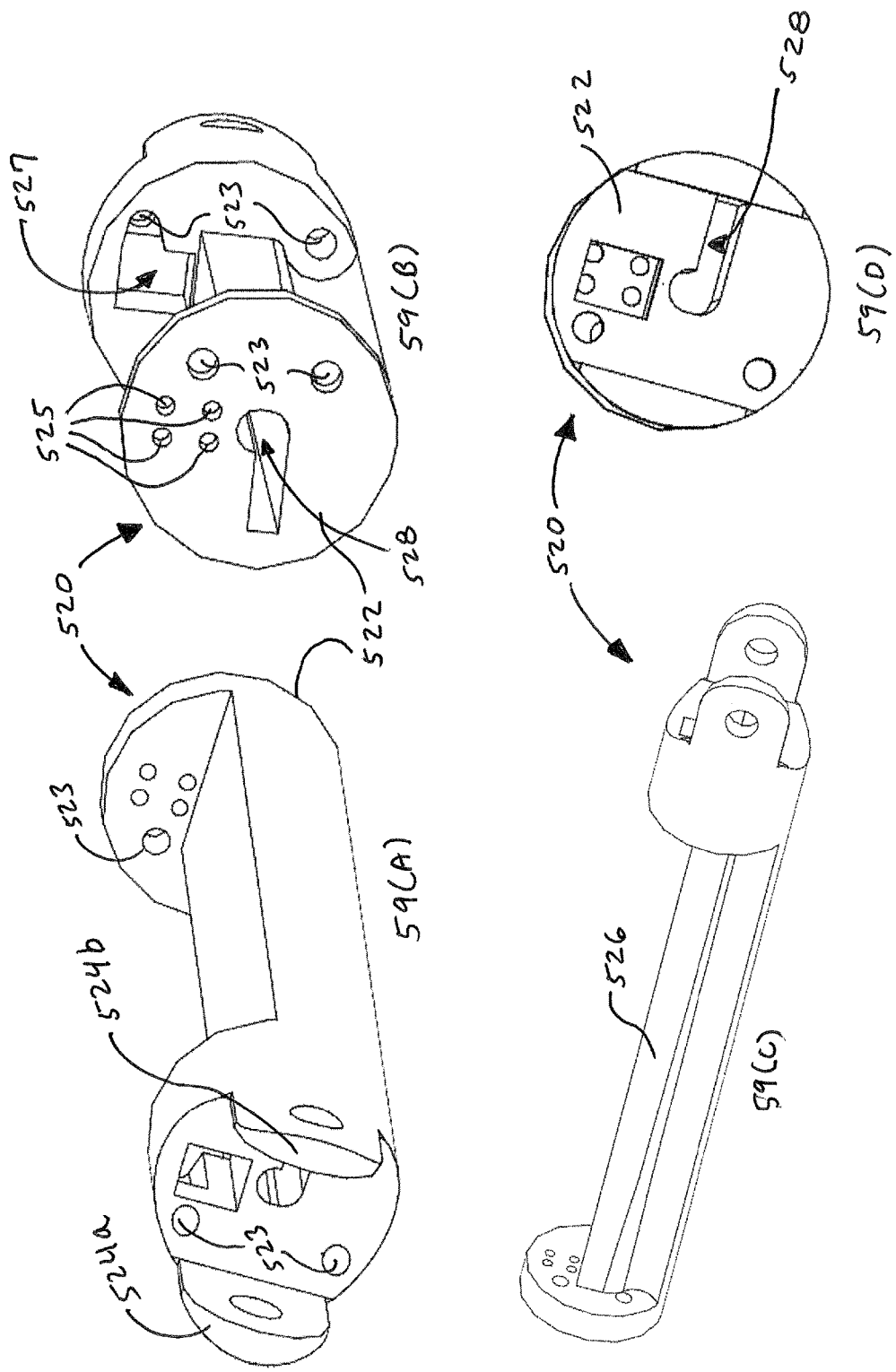

FIG. 46 illustrates a fourth embodiment of a suturing needle 450. Needle 450 is essentially the same as needle 300, except that it further includes an arcuate keel 475, or raised surface, along its length. Keel 475 is adapted and configured to ride in grooves 124b, 134b of guides 120, 130 to stabilize the needle 450 as it crosses the gap 110 of suture head and re-enters suture head with superior alignment as compared to needle 300.

FIGS. 47(F)-55 illustrate aspects of an alternative embodiment of a suture head 100' made in accordance with the disclosure. The principal difference between suture head 100 and suture head 100' lies in the path of travel of the drive element 150.

Embodiment 100 of suture head includes a drive member 150 that defines a narrowed, or notched region 158, as illustrated in FIG. 12, for example. In operation, notched region 158 is located to coincide with bosses 106W, 108W (FIGS. 47(A)-47(D)) when pawl 160 is located at the distal extremity of its range of motion within groove 135 of distal guide 130. When in this position, drive member 150 extends into groove 125 of proximal guide 120 (FIG. 14). However, as soon as tension is then applied to bring pawl 160 (and needle 300) proximally along the needle track, the narrowed region 158 of drive member 150 slips past bosses 106W, 108W, so that pawl 160 will travel up lower leg of passage 106T when moving proximally until it passes boss 106W and emerges from the passage, ready to begin another cycle. Stated another way, bosses 106W, 108W result in a passageway between them that permits narrowed region 158 to slip through, but not the rest of member 150 or pawl 160. Thus, narrowed region 158 permits the drive member 150 to travel along an upper path above bosses 106W, 108W when advancing distally, and slip past bosses 106W, 108W when region 158 aligns with the bosses, thus permitting drive member 150 and pawl 160 to move proximally along a lower path below bosses 106W, 108W. Housing portion 112 is illustrated in FIG. 47(E).

Accordingly, it can be appreciated that drive member 150 should ideally be metallic. Preferably, member 150 is made from hardened stainless steel that has been heat treated to HR 900, and may have a chromium coating, such as an Armoloy ME 92® coating commercially available from ME-92® West/Armoloy® of Illinois, 118 Simonds Avenue, DeKalb, Ill. 60115, (815) 758-6691. Preferably, member 150 is 17-7 PH Stainless steel, condition "C" that is then hardened to condition CH900, and then coated with a ME 92® coating. Preferably, the ME-92® coating is applied after 900 Heat Treatment. The sequence of operations in manufacturing member 150 includes providing 17-7 PH strip stock material that is machined to size by any number of known methods (e.g., electrical discharge machining ("EDM"), shearing, milling, etc.). The drive ribbon is heat treated, and then cleaned to remove heat treatment surface oxidation, and the ME-92® coating is then applied. By way of further example, 17-7PH condition "A" material can be heat treated to RH950. In other embodiments, the drive member 150 can be made, for example, from shape memory material such as nickel-titanium alloys sold under the trade name of NITINOL® and the like. In another embodiment, member 150 is made from a polymeric material. In one aspect, member 150 can include polyethylene terephthalate material or nylon material of high strength. If desired, a laminate of plastic and metal materials or multiple materials can be used. By way of further example, member 150 can be comprised of a bundle of wires or filaments, a single wire or filament, or any material in any configuration that permits driving the needle around the needle track.

The other components of suture head 100 including the needle (300, etc.) are preferably formed by metal injection molding ("MIM") techniques, as are known in the art from various materials, preferably stainless steel. In accordance with a preferred embodiment, 17-4 PH stainless steel alloy is preferably used. Device 1000 is preferably a disposable device, and handle components are preferably made from injection molded plastic wherever desirable.

A further embodiment of a suture head 100' is set forth in FIGS. 47(F)-55. The principal difference between suture head 100' and suture head 100 is that the drive member 150 in suture head 100' follows a single path during reciprocation, in contrast with the alternating path of embodiment 100. FIG. 47(F) illustrates suture head 100' including a needle 300 with guides 120', 130' in a deployed configuration. Guides 120' 130' are only partially represented and are not depicted including crimps at their extremities for mating with deployment or retraction cables as with embodiment 100 discussed earlier. Suture head 100' defines a guide path 153' between housing components 106', 112' (FIG. 48), similar to the manner in which suture head 100 defines a guide path between housing components 106 and 112 (FIG. 21). FIG. 48 further illustrates an alternate path 1001 that can be traversed by drive member 150' by modifying components 106', 112' by removing material 112a' that acts as a pawl stop and adding material 106'b in component 106' to act as a new pawl stop. The end result is a different angle of incidence for the drive member 150.

FIG. 49 illustrates the "left" housing component 108' from various angles, while FIGS. 50(A)-50(E) illustrate the "right" housing component from various angles. Apparent from the figures is the path 153' followed by the drive member 150' and pawl 160' (not shown). It will be appreciated that drive member 150' and pawl 160' can be substantially identical to embodiments 150, 160, but need not have the notched region 158, as a single path for traversal of pawl 160' is defined by cooperation of housing components 106', 108'. Guard 109' is illustrated in FIGS. 51(A)-51(B), and illustrates the location of pawl 115' that helps prevent needle (e.g., 300) from moving against the direction of desired travel. FIG. 52 illustrates the spatial relationship of guides 120', 130' with respect to pin face 168a' and pawl 160' in their two respective locations, for purposes of illustration only. FIGS. 53(A)-53(D) illustrate various views of housing portion 112'. FIGS. 54-55 illustrate the spatial orientation of guides 120', 130' (which are substantially identical to guides 120, 130) with respect to pawl 115' and further illustrates guide stops 117', which help guides 120', 130' stop in a predetermined location when in an undeployed condition.

FIGS. 56-59 illustrate aspects of the intermediate region 500 of device 1000. Intermediate region 500 includes an elongate, preferably metallic tube 510 having a proximal end and a distal end 514. Distal end 514 of tube 510 is attached to a knuckle assembly 520, which in turn is pivotally attached at pivot 114 to suture head 110. A pulley 515 is located at pivot 114 to serve as a bearing surface for adjoined articulation cables 532, 534 and cables 532, 534 are preferably affixed to pulley 515 to provide leverage for accomplishing articulation. Articulation cables 532, 534 can take any suitable form, most preferably multi-strand 300 series Stainless Steel cables that are 0.020" in diameter. By pulling on one of the articulation cables, the suture head 100 will articulate with respect to intermediate region 500 about the pivot 114. Knuckle 520 includes a proximal end 522 and a distal end 524 (in the form of a yoke 524a, 524b for receiving suture head 100) separated by an intermediate region 526. Intermediate region 526 defines a longitudinal channel 528 therethrough for receiving drive member 150. Preferably, member 150 is attached to a pull rod 151 in this region, and the cross-sectional profile of channel 528 is adapted to accommodate such a geometry, as depicted in the Figures. Openings 523 are also defined for receiving members 532, 534. Moreover, openings 525, 527 are also provided to permit passage of pull wires/cables 172, 174, 176, 178 for controlling the movement of guides 120, 130. The proximal end of tubular member 510 is attached to a roticulation mechanism that rotates the tube 510 and suture head 100 with respect to a handle 600 of the device, discussed below. The distal end 514a of tube 510 may be extended slightly to provide for tighter control of drive element 150 as it passes into intermediate region 500.

Figure 63:
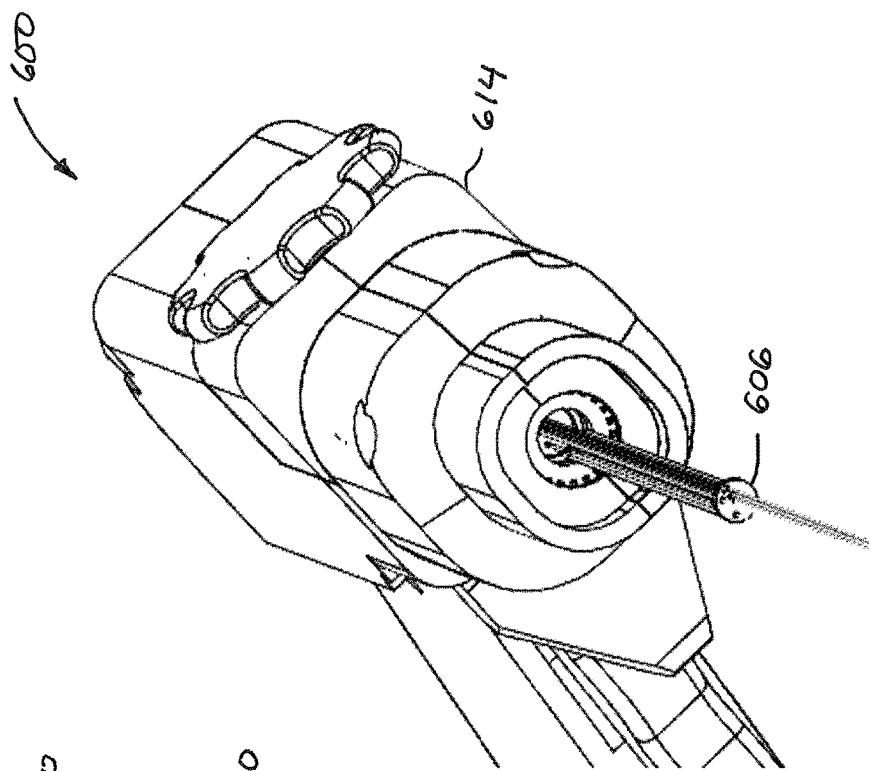
Figure 62:
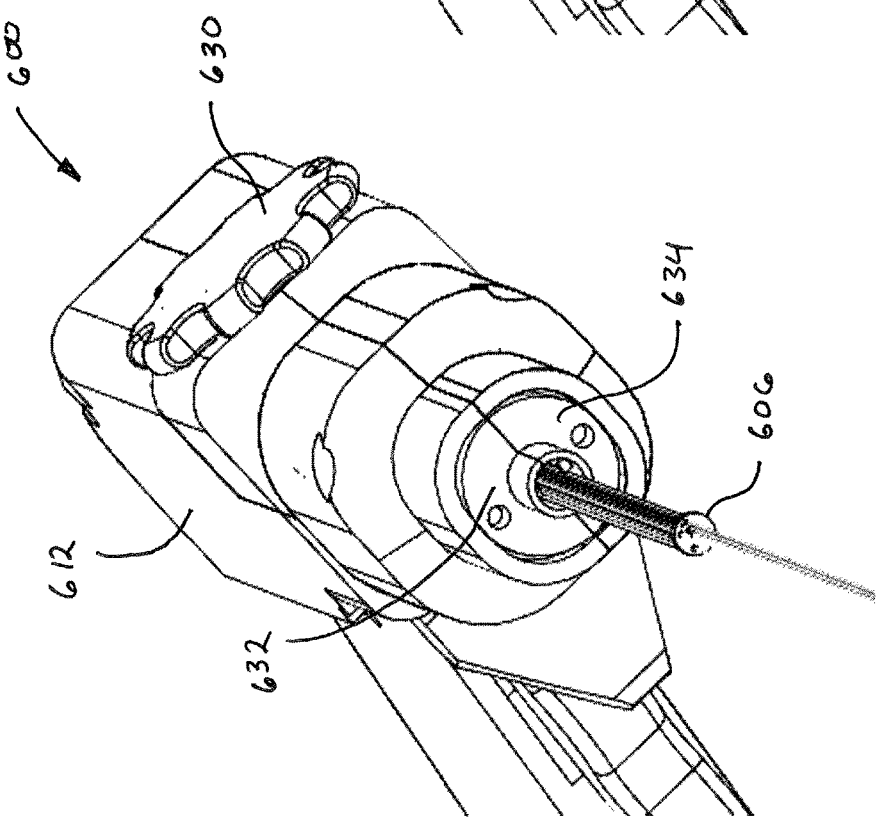
Figure 71:
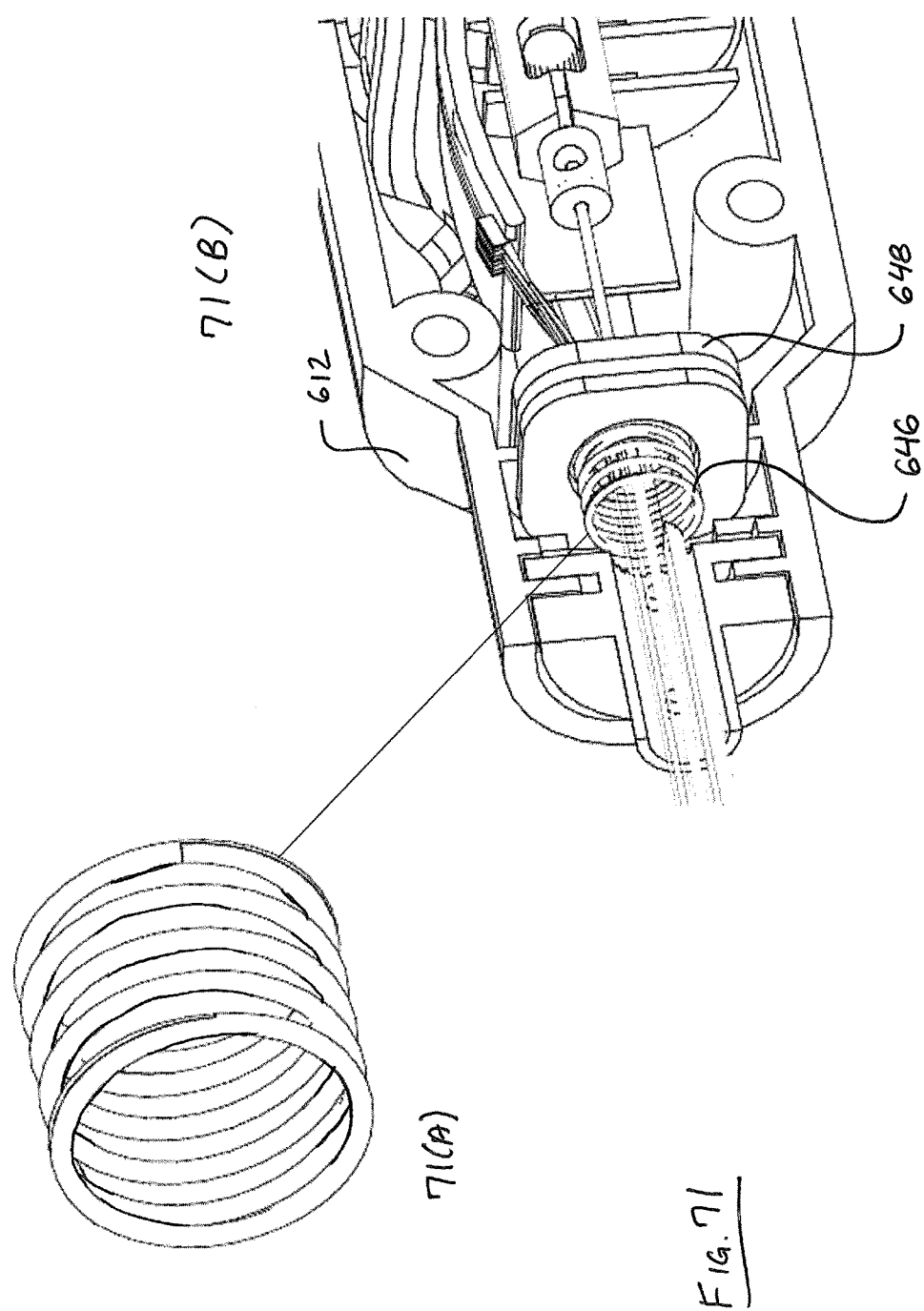
Figure 72:
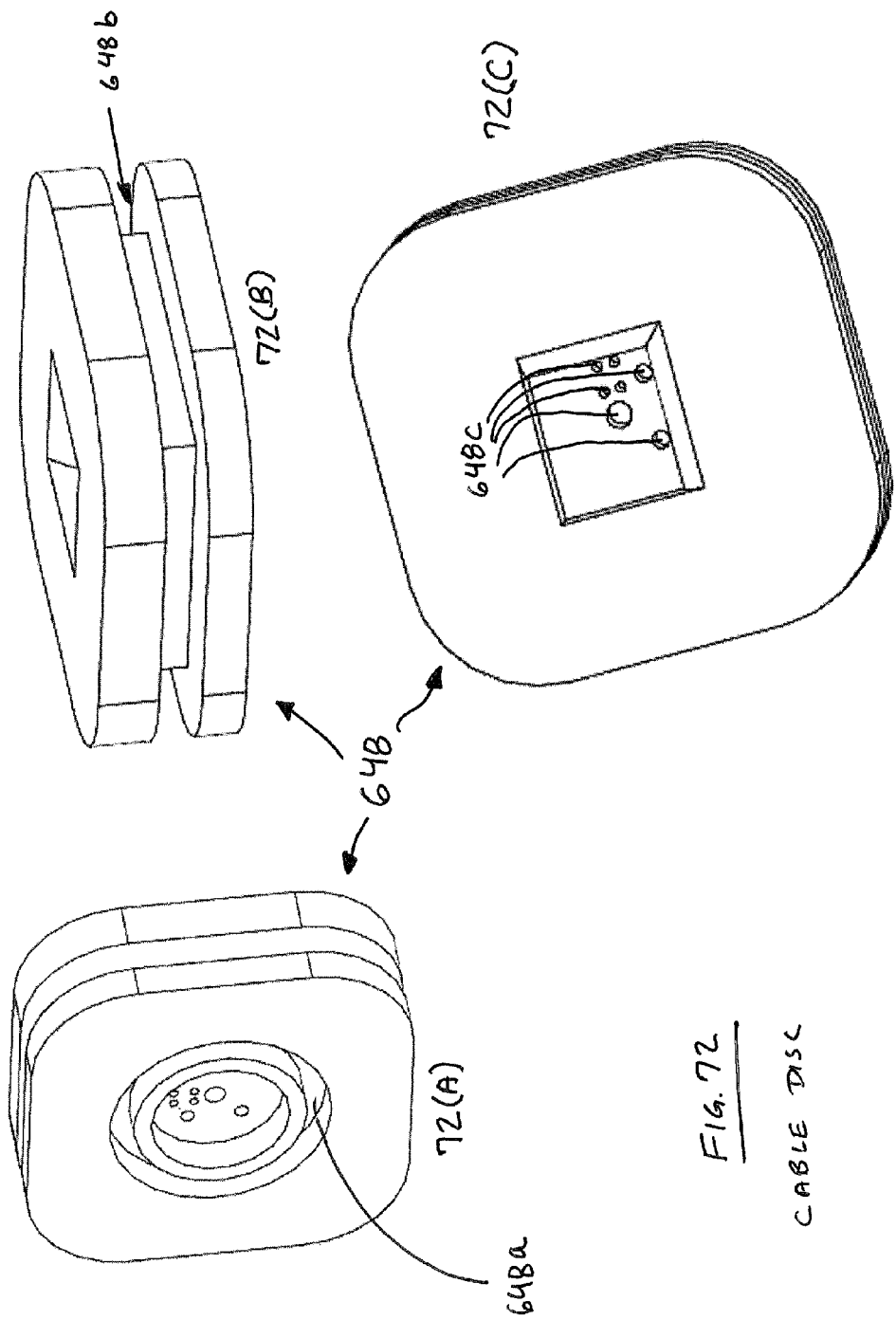
Figure 79:
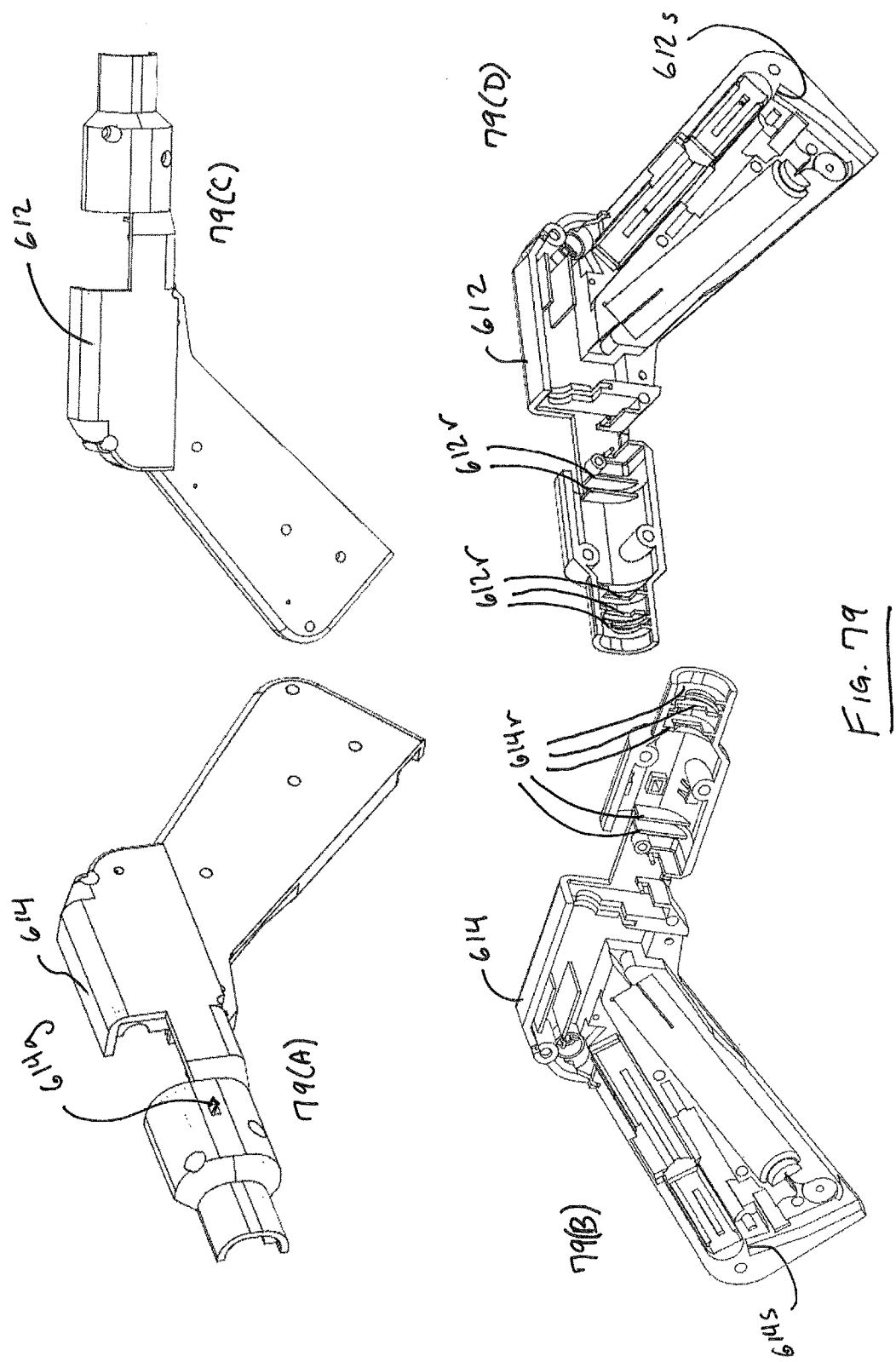

For purposes of illustration, and not limitation, handle 600 of device 1000 is illustrated from FIGS. 60-122. Handle 600 includes many components and systems for operating suture head 100, 100'. FIG. 61 illustrates a head-on view of handle with tube 510 removed, illustrating roticulation handle 620, wherein relative rotational motion of handle 620 with respect to handle 600 will cause the suture head 100, 100' to rotate with respect to handle 600. FIG. 60 depicts a rear view of handle 600. FIG. 62 depicts handle with roticulation handle 620 removed, and depicting proximal cable guide 606, left tube collar 634 and right tube collar 632. Tube collar portions 632, 634 cooperate to capture the proximal end 512 of tube 510, which can be, for example and not limitation, a 5 mm nominal outside diameter stainless steel hypotube. Also illustrated is articulation handle 630 that can be used to articulate suture head 100 about its pivot point as discussed above. Housing 600 includes two main housing halves including a right side 612 and a left side 614. FIG. 63 illustrates handle 600 with tube collars 632, 634 removed. Proximal cable guide 606 is anchored within hypotube, such as by interference fit. The longitudinal distance along tube 510 between the distal disc 606b of proximal cable guide 606 and cable disc 648 (FIGS. 71-72) represents a twist region over which all cables routed through tube 510 can rotate and twist about each other when the suture head is roticulated, or rotated with respect to the handle 600. The twist region is preferably between about three and six inches long, most preferably about four inches long. In a preferred embodiment, suture head has a total angular range of motion of about 270 degrees with respect to handle 600, desirably about 135 degrees in either direction from the home position illustrated in the Figures. Detents in roticulation handle 620 (FIG. 64) are adapted and configured to engage with a pawl 614g housed in an opening in left handle portion 614 (FIG. 79(A)).

Figure 66:
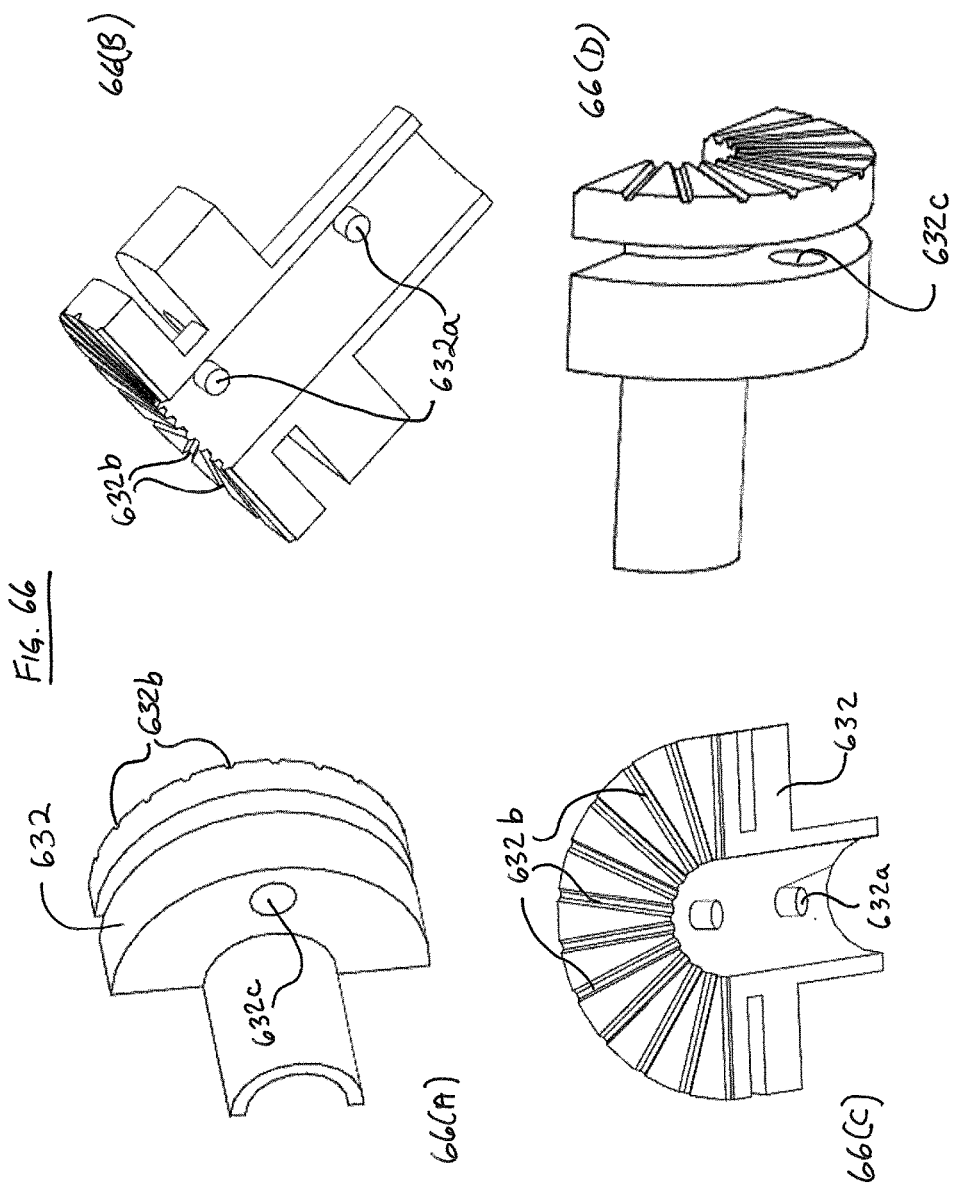

Tube collars (FIGS. 66-67) are essentially mirror images of each other (across a vertical centerplane of the device 1000) and cooperate to define a hollow, generally cylindrical interior for receiving proximal end 512 of tube 510. In particular, lugs 632a, 634a are provided to mate with openings 518 near the proximal end 512 of tube 510 (FIG. 69). Tube collars also define radially oriented detents 632b, 634b along their proximal faces to mate with raised portions 644b on the distal face of roticulator plate 644 (FIG. 68). Roticulator plate 644 further includes a proximal portion 644c having a square cross section for being received by the left and right housing side portions 612, 614.

Roticulator plate 644 is received in housing 614 between adjacent ribs 614r (FIG. 70) as is cable disc 648. Cable disc 648 (FIGS. 71-72) defines a circumferential groove 648b about its periphery for mating with a rib 614r as well as an annularly-shaped channel 648a in its distal face for receiving a roticulator spring 646. Spring 646 is adapted and configured to urge roticulator plate into contact with detents 632b, 634b to facilitate stepwise rotational movement. cable disc 648 further defines a plurality of openings 648c therethrough to permit passage of cables/wires 172, 174, 176, 178, 532, 534 and 551.

Figure 73:
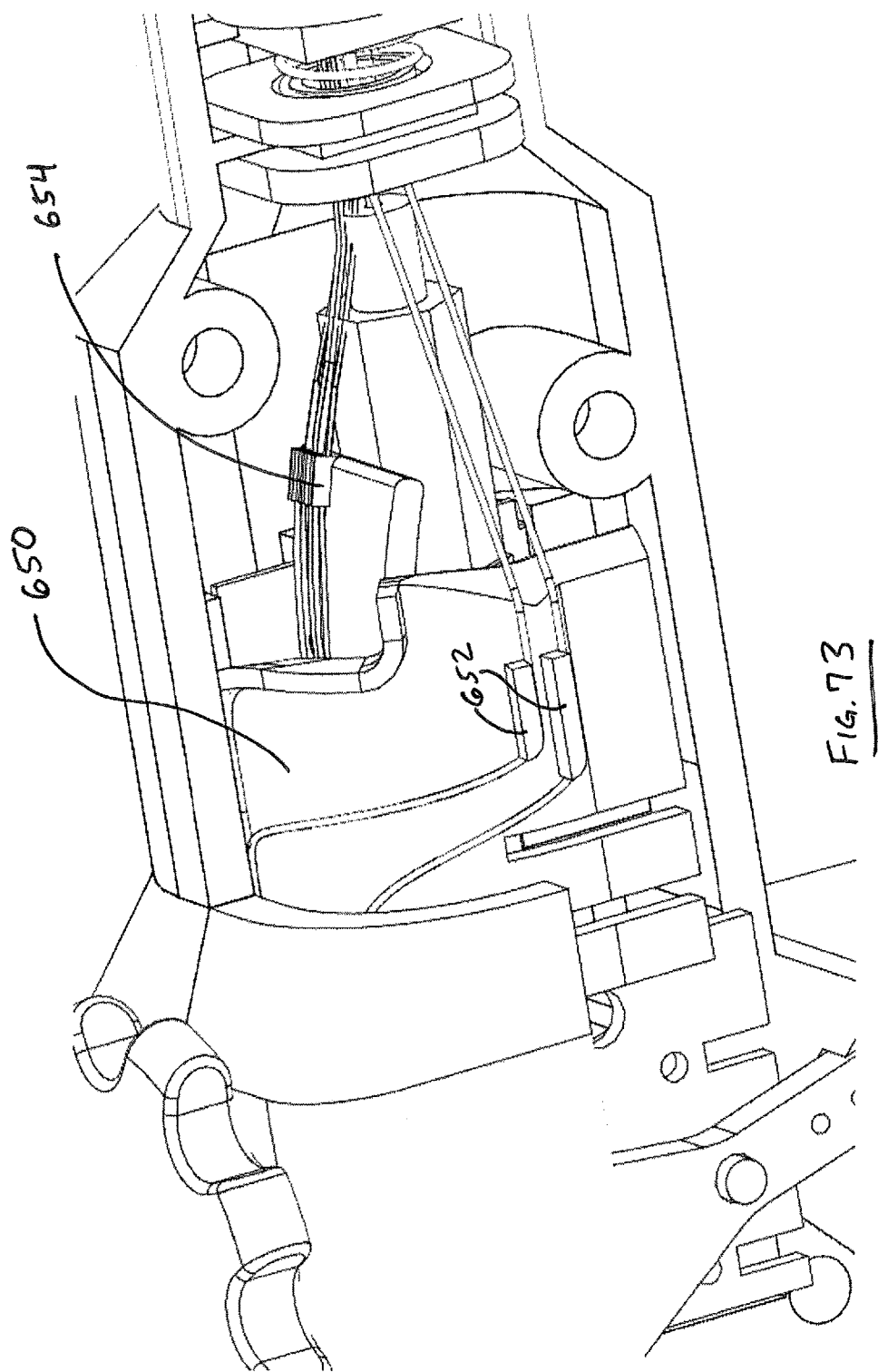
Figure 74:
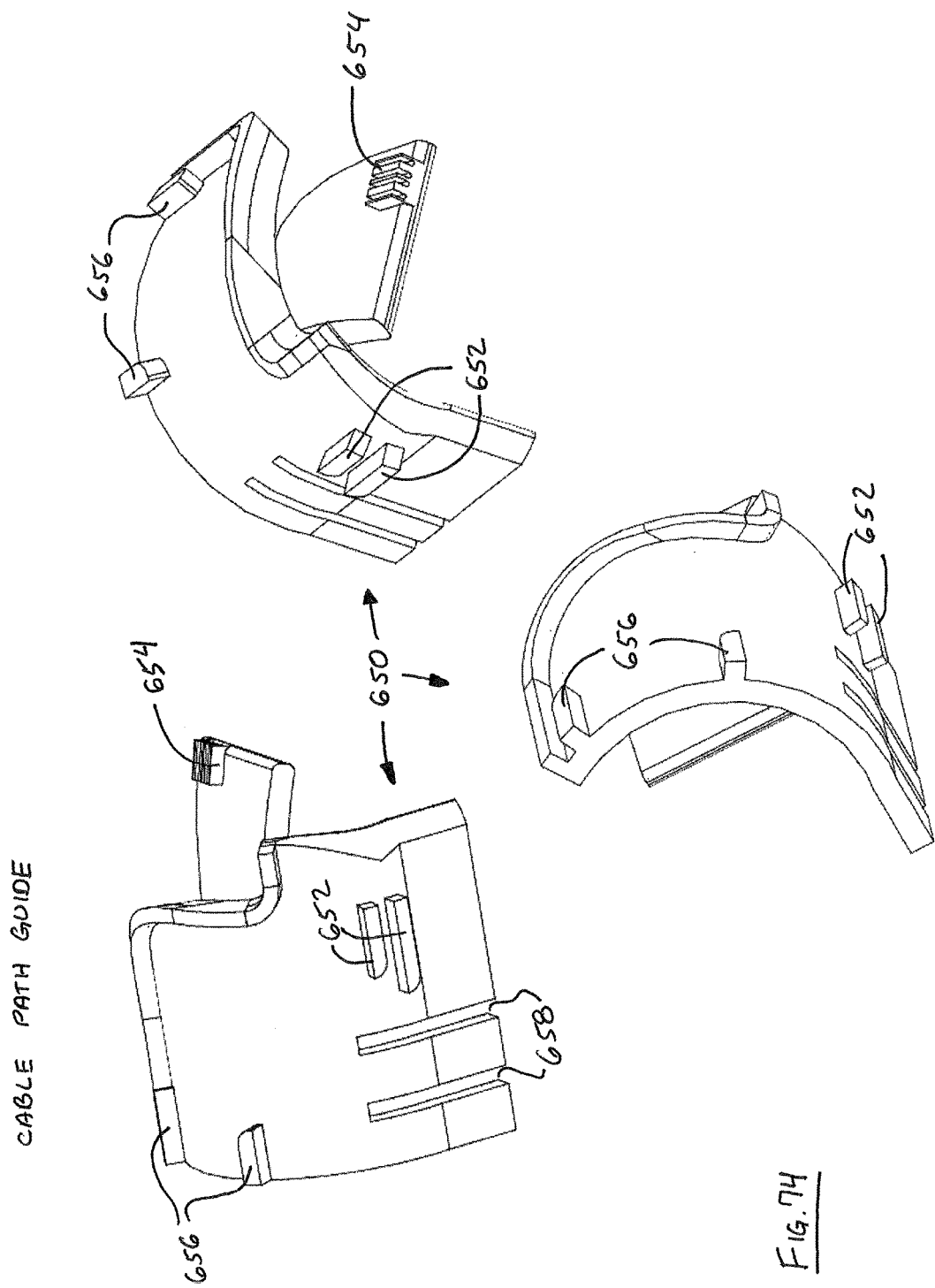

As illustrated in FIGS. 73-74, a cable path guide 650 is provided for directing cables 172, 174, 176, 178, 532, 534 through the handle 600. In particular, guide 650 provides a first set of guides 654 for guiding cables 172, 174, 176, 178, and a second set of guides, or bosses, 652, 654 for directing cables 532, 534 through the handle 600. Grooves 658 are provided in guide 650 for receiving ribs 612r of right housing portion 612 (FIG. 79(D)).

Figure 75:
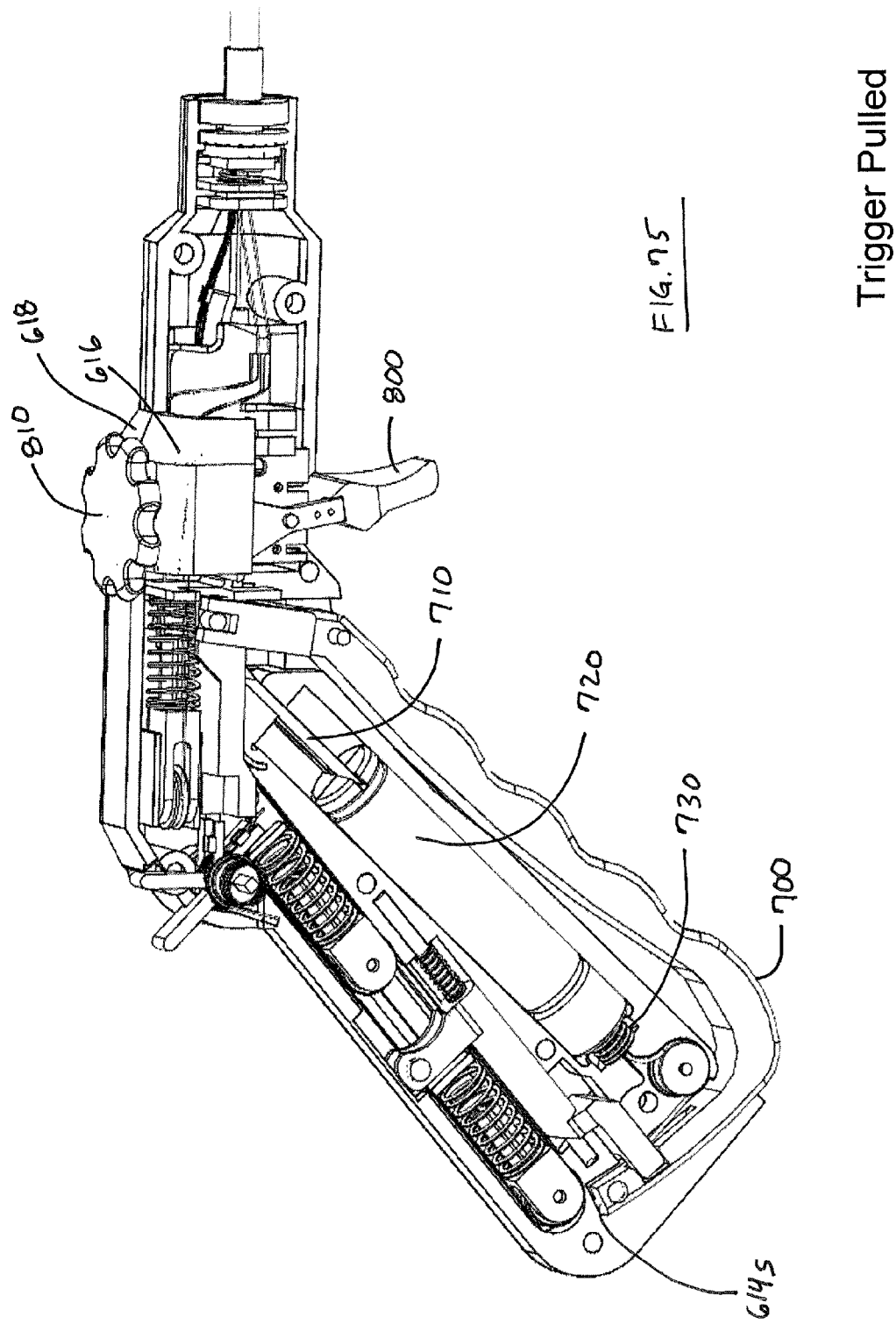
Figure 76:
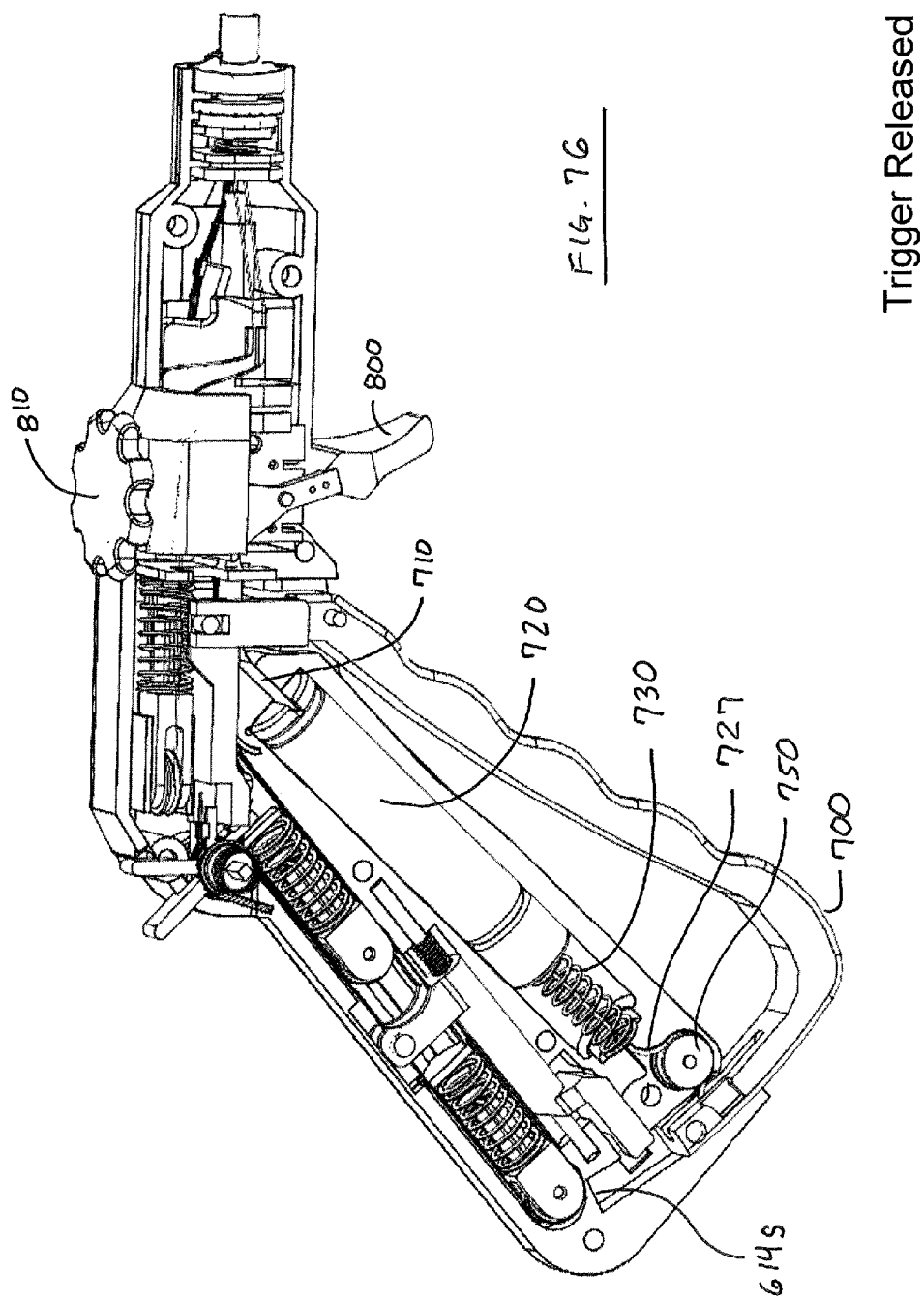
Figure 77:
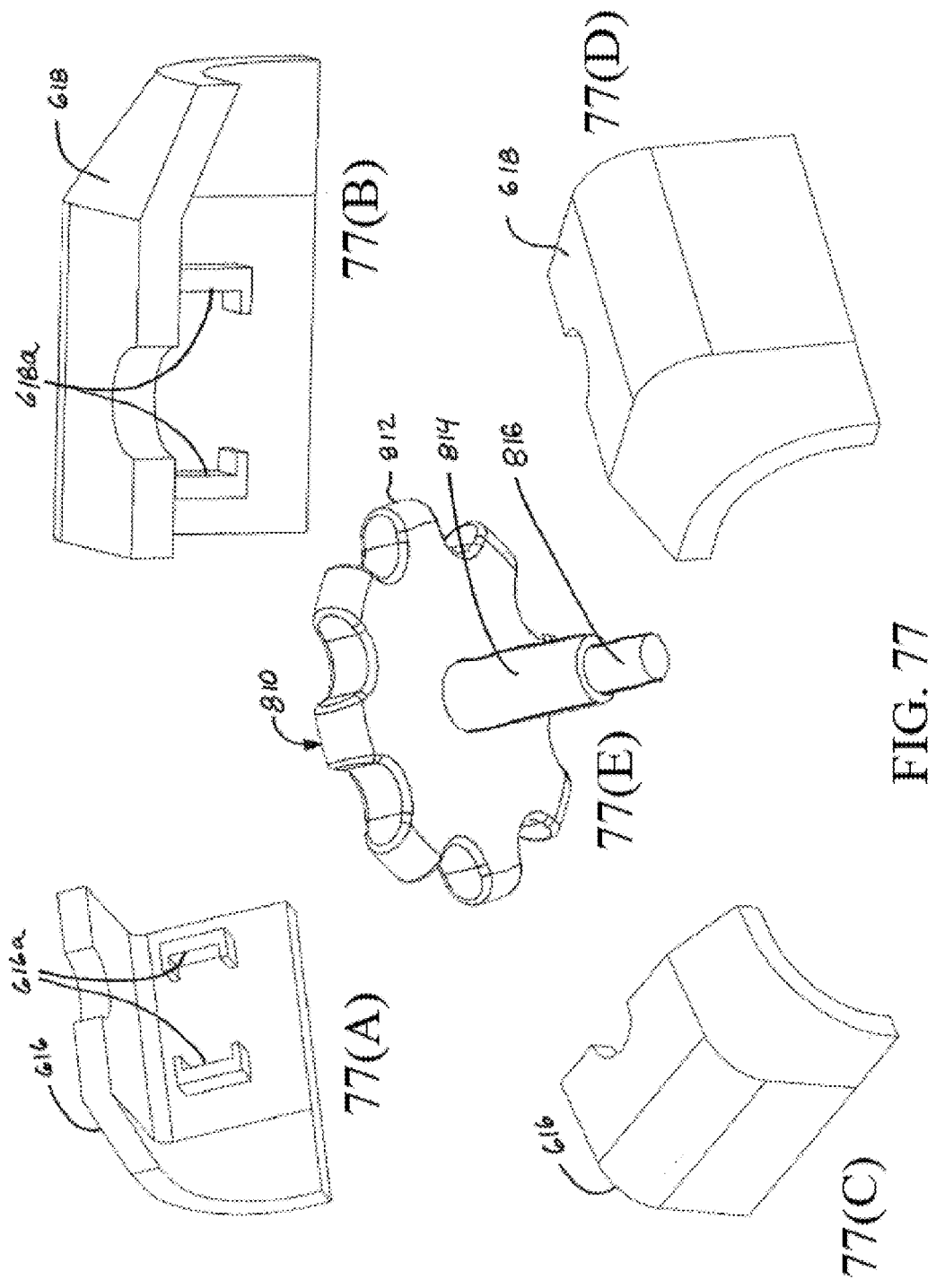
Figure 78:
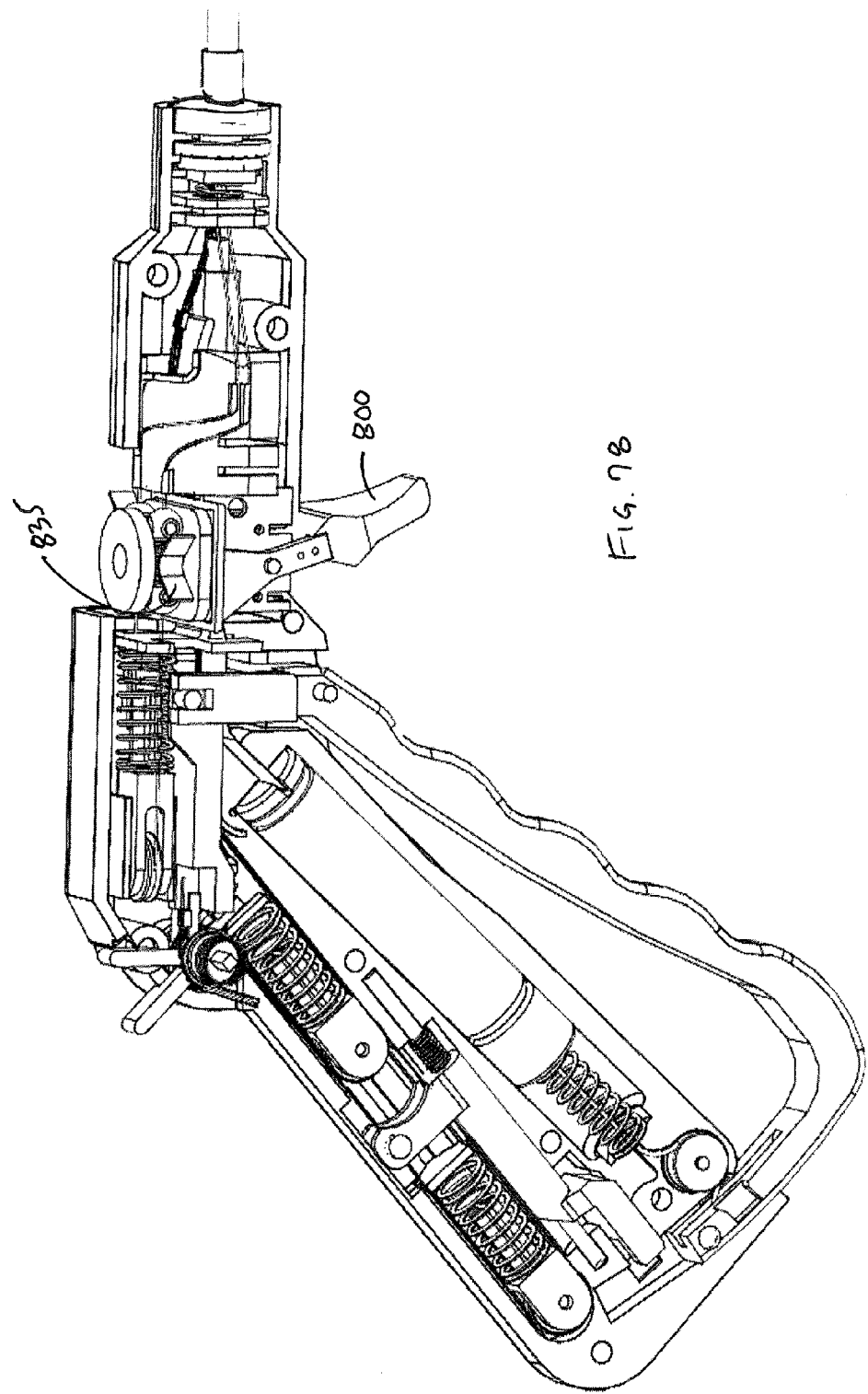
Figure 80:
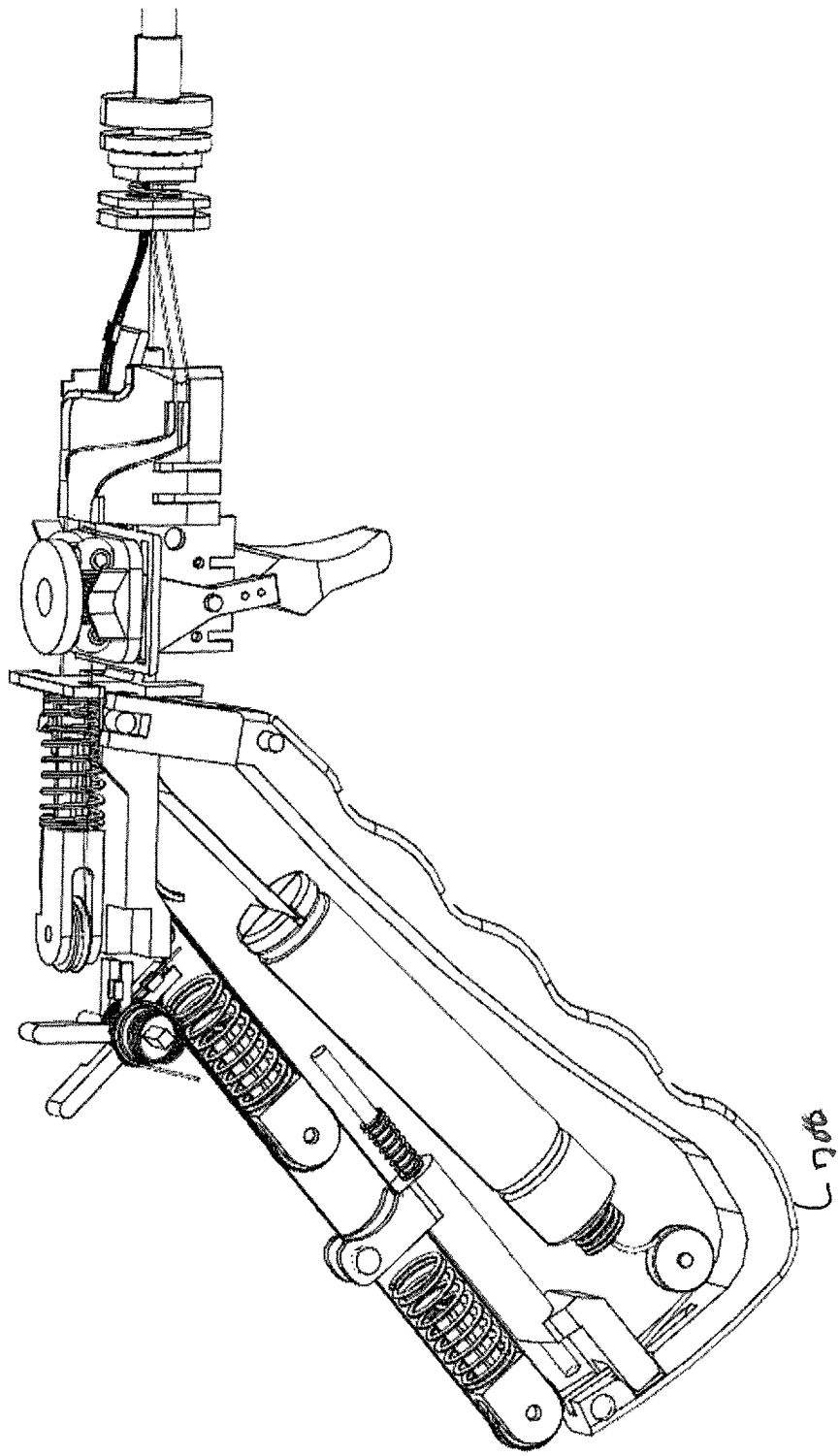
Figure 81:
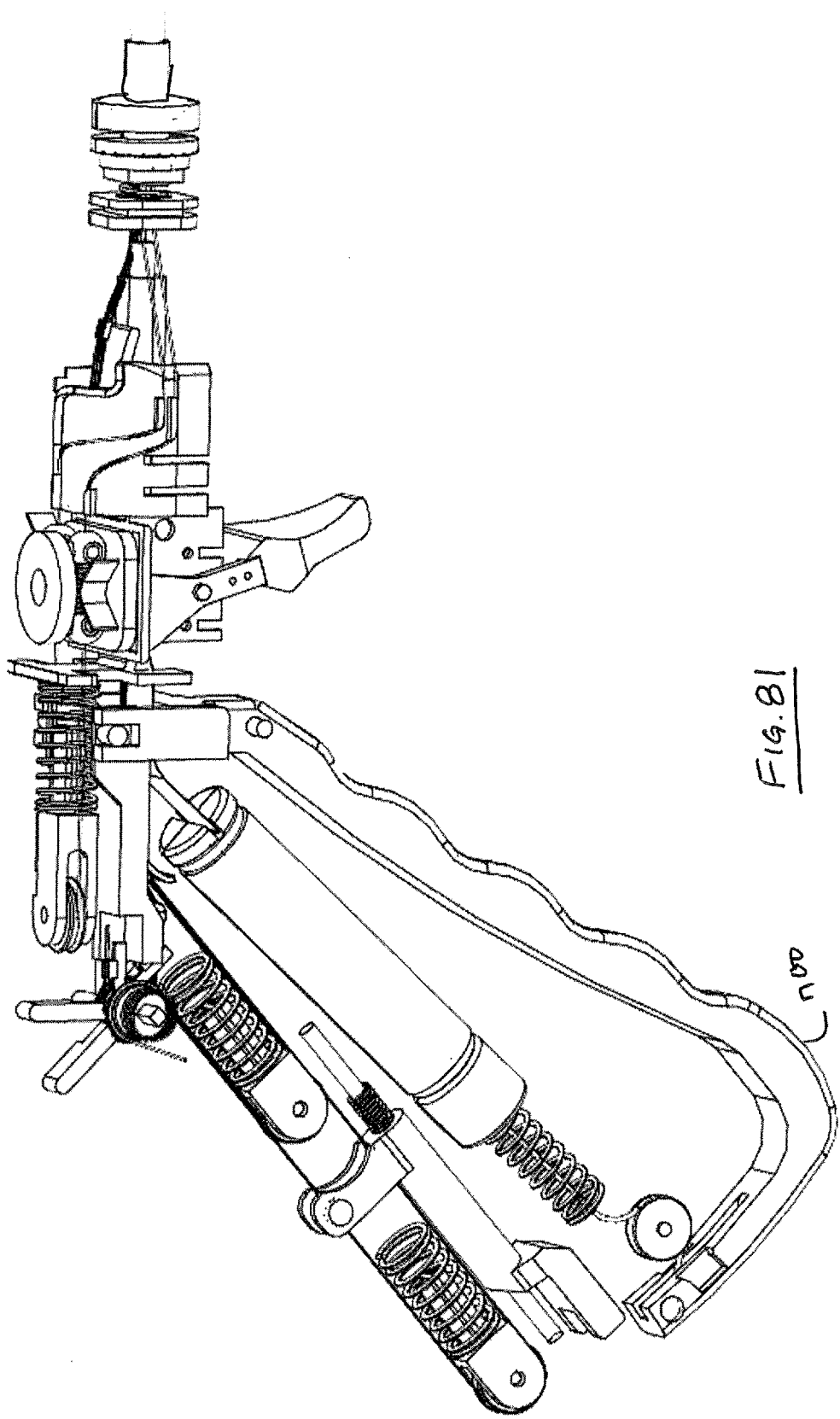
Figure 82:
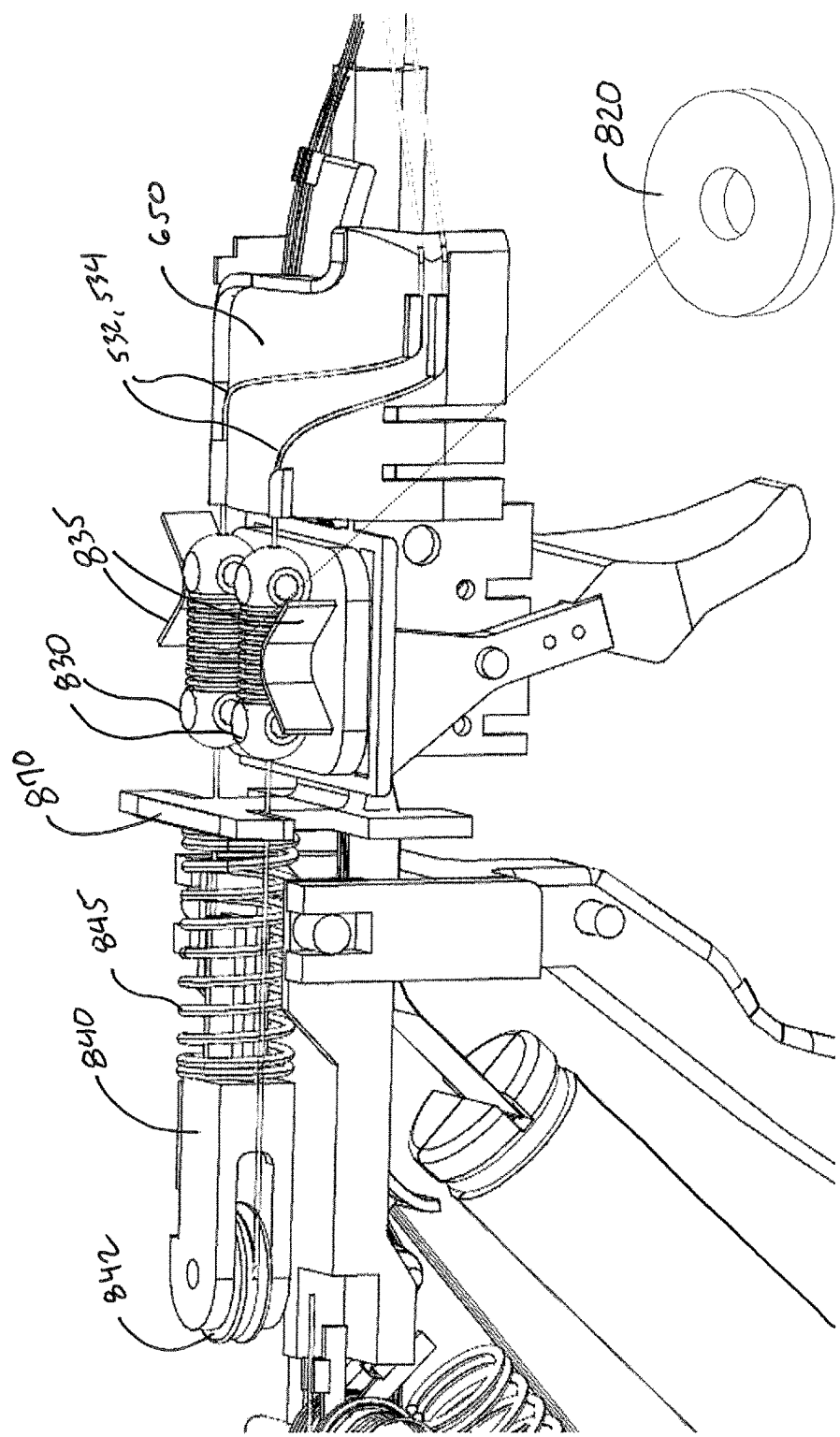

FIGS. 75-76 illustrate a cutaway view of handle 600 wherein right housing portion 612 has been removed to permit view of interior components of handle 600. FIG. 75 illustrates trigger 700, or actuator, in a locked position, whereas FIG. 76 illustrates trigger 700 in a released position wherein the trigger can be depressed, thus advancing needle (e.g., 300) about needle track 140. As illustrated in FIGS. 75-76, handle includes trigger 700, pull cable/ribbon 710, trigger spring capsule 720, trigger return spring 730, pull cable 727, pulley 750 and brake handle 800 for preventing articulation knob 810 from being rotated. As stop surface 614s is defined in left housing 614 to define a stop point for trigger 700 when trigger 700 is locked. Right housing 612 includes a similar stop feature 612s (FIG. 79(D)). Articulation knob 810 (FIG. 77(E)) includes a handle portion 812, an elongate shaft 814 for engaging with brake rotate fitting 830 (FIG. 83), and a distal portion 816 that is preferably threaded for receiving a hex nut 886 (FIG. 90). Right and left handle cap portions 616, 618 (FIGS. 77(A)-77(D)) are provided with bosses 616a, 618a for receiving and supporting the edges 835b of brake springs 835 (FIG. 84). Bearing portion 835a of brake springs 835 bear against brake rotate fittings 830, which in turn urges brake rotate fittings 830 against shaft 814 of knob 810. Portion 814 of knob 810 preferably includes a resilient layer or coating that can grip serrated portion 834 of fittings 830, wherein rotation of the knob 810 causes the fittings 830, and hence cables 532, 534 to advance along a proximal-distal direction with respect to device 1000, resulting in articulation of suture head 100, 100'. FIG. 78 illustrates handle 600 with components 810, 616, 618 removed. FIGS. 79(A)-79(D) illustrate inner and outer views of left and right handle portions 612, 614. FIGS. 80-81 illustrate the inner workings of handle 600 with both handle portions 612, 614 removed with the trigger 700 locked, and released, respectively. FIG. 82 illustrates a close up view of the inner workings of handle 600, showing the upper brake pad 820 removed, fully revealing the positioning of fittings 830 and springs 835 with the trigger 700 released. Also illustrated is knuckle pulley 842, which is rotationally supported by knuckle pulley holder 840, which in turn is biased by a guide spring 845 against bracket 870 to maintain tension on cables 532, 534. FIGS. 83-85 further illustrate fittings 830, spring 835 and spring 845.

Figure 87:
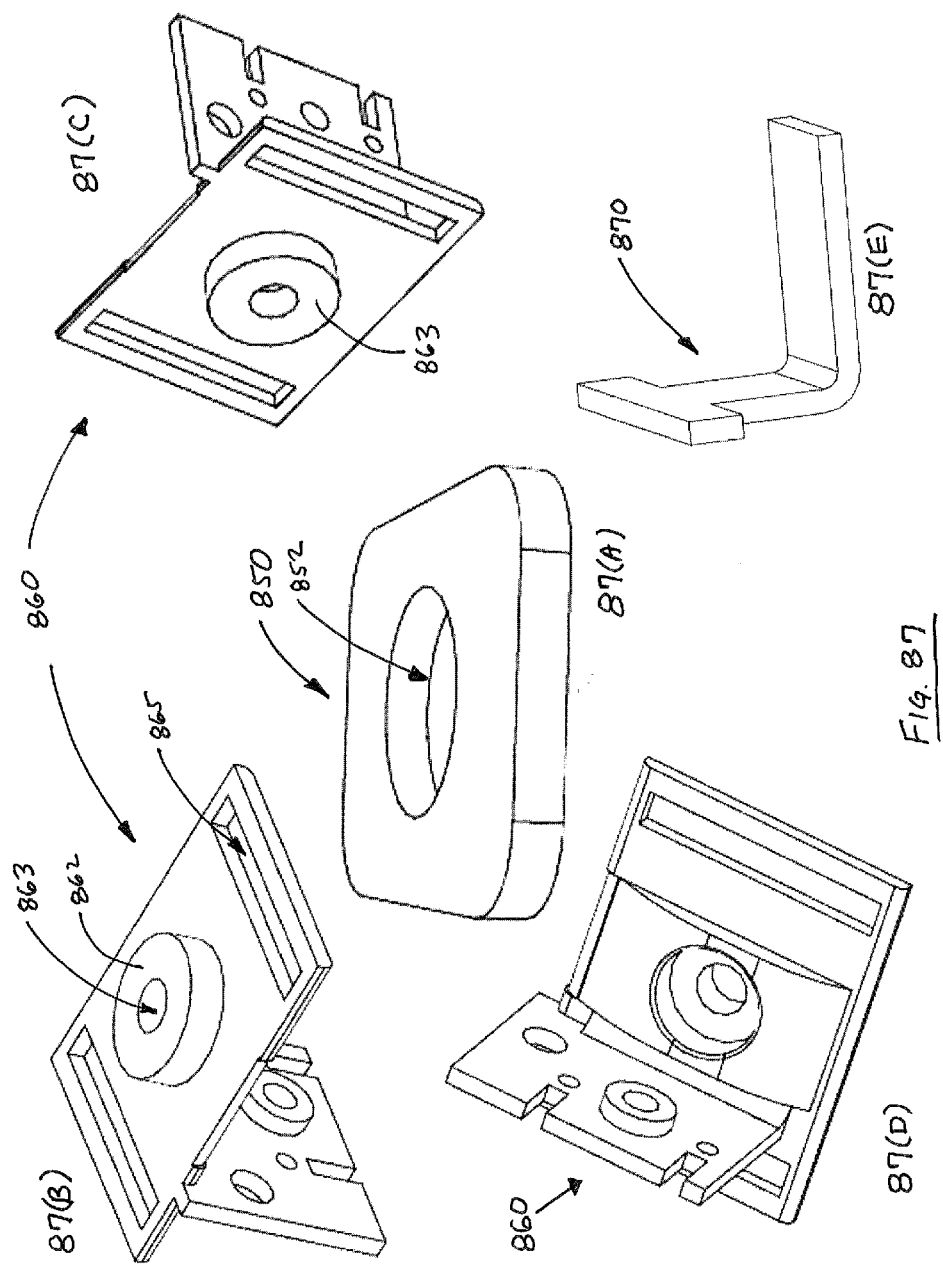
Figure 88:
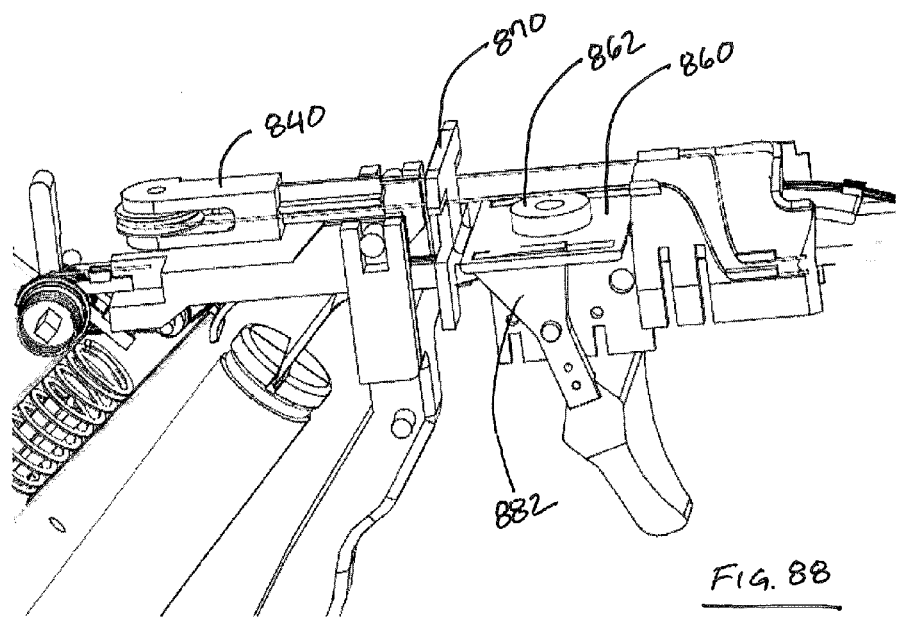
Figure 89A:
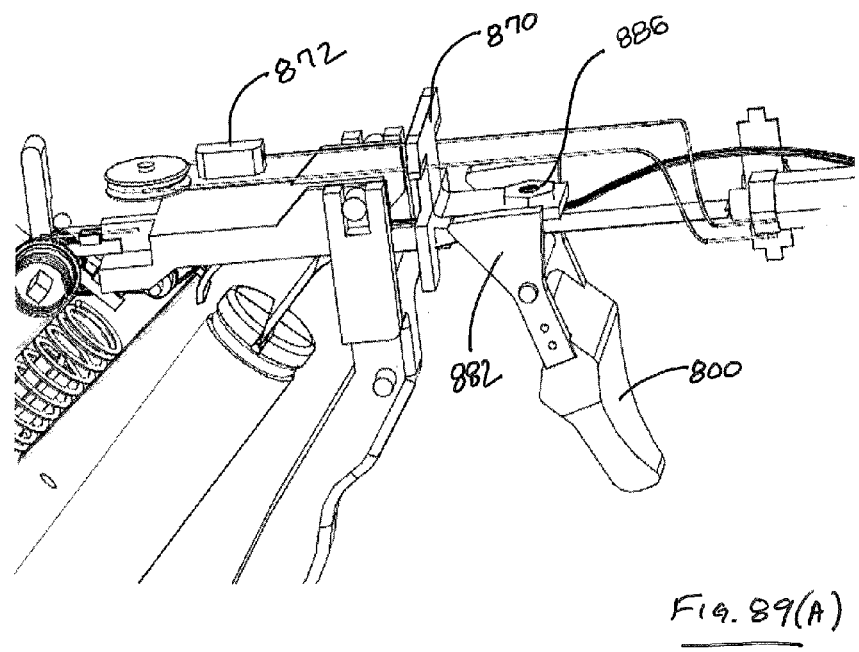
Figure 89B:
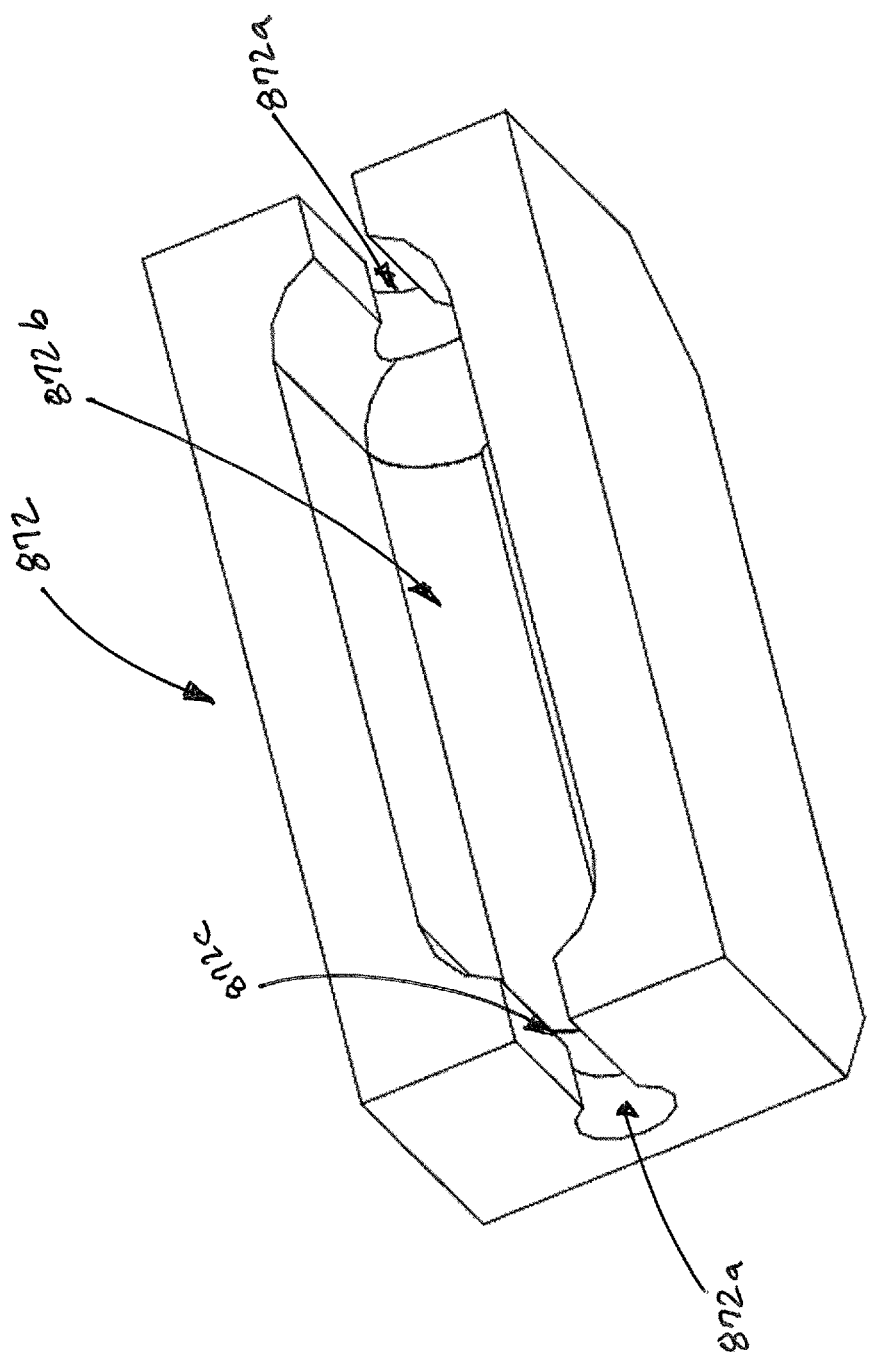
Figure 91A:
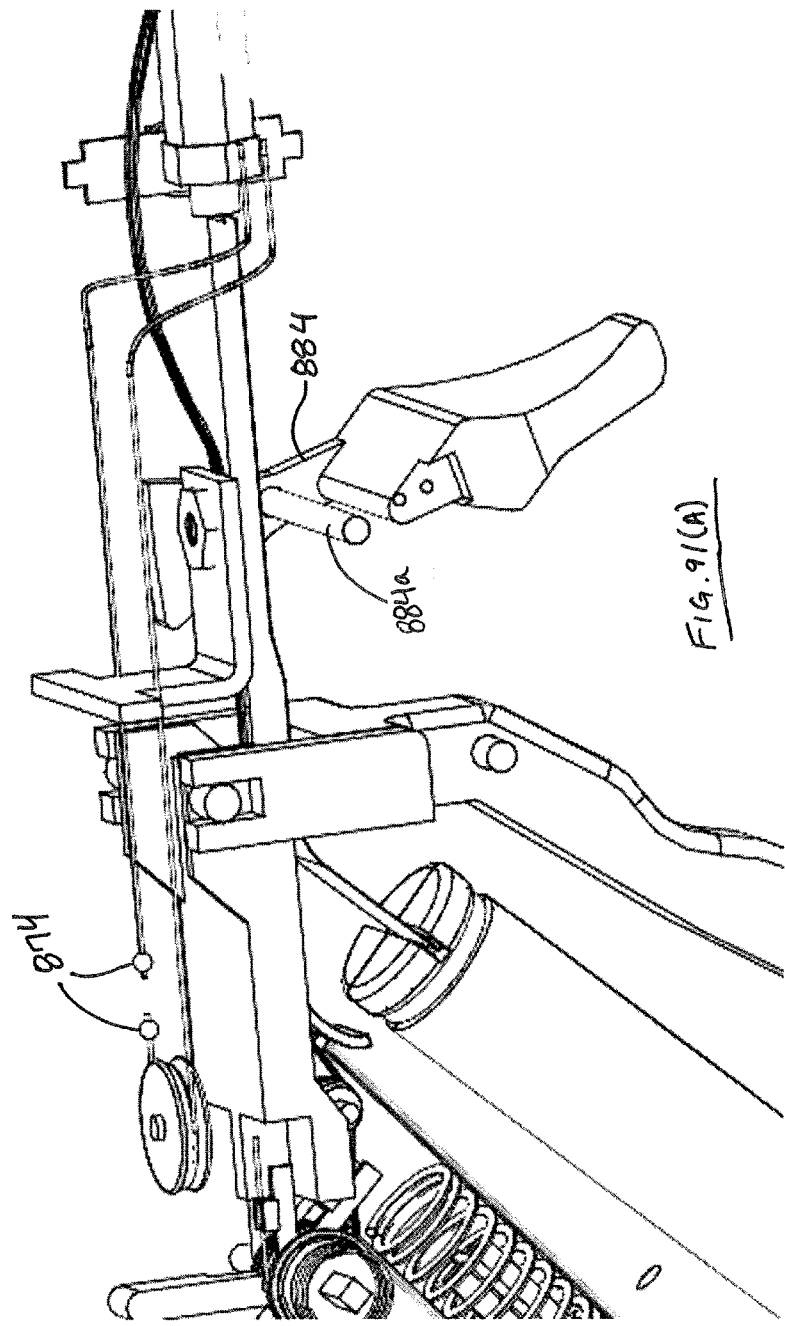
Figure 91B:
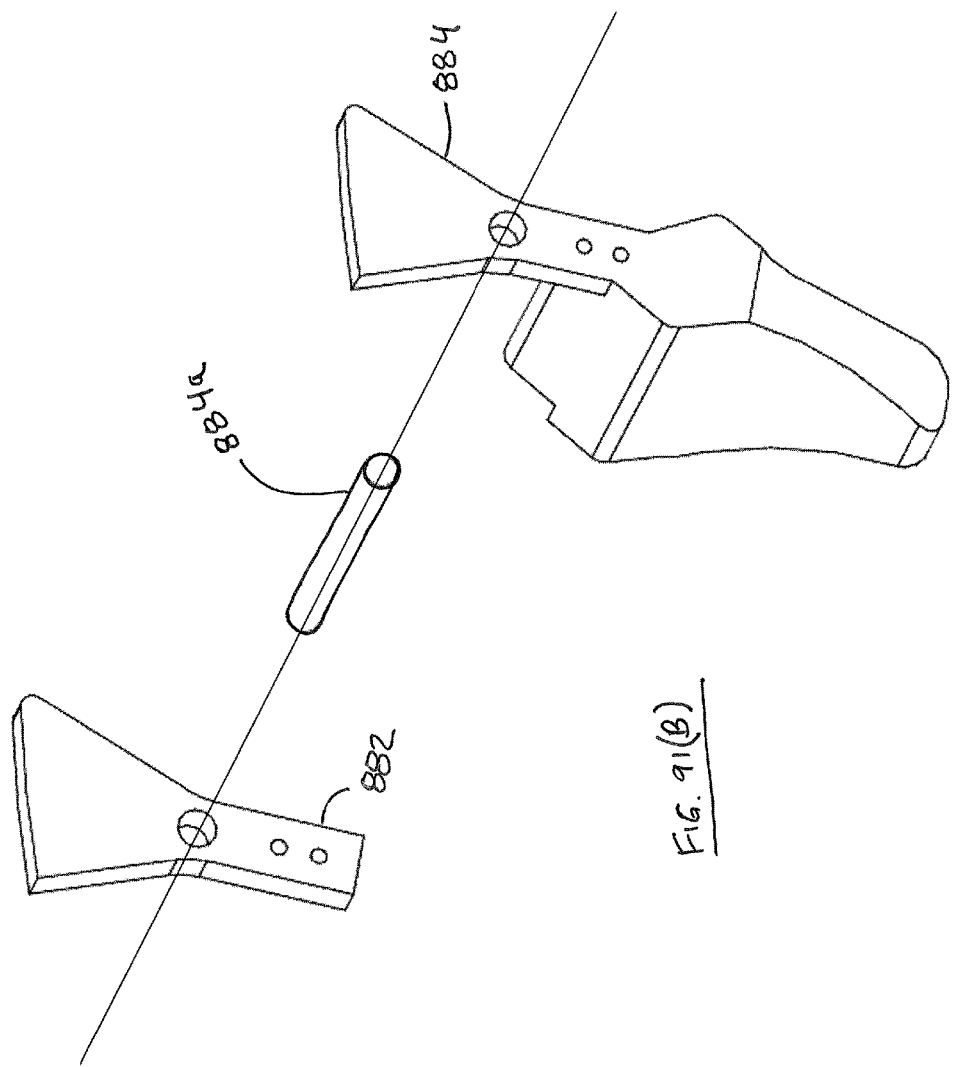
Figure 93:
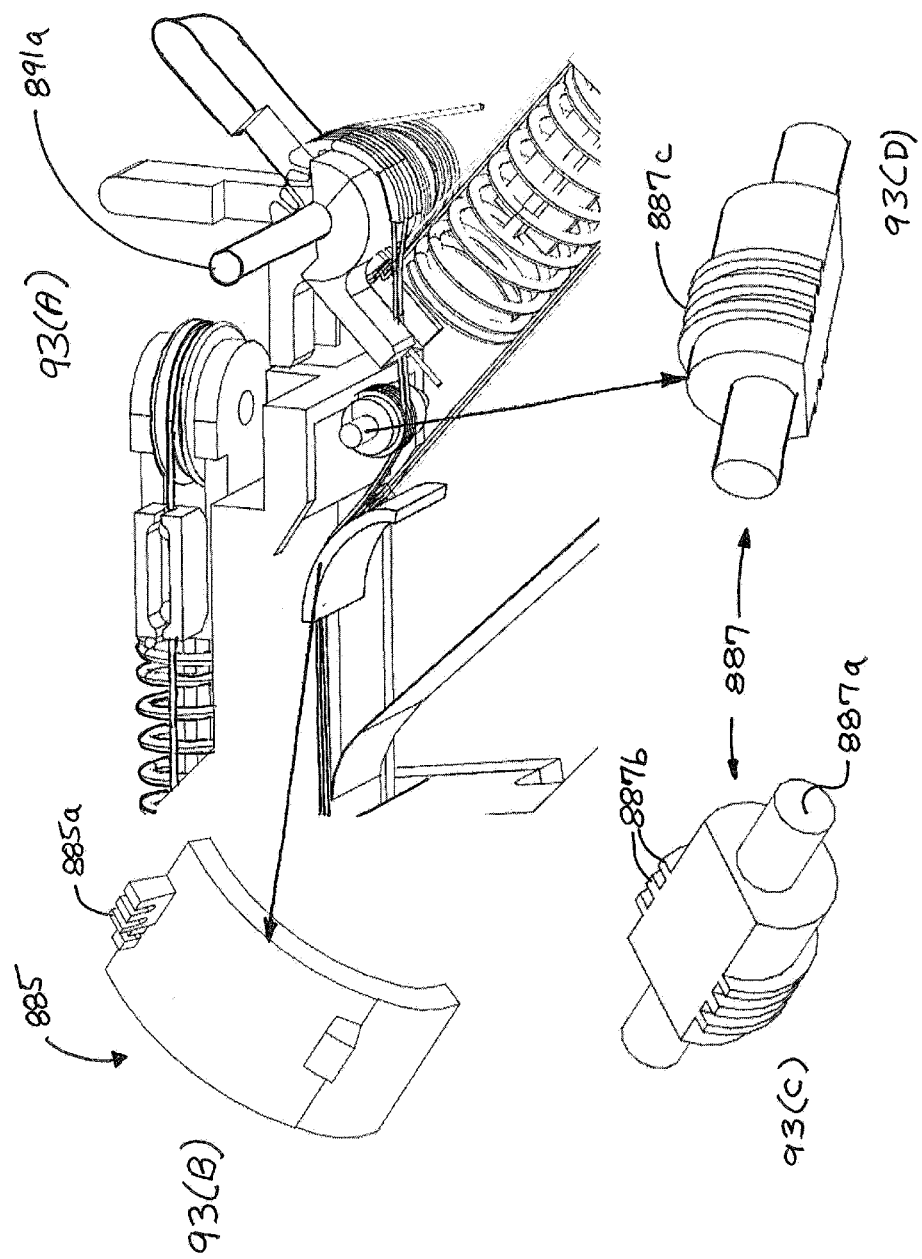
Figure 98:
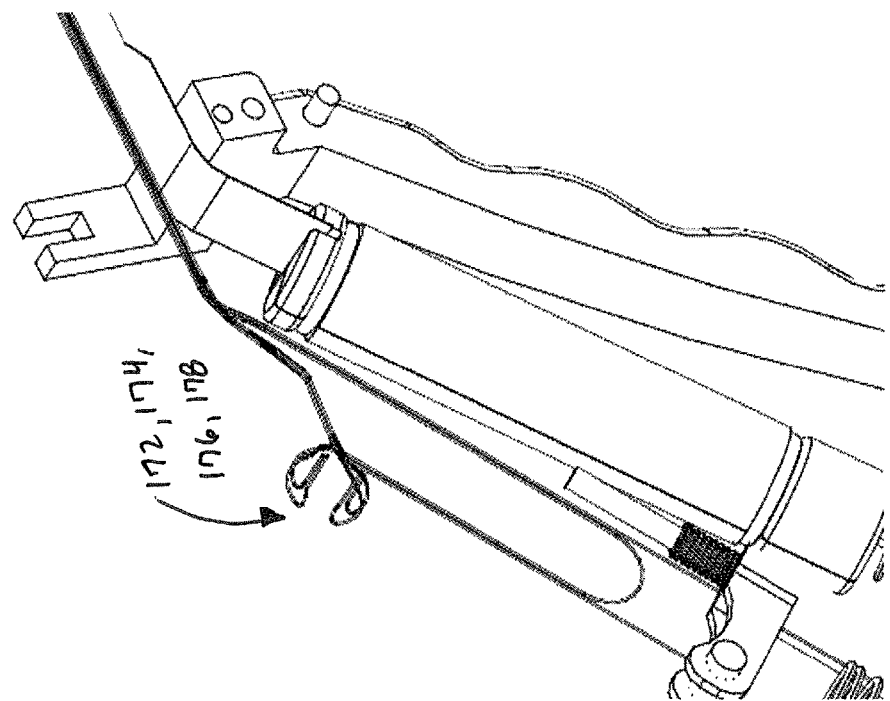
Figure 97:
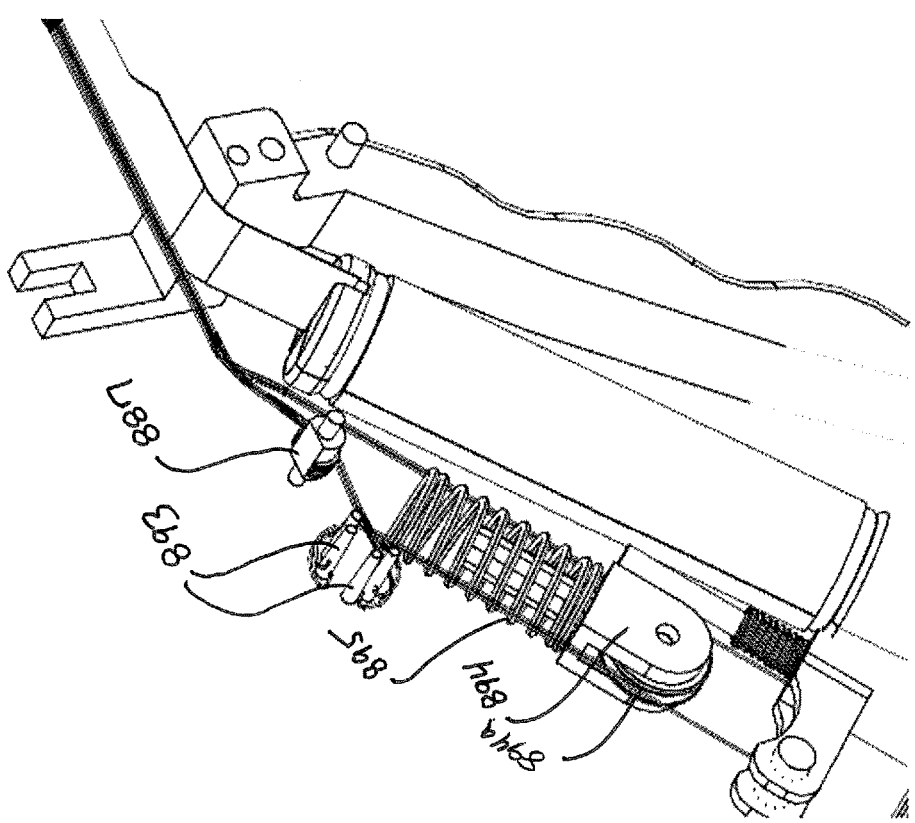

FIGS. 86(A)-86(B) illustrate the movement of shuttle 888 (FIGS. 99(A)-99(B)), which moves proximally upon the release of trigger 700. Proximal movement of shuttle 888 prevents handle 892r from being articulated, which, in turn, prevents guides 120, 130 from being withdrawn into suture head 100, 100' while trigger 700 is actuated, advancing the needle (e.g., 300) about circular needle track 140, 140'. Components 830, 835 have been removed in FIG. 86 to better illustrate lower brake pad 850. Brake pads 820, 850 are preferably made from resilient and somewhat compressible material, such as silicone. FIG. 87(A) further illustrates lower brake pad 850, while FIGS. 87(B)-87(D) illustrate brake bracket 860. Bracket 860 defines a circular boss 862 thereon for receiving lower brake pad 850, as well as brake handle components 882, 884, 884a (FIG. 91(B)). FIGS. 88-89(A) illustrate remaining inner workings of handle with brake pad removed (FIG. 88) and further with pulley holder 840 and brake bracket 860 removed. FIGS. 89(A)-89(B) further illustrates coupling knuckle 872, which includes longitudinal openings 872a having narrowed portions 872c that are wide enough to permit passage of a cable 532, 534, but not wide enough to permit passage of cable terminations 874 (FIG. 91). Opening 872b, in contrast, is large enough to permit terminations 874 to pass into knuckle 872, thus joining cable 532 to cable 534, and providing a closed loop to facilitate articulation by way of articulation and brake control 800. Brake trigger 884 can be pulled, causing a camming effect of by moving an upper portion of handle component 882 (and its counterpart on the left side of the device) into contact with lower brake pad 850, causing the brake pad 850 to compress components 830 between the upper and lower brake pads 820, 850.

FIGS. 92-102 illustrate aspects of the operation and control for the guides 120, 130 as well as the locking mechanism for trigger 700. Guides 120, 130 are deployed or withdrawn by rotating handles 892. Cables 172-178 are routed over guide 885, which is held in place by housing components 612, 614 and are split up into two pairs of wires, wherein one set of wires is directed downwardly around spring loaded pulleys 894a, 896a and routed up to handles 192 where all four cables, 172, 174, 176, 178 are held in place in openings 892b in handles 892 by tapered pins 893. The other pair of cables is routed about guide 887 directly into handles 892. Guide 885 (FIG. 93(B)) is a generally curved planar member having a plurality of cable guides 885a, wherein the cables 172-178 bear over its upper surface on their route to handles 892. FIG. 93(A) illustrates guides 887 and 885 in situ in relation to other internal components of handle 600. Guide 887 (FIGS. 93(C)-93(D)) include bosses 887a to be received by housing portions 612, 614, and grooves 887b defined by fins 887c for routing cables/wires. Handles 892 include grips 892a and grooves 892c and channels 892d for directing cables/wires into openings 892b (FIGS. 94(A)-94E). Both handles 892 can be essentially identical in form.

Guide handles 892 also play a role in releasing trigger lock 780, thereby permitting trigger 700 to actuate the movement of needle (e.g., 300). As illustrated in FIGS. 95(A)-95(B), trigger lock 780 is attached to a cable at ferrule 781, which is disposed in opening 783 at bifurcation 782 of trigger lock (FIGS. 95(C)-95(D)). Trigger lock 780 is slidably disposed on a cylindrical rail 786, and is biased toward a locked position by spring 787. A bifurcation 784 at the opposite end of trigger lock 780 is adapted and configured to interlock with trigger 700. When the cable to which ferrule 781 is attached is advanced upwardly (FIG. 95(B)) by rotating handle 892L, bifurcation 784 of trigger lock 780 disengages from trigger 700, permitting free movement of trigger. Handles 892L, 892R are pivotally disposed on axle 891 (FIGS. 96, 122). FIGS. 97-101 further illustrate additional features of the actuation system for guides 120, 130 with progressively additional components removed to better illustrate other components, and their relative positions. FIG. 102 further illustrates additional aspects and views of components 840, 894, 896.

Figure 105:
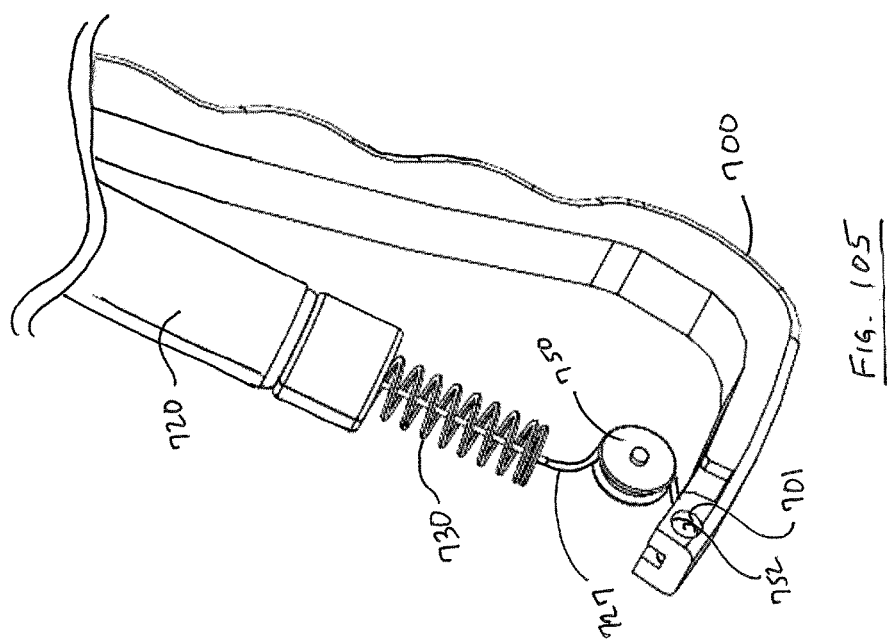

FIGS. 103-113 illustrate aspects of the operation of reciprocating trigger mechanism 700. FIG. 103 illustrates the relative positions of trigger 700, pull cable/ribbon 710, trigger spring capsule 720, trigger return spring 730, pull cable 727 and pulley 750. FIG. 103 removes components 786, 787 and handle 700 to reveal ferrule 752, which is fixed to a terminal end of pull cable 727 and resides within an opening 701 within handle 700 (FIG. 105). Trigger 700 is further illustrated in FIGS. 106(A)-106(B) from two additional angles, showing bifurcated yoke 702 proximate the top end of trigger 700. Yoke cap 704 is received in trigger handle 700 by securing studs 704a into holes 700a by interference fit and/or ultrasonic welding, adhesive or the like. Yoke 702 and yoke cap 704 define openings 702a, 704a therein for receiving bosses 888a of shuttle link 888 (FIG. 99(B)). FIG. 107(A) illustrates the interior of capsule 720, revealing clutch spring 724. FIGS. 107(B)-107(C) illustrate housing portion 720a, which mates with housing portion 720b. Housing portion 720b is an identical minor image of portion 720a, so only 720a is illustrated. Clutch spring 724 is removed in FIG. 108, clearly illustrating pull cable 727, clutch spring ferrule 723 and clutch washer 726. FIG. 109 illustrates the assembly with spring 730 and housing portion 720b removed. FIG. 110 illustrates a closeup of the connection of drive member 710 to assembly 720, showing the manner in which tabs 711, 712 at proximal end of drive member 710 are bent and inserted through the slot 721a in washer plate 721. O-rings 720, which may be silicone or other suitable material, are illustrated in FIGS. 104 and 109. O-rings 729 provide a seal against housing segments 612, 614. Ferrule 723 is secured to cable 727. FIGS. 111-113 provide closer views of ferrule 723, washer plate 721 and proximal end of member 710, respectively.

FIGS. 114-120 further illustrate the connections between drive member 710 and drive members 150/551. As illustrated in FIG. 114, proximal drive member, which can include ribbon-element 150 described above attached to intermediate cable section 551 in intermediate region 500, is received by a ferrule 910 which is affixed in place after termination 930 is attached, and positioned into cavity 922 in coupling by passing cable/rod 551 through slot 924 in coupling 920. Rounded portion 932 of termination faces distally, permitting movement between member 551 and coupling 920. As illustrated in FIGS. 115-117, termination 930 defines a passage 936 therethrough for receiving cable 551, and defines a generally cylindrical proximal section 934. Ferrule 910 defines a passage 912 therethrough for receiving cable 551, and a transverse opening 914 therethrough, such as for receiving brazing or soldering material or other material for holding ferrule in place on cable 551. Coupling 920 includes a proximal face 922a, a distal face 928 and a bore 922 therethrough. As illustrated in FIG. 114 in cooperation with FIGS. 118-120, threaded male fitting 940 is received within threaded opening 922 of coupling, and receives a retaining hex nut 950 thereon. Proximal end 943 of fitting 940 faces proximally, and defines a cavity 946 therein for receiving distal tip 717 of drive ribbon/cable 710. Tip 717 is inserted into cavity 946 until stop 719 contacts proximal face 943. Threads 942, 952 are defined on fitting 940 and nut 950. Components 940, 710 may be coupled by any suitable means, including but not limited to interference fit and/or welding, soldering, brazing, adhesive and the like. FIGS. 121-122 illustrate torsion spring 960 and guide spring 970 and their positioning with respect to the other components within handle 600. Springs 960, 970 are a part of the control mechanism for deploying and retracting guides 120, 130. Return spring 895, 897 is illustrated in FIG. 121(C).

An exemplary method of operation of suture head 100 is set forth in FIGS. 123-131. FIG. 123 illustrates a cutaway view of suture head 100 with needle 300 disposed therein in a delivery configuration with guides 120, 130 retracted. Needle 300 is wholly contained within device 1000, and pawl spring 115b prevents needle 300 from moving in a counterclockwise direction. Similarly, pawl spring 115a is biased against the inner circumferential surface 322 of needle, tending to prevent needle from moving in a clockwise direction. As set forth in FIGS. 123-131, it is apparent from the instant disclosure that the drive system of the device 1000 is adapted and configured to advance the needle 300 in multiple 360° revolutions about the needle track when the needle track is in a deployed condition. It is further evident that the needle track is about 180° in extent prior to deployment, and greater than 180° in angular extent after deployment.

FIG. 124 illustrates the initial deployment of guides. Pawl 115a is dragged along surface 322 of needle 300 until it engages with notch 308 and pawl 115b engages with notch 306. Guides are then fully retracted in FIG. 125, and pawl 115a situated in guide 120 drags needle 300 in a clockwise direction to present it for suturing. Pawl 160 meanwhile is advanced along its arcuate track along guides 120, 130 to its distalmost extent, causing notch 158 in the drive member 150 to align with boss 108a, and pawl 115b bears against surface 122 of needle 300. When drive member 150 is then pulled proximally, notched region 158 of member 150 slips past bosses 106a, 108a and drive member 150 drops into lower passage defined in part by passage 108T. Further proximal movement of drive member 150 causes the distally located wider portion of ribbon 150 to bear against the underside of bosses 106a, 108a, and pawl 160 makes contact with the trailing end of the needle 300, and needle is advanced about 180°, as illustrated in FIG. 126. The distal movement of pawl 160 is then repeated, such that pawl 160 engages with notch 310 in needle 300. Region 158 slips past bosses 106a, 108a as before, and pawl 160 and the leading tip 302 of needle are pulled along the arcuate needle track 140, resulting in the needle being returned to its starting point, as illustrated in FIG. 128. FIG. 129 illustrates guides 120, 130 in partial retraction such that needle is moved counterclockwise until notch 306 meets with pawl 115b. FIG. 130 illustrates guides 120, 130 retracted even further, illustrating how pawl 115a is pulled out of notch 308 and is dragged along surface 322 of needle. further counterclockwise movement of needle 300 is prevented by pawl 115b being locked into notch 306. FIG. 131 illustrates suture head 110 once again in delivery or removal configuration with guides 120, 130 fully withdrawn. Thus, a device is provided herein that can rotate the disclosed needle through 180°, 360°, or any further multiple of 180° as desired. If desired, the angular increments of advancement could be increments of more or less than 180° as desired.

The suturing devices of the presently disclosed embodiments can be used for laparoscopic procedures, including but not limited to laparoscopic colostomy, colectomy, adrenalectomy, splenectomy, repair of paraesophageal hernia, inguinal hernia repair, ventral hernia repair, Nissen fundoplication, liver lobectomy, gastrectomy, small bowel resection, treatment of small bowel obstruction, distal pancreatectomy, nephrectomy and gastric bypass. Those skilled in the art will recognize that the presently disclosed embodiments can be used in other laparoscopic procedures.

In using the devices of the presently disclosed embodiments, the abdomen is insufflated with gas to create a working space for the user. Any gas known to those skilled in the art including, but not limited to, nitrogen or carbon dioxide, can be used. Access portals are established using trocars in locations to suit the particular surgical procedure. A variety of surgical instruments may then be inserted into the body through these access ports/cannulas. The user then introduces the distal end portion of the suturing device into a cannula, and then articulates the suture head assembly (e.g., 100, 100'). The suture head assembly is then positioned relative to the tissue/vessel to be sutured together, and the user preferably locks the suture head assembly in place. The user then, through manipulation of the suturing device, positions a plurality of separated tissue segments into the opening defined at the distal end portion of the suture head assembly. The user, using only one hand, may manipulate the device while actuating the handle to close an incision with a continuous suture whose stitches may be individually tensioned precisely and uniformly along the length of the suture similar to suturing done by hand in the conventional way. The user may employ a single suture which would extend the entire length of the incision or multiple sutures. Thus, by placement of the device spanning the incised tissue segments and actuating the handle, the suturing device enables the user to lay down a running stitch or interrupted stitch to close the tissue incision in a time efficient manner. Those skilled in the art will recognize that any conventional procedure for conducting laparoscopic surgery can be used with the device.

The minimalized structural design of the suture head assembly enables the user to have a clear, unobstructed view of the suturing needle during advancement through the tissue segments during the course of a suturing operation, thereby enabling precise placement of the suturing device to provide uniform sutures and precluding the risk of tearing tissue by placement too close to the edge of the incision. The suturing device is then advanced a short distance along the incision and the aforementioned operation is repeated to produce another stitch comprising the suturing material or thread.

The user may continue to manipulate the suturing device, alternately advancing and actuating rotation of the needle about an axis that is generally parallel to the direction of advancement to create a continuous suture which may extend through the entire length of the incision or a series of interrupted stitches. After each individual stitch is laid down, the stitch is tightened by exerting a pull on the suturing material or thread so that the resultant suture is tensioned uniformly along the length of the incised tissue segments. Therefore, a tight closure of the segments is accomplished and bleeding and tearing of tissue are minimized. Once the appropriate amount of suture material or thread 246 has been placed, the user can use a needle grasper to tighten and knot the formed stitches.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the present disclosure.

What is claimed is:

1. A suturing device comprising:
    an arced needle having a leading end, a trailing end, and a length of suture, the arced needle being disposed within a suturing head located at a distal end of the suturing device;
    an arced needle track defined in the suturing head for receiving the needle, the arced needle track defining a circular path;
    a needle driver configured to drive the needle along the circular path in a first rotational direction, the needle driver including a drive pawl that is configured to engage the needle and advance the needle along the needle track in the first rotational direction, and
    a plurality of anti-rotate pawls projecting into the arced needle track, the plurality of anti-rotate pawls being spaced apart from one another along the circular path defined by the needle track, each anti-rotate pawl being configured to engage the trailing end of the needle to prevent the needle from rotating in a second rotational direction opposite the first rotational direction when the needle driver reciprocates between a drive stroke and a return stroke, wherein the drive stroke drives the needle about 180 degrees along the needle track.

2. The suturing device of claim 1, wherein the plurality of anti-rotate pawls are spaced apart a multiple of about 90 degrees from one another along the circular path defined by the needle track.

3. The suturing device of claim 2, wherein the plurality of anti-rotate pawls includes two pawls that are spaced apart a multiple of about 90 degrees from one another along the circular path defined by the needle track.

4. The suturing device of claim 1, wherein at least one of the anti-rotate pawls is positioned to be adjacent the trailing end of the needle after the drive stroke is completed.

5. The suturing device of claim 1, wherein at least one of the anti-rotate pawls and a portion of a housing of the suturing device are unitary.

6. The suturing device of claim 1, wherein each of the anti-rotate pawls interferes with the needle in the needle track when the needle is present in the same location of the needle track as each of the anti-rotate pawls.

7. A suturing device comprising:
    an arced needle having a leading end, a trailing end, and a length of suture, the arced needle being disposed within a suturing head located at a distal end of the suturing device;
    an arced needle track defined in the suturing head for receiving the needle, the arced needle track defining a circular path;
    a needle driver configured to drive the needle along the circular path in a first rotational direction, the needle driver including a drive pawl that is configured to engage the needle and advance the needle along the needle track in the first rotational direction; and a pair of pawls projecting into the arced needle track, the pair of pawls being spaced apart from one another along the circular path defined by the needle track, both pawls being configured to simultaneously engage anti-rotate surfaces of the needle to prevent the needle from rotating in a second rotational direction opposite the first rotational direction when the needle driver reciprocates between a drive stroke and a return stroke, wherein the drive stroke drives the needle about 180 degrees.

8. The suturing device of claim 7, wherein at least one of the pawls is positioned to be adjacent the trailing end of the needle after the drive stroke is completed.

9. The suturing device of claim 7, wherein at least one of the pawls and a portion of the suturing head are unitary.

10. The suturing device of claim 7, wherein each of the pawls interferes with the needle in the needle track when the needle is present in the same location of the needle track as each of the pawls.

11. A suturing device comprising:
an arced needle having a leading end, a trailing end, an inner radial surface, an outer radial surface and a length of suture, the needle being disposed within a suturing head located at a distal end of the suturing device, the arced needle including at least one engagement surface formed into the inner radial surface;
an arced needle track defined in the suturing head for receiving the needle, the arced needle track defining a circular path;
a needle driver configured to drive the needle along the circular path in a first rotational direction, the needle driver including a drive pawl that is configured to engage the needle and advance the needle along the needle track in the first rotational direction, wherein the needle driver reciprocates between a drive stroke and a return stroke, and further wherein the drive stroke drives the needle about 180 degrees; and
at least one anti-rotate pawl projecting from a location within the circular path of the needle radially outwardly into the arced needle track, the at least one anti-rotate pawl being configured to engage the at least one engagement surface formed into the inner radial surface of the needle, the at least one anti-rotate pawl remaining stationary with respect to the needle track as the needle driver reciprocates with respect to the needle track.

12. The suturing device of claim 11, further comprising a second anti-rotate pawl projecting radially outwardly into the arced needle track, the second anti-rotate pawl being configured to engage the at least one engagement surface formed into the inner radial surface of the needle.

13. The suturing device of claim 12, wherein the anti-rotate pawls are spaced apart from one another along the circular path defined by the needle track by a multiple of about 90 degrees.

14. The suturing device of claim 13, wherein the needle further defines a second engagement surface formed into the inner radial surface of the arced needle, the engagement surfaces of the needle being spaced apart from each other along the inner radial surface of the needle by a multiple of about 90 degrees.

15. The suturing device of claim 14, wherein the engagement surfaces of the needle are configured to engage the anti-rotate pawls simultaneously to prevent the needle from moving in a direction opposite to the first rotational direction.

* * * * *